United States Patent
Sasmal et al.

(10) Patent No.: US 9,394,305 B2
(45) Date of Patent: Jul. 19, 2016

(54) SUBSTITUTED IMIDAZO[1,2-A]PYRIDINE COMPOUNDS AS TROPOMYOSIN RECEPTOR KINASE A (TRKA) INHIBITORS

(71) Applicant: Dr. Reddy's Laboratories Ltd., Hyderabad (IN)

(72) Inventors: Pradip Kumar Sasmal, Hyderabad (IN); Shahadat Ahmed, Bangalore (IN); Ashok Tehim, Ridgewood, NJ (US); Vidyadhar Paradkar, Branchburg, NJ (US)

(73) Assignee: Dr. Reddy's Laboratories Ltd. (IN)

( * ) Notice: Subject to any disclaimer, the term of this patent is extended or adjusted under 35 U.S.C. 154(b) by 0 days.

(21) Appl. No.: 14/747,485

(22) Filed: Jun. 23, 2015

(65) Prior Publication Data
US 2015/0368238 A1    Dec. 24, 2015

Related U.S. Application Data

(60) Provisional application No. 62/015,677, filed on Jun. 23, 2014.

(51) Int. Cl.
C07D 471/04 (2006.01)
A61K 31/4025 (2006.01)
C07K 5/06 (2006.01)

(52) U.S. Cl.
CPC ............... *C07D 471/04* (2013.01); *C07K 5/06* (2013.01); *A61K 31/4025* (2013.01)

(58) Field of Classification Search
CPC ................ C07D 471/04; A61K 31/4025
See application file for complete search history.

(56) References Cited

U.S. PATENT DOCUMENTS 9,145,433 B2 *   9/2015   Bhamidipati ........ C07D 405/04

FOREIGN PATENT DOCUMENTS

| JP | 2003231687 A | 8/2003 |
|---|---|---|
| WO | 2004011461 A1 | 2/2004 |
| WO | 2005005427 A1 | 1/2005 |
| WO | 2013088256 A1 | 6/2013 |
| WO | 2013088257 A1 | 6/2013 |
| WO | WO2014055548 * | 4/2014 |
| WO | WO2014082979 * | 6/2014 |

OTHER PUBLICATIONS

Ardem Patapoutian and Louis F. Reichardt, Trk receptors: mediators of neurotrophin action, Curr OpinNeurobiol, 2001, 11, 272-280.
Wang, et al., Trk kinase inhibitors as new treatments for cancer and pain, Expert Opin. Ther. Patents, 2009, 19 (3):305-319.
Ghilardi, et al., Sustained blockade of neurotrophin receptors TrkA, TrkB and TrkC reduces non-malignant skeletal pain but not the maintenance of sensory and sympathetic nerve fibers, Bone, 2011, 48(2), 389-398.
Hayashi, et al., Involvement of NGF in the Rat Model of Persistent Muscle Pain Associated With Taut Band, J. Pain, Article in Press, 2011, 12(10), 1059-1068.
Woolf, et al., Nerve growth factor contributes to the generation of inflammatory sensory hypersensitivity, Neuroscience, 1994, 62,327-331.
Zahn, et al., Effect of blockade of nerve growth factor and tumor necrosis factor on pain behaviors after plantar incision, J. Pain, 2004, 5, 157-163.
McMahon, et al., The biological effects of endogenous nerve growth factor on adult sensory neurons revealed by a trkA-IgG fusion molecule, Nat. Med., 1995, 1, 774-780.
Shelton, et al., Nerve growth factor mediates hyperalgesia and cachexia in auto-immune arthritis, Pain, 2005, 116, 8-16.
Delafoy, et al., Role of nerve growth factor in the trinitrobenzene sulfonic acid-induced colonic hypersensitivity, Pain, 2003, 105, 489-497.
Matt S. Ramer and Mark A. Bisby, Adrenergic innervation of rat sensory ganglia following proximal or distal painful sciatic neuropathy: distinct mechanisms revealed by anti-NGF treatment, Eur. J. Neurosci., 1999, 11, 837-846.
Ro, et al., Effect of NGF and anti-NGF on neuropathic pain in rats following chronic constriction injury of the sciatic nerve, Pain, 1999, 79, 265-274.
Theodosiou, et al., Hyperalgesia due to nerve damage: role of nerve growth factor, Pain, 1999, 81, 245-255.
Gwak, et al., Attenuation of mechanical hyperalgesia following spinal cord injury by administration of antibodies to nerve growth factor in the rat, Neurosci. Lett., 2003, 336, 117-120.
Matayoshi, et al., Actions of brain-derived neurotrophic factor on spinal nociceptive transmission during inflammation in the rat, J. Physiol. 2005, 569:685-95.
Thompson, et al., Brain-derived neurotrophic factor is an endogenous modulator of nociceptive responses in the spinal cord, Proc. Natl. Acad. Sci. USA 1999, 96:7714-18.
Hiroshi Ueda, Peripheral mechanisms of neuropathic pain—involvement of lysophosphatidic acid receptor-mediated demyelination, Molecular Pain, 2008, 4(28), 1-11.
V. Freund-Michel, N. Frossard, The nerve growth factor and its receptors in airway inflammatory diseases, Pharmacol. Therapeut. 2008, 117(1), 52-76.

(Continued)

*Primary Examiner* — D M Seaman
(74) *Attorney, Agent, or Firm* — Lerner, David, Littenberg, Krumholz & Mentlik, LLP

(57) ABSTRACT

The present application relates to a series of substituted imidazo[1,2-a]pyridine compounds of formula (I),

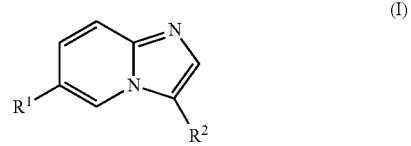

(I)

pharmaceutically acceptable salts, pharmaceutically acceptable solvates or stereoisomers thereof, their use as tropomyosin receptor kinase (Trk) family protein kinase inhibitors, method of making and pharmaceutical compositions comprising such compounds.

19 Claims, No Drawings

(56) References Cited

OTHER PUBLICATIONS

Hu, et al., Decrease in bladder overactivity with REN1820 in rats with cyclophosphamide induced cystitis, J. Urology, 2005, 173(3), 1016-21.

Mola, et al., Nerve growth factor and Trk high aYnity receptor (TrkA) gene expression in inflammatory bowel disease, Gut, 2000, 46(5), 670-678.

Dou, et al., Increased nerve growth factor and its receptors in atopic dermatitis: an immunohistochemical study, Arc Dermatol Res., 2006, 298(1), 31-37.

Raychaudhuri, et al., K252a, a high-affinity nerve growth factor receptor blocker, improves psoriasis: an in vivo study using the severe combined immunodeficient mouse-human skin model, J. Investig Dermatol., 2004, 122(3), 812-819.

International Search Report and Written Opinion for Application No. PCT/US2015/037214 dated Aug. 14, 2015.

Nwosu, Lilian N., et al., Blocking the tropomyosin receptor kinase A (TrkA) receptor inhibits pain behaviour in two at models of osteoarthritis, Ann Rheum Dis 2015, 2015, doi:10.1136/annrheumdis-2014-207203.

Roblin, David, et al., Topical TrkA Kinase Inhibitor CT327 is an Effective, Novel Thereapy for the Treatment of Pruritus due to Psoriasis: Results from Experimental Studies, and Efficacy and Safety of CT327 in Phase 2b Clinical Trial in Patients with Psoriasis, Acta Derm Vereal 95, pp. 542-548, 2015.

\* cited by examiner

SUBSTITUTED IMIDAZO[1,2-A]PYRIDINE COMPOUNDS AS TROPOMYOSIN RECEPTOR KINASE A (TRKA) INHIBITORS

RELATED APPLICATIONS

This application claims the benefit of U.S. Provisional Application No. 62/015,677 filed on Jun. 23, 2014; which is hereby incorporated by reference in its entirety.

TECHNICAL FIELD

The present application relates to a series of substituted imidazo[1,2-a]pyridine compounds. The present application is further directed to use such compounds as tropomyosin receptor kinase (Trk) family protein kinase inhibitors. The present application also describes method of making such compounds and pharmaceutical compositions comprising such compounds.

BACKGROUND

TrkA, TrkB and TrkC, which make up the Trk receptor family, are high affinity receptor tyrosine kinases activated by a group of soluble growth factors called neurotrophins (NT) (CurrOpinNeurobiol, 2001, 11, 272-280). Trks play important roles in pain sensation, tumour cell growth and survival signaling (Expert Opin. Ther. Patents, 2009, 19(3):305-319).

Inhibitors of the Trk/neurotrophin pathway have been demonstrated to be effective in numerous animal models of pain. For example, sustained blockade of neurotrophin receptors TrkA, TrkB and TrkC reduces non-malignant skeletal pain (Bone, 2011, 48(2), 389-398). Administration of NGF receptor (TrkA) inhibitor K252a showed significant suppression of mechanical hyperalgesia (relevant to the pathogenesis of myofascial pain syndrome (MPS) in animal models (J. Pain, Article in Press, 2011, 12(10), 1059-1068). Antagonistic NGF and TrkA antibodies have been shown to be efficacious in inflammatory and neuropathic pain animal models (Neuroscience, 1994, 62, 327-331 J. Pain, 2004, 5, 157-163 Nat. Med., 1995, 1, 774-780 Pain, 2005, 116, 8-16 Pain, 2003, 105, 489-497) and neuropathic pain animal models (Eur. J. Neurosci., 1999, 11, 837-846 Pain, 1999, 79, 265-274 Pain, 1999, 81, 245-255 Neurosci. Lett., 2003, 336, 117-120).

NGF secreted by tumor cells and tumor invading macrophages has been shown to directly stimulate TrkA located on peripheral pain fibers. It has also been demonstrated in various tumor models in both mice and rats that neutralizing NGF with a monoclonal antibody inhibits cancer related pain. Further, activation of the BDNF/TrkB pathway has been implicated in numerous studies as a modulator of various types of pain including inflammatory pain (J. Physiol. 2005, 569:685-95), neuropathic pain (Proc. Natl. Acad. Sci. USA 1999, 96:7714-18) and surgical pain (Molecular Pain, 2008, 4(28), 1-11). Since TrkA kinases have been demonstrated to serve as a mediator of NGF driven biological responses, inhibitors of TrkA and/or other Trk kinases may provide an effective treatment for various pain conditions.

Inhibition of the neurotrophin/Trk pathway with NGF antibodies or non-selective small molecule inhibitors of Trk A, B and C has been shown to be effective in treatment of preclinical models of inflammatory diseases such as asthma (Pharmacol. Therapeut., 2008, 117(1), 52-76), interstitial cystitis (J. Urology, 2005, 173(3), 1016-21), inflammatory bowel diseases including ulcerative colitis and Crohn's disease (Gut, 2000, 46(5), 670-678) and inflammatory skin diseases such as atopic dermatitis (Arc Dermatol Res., 2006, 298(1), 31-37), eczema and psoriasis (J. InvestigDermatol., 2004, 122(3), 812-819).

The current treatment regimes for pain conditions utilize several classes of compounds. The opiates apart from being potentially addictive have several adverse effects such as emesis, constipation, dose-related respiratory depression. Nonsteroidal anti-inflammatory analgesics (NSAID) also have drawbacks such as gastric ulceration, dyspepsia and insufficient efficacy in treating severe pain. Accordingly, there is a continuing need for new and more effective treatments for the relief of pain, especially chronic pain. Several classes of small molecule inhibitors of Trk kinases said to be useful for treating pain or cancer are known (Expert Opin. Ther. Patents, 2009, 19(3), 305-319).

JP Publication No. 2003231687 describes a series of pyrazolyl condensed cyclic compounds as Trk inhibitors.

PCT Publication No. 200505427 describes compounds containing a 1,4,5,6-tetrahydropyrrolo[3,4-c]pyrazole bicyclic scaffold as TrkA inhibitors.

PCT Publication No. 2004011461 describes a series of isothiazole derivatives as Trk inhibitors.

PCT Publication No. 2013088256 describes a series of pyrazolo[1,5-a]pyridine derivatives as Trk inhibitors.

PCT Publication No. 2013088257 describes a series of pyrazolo[1,5-a]pyridine derivatives as Trk inhibitors.

SUMMARY

The present applications relates to substituted imidazo[1,2-a]pyridine compounds of formula (I),

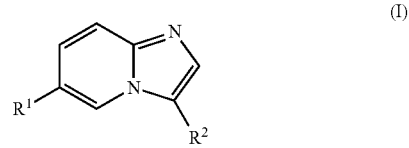

pharmaceutically acceptable salts, pharmaceutically acceptable solvates or stereoisomers thereof, wherein,
$R^1$ is —$X^a$—$R^a$;
$R^2$ is —$X^b$—$R^b$;
$X^a$ is a 3-7 membered heterocyclyl selected from aziridinyl, azetidinyl, pyrrolidinyl, piperidinyl, piperazinyl, azapanyl, thiomorpholinyl, 1,1-dioxo-thiomorphonyl and morpholinyl, any of which is optionally substituted with 1-3 times with $R^3$;
$R^3$, in each occurrence, is selected independently from halogen, hydroxy, —($C_1$-$C_6$)alkyl, —($C_1$-$C_6$)alkoxy and halo($C_1$-$C_6$)alkoxy;
$R^a$ is a phenyl ring optionally substituted 1-3 times with $R^4$;
$R^4$, in each occurrence, is selected independently from halogen, —($C_1$-$C_6$)alkyl, and —O—$R^5$;
Alternatively, two $R^4$, on adjacent carbon atoms, together with the carbon atoms to which they are attached may form a 5-6 membered heterocyclyl or a 5-6 membered heteroaryl ring;
$R^5$ is selected from —($C_1$-$C_6$)alkyl, halo($C_1$-$C_6$)alkyl, and 5-6 membered heterocyclyl;
$X^b$ is selected from —CO—, —CONR⁶—, —NR⁶CO—, —C(=N—OR⁶)—, —CONR⁶—$SO_2$—, —CONR⁶—$SO_2$—NR⁶— and —R⁶N—CO—NR⁶;
$R^b$ is selected from
(i) alkyl, optionally substituted with 1-3 substituents selected independently from halogen, —($C_1$-$C_6$)alkoxy, hydroxyl and —CO—$(CR^7R^8)_p$—$OR^9$;

(ii) aryl, heteroaryl or cycloalkyl, any of which is optionally substituted with 1-3 substituents selected independently from halogen, halo($C_1$-$C_6$)alkyl, -halo($C_1$-$C_6$)alkoxy, —($C_1$-$C_6$)alkoxy, hydroxyl, —($C_1$-$C_6$)alkyl and —$R^{10}$; and (iii) heterocyclyl, optionally substituted with 1-3 substituents selected independently from halogen, halo($C_1$-$C_6$)alkyl, halo($C_1$-$C_6$)alkoxy, —($C_1$-$C_6$)alkoxy, hydroxyl, —($C_1$-$C_6$)alkyl and $N(R^i)_2$, wherein $R^i$, in each occurrence, independently selected from hydrogen, —($C_1$-$C_6$)alkyl or —($C_3$-$C_6$)alkyl;

Alternatively, $R^6$ and $R^b$ together with Nitrogen atom to which they are attached, may form a 3-10 membered heterocyclic ring optionally substituted 1-3 times with $R^{11}$;

$R^6$, in each occurrence, is independently selected from hydrogen, —($C_1$-$C_6$)alkyl and —($C_1$-$C_6$)alkyl-($C_3$-$C_6$)cycloalkyl;

$R^7$, $R^8$, or $R^9$, in each occurrence, is independently selected from hydrogen and —($C_1$-$C_6$)alkyl;

$R^{10}$ is a 5-6 membered heterocyclyl or a 5-6 membered heteroaryl, any of which is optionally substituted with 1-2 substituents selected independently from —($C_1$-$C_6$)alkyl, halogen, halo($C_1$-$C_6$)alkyl, halo($C_1$-$C_6$)alkoxy, —($C_1$-$C_6$)alkoxy and hydroxyl;

$R^{11}$ is selected from halogen, hydroxyl, alkyl and —$NH_2$; and p is 0, 1, 2 or 3.

The present application further relates to methods of treating or preventing conditions, diseases and/or disorders associated with abnormal or deregulated Trk kinase activity by administering effective amount of a compound of formula (I), to a patient in need thereof.

One aspect of the present application provides methods of treating or preventing conditions, diseases and/or disorders associated with abnormal or deregulated TrkA kinase activity by administering effective amount of a compound of formula (I), to a patient in need thereof.

One aspect of the present application provides conditions. diseases and/or disorders treatable or preventable by inhibition of Trk kinase activity, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative disease or a disease, disorder or injury relating to dysmyelination or demyelination by administering a therapeutically effective amount of compound of formula (I), to a patient in need thereof.

The present application also relates to pharmaceutical compositions comprising effective amount of a compound of formula (I), and a pharmaceutically acceptable carrier or diluent, and the use of such compositions in the treatment and/or prevention of diseases associated with inhibiting TrkA in a patient in need thereof, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative disease, a disease, disorder, or injury relating to dysmyelination or demyelination or certain infectious diseases such as Trypanosomacruzi infection.

DETAILED DESCRIPTION

As used herein, 'halogen' or 'halo' represents fluorine, chlorine, bromine, or iodine.

As used herein, 'hydroxy' or 'hydroxyl' represents —OH.

As used herein, 'alkyl' group refers to linear or branched alkyl group with 1 to 10 carbon atoms (i.e. '($C_1$-$C_{10}$)alkyl'). Exemplary alkyl group includes, but is not limited to, methyl, ethyl, n-propyl, iso-propyl, n-butyl, iso-butyl, t-butyl, n-pentyl, iso-pentyl, hexyl, heptyl, octyl and the like. As used herein, '—($C_1$-$C_6$)alkyl' refers to an alkyl group having 1 to 6 carbon atoms.

As used herein, 'haloalkyl' means at least one halogen atom is substituted on an alkyl group. Both halogen and alkyl have the meaning as defined above. Representative examples of haloalkyl groups include, but are not limited to, fluoromethyl, chloromethyl, fluoroethyl, chloroethyl, difluoromethyl, trifluoromethyl, dichloroethyl, trichloroethyl and the like. Unless otherwise specified, a haloalkyl group typically has from 1 to 10 carbon atoms and 1 to 5 halogen atoms (i.e. halo($C_1$-$C_{10}$)alkyl). As used herein, 'halo($C_1$-$C_6$)alkyl' refers to an haloalkyl group having 1 to 6 carbon atoms.

As used herein, 'alkoxy' group refers to an —O(alkyl) group, wherein alkyl group is as defined above. Exemplary alkoxy groups include methoxy, ethoxy, n-propoxy, iso-propoxy, n-butoxy, iso-butoxy, t-butoxy, and the like. Unless otherwise specified, an alkoxy group has from 1 to 10 carbon atoms (i.e. ($C_1$-$C_{10}$)alkoxy). As used herein '—($C_1$-$C_6$) alkoxy' refers to an alkoxy group having 1 to 6 carbon atoms.

As used herein, 'aryl' is a monocyclic or polycyclic aromatic ring system. Exemplary aryl groups include, but are not limited to, phenyl, naphthyl, and the like. Unless otherwise specified, an aryl group typically has from 6 to about 14 carbon atoms (i.e. ($C_6$-$C_{14}$)aryl) but the invention is not limited in that respect.

As used herein, 'cycloalkyl' group refers to a cyclic alkyl group which may be mono, bicyclic, polycyclic, or a fused/bridged ring system. Exemplary cycloalkyl groups include, but are not limited to, cyclopropyl, cyclobutyl, cyclopentyl, cyclohexyl, cycloheptyl, cyclooctyl, and the like. Unless otherwise specified, a cycloalkyl group typically has from 3 to about 10 carbon atoms (i.e ($C_3$-$C_{10}$)cycloalkyl). Typical bridged cycloalkyls include, but are not limited to adamantyl, noradamantyl, bicyclo[1.1.0]butanyl, norbornyl(bicyclo [2.2.1]heptanyl), and the like. As used herein, '—($C_3$-$C_6$) cycloalkyl' refers to a cycloalkyl group having 3 to 6 carbon atoms.

As used herein '—($C_1$-$C_6$)alkyl-($C_3$-$C_6$)cycloalkyl' refers to alkyl group having 1 to 6 carbon atoms (i.e. ($C_1$-$C_6$)alkyl), which is substituted with at least one cycloalkyl group having 3 to 6 carbon atoms (i.e. ($C_3$-$C_6$)cycloalkyl). Exemplary —($C_1$-$C_6$)alkyl-($C_3$-$C_6$)cycloalkyl groups include, but are not limited to, methylcyclopropyl, methyl-cyclobutyl, ethyl-clcobutyl, methyl-cyclopentyl and the like.

As used herein, 'haloalkoxy' means at least one halogen atom is substituted on an alkoxy group, wherein alkoxy and halogen groups are as defined above. Exemplary haloalkoxy groups include, but not limited to, fluoromethoxy, chloromethoxy, trifluoromethoxy, trichloroethoxy, fluoroethoxy, chloroethoxy, trifloroethoxy, perfluoroethoxy (—$OCF_2CF_3$), trifluoro-t-butoxy, hexafluoro-t-butoxy, perfluoro-t-butoxy (—$OC(CF_3)_3$), and the like. Unless otherwise specified, a haloalkoxy group typically has from 1 to 10 carbon atoms and 1 to 5 halogen atoms (i.e halo($C_1$-$C_{10}$)alkoxy). As used herein, halo($C_1$-$C_6$)alkoxy refers to an haloalkoxy group having 1 to 6 carbon atoms.

As used herein, 'heterocyclyl' or 'heterocyclic' or 'heterocycle' is a saturated, unsaturated, aromatic or non-aromatic, monocyclic or polycyclic ring system, having at least one heteroatom or heterogroup selected from —O—, —N—, —S—, —SO, —$SO_2$, or —CO. Exemplary heterocyclyl ring groups include, but are not limited to, aziridinyl, azetidinyl, pyrrolidinyl, piperidinyl, piperazinyl, tetrahydrofuranyl, tetrahydro-2H-pyranyl, 1,4-dioxane, morpholinyl, thiomorpholinyl, 1,1-dioxo-thiomorphonyl, azepanyl or azapanyl, furanyl, oxazolyl, isoxazole, imidazolyl, triazolyl, thiophenyl, thiazolyl, thiadiazolyl, pyridinyl, thiazinyl, pyrazinyl, pyrazolyl, tetrazolyl and the like. Unless otherwise specified, a heterocyclyl group typically has from 3 to about 10 carbon atoms and 1 to 6 heteroatoms or heterogroups. As used herein, '3-10 membered heterocyclyl' refers to a heterocyclyl with 3-10 ring atoms or groups. As used herein, '5-6 membered heterocyclyl' refers to a heterocyclyl with 5-6 ring atoms or groups. As used herein, '3-7 membered heterocyclyl' refers to a heterocyclyl with 3 to 7 ring atoms or groups.

As used herein, 'heteroaryl' is an unsaturated, aromatic or non-aromatic, monocyclic or polycyclic ring system, having at least one heteroatom or heterogroup selected from —O—, —N—, —S—, —SO, —$SO_2$, or —CO. Unless otherwise specified, a heteroaryl group typically has from 3 to about 10 carbon atoms and 1 to 6 heteroatoms or heterogroups. Exemplary heteroaryl ring groups, aromatic or non-aromatic rings, include, but not limited to, furanyl, oxazolyl, isoxazole, imidazolyl, triazolyl, thiophenyl, thiazolyl, thiadiazolyl, pyridinyl, thiazinyl, pyrazinyl, pyrazolyl, tetrazolyl, quinolinyl. As used herein, '5-6 membered heteroaryl' refers to a heteroaryl group having 5 or 6 ring atoms or groups. Exemplary heteroaryl ring groups, aromatic or non-aromatic rings, include, but not limited to, furanyl, oxazolyl, isoxazole, imidazolyl, triazolyl, thiophenyl, thiazolyl, thiadiazolyl, pyridinyl, thiazinyl, pyrazinyl, pyrazolyl, tetrazolyl.

The Trk's are made up of three family members TrkA, TrkB and TrkC that bind to and mediate the signal transduction derived from the Neurotrophins Inhibitors of the Trk/neutrophin pathway have been demonstrated to be highly effective in numerous pre-clinical animal models of pain. The compounds of the invention are modulators of the Trk receptors, particularly TrkA.

As used herein, the term TrkA refers to one of Trk's high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5).

'Optionally substituted' means that the substitution is optional and therefore it is possible for the designated atom or group to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example, in formula (I) when a substituent is oxo (i.e., =O), then two hydrogens on the atom are replaced and when the substitution is fluoro, then one hydrogen on the atom is replaced and the like. When more than one substituent is present on an atom or group, the chosen substituents are independent of each other (i.e same or different).

As used herein and in the appended claims, the singular forms "a", "an", and "the" include plural reference unless the context clearly indicates otherwise.

As used herein, the term 'subject' or 'patient' means mammals, such as humans and other animals, including horses, dogs, cats, rats, mice, sheep, pigs, monkeys, chimpanzees or other apes or primates. In exemplary embodiments, the subject may include subjects for which treatment and/or prevention of the conditions described herein would be beneficial.

For ease of reference, in this application it will be described in terms of administration to human subjects. It will be understood, however, that such descriptions are not limited to administration to humans, but will also include administration to other animals unless explicitly stated otherwise.

A 'therapeutically effective amount' is the amount of compound of the present application that is effective in generating biological or medical response of a subject, for example, reduction or inhibition of an enzyme or a protein activity, or ameliorate symptoms, alleviate conditions, slow or delay disease progression, or prevent a disease.

In one embodiment, the term 'a therapeutically effective amount' refers to the amount of the compound of the present application that, when administered to a subject, is effective in (i) at least partially alleviating, inhibiting, preventing and/or ameliorating a condition, or a disorder or a disease mediated by TrkA, TrkB and/or TrkC, associated with TrkA, TrkB and/or TrkC activity or characterized by activity (normal or abnormal) of TrkA, TrkB and/or TrkC (ii) reducing or inhibiting the activity of TrkA, TrkB and/or TrkC or (iii) reducing or inhibiting the expression of TrkA, TrkB and/or TrkC.

In another embodiment, the term "a therapeutically effective amount" refers to the amount of the compound of the present invention that, when administered to a cell, or a tissue, or a non-cellular biological material, or a medium, is effective to at least partially reducing or inhibiting the activity of TrkA, TrkB and/or TrkC or at least partially reducing or inhibiting the expression of TrkA, TrkB and/or TrkC.

The terms 'treating' or 'to treat' means to alleviate symptoms, eliminate the causation either on a temporary or permanent basis, or to prevent or slow the appearance of symptoms. The term 'treatment' includes alleviation, elimination of causation of or prevention of any of the diseases or disorders described above. The compounds described herein are typically administered in admixture with one or more pharmaceutically acceptable excipients or carriers in the form of a pharmaceutical composition. A 'composition' may contain one compound or a mixture of compounds. A 'pharmaceutical composition' is any composition useful in producing at least one physiological response in a subject to which such pharmaceutical composition is administered.

The term 'substantially pure' means that the isolated material is at least 80% pure, preferably 90% pure, more preferably 95% pure, and even more preferably 99% pure as measured by a suitable analytical techniques known in the art.

Unless defined otherwise, all technical and scientific terms used herein have the same meaning as commonly understood to one of ordinary skill in the art.

One or more compounds of formula (I) can be supplied in the form of a therapeutic composition that is within the scope of the present application.

The term 'Pharmaceutically acceptable salts' refers to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the application. The preparation of salts can be carried out using known methods.

For example, pharmaceutically acceptable salts of compound of formula (I) contemplated refers to salts prepared from acids or bases including inorganic or organic acids and inorganic or organic bases by conventional chemical methods using a compound of formula (I). Generally, such salts may be prepared, for example, by making free base of the compounds and reacting with a stoichiometric quantity of the appropriate acid and vice-versa in water or in an organic solvent, or in a mixture of the two. The compounds of the present applications may form mono, di or tris salts.

When the compound of formula (I) is basic, salts may be prepared from acids, including inorganic or organic acids (acid addition salts). Examples of such acids include, but not limited to formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), nitric, hydrochloride, hydrobromide, isoethionic, hydroiodide, phosphoric, sulfuric, succinic, tartaric, methanesulfonic, ethanesulfonic, benzenesulfonic, benzoic, mucic, pantothenic, p-toluenesulfonic, camphorsulfonic, 2-hydroxyethanesulfonic, sulfanilic, cyclohexylaminosulfonic, algenic, β-hydroxybutyric, galactaric, and galacturonic acid, and the like.

Salts formed from inorganic bases include sodium, potassium, lithium, calcium, copper, magnesium, manganic salts, manganous, zinc, aluminum, ammonium, ferric, ferrous and the like.

Salts derived from organic bases include salts of primary, secondary, and tertiary amines, substituted amines including naturally occurring substituted amines, cyclic amines, and basic ion exchange resins, such as arginine, betaine, caffeine, choline, N,N-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

'Pharmaceutically acceptable salts' in the solid form may exist in more than one crystal structure, and may also be in the form of hydrates.

The term 'stereoisomers' is a general term used for all isomers of an individual molecule that differ only in the orientation of their atoms in space. Where the compounds according to the present application possess one or more asymmetric centers and compounds with asymmetric centers give rise to enantiomers, diastereomers or both as pure or partially purified compounds. It is to be understood that all stereoisomeric forms of the compounds of the invention, including but not limited to, diastereomers, enantiomers and atropisomers, as well as mixtures thereof such as forms, are included in the scope of the present application. Preparation of such stereoisomeric forms of compound of formula (I), may be achieved by appropriate modification of the methodology known in the art. Their absolute stereochemistry may be determined by the suitable methods. If required, racemic mixtures of the compound of formula (I) may be separated to isolate individual enantiomers or diastereomers. Such separation can be carried out by methods known in the art, such as the coupling of a racemic mixture of compound of formula (I) to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer or diastereomer of a compound may be obtained by stereoselective synthesis using optically pure starting materials or known reagents.

For any particular compound disclosed herein, wherein the stereochemistry of any particular chiral atom is not specified, then all stereoisomers are contemplated and included as the compounds of the application. Where stereochemistry is specified by a solid wedge or a dashed wedge bond or dashed line representing a particular configuration then that stereoisomer is so specified and defined. Following the standard chemical literature description practice and as used herein, a full wedge bond means above the ring plane, and a dashed wedge bond or dashed line means below the ring plane. For example, N—(N-ethyl-N-methylsulfamoyl)-6-((2R,4S)-4-fluoro-2-(7-fluoro-2,3-dihydrobenzo[b][1,4]dioxin-5-yl)pyrrolidin-1-yl)imidazo[1,2-a]pyridine-3-carboxamide exemplified herein can be represented as follows, specifying the orientation of each stereocenter:

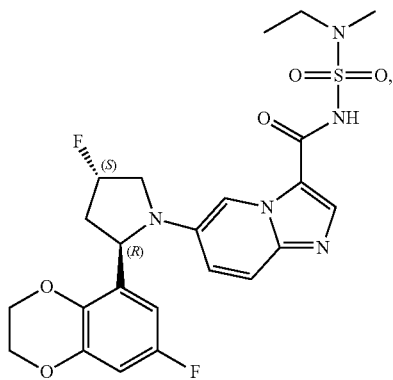

6-((2R,4S)-4-fluoro-2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide exemplified herein can be represented as follows, specifying the orientation of each stereocenter:

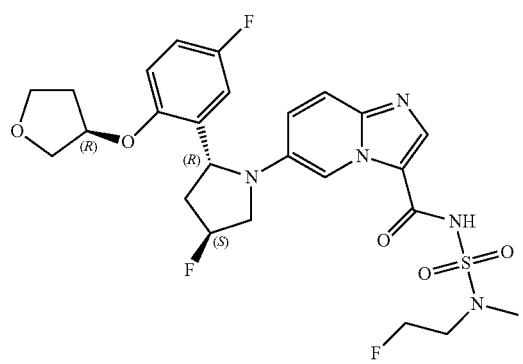

Pharmaceutically acceptable solvates of compound of formula (I) may be hydrates or comprising other solvents of crystallization such as alcohols. Pharmaceutically acceptable solvates of compound of formula (I) may be prepared by conventional methods such as dissolving the compounds of formula (I) in solvents such as water, methanol, ethanol etc., preferably water and recrystallizing by using different crystallization techniques.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position.

Reference will now be made in detail to the embodiments of the invention, one or more examples of which are set forth below. Each example is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present application.

Thus in accordance of this application there is provided a series of substituted imidazo[1,2-a]pyridine compounds having the general formula (I),

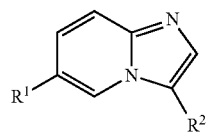
(I)

or pharmaceutically acceptable salts thereof, or pharmaceutically acceptable solvates thereof or stereoisomers thereof,
wherein,
$R^1$ is —$X^a$—$R^a$;
$R^2$ is —$X^b$—$R^b$;
$X^a$ is a 3-7 membered heterocyclyl selected from aziridinyl, azetidinyl, pyrrolidinyl, piperidinyl, piperazinyl, azepanyl, thiomorpholinyl, 1,1-dioxo-thiomorphonyl and morpholinyl, any of which is optionally substituted with 1-3 times with $R^3$;
$R^3$, in each occurrence is selected independently from halogen, hydroxy, —($C_1$-$C_6$)alkyl, —($C_1$-$C_6$)alkoxy and halo($C_1$-$C_6$)alkoxy;
$R^a$ is a phenyl ring optionally substituted 1-3 times with $R^4$;
$R^4$, in each occurrence is selected independently from halogen, —($C_1$-$C_6$)alkyl and —O—$R^5$;
Alternatively, two $R^4$, on adjacent carbon atoms, together with the carbon atoms to which they are attached may form a 5-6 membered heterocyclyl or a 5-6 membered heteroaryl ring;
$R^5$ is selected from —($C_1$-$C_6$)alkyl, halo($C_1$-$C_6$)alkyl and 5-6 membered heterocyclyl;
$X^b$ is selected from —CO—, —CONR$^6$—, —NR$^6$CO—, —C(=N—OR$^6$)—, —CONR$^6$—SO$_2$—, —CONR$^6$—SO$_2$—NR$^6$— and —R$^6$N—CO—NR$^6$;
$R^b$ is selected from
(i) alkyl, optionally substituted with 1-3 substituents selected independently from halogen, —($C_1$-$C_6$)alkoxy, hydroxyl and —CO—(CR$^7$R$^8$)$_p$—OR$^9$;
(ii) aryl, heteroaryl or cycloalkyl, any of which is optionally substituted with 1-3 substituents selected independently from halogen, halo($C_1$-$C_6$)alkyl, halo($C_1$-$C_6$)alkoxy, —($C_1$-$C_6$)alkoxy, hydroxyl, —($C_1$-$C_6$)alkyl and —R$^{10}$;
(iii) heterocyclyl, optionally substituted with 1-3 substituents selected independently from halogen, halo($C_1$-$C_6$)alkyl, halo($C_1$-$C_6$)alkoxy, —($C_1$-$C_6$)alkoxy, hydroxyl, —($C_1$-$C_6$)alkyl and N($R^i$)$_2$, wherein $R^i$, in each occurrence, independently selected from hydrogen, —($C_1$-$C_6$)alkyl or —($C_3$-$C_6$)alkyl;

Alternatively, $R^6$ and $R^b$ together with Nitrogen atom to which they are attached, may form a 3-10 membered heterocyclic ring optionally substituted 1-3 times with $R^{11}$;
$R^6$, in each occurrence, is independently selected from hydrogen, —($C_1$-$C_6$)alkyl and —($C_1$-$C_6$)alkyl-($C_3$-$C_6$)cycloalkyl;
$R^7$, $R^8$ or $R^9$, in each occurrence, is independently selected from hydrogen and —($C_1$-$C_6$)alkyl;
$R^{10}$ is a 5-6 membered heterocyclyl or a 5-6 membered heteroaryl, any of which is optionally substituted with 1-2 substituents selected independently from —($C_1$-$C_6$)alkyl, halogen, halo($C_1$-$C_6$)alkyl, halo($C_1$-$C_6$)alkoxy, —($C_1$-$C_6$)alkoxy and hydroxyl;
$R^{11}$ is selected from halogen, hydroxyl, alkyl and —NH$_2$; and p is 0, 1, 2 or 3.

In one embodiment, the compounds of formula (I) are represented as compounds of formula (Ia),

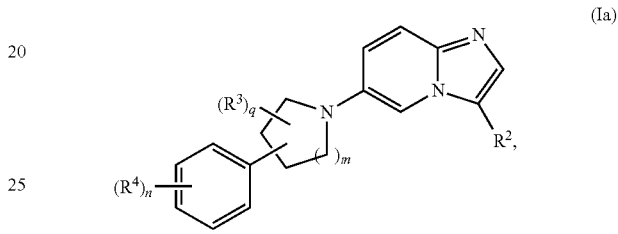
(Ia)

or pharmaceutically acceptable salts thereof, or pharmaceutically acceptable solvates thereof or stereoisomers thereof, wherein
'n' is 1, 2 or 3;
'm' is 1, 2 or 3;
'q' is 0, 1, 2 or 3;
and the values of all other variables are as described for compound of formula (I).

In another embodiment, the compounds of formula (I) are represented as compounds of formula (Ib),

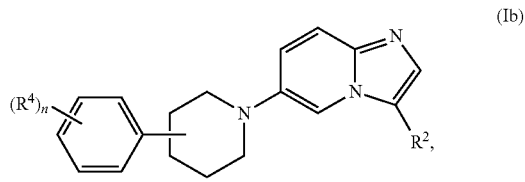
(Ib)

or pharmaceutically acceptable salts thereof, or pharmaceutically acceptable solvates thereof or stereoisomers thereof, wherein 'n' is 1, 2 or 3 and the values of all other variables are as described for compound of formula (I).

In another embodiment, the compounds of formula (I) are represented as compounds of formula (Ic),

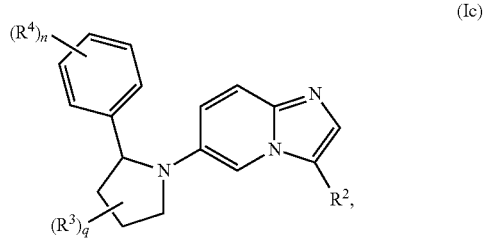
(Ic)

or pharmaceutically acceptable salts thereof, or pharmaceutically acceptable solvates thereof or stereoisomers thereof, wherein
'n' is 1, 2 or 3
'q' is 0, 1, 2 or 3; and the values of all other variables are as described for compound of formula (I).

In another embodiment, the compounds of formula (I) are represented as compounds of formula (Id),

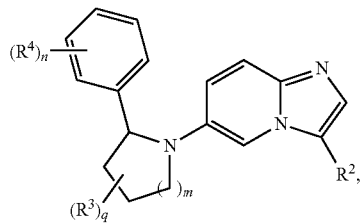

(Id)

or pharmaceutically acceptable salts thereof, or pharmaceutically acceptable solvates thereof or stereoisomers thereof, wherein
'm' is 1 or 2;
'n' is 1, 2 or 3;
'q' is 0 or 1;
and the values of all other variables are as described for compound of formula (I).

In another embodiment, the compounds of formula (I) are represented as compounds of formula (Ie),

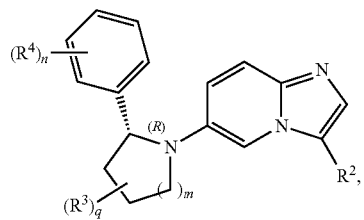

(Ie)

or pharmaceutically acceptable salts thereof, or pharmaceutically acceptable solvates thereof or stereoisomers thereof,
wherein,
'm' is 1 or 2;
'n' is 1, 2 or 3;
'q' is 0 or 1;
and the values of all other variables are as described for compound of formula (I).

In another embodiment, the compounds of formula (I) are represented as compounds of formula (If),

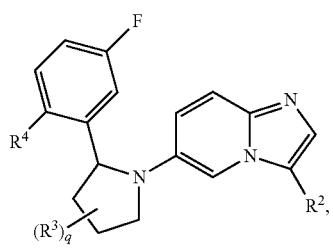

(If)

or pharmaceutically acceptable salts thereof, or pharmaceutically acceptable solvates thereof or stereoisomers thereof,
wherein,
$R^3$ is halogen;
'q' is 0 or 1;
and the values of all other variables are as described for compound of formula (I).

In another embodiment, the compounds of formula (I) are represented as compounds of formula (Ig),

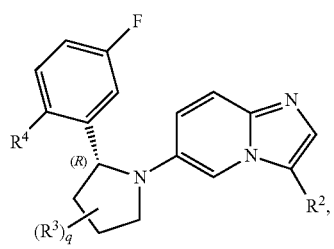

(Ig)

or pharmaceutically acceptable salts thereof, or pharmaceutically acceptable solvates thereof or stereoisomers thereof,
wherein,
$R^3$ is halogen;
'q' is 0 or 1;
and the values of all other variables are as described for compound of formula (I).

In another embodiment, the compounds of formula (I) are represented as compounds of formula (Ih),

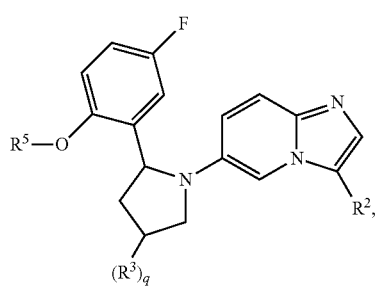

(Ih)

or pharmaceutically acceptable salts thereof, or pharmaceutically acceptable solvates thereof or stereoisomers thereof,
wherein,
$R^3$ is halogen;
'q' is 0 or 1;
and the values of all other variables are as described for compound of formula (I).

In another embodiment, the compounds of formula (I) are represented as compounds of formula (Ii),

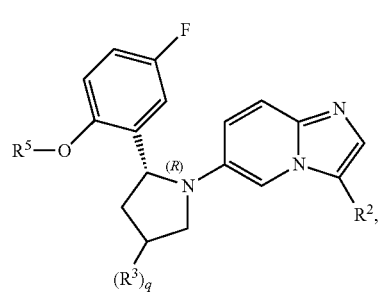

(Ii)

or pharmaceutically acceptable salts thereof, or pharmaceutically acceptable solvates thereof or stereoisomers thereof,
wherein,
R³ is halogen;
'q' is 0 or 1;
and the values of all other variables are as described for compound of formula (I).

In another embodiment, the compounds of formula (I) are represented as compounds of formula (Ij),

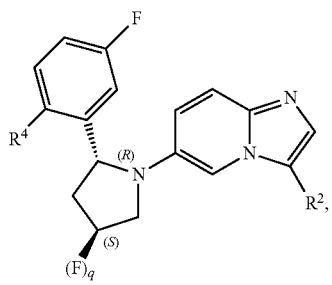

(Ij)

or pharmaceutically acceptable salts thereof, or pharmaceutically acceptable solvates thereof or stereoisomers thereof,
wherein
'q' is 0 or 1;
and values of all other variables are as described for compound of formula (I).

In another embodiment, the compounds of formula (I) are represented as compounds of formula (Ik),

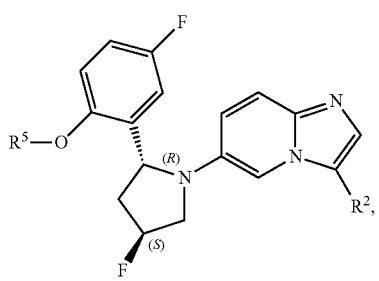

(Ik)

or pharmaceutically acceptable salts thereof, or pharmaceutically acceptable solvates thereof or stereoisomers thereof,
wherein values of all other variables are as described for compound of formula (I).

In another embodiment, the compounds of formula (I) are represented as compounds of formula (Il),

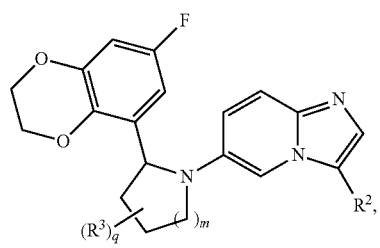

(Il)

or pharmaceutically acceptable salts thereof, or pharmaceutically acceptable solvates thereof or stereoisomers thereof,
wherein
R³ is halogen;
'm' is 1 or 2;
'q' is 0 or 1;
and the values of all other variables are as described for compound of formula (I).

In another embodiment, the compounds of formula (I) are represented as compounds of formula (Im),

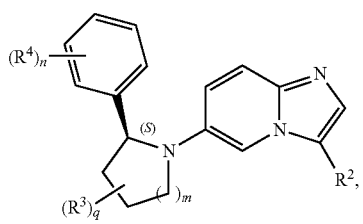

(Im)

or pharmaceutically acceptable salts thereof, or pharmaceutically acceptable solvates thereof or stereoisomers thereof,
wherein
'm' is 1 or 2;
'n' is 1, 2 or 3;
'q' is 0 or 1;
and the values of all other variables are as described for compound of formula (I).

In one embodiment of formula (I), $R^1$ is $—X^a—R^a$.

In another embodiment of formula (I), $X^a$ is pyrrolidinyl or piperidinyl ring, optionally substituted 1-3 times with $R^3$.

In another embodiment of formula (I), $X^a$ is pyrrolidinyl or piperidinyl ring, optionally substituted with fluorine.

In another embodiment of formula (I), $R^a$ is a phenyl, optionally substituted 1-3 times with $R^4$.

In another embodiment of formula (I), $R^1$ is $—X^a—R^a$; In this embodiment, $X^a$ is pyrrolidinyl or piperidinyl ring, optionally substituted with 1-3 times with $R^3$; and $R^a$ is a phenyl, optionally substituted 1-3 times with $R^4$.

In another embodiment of formula (I), $R^4$ is halogen, $—(C_1-C_6)$alkyl or $—O—R^5$; or $R^4$ on two adjacent carbon atoms, together with the carbon atoms to which they are attached form a 5-6 membered heterocyclyl ring or a 5-6 membered heteroaryl ring.

In another embodiment of formula (I), $R^4$ is independently selected from fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy and (R)-(tetrahydrofuran-3-yl)oxy; or $R^4$ on two adjacent carbon atoms, together with the carbon atoms to which they are attached form a 1,4-dioxine ring.

In another embodiment of formula (I), $R^1$ is $—X^a—R^a$; In this embodiment, $X^a$ is pyrrolidinyl or piperidinyl ring, optionally substituted with 1-3 times with $R^3$; and $R^a$ is a phenyl, optionally substituted 1-3 times with $R^4$; wherein $R^4$ is independently selected from fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy and (R)-(tetrahydrofuran-3-yl)oxy; or $R^4$ on two adjacent carbon atoms, together with the carbon atoms to which they are attached form a 1,4-dioxine ring.

In one embodiment of formula (Ia), $R^3$ is halogen; $R^4$ is a halogen, —$(C_1$-$C_6)$alkyl or —O—$R^5$; or $R^4$ on two adjacent carbon atoms, together with the carbon atoms to which they are attached form a 5-6 membered heterocyclyl ring or a 5-6 membered heteroaryl ring; 'm' is 1 or 2; 'n' is 2 or 3; and 'q' is 0 or 1.

In another embodiment of formula (Ia), $R^3$ is fluorine; and 'q' is 0 or 1.

In another embodiment of formula (Ia), at each occurrence, $R^4$ is independently selected from fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy and (R)-(tetrahydrofuran-3-yl)oxy; or $R^4$ on two adjacent carbon atoms, together with the carbon atoms to which they are attached form a 1,4-dioxine ring; and 'n' is 2 or 3.

In another embodiment of formula (Ib), $R^4$ is independently selected from fluorine; (tetrahydro-2H-pyran-4-yl)oxy and (R)-tetrahydrofuran-3-yl)oxy; and 'n' is 2 or 3.

In one embodiment of formula (Ic), $R^3$ is halogen; $R^4$ is a halogen, —$(C_1$-$C_6)$alkyl or —O—$R^5$; or $R^4$ on two adjacent carbon atoms, together with the carbon atoms to which they are attached form a 1,4-dioxine ring; 'n' is 2 or 3; and 'q' is 0 or 1.

In one embodiment of formula (Id), $R^3$ is halogen; $R^4$ is a halogen, —$(C_1$-$C_6)$alkyl or —O—$R^5$; or $R^4$ on two adjacent carbon atoms, together with the carbon atoms to which they are attached form a 5-6 membered heterocyclyl ring; 'm' is 1 or 2; 'n' is 2 or 3; and 'q' is 0 or 1.

In another embodiment of formula (Id), at each occurrence, $R^4$ is independently selected from fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy and (R)-(tetrahydrofuran-3-yl)oxy; or $R^4$ on two adjacent carbon atoms, together with the carbon atoms to which they are attached form a 1,4-dioxine ring; and 'n' is 2 or 3.

In another embodiment, the compound of formula (Id) of the above embodiments is defined as compound of formula (Ie).

In one embodiment of formula (If), $R^3$ is fluorine; $R^4$ is a halogen, —$(C_1$-$C_6)$alkyl or —O—$R^5$. In this embodiment $R^5$ is methyl, 2-fluoroethyl, tetrahydrofuranyl, tetrahydropyranyl, (tetrahydropyran-4-yl), (tetrahydro-2H-pyran-4-yl) or (R)-(tetrahydrofuran-3-yl).

In another embodiment of formula (If), $R^3$ is fluorine; $R^4$ is fluorine, methoxy, 2-fluoroethoxy, (tetrahydrofuranyl)oxy, (tetrahydropyranyl)oxy, (tetrahydropyran-4-yl)oxy, (tetrahydro-2H-pyran-4-yl)oxy or (R)-(tetrahydrofuran-3-yl)oxy; and 'q' is 0 or 1.

In another embodiment, the compound of formula (If) of the above embodiments is defined as compound of formula (Ig).

In one embodiment of formula (Ih), $R^3$ is fluorine; $R^5$ is —$(C_1$-$C_6)$alkyl, halo$(C_1$-$C_6)$alkyl, or 5-6 membered heterocyclyl; and 'q' is 0 or 1.

In another embodiment of formula (Ih), $R^3$ is fluorine; $R^5$ is methyl, 2-fluoroethyl, tetrahydrofuranyl, tetrahydropyranyl, tetrahydropyran-4-yl, tetrahydro-2H-pyran-4-yl or (R)-tetrahydrofuran-3-yl; and 'q' is 0 or 1.

In another embodiment, the compound of formula (Ih) of the above embodiments is defined as compound of formula (Ii).

In one embodiment of formula (Ij), $R^4$ is a halogen, —$(C_1$-$C_6)$alkyl or —O—$R^5$. In this embodiment $R^5$ is methyl, 2-fluoroethyl, tetrahydrofuranyl, tetrahydropyranyl, (tetrahydropyran-4-yl), (tetrahydro-2H-pyran-4-yl) or (R)-(tetrahydrofuran-3-yl).

In another embodiment of formula (Ij), $R^4$ is fluorine, methoxy, 2-fluoroethoxy, (tetrahydrofuranyl)oxy, (tetrahydropyranyl)oxy, (tetrahydropyran-4-yl)oxy, (tetrahydro-2H-pyran-4-yl)oxy or (R)-(tetrahydrofuran-3-yl)oxy.

In one embodiment of formula (Ik), $R^5$ is —$(C_1$-$C_6)$alkyl, halo$(C_1$-$C_6)$alkyl, or 5-6 membered heterocyclyl.

In another embodiment of formula (Ik), $R^5$ is methyl, 2-fluoroethyl, tetrahydrofuranyl, tetrahydropyranyl, tetrahydropyran-4-yl, tetrahydro-2H-pyran-4-yl or (R)-tetrahydrofuran-3-yl.

In one embodiment of formula (Il), $R^3$ is fluorine;

In another embodiment of formula (Il), $R^3$ is fluorine; 'm' is 1 or 2; and 'q' is 0 or 1.

In one embodiment, the compound of formula (Id) of the above embodiments is defined as compound of formula (Im).

In certain embodiments of formula (I), (Ia), (Ib), (Ic), (Id), (Ie), (If), (Ig), (Ih), (Ii), (Ij), (Ik), (Il) or (Im), $R^2$ is —$X^b$—$R^b$;

In certain embodiments of formula (I), (Ia), (Ib), (Ic), (Id), (Ie), (If), (Ig), (Ih), (Ii), (Ij), (Ik), (Il) or (Im), $R^2$ is —CO—$R^b$, —CONR$^6$—$R^b$, —NR$^6$CO—$R^b$, —C(=N—OR$^6$)—$R^b$, —CONR$^6$—SO$_2$—$R^b$, —CONR$^6$—SO$_2$—NR$^6$—$R^b$ or —R$^6$N—CO—NR$^6$—$R^b$.

In certain embodiments of formula (I), (Ia), (Ib), (Ic), (Id), (Ie), (If), (Ig), (Ih), (Ii), (Ij), (Ik), (Il) or (Im), $R^2$ is —CO—$R^b$, —CONR$^6$—$R^b$, —NR$^6$CO—$R^b$, —C(=N—OR$^6$)—$R^b$, —CONR$^6$—SO$_2$—$R^b$, —CONR$^6$—SO$_2$—NR$^6$—$R^b$ or —R$^6$N—CO—NR$^6$—$R^b$. In this embodiment, each occurrence of $R^6$ is hydrogen, methyl, ethyl, propyl or cyclopropylmethyl.

In certain embodiments of formula (I), (Ia), (Ib), (Ic), (Id), (Ie), (If), (Ig), (Ih), (Ii), (Ij), (Ik), (Il) or (Im), $R^2$ is —CO—$R^b$, —CONH—$R^b$, —CONCH$_3$—$R^b$, —NHCO—$R^b$, —C(=N—OH)—$R^b$, —CONH—SO$_2$—$R^b$, —CON(CH$_3$)—SO$_2$—$R^b$, —CONH—SO$_2$—NH—$R^b$, —CONH—SO$_2$—N(CH$_3$)—$R^b$, —CONH—SO$_2$—N(CH$_2$CH$_3$)—$R^b$, —CONH—SO$_2$—N(CH$_2$CH$_2$CH$_3$)—$R^b$, —CONH—SO$_2$—N(cyclopropylmethyl)-$R^b$ or —NH—CO—NH—$R^b$.

In certain embodiments of formula (I), (Ia), (Ib), (Ic), (Id), (Ie), (If), (Ig), (Ih), (Ii), (Ij), (Ik), (Il) or (Im), $R^2$ is —CO—$R^b$, —CONR$^6$—$R^b$, —NR$^6$CO—$R^b$, —C(=N—OR$^6$)—$R^b$, —CONR$^6$—SO$_2$—$R^b$, —CONR$^6$—SO$_2$—NR$^6$—$R^b$ or —R$^6$N—CO—NR$^6$—$R^b$. In this embodiment, each occurrence of $R^6$ is hydrogen, methyl, ethyl, propyl or cyclopropylmethyl; and $R^b$ is (i) methyl, ethyl, propyl, tert-butyl and 2-methylpropyl, any of which is optionally substituted with 1-3 substituents independently selected from fluorine, methoxy, hydroxyl, —COOCH$_2$CH$_3$ and —COOH;

(ii) phenyl, pyridinyl, pyrazinyl, pyridazinyl, thiazolyl, thiadiazolyl, pyrazolyl, cyclopropyl, cyclohexyl or adamantanyl, any of which is optionally substituted with 1-3 substituents independently selected from halogen, fluoromethyl, difluoromethyl, trifluoromethyl, fluoromethoxy, methoxy, ethoxy, hydroxyl, methyl, piperidinyl, 3-hydroxypyrrolidin-1-yl, 1,2,4-triazol-1-yl and 1H-imidazol-1-yl; or (iii) pyrrolidinyl, azetidinyl, piperidinyl, morpholino, methylpiperazinyl, azepanyl or pyranyl, any of which is optionally substituted with 1-3 substituents independently selected from halogen, fluoromethyl, difluoromethyl, trifluoromethyl, fluoromethoxy, methoxy, ethoxy, hydroxyl, —NH$_2$ and methyl.

In certain embodiments of formula (I), (Ia), (Ib), (Ic), (Id), (Ie), (If), (Ig), (Ih), (Ii), (Ij), (Ik), (Il) or (Im), $R^2$ is —CO—$R^b$, —CONH—$R^b$, —CONCH$_3$—$R^b$, —NHCO—$R^b$, —C(=N—OH)—$R^b$, —CONH—SO$_2$—$R^b$, —CON(CH$_3$)—SO$_2$—$R^b$, —CONH—SO$_2$—NH—$R^b$, —CONH—SO$_2$—N(CH$_3$)—$R^b$, —CONH—SO$_2$—N(CH$_2$CH$_3$)—$R^b$, —CONH—SO$_2$—N(CH$_2$CH$_2$CH$_3$)—R$^b$, —CONH—SO$_2$—N(cyclopropylmethyl)-R$^b$ or —NH—CO—NH—R$^b$. In this embodiment, R$^b$ is (i) methyl, ethyl, propyl, tert-butyl, isobutyl, propan-2-yl or 2-methylpropan-2-yl, any of which is optionally substituted with 1-3 substituents independently selected from fluorine, methoxy, hydroxyl, —COOCH$_2$CH$_3$ and —COOH;

(ii) phenyl, pyridin-2-yl, pyridin-3-yl, pyrazin-2-yl, pyridazin-3-yl, thiazol-2-yl, 1,3,4-thiadiazol-2-yl, 1H-pyrazol-3-yl, cyclopropyl, cyclohexyl or amantan-1-yl, any of which is optionally substituted with 1-3 substituents independently selected from fluorine, fluoromethyl, difluoromethyl, trifluoromethyl, fluoromethoxy, methoxy, ethoxy, hydroxyl, methyl, 3-hydroxypyrrolidin-1-yl, piperidin-1-yl, 1,2,4-triazol-1-yl and 1H-imidazol-1-yl; or (iii) pyrrolidin-1-yl, azetidin-1-yl, piperidin-1-yl, morpholino, piperazin-1-yl, azepan-1-yl or tetrahydro-2H-pyran-4-yl, optionally substituted with 1-3 substituents independently selected from fluorine, fluoromethyl, difluoromethyl, trifluoromethyl, fluoromethoxy, methoxy, hydroxyl, —NH$_2$ and methyl;

In certain embodiments of formula (I), (Ia), (Ib), (Ic), (Id), (Ie), (If), (Ig), (Ih), (Ii), (Ij), (Ik), (Il) or (Im), R$^2$ is —CO—R$^b$, —CONH—R$^b$, —CONCH$_3$—R$^b$, —NHCO—R$^b$, —C(=N—OH)—R$^b$, —CONH—SO$_2$—R$^b$, —CON(CH$_3$)—SO$_2$—R$^b$, —CONH—SO$_2$—NH—R$^b$, —CONH—SO$_2$—N(CH$_3$)—R$^b$, —CONH—SO$_2$—N(CH$_2$CH$_3$)—R$^b$, —CONH—SO$_2$—N(CH$_2$CH$_2$CH$_3$)—R$^b$, —CONH—SO$_2$—N(cyclopropylmethyl)-R$^b$ or —NH—CO—NH—R$^b$. In this embodiment, R$^b$ is methyl, ethyl, propyl, tert-butyl, —CH$_2$C(O)OCH$_2$CH$_3$, —CH$_2$C(O)OH, 2-hydroxyethyl, 1,3-dihydroxypropan-2-yl, 1,3-dihydroxy-2-methylpropan-2-yl, 1-hydroxy-2-methylpropan-2-yl, (S)-2,3-dihydroxypropyl, (S)-1-hydroxypropan-2-yl, 2-fluoroethyl, 2,2-difluoroethyl, 2-fluoro-2-methylpropyl, 2,2,2-trifluoroethyl, 2-methoxyethyl, 2-ethoxyethyl, cyclopropyl, 1-methylcyclopropyl, (1r,4r)-4-hydroxycyclohexyl, 3-hydroxyadamantan-1-yl, 3-hydroxyazetidin-1-yl, 3-hydroxy-3-methylazetidin-1-yl, (S)-3-aminopyrrolidin-1-yl), (S)-3-hydroxypyrrolidin-1-yl, piperidin-1-yl, 4-hydroxypiperidin-1-yl, morpholinyl, 4-methylpiperazinyl, tetrahydro-2H-pyran-4-yl, 4-hydroxyazepan-1-yl, thiazol-2-yl, 5-methyl-1,3,4-thiadiazol-2-yl, 1,3,4-thiadiazol-2-yl, 1H-1,2,4-triazol-1-yl, (1-methyl-1H-pyrazol-3-yl), 1H-imidazol-1-yl, 6-methylpyridazin-3-yl, pyridin-2-yl, pyridin-3-yl, pyrazin-2-yl, 4-fluorophenyl, ((S)-3-hydroxypyrrolidin-1-yl)phenyl or ((S)-3-hydroxypyrrolidin-1-yl)pyridin-3-yl.

In certain embodiments of formula (I), (Ia), (Ib), (Ic), (Id), (Ie), (If), (Ig), (Ih), (Ii), (Ij), (Ik), (Il) or (Im), X$^b$ is —CO—, —CONH—, CONCH$_3$—, —NHCO—, —C(=N—OH)—, —CONH—SO$_2$—, —CON(CH$_3$)—SO$_2$—, —CONH—SO$_2$—NH—, —CONH—SO$_2$—N(CH$_3$)—, —CONH—SO$_2$—N(CH$_2$CH$_3$)—, —CONH—SO$_2$—N(CH$_2$CH$_2$CH$_3$)—, —CONH—SO$_2$—N(cyclopropylmethyl)-R$^b$ or —NH—CO—NH—.

In certain embodiments of formula (I), (Ia), (Ib), (Ic), (Id), (Ie), (If), (Ig), (Ih), (Ii), (Ij), (Ik), (Il) or (Im), R$^b$ is (i) methyl, ethyl, propyl, tert-butyl and 2-methylpropyl, any of which is optionally substituted with 1-3 substituents independently selected from fluorine, methoxy, hydroxyl, —COOCH$_2$CH$_3$ and —COOH;

(ii) phenyl, pyridinyl, pyrazinyl, pyridazinyl, thiazolyl, thiadiazolyl, pyrazolyl, cyclopropyl, cyclohexyl or adamantanyl, any of which is optionally substituted with 1-3 substituents independently selected from halogen, fluoromethyl, difluoromethyl, trifluoromethyl, fluoromethoxy, methoxy, ethoxy, hydroxyl, methyl, piperidinyl, 3-hydroxypyrrolidin-1-yl, 1,2,4-triazol-1-yl and 1H-imidazol-1-yl; or (iii) heterocyclyl ring selected from pyrrolidinyl, azetidinyl, piperidinyl, morpholino, methylpiperazinyl, azepanyl and pyranyl, any of which is optionally substituted with 1-3 substituents independently selected from halogen, fluoromethyl, difluoromethyl, trifluoromethyl, fluoromethoxy, methoxy, ethoxy, hydroxyl, —NH$_2$ and methyl.

In certain embodiments of formula (I), (Ia), (Ib), (Ic), (Id), (Ie), (If), (Ig), (Ih), (Ii), (Ij), (Ik), (Il) or (Im), R$^b$ is (i) methyl, ethyl, propyl, tert-butyl, isobutyl, propan-2-yl or 2-methylpropan-2-yl, any of which is optionally substituted with 1-3 substituents independently selected from fluorine, methoxy, hydroxyl, —COOCH$_2$CH$_3$ and COOH;

(ii) phenyl, pyridin-2-yl, pyridin-3-yl, pyrazin-2-yl, pyridazin-3-yl, thiazol-2-yl, 1,3,4-thiadiazol-2-yl, 1H-pyrazol-3-yl, cyclopropyl, cyclohexyl or amantan-1-yl, any of which is optionally substituted with 1-3 substituents independently selected from fluorine, fluoromethyl, difluoromethyl, trifluoromethyl, fluoromethoxy, methoxy, ethoxy, hydroxyl, methyl, 3-hydroxypyrrolidin-1-yl, piperidin-1-yl, 1,2,4-triazol-1-yl and 1H-imidazol-1-yl; or (iii) pyrrolidin-1-yl, azetidin-1-yl, piperidin-1-yl, morpholino, piperazin-1-yl, azepan-1-yl or tetrahydro-2H-pyran-4-yl, optionally substituted with 1-3 substituents independently selected from fluorine, fluoromethyl, difluoromethyl, trifluoromethyl, fluoromethoxy, methoxy, hydroxyl, —NH$_2$ and methyl.

In certain embodiments of formula (I), (Ia), (Ib), (Ic), (Id), (Ie), (If), (Ig), (Ih), (Ii), (Ij), (Ik), (Il) or (Im), R$^2$ is —CO—R$^6$, —CONR$^6$—R$^b$, —NR$^6$CO—R$^b$, —C(=N—OR$^6$)—R$^b$, —CONR$^6$—SO$_2$—R$^b$, —CONR$^6$—SO$_2$—NR$^6$—R$^b$ or —R$^6$N—CO—NR$^6$—R$^b$. In this embodiment, each occurrence of R$^6$ is hydrogen, methyl, ethyl, propyl or cyclopropylmethyl; and R$^b$ is methyl, ethyl, propyl, tert-butyl, —CH$_2$C(O)OCH$_2$CH$_3$, —CH$_2$C(O)OH, 2-hydroxyethyl, 1,3-dihydroxypropan-2-yl, 1,3-dihydroxy-2-methylpropan-2-yl, 1-hydroxy-2-methylpropan-2-yl, (S)-2,3-dihydroxypropyl, (S)-1-hydroxypropan-2-yl, 2-fluoroethyl, 2,2-difluoroethyl, 2-fluoro-2-methylpropyl, 2,2,2-trifluoroethyl, 2-methoxyethyl, 2-ethoxyethyl, cyclopropyl, 1-methylcyclopropyl, (1r,4r)-4-hydroxycyclohexyl, 3-hydroxyadamantan-1-yl, 3-hydroxyazetidin-1-yl, 3-hydroxy-3-methylazetidin-1-yl, (S)-3-aminopyrrolidin-1-yl), (S)-3-hydroxypyrrolidin-1-yl, piperidin-1-yl, 4-hydroxypiperidin-1-yl, morpholinyl, 4-methylpiperazinyl, tetrahydro-2H-pyran-4-yl, 4-hydroxyazepan-1-yl, thiazol-2-yl, 5-methyl-1,3,4-thiadiazol-2-yl, 1,3,4-thiadiazol-2-yl, 1H-1,2,4-triazol-1-yl, (1-methyl-1H-pyrazol-3-yl), 1H-imidazol-1-yl, 6-methylpyridazin-3-yl, pyridin-2-yl, pyridin-3-yl, pyrazin-2-yl, 4-fluorophenyl, ((S)-3-hydroxypyrrolidin-1-yl)phenyl or ((S)-3-hydroxypyrrolidin-1-yl)pyridin-3-yl.

In another embodiment of formula (I), wherein,

R$^1$ is —X$^a$—R$^a$;

R$^2$ is —CO—R$^6$, —CONH—R$^b$, —CONCH$_3$—R$^b$, —NHCO—R$^6$, —C(=N—OH)—R$^b$, —CONH—SO$_2$—R$^b$, —CON(CH$_3$)—SO$_2$—R$^b$, —CONH—SO$_2$—NH—R$^b$, —CONH—SO$_2$—N(CH$_3$)—R$^b$, —CONH—SO$_2$—N(CH$_2$CH$_3$)—R$^b$, —CONH—SO$_2$—N(CH$_2$CH$_2$CH$_3$)—R$^b$, —CONH—SO$_2$—N(cyclopropylmethyl)-R$^b$ or —NH—CO—NH—R$^b$;

X$^a$ is pyrrolidinyl or piperidinyl ring, optionally substituted with 1-3 times fluorine.

R$^a$ is a phenyl ring optionally substituted 1-3 times with R$^4$;

R$^4$ is independently selected from fluorine, methoxy, 2-fluoroethoxy, (tetrahydrofuranyl)oxy, (tetrahydropyranyl)

oxy, (tetrahydrofuran-3-yl)oxy, (tetrahydro-2H-pyran-4-yl) oxy or (R)-(tetrahydrofuran-3-yl)oxy; or $R^4$ on two adjacent carbon atoms, together with the carbon atoms to which they are attached form a 1,4-dioxine ring.

$R^b$ is methyl, ethyl, propyl, tert-butyl, —CH$_2$C(O) OCH$_2$CH$_3$, —CH$_2$C(O)OH, 2-hydroxyethyl, 1,3-dihydroxypropan-2-yl, 1,3-dihydroxy-2-methylpropan-2-yl, 1-hydroxy-2-methylpropan-2-yl, (S)-2,3-dihydroxypropyl, (S)-1-hydroxypropan-2-yl, 2-fluoroethyl, 2,2-difluoroethyl, 2-fluoro-2-methylpropyl, 2,2,2-trifluoroethyl, 2-methoxyethyl, 2-ethoxyethyl, cyclopropyl, 1-methylcyclopropyl, (1r, 4r)-4-hydroxycyclohexyl, 3-hydroxyadamantan-1-yl, 3-hydroxyazetidin-1-yl, 3-hydroxy-3-methylazetidin-1-yl, (S)-3-aminopyrrolidin-1-yl), (S)-3-hydroxypyrrolidin-1-yl, piperidin-1-yl, 4-hydroxypiperidin-1-yl, morpholinyl, 4-methylpiperazinyl, tetrahydro-2H-pyran-4-yl, 4-hydroxyazepan-1-yl, thiazol-2-yl, 5-methyl-1,3,4-thiadiazol-2-yl, 1,3,4-thiadiazol-2-yl, 1H-1,2,4-triazol-1-yl, (1-methyl-1H-pyrazol-3-yl), 1H-imidazol-1-yl, 6-methylpyridazin-3-yl, pyridin-2-yl, pyridin-3-yl, pyrazin-2-yl, 4-fluorophenyl, ((S)-3-hydroxypyrrolidin-1-yl)phenyl or ((S)-3-hydroxypyrrolidin-1-yl)pyridin-3-yl.

The compounds of formula (I) can also exist in the form of pharmaceutically acceptable salts, pharmaceutically acceptable solvates or stereoisomers thereof.

In one embodiment, the present application provides compounds of formula (1d):

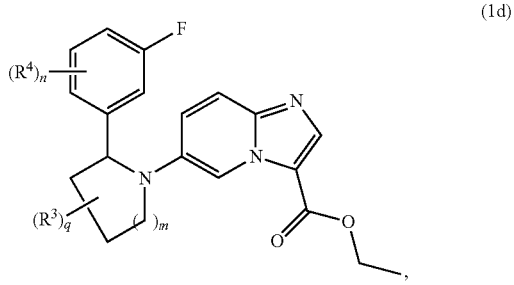

(1d)

or pharmaceutically acceptable salts thereof, or pharmaceutically acceptable solvates thereof or stereoisomers thereof, wherein $R^3$ is halogen; 'm' is 1 or 2; q' is 0, 1, 2 or 3;

and the values of all other variables are as described for compound of formula (I).

In another embodiment, the present application provides compounds of formula (1e):

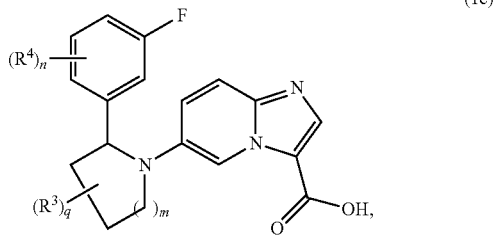

(1e)

or pharmaceutically acceptable salts thereof, or pharmaceutically acceptable solvates thereof or stereoisomers thereof, wherein $R^3$ is halogen; 'm' is 1 or 2; 'q' is 0, 1, 2 or 3;

and the values of all other variables are as described for compound of formula (I).

In another embodiment, the compounds of formula (I) are represented as compounds of formula (1f):

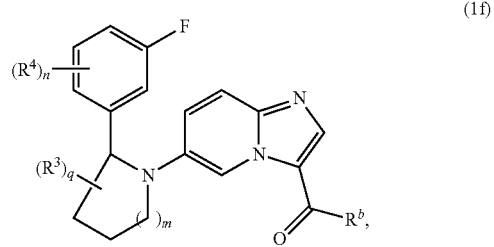

(1f)

or pharmaceutically acceptable salts thereof, or pharmaceutically acceptable solvates thereof or stereoisomers thereof, wherein $R^3$ is fluorine; 'm' is 1 or 2; 'n' is 1 or 2; 'q' is 0 or 1;

and the values of all other variables are as described for compound of formula (I).

In another embodiment, the compounds of formula (I) are represented as compounds of formula (1g):

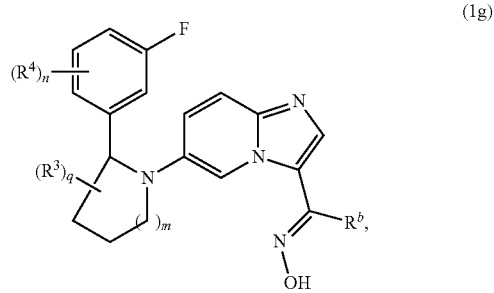

(1g)

or pharmaceutically acceptable salts thereof, or pharmaceutically acceptable solvates thereof or stereoisomers thereof, wherein $R^3$ is fluorine; 'm' is 1 or 2; 'n' is 1 or 2; 'q' is 0 or 1;

and the values of all other variables are as described for compound of formula (I).

In another embodiment, the compounds of formula (I) are represented as compounds of formula (2a):

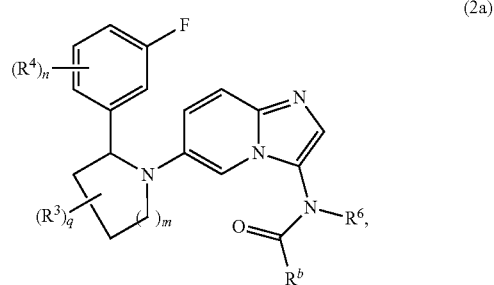

(2a)

or pharmaceutically acceptable salts thereof, or pharmaceutically acceptable solvates thereof or stereoisomers thereof, wherein $R^3$ is fluorine; 'm' is 1 or 2; 'n' is 1 or 2; 'q' is 0 or 1;

and the values of all other variables are as described for compound of formula (I).

In another embodiment, the compounds of formula (I) are represented as compounds of formula (2b):

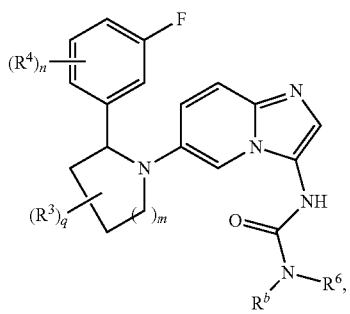

(2b)

or pharmaceutically acceptable salts thereof, or pharmaceutically acceptable solvates thereof or stereoisomers thereof, wherein
R³ is fluorine; 'm' is 1 or 2; 'n' is 1 or 2; 'q' is 0 or 1;
and the values of all other variables are as described for compound of formula (I).

In another embodiment, the compounds of formula (I) are represented as compounds of formula (2c):

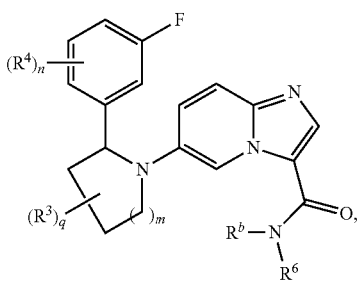

(2c)

or pharmaceutically acceptable salts thereof, or pharmaceutically acceptable solvates thereof or stereoisomers thereof, wherein
R³ is fluorine; 'm' is 1 or 2; 'n' is 1 or 2; 'q' is 0 or 1;
and the values of all other variables are as described for compound of formula (I).

In another embodiment, the compounds of formula (I) are represented as compounds of formula (2d):

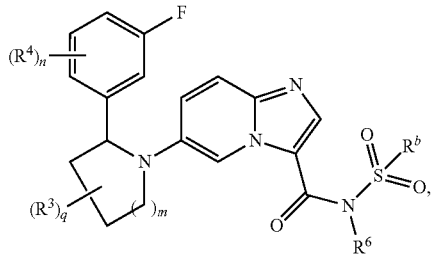

(2d)

or pharmaceutically acceptable salts thereof, or pharmaceutically acceptable solvates thereof or stereoisomers thereof, wherein
R³ is fluorine; 'm' is 1 or 2; 'n' is 1 or 2; 'q' is 0 or 1;
and the values of all other variables are as described for compound of formula (I).

In another embodiment, the compounds of formula (I) are represented as compounds of formula (2e):

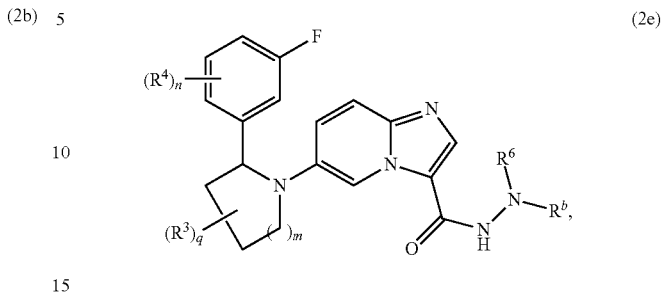

(2e)

or pharmaceutically acceptable salts thereof, or pharmaceutically acceptable solvates thereof or stereoisomers thereof, wherein
R³ is fluorine; 'm' is 1 or 2; 'n' is 1 or 2; 'q' is 0 or 1;
and the values of all other variables are as described for compound of formula (I).

In another embodiment, the compounds of formula (I) are represented as compounds of formula (2f):

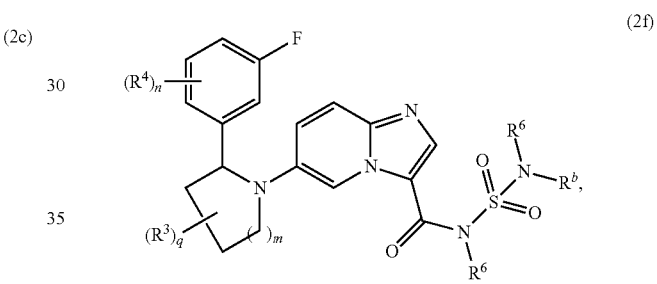

(2f)

or pharmaceutically acceptable salts thereof, or pharmaceutically acceptable solvates thereof or stereoisomers thereof, wherein
R³ is fluorine; 'm' is 1 or 2; 'n' is 1 or 2; 'q' is 0 or 1;
and the values of all other variables are as described for compound of formula (I).

In certain embodiments of formula (1f), (1g), (2a), (2b), (2c), (2d), (2e) or (2f), group

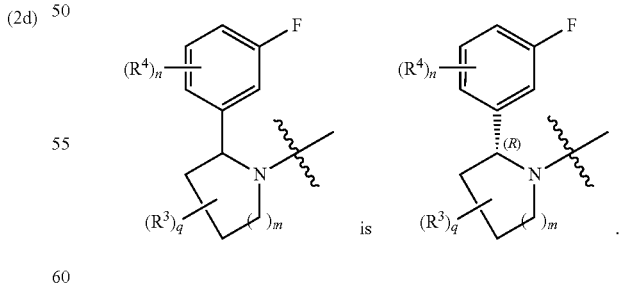

In certain embodiments of formula (1f), (1g), (2a), (2b), (2c), (2d), (2e) or (2f), R⁴ is independently selected from fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy and (R)-(tetrahydrofuran-3-yl)oxy; or R⁴ on two adjacent carbon atoms, together with the carbon atoms to which they are attached form a 1,4-dioxine ring.

In certain embodiments of formula (1g), (2a), (2b), (2c), (2d), (2e) or (2f), $R^6$ is hydrogen, methyl, ethyl, propyl or cyclopropylmethyl.

In certain embodiments of formula (1f), (1g), (2a), (2b), (2c), (2d), (2e) or (2f), $R^b$ is (i) methyl, ethyl, propyl, tert-butyl and 2-methylpropyl, any of which is optionally substituted with 1-3 substituents independently selected from fluorine, methoxy, hydroxyl, —COOCH$_2$CH$_3$ and —COOH;

(ii) phenyl, pyridinyl, pyrazinyl, pyridazinyl, thiazolyl, thiadiazolyl, pyrazolyl, cyclopropyl, cyclohexyl or adamantanyl, any of which is optionally substituted with 1-3 substituents independently selected from halogen, fluoromethyl, difluoromethyl, trifluoromethyl, fluoromethoxy, methoxy, ethoxy, hydroxyl, methyl, piperidinyl, 3-hydroxypyrrolidin-1-yl, 1,2,4-triazol-1-yl and 1H-imidazol-1-yl; or (iii) pyrrolidinyl, azetidinyl, piperidinyl, morpholino, methylpiperazinyl, azepanyl or pyranyl, any of which is optionally substituted with 1-3 substituents independently selected from halogen, fluoromethyl, difluoromethyl, trifluoromethyl, fluoromethoxy, methoxy, ethoxy, hydroxyl, —NH$_2$ and methyl.

In certain embodiments of formula (1f), (1g), (2a), (2b), (2c), (2d), (2e) or (2f), $R^b$ is (i) methyl, ethyl, propyl, tert-butyl, isobutyl, propan-2-yl or 2-methylpropan-2-yl, any of which is optionally substituted with 1-3 substituents independently selected from fluorine, methoxy, hydroxyl, —COOCH$_2$CH$_3$ and —COOH, (ii) phenyl, pyridin-2-yl, pyridin-3-yl, pyrazin-2-yl, pyridazin-3-yl, thiazol-2-yl, 1,3,4-thiadiazol-2-yl, 1H-pyrazol-3-yl, cyclopropyl, cyclohexyl or amantan-1-yl, any of which is optionally substituted with 1-3 substituents independently selected from fluoro, fluoromethyl, difluoromethyl, trifluoromethyl, fluoromethoxy, methoxy, ethoxy, hydroxyl, methyl, 3-hydroxypyrrolidin-1-yl, piperidin-1-yl, 1,2,4-triazol-1-yl and 1H-imidazol-1-yl; or (iii) pyrrolidin-1-yl, azetidin-1-yl, piperidin-1-yl, morpholino, piperazin-1-yl, azepan-1-yl or tetrahydro-2H-pyran-4-yl, optionally substituted with 1-3 substituents independently selected from fluorine, fluoromethyl, difluoromethyl, trifluoromethyl, fluoromethoxy, methoxy, hydroxyl, —NH$_2$ and methyl.

In another embodiment, the compounds of formula (I) are represented as compound of formula (2g):

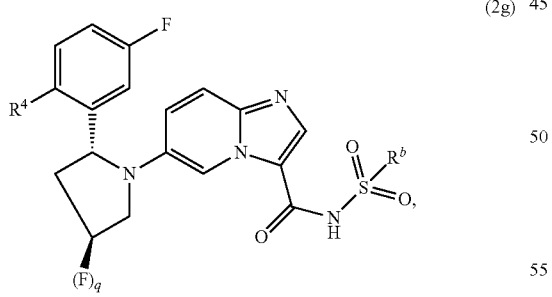

(2g)

or pharmaceutically acceptable salts thereof, or pharmaceutically acceptable solvates thereof or stereoisomers thereof,
wherein,
'q' is 0 or 1;
$R^4$ is fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy or (R)-(tetrahydrofuran-3-yl)oxy; and
$R^b$ is methyl, ethyl, propyl or 1-methylcyclopropyl.

In another embodiment, the compounds of formula (I) are represented as compound of formula (2h):

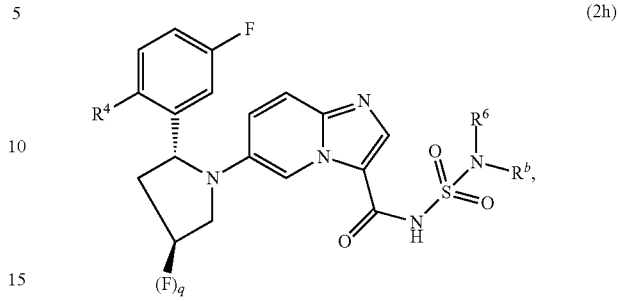

(2h)

or pharmaceutically acceptable salts thereof, or pharmaceutically acceptable solvates thereof or stereoisomers thereof,
wherein,
'q' is 0 or 1;
$R^4$ is fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy or (R)-(tetrahydrofuran-3-yl)oxy;
$R^6$ is hydrogen, methyl, ethyl, propyl, or cyclopropylmethyl; and
$R^b$ is methyl, ethyl, propyl, 1-methylcyclopropyl, thiazol-2-yl, 5-methyl-1,3,4-thiadiazol-2-yl, 1-methyl-1H-pyrazol-3-yl or pyridin-2-yl.

In another embodiment, the compounds of formula (I) are represented as compound of formula:

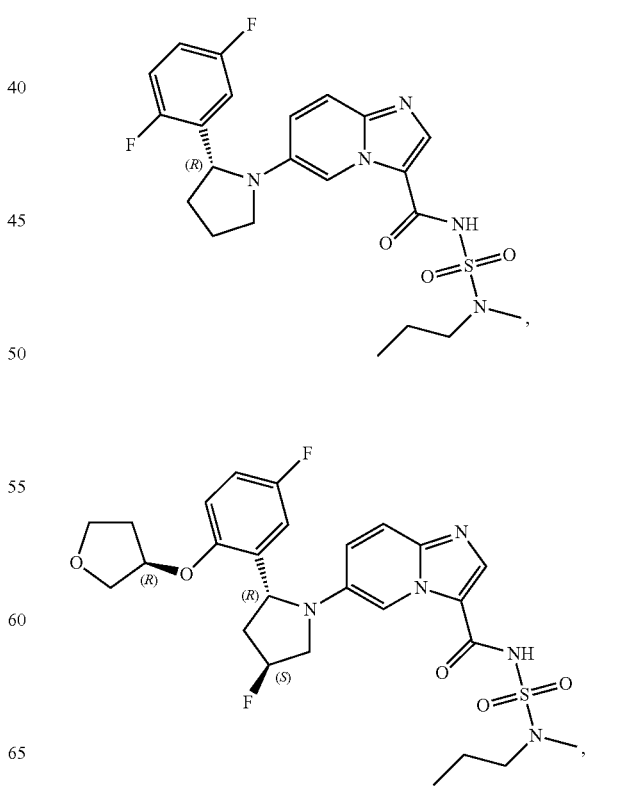

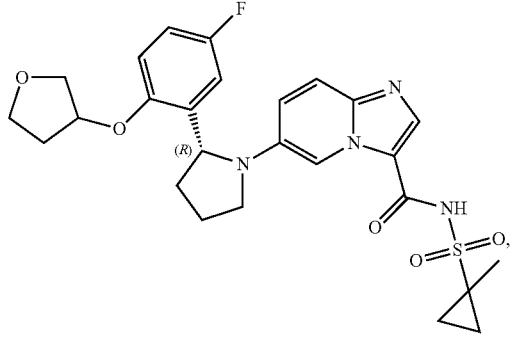
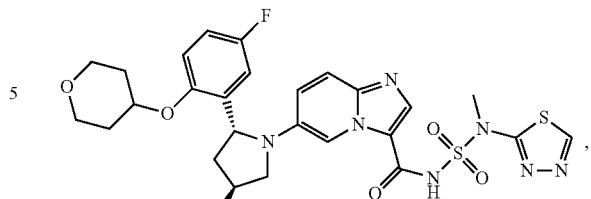
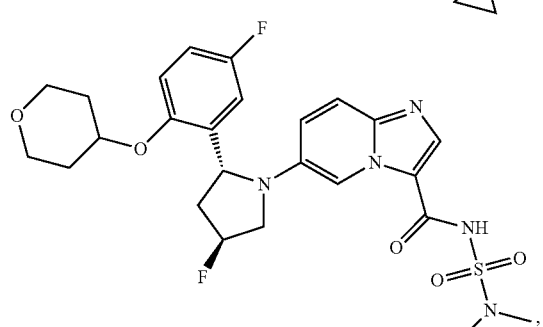
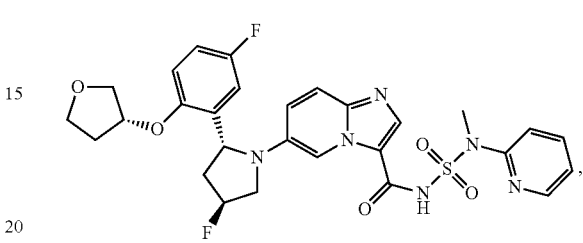
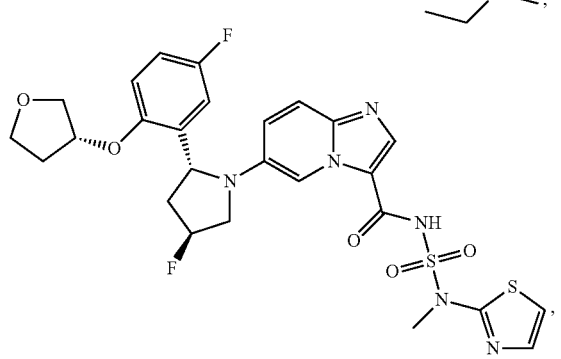
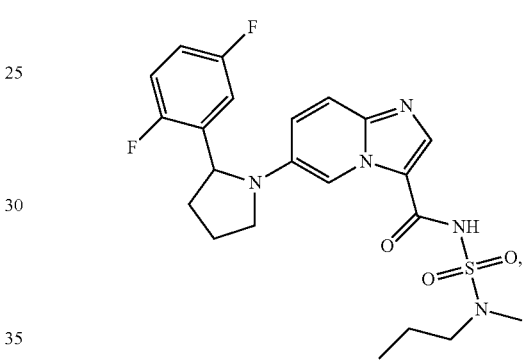
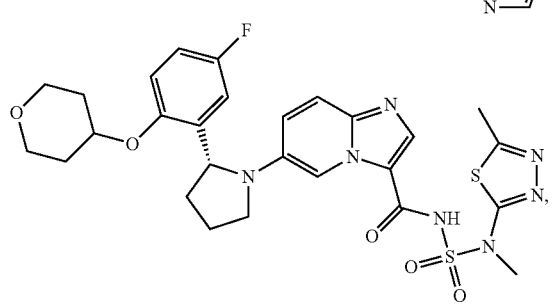
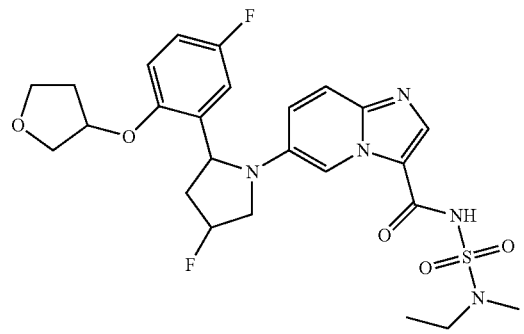
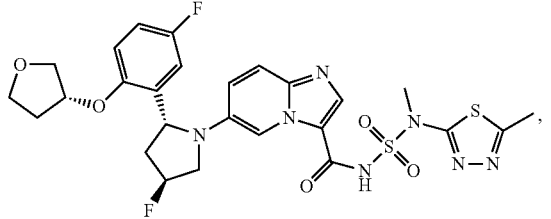
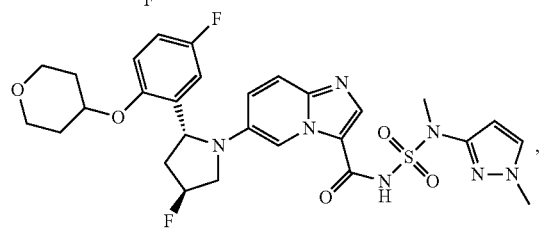
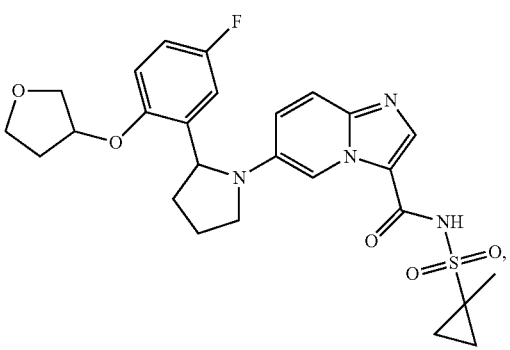

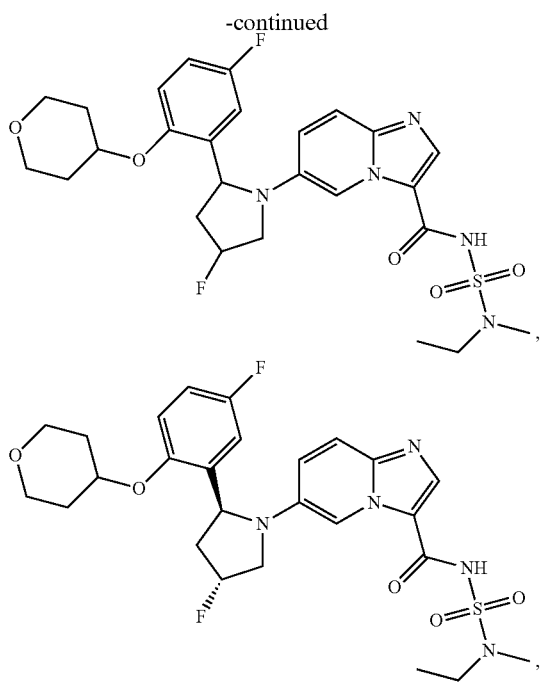

or pharmaceutically acceptable salts thereof, or pharmaceutically acceptable solvates thereof or stereoisomers thereof.

The present application relates to the compounds of formula (I), which are inhibitors of TrkA, TrkB and/or TrkC kinase activity, for the treatment or prevention of diseases or conditions or disorders associated with TrkA, TrkB and/or TrkC kinase activity.

One embodiment of the present application further provides methods of treating or preventing conditions, diseases and/or disorders associated TrkA, TrkB and/or TrkC kinase activity, wherein the method includes administration of a therapeutically effective amount of a compound formula (I), to a patient in need thereof.

One embodiment of the present application provides conditions. diseases and/or disorders treatable or preventable by inhibition of Trk kinase activity, such as pain, inflammation, cancer, restenosis, atherosclerosis, psoriasis, thrombosis, psoriatic arthritis, rheumatoid arthritis, inflammatory bowel disease, ulcerative colitis, Crohn's disease, fibrosis, neurodegenerative a disease, disorder or injury relating to dysmyelination or demyelination or infectious diseases such as Trypanosomacruzi infection by administering a therapeutically effective amount of compound of formula (I), to a patient in need thereof.

One embodiment of the present application further provides methods of treating or preventing conditions, diseases and/or disorders associated TrkA, wherein the method includes administration of a therapeutically effective amount of a compound formula (I) to a patient in need thereof.

In another embodiment, there is provided a method of treating or preventing pain or pain disorder in a patient in need of such a treatment comprising the administration of a therapeutically effective amount of the compound of formula (I) to said patient.

In another embodiment, pain includes chronic and acute pain but is not limited to, pain related to cancer, surgery, bone fracture, skeletal pain caused by tumor metastasis, osteoarthritis, psoriatic arthritis, rheumatoid arthritis, interstitial cystitits, chronic pancreatitis, visceral pain, inflammatory pain, migraine, chronic lower back pain, bladder pain syndrome and neuropathic pain.

In one embodiment, there is provided a method of binding TrkA protein in a patient in need of such a treatment comprising the administration of a therapeutically effective amount of the compound of formula (I) to said patient.

The present application further relates to use of compound of formula (I) for treating or preventing conditions, diseases and/or disorders associated with abnormal or deregulated Trk kinase activity.

One aspect of the present application provides use of compound of formula (I) for treating or preventing conditions, diseases and/or disorders associated with abnormal or deregulated TrkA kinase activity, in a patient in need thereof.

In another embodiment, there is provided an use of the compound for formula (I) for treating or preventing pain or pain disorder in a patient in need of such a treatment, comprising the administration of a therapeutically effective amount of the compound of formula (I), to said patient.

In another embodiment of the present application, pain includes chronic and acute pain but is not limited to, pain related to cancer, surgery and bone fracture, skeletal pain caused by tumor metastasis, osteoarthritis, visceral pain, inflammatory pain and neuropathic pain.

In yet another embodiment, the compounds of the present application may be useful for the pain disorders include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy) central pain syndromes (potentially caused by virtually any lesion at any level of the nervous system) postsurgical pain syndromes (eg, postmastectomy syndrome, postthoracotomy syndrome, stump pain) bone and joint pain (osteoarthritis), repetitive motion pain, denial pain, cancer pain, myofascial pain (muscular injury, fibromyalgia) perioperative pain (general surgery, gynecological), chronic pain, dysmenorrhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

In another embodiment of the above aspect, there is provided a method of treating or preventing pain which comprises administering to said subject a pharmaceutical composition comprising an effective amount of a compound of formula (I).

Another embodiment of the application provides the use of such compositions in the treatment and/or prevention of diseases associated with inhibition of TrkA, such as pain, cancer, restenosis, atherosclerosis, psoriasis, thrombosis, neurodegenerative disease, a disease, disorder, or injury relating to dysmyelination or demyelination or certain infectious diseases such as Trypanosomacrurzi infection.

In another embodiment, the compounds of formula (I) are useful in treating or preventing neurodegenerative disease.

In one embodiment, neurodegenerative disease is Parkinson's disease or Alzheimer's disease.

In another aspect, the present application provides a method of treating or preventing neurodegenerative disease.

In one embodiment, neurodegenerative disease, as described above, is Parkinson's disease or Alzheimer's disease.

In another embodiment, the present application provides method of treating or preventing certain infectious diseases, for example Trypanosomacruzi infection, by administering effective amount of compound of formula (I) to a patient in need thereof.

In another embodiment, the present application provides method of treating or preventing Trypanosomacruzi infection by administering effective amount of compound of formula (I), to a patient in need thereof.

In one embodiment of the present application, there is provided a pharmaceutical composition comprising a therapeutically effective amount of one or more compounds of formula (I) and pharmaceutically acceptable carrier.

Another embodiment of the present application provides a method of administering TrkA inhibitors in a subject (i.e., a patient), which comprises administering to said subject (i.e., a patient) a pharmaceutical composition comprising a therapeutically effective amount of a compound of formula (I). As used herein the term "subject" and "patient" can be the same and can be used interchangeably.

In another embodiment, there is provided a method of inhibiting TrkA comprising administering to said subject a pharmaceutical composition comprising an effective amount of a compound of formula (I).

In an embodiment of the invention are provided specific compounds of formula (I), as enumerated below List-1, pharmaceutically acceptable salts thereof, pharmaceutically acceptable solvates thereof or stereoisomers thereof or any combinations thereof.

In an embodiment, specific compounds of formula (I) without any limitation are enumerated in List-1 or List-2:

In one embodiment, specific compounds of formula (I) are represented by List-1 below:

List-1

6-(2-(2,5-difluorophenyl)pyrrolidin-1-yl)-N-(4-fluorophenyl)imidazo[1,2-a]pyridine-3-carboxamide;
N-(6-(2-(2,5-difluorophenyl)pyrrolidin-1-yl)imidazo[1,2-a]pyridin-3-yl)-3-hydroxypyrrolidine-1-carboxamide;
(6-(2-(2,5-difluorophenyl)pyrrolidin-1-yl)imidazo[1,2-a]pyridin-3-yl)(3-hydroxypyrrolidin-1-yl)methanone;
(6-(2-(2,5-difluorophenyl)pyrrolidin-1-yl)imidazo[1,2-a]pyridin-3-yl)(3-hydroxyazetidin-1-yl)methanone;
6-(2-(2,5-difluorophenyl)pyrrolidin-1-yl)-N-(1,3-dihydroxypropan-2-yl)imidazo[1,2-a]pyridine-3-carboxamide;
(6-(2-(2,5-difluorophenyl)pyrrolidin-1-yl)imidazo[1,2-a]pyridin-3-yl)(morpholino)methanone;
N-(6-(2-(2,5-difluorophenyl)pyrrolidin-1-yl)imidazo[1,2-a]pyridin-3-yl)morpholine-4-carboxamide;
6-(2-(2,5-difluorophenyl)pyrrolidin-1-yl)-N,N-dimethylimidazo[1,2-a]pyridine-3-carboxamide;
(6-(2-(2,5-difluorophenyl)pyrrolidin-1-yl)imidazo[1,2-a]pyridin-3-yl)(4-methylpiperazin-1-yl)methanone;
(6-(2-(2,5-difluorophenyl)pyrrolidin-1-yl)imidazo[1,2-a]pyridin-3-yl)(4-fluorophenyl)methanone;
3-(6-(2-(2,5-difluorophenyl)pyrrolidin-1-yl)imidazo[1,2-a]pyridin-3-yl)-1,1-dimethylurea;
(6-(2-(2,5-difluorophenyl)pyrrolidin-1-yl)imidazo[1,2-a]pyridin-3-yl)(3-hydroxypyrrolidin-1-yl)methanone;
N-(6-(2-(2,5-difluorophenyl)pyrrolidin-1-yl)imidazo[1,2-a]pyridin-3-yl)acetamide;
(6-(2-(2,5-difluorophenyl)pyrrolidin-1-yl)imidazo[1,2-a]pyridin-3-yl)(4-fluorophenyl)methanone oxime;
6-(2-(2,5-difluorophenyl)pyrrolidin-1-yl)-N-(4-fluorophenyl)-N-methylimidazo[1,2-a]pyridine-3-carboxamide;
6-(2-(2,5-difluorophenyl)pyrrolidin-1-yl)-N-(4-hydroxycyclohexyl)imidazo[1,2-a]pyridine-3-carboxamide;
(6-(2-(2,5-difluorophenyl)pyrrolidin-1-yl)imidazo[1,2-a]pyridin-3-yl)(4-hydroxypiperidin-1-yl)methanone;
6-(2-(2,5-difluorophenyl)pyrrolidin-1-yl)-N-(3-ethoxy-2-oxopropyl)imidazo[1,2-a]pyridine-3-carboxamide;
(6-(2-(2,5-difluorophenyl)pyrrolidin-1-yl)imidazo[1,2-a]pyridine-3-carbonyl)glycine;
2-(6-(2-(2,5-difluorophenyl)pyrrolidin-1-yl)imidazo[1,2-a]pyridine-3-carboxamido)acetic acid;
(3-aminopyrrolidin-1-yl)(6-(2-(2,5-difluorophenyl)pyrrolidin-1-yl)imidazo[1,2-a]pyridin-3-yl)methanone;
6-(2-(2,5-difluorophenyl)pyrrolidin-1-yl)-N-(2-hydroxyethyl)imidazo[1,2-a]pyridine-3-carboxamide;
6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide;
6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide;
6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide;
6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide;
N-(tert-butylsulfonyl)-6-(2-(5-fluoro-2-((tetrahydrofuran-3-yl)oxy)phenyl)pyrrolidin-1-yl)imidazo[1,2-a]pyridine-3-carboxamide;
N—(N-ethyl-N-methylsulfamoyl)-6-(2-(5-fluoro-2-((tetrahydrofuran-3-yl)oxy)phenyl)pyrrolidin-1-yl)imidazo[1,2-a]pyridine-3-carboxamide;
6-(2-(2,5-difluorophenyl)pyrrolidin-1-yl)-N-(2-hydroxyethyl)imidazo[1,2-a]pyridine-3-carboxamide;
(6-(2-(2,5-difluorophenyl)pyrrolidin-1-yl)imidazo[1,2-a]pyridin-3-yl)((S)-3-hydroxypyrrolidin-1-yl)methanone;
(6-(2-(2,5-difluorophenyl)pyrrolidin-1-yl)imidazo[1,2-a]pyridin-3-yl)(4-fluorophenyl)methanone oxime;
6-(2-(2,5-difluorophenyl)pyrrolidin-1-yl)-N-(4-fluorophenyl)-N-methylimidazo[1,2-a]pyridine-3-carboxamide;
6-(2-(2,5-difluorophenyl)pyrrolidin-1-yl)-N-((1r,4R)-4-hydroxycyclohexyl)imidazo[1,2-a]pyridine-3-carboxamide;
(6-(2-(2,5-difluorophenyl)pyrrolidin-1-yl)imidazo[1,2-a]pyridin-3-yl)(4-hydroxypiperidin-1-yl)methanone;
6-(2-(2,5-difluorophenyl)pyrrolidin-1-yl)-N-(3-ethoxy-2-oxopropyl)imidazo[1,2-a]pyridine-3-carboxamide;
Ethyl 2-(6-(2-(2,5-difluorophenyl)pyrrolidin-1-yl)imidazo[1,2-a]pyridine-3-carboxamido)acetate;
(6-(2-(2,5-difluorophenyl)pyrrolidin-1-yl)imidazo[1,2-a]pyridine-3-carbonyl)glycine;
2-(6-(2-(2,5-difluorophenyl)pyrrolidin-1-yl)imidazo[1,2-a]pyridine-3-carboxamido)acetic acid;
6-(2-(2,5-difluorophenyl)pyrrolidin-1-yl)-N-(2-hydroxyethyl)imidazo[1,2-a]pyridine-3-carboxamide;
(6-(2-(2,5-difluorophenyl)pyrrolidin-1-yl)imidazo[1,2-a]pyridin-3-yl)(4-hydroxyazepan-1-yl)methanone;
6-(2-(2,5-difluorophenyl)pyrrolidin-1-yl)-N-((1r,3S,5R,7S)-3-hydroxyadamantan-1-yl)imidazo[1,2-a]pyridine-3-carboxamide;
6-(2-(2,5-difluorophenyl)pyrrolidin-1-yl)-N-(1,3-dihydroxy-2-methylpropan-2-yl)imidazo[1,2-a]pyridine-3-carboxamide;
6-(2-(2,5-difluorophenyl)pyrrolidin-1-yl)-N—((S)-2,3-dihydroxypropyl)imidazo[1,2-a]pyridine-3-carboxamide;
(6-(2-(2,5-difluorophenyl)pyrrolidin-1-yl)imidazo[1,2-a]pyridin-3-yl)(3-hydroxy-3-methylazetidin-1-yl)methanone;
6-(2-(2,5-difluorophenyl)pyrrolidin-1-yl)-N-(piperidin-1-yl)imidazo[1,2-a]pyridine-3-carboxamide;

6-(2-(2,5-difluorophenyl)pyrrolidin-1-yl)-N—((S)-1-hydroxypropan-2-yl)imidazo[1,2-a]pyridine-3-carboxamide;

6-(2-(2,5-difluorophenyl)pyrrolidin-1-yl)-N-(1-hydroxy-2-methylpropan-2-yl)imidazo[1,2-a]pyridine-3-carboxamide;

6-(2-(2,5-difluorophenyl)pyrrolidin-1-yl)-N-(tetrahydro-2H-pyran-4-yl)imidazo[1,2-a]pyridine-3-carboxamide;

N-(tert-butylsulfonyl)-6-(2-(2,5-difluorophenyl)pyrrolidin-1-yl)imidazo[1,2-a]pyridine-3-carboxamide;

6-(2-(2,5-difluorophenyl)pyrrolidin-1-yl)-N-((1-methylcyclopropyl)sulfonyl)imidazo[1,2-a]pyridine-3-carboxamide;

6-(2-(2,5-difluorophenyl)pyrrolidin-1-yl)-N-((6-((S)-3-hydroxypyrrolidin-1-yl)pyridin-3-yl)sulfonyl)imidazo[1,2-a]pyridine-3-carboxamide;

6-(2-(2,5-difluorophenyl)pyrrolidin-1-yl)-N—(N-ethyl-N-methylsulfamoyl)imidazo[1,2-a]pyridine-3-carboxamide;

N-((4-(1H-1,2,4-triazol-1-yl)phenyl)sulfonyl)-6-(2-(2,5-difluorophenyl)pyrrolidin-1-yl)imidazo[1,2-a]pyridine-3-carboxamide;

6-(2-(2,5-difluorophenyl)pyrrolidin-1-yl)-N-((4-((S)-3-hydroxypyrrolidin-1-yl)phenyl)sulfonyl)imidazo[1,2-a]pyridine-3-carboxamide;

6-(2-(2,5-difluorophenyl)pyrrolidin-1-yl)-N—(N-methyl-N-propylsulfamoyl)imidazo[1,2-a]pyridine-3-carboxamide;

6-(2-(2,5-difluorophenyl)pyrrolidin-1-yl)-N—(N-(2-fluoroethyl)-N-methylsulfamoyl)imidazo[1,2-a]pyridine-3-carboxamide;

6-(2-(2,5-difluorophenyl)pyrrolidin-1-yl)-N—(N-(2-methoxyethyl)-N-methylsulfamoyl)imidazo[1,2-a]pyridine-3-carboxamide;

6-(2-(2,5-difluorophenyl)pyrrolidin-1-yl)-N—(N-ethyl-N-(2-fluoroethyl)sulfamoyl)imidazo[1,2-a]pyridine-3-carboxamide;

6-(2-(2,5-difluorophenyl)pyrrolidin-1-yl)-N—(N-methyl-N-(2,2,2-trifluoroethyl)sulfamoyl)imidazo[1,2-a]pyridine-3-carboxamide;

6-(2-(2,5-difluorophenyl)pyrrolidin-1-yl)-N—(N-(2-fluoro-2-methylpropyl)-N-methylsulfamoyl)imidazo[1,2-a]pyridine-3-carboxamide;

6-(2-(2,5-difluorophenyl)pyrrolidin-1-yl)-N—(N-methyl-N-(pyridin-3-yl)sulfamoyl)imidazo[1,2-a]pyridine-3-carboxamide;

N—(N-(cyclopropylmethyl)-N-(pyridin-3-yl)sulfamoyl)-6-(2-(2,5-difluorophenyl)pyrrolidin-1-yl)imidazo[1,2-a]pyridine-3-carboxamide;

6-(2-(2,5-difluorophenyl)pyrrolidin-1-yl)-N—(N-methyl-N-(pyrazin-2-yl)sulfamoyl)imidazo[1,2-a]pyridine-3-carboxamide;

N-((6-(1H-imidazol-1-yl)pyridin-3-yl)sulfonyl)-6-(2-(2,5-difluorophenyl)pyrrolidin-1-yl)imidazo[1,2-a]pyridine-3-carboxamide;

6-(2-(2,5-difluorophenyl)pyrrolidin-1-yl)-N—(N-methyl-N-(pyridin-2-yl)sulfamoyl)imidazo[1,2-a]pyridine-3-carboxamide;

6-(2-(2,5-difluorophenyl)pyrrolidin-1-yl)-N—(N-methyl-N-(thiazol-2-yl)sulfamoyl)imidazo[1,2-a]pyridine-3-carboxamide;

6-(2-(2,5-difluorophenyl)piperidin-1-yl)-N-((4-(3-hydroxypyrrolidin-1-yl)phenyl)sulfonyl)imidazo[1,2-a]pyridine-3-carboxamide;

6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide;

6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide;

6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide;

6-(2-(5-fluoro-2-methoxyphenyl)pyrrolidin-1-yl)-N—(N-methyl-N-propylsulfamoyl)imidazo[1,2-a]pyridine-3-carboxamide;

6-(2-(5-fluoro-2-methoxyphenyl)pyrrolidin-1-yl)-N—(N-(2-fluoro-2-methylpropyl)-N-methylsulfamoyl)imidazo[1,2-a]pyridine-3-carboxamide;

N—(N-ethyl-N-methylsulfamoyl)-6-(2-(5-fluoro-2-methoxyphenyl)pyrrolidin-1-yl)imidazo[1,2-a]pyridine-3-carboxamide;

6-(2-(5-fluoro-2-methoxyphenyl)pyrrolidin-1-yl)-N—(N-(2-fluoroethyl)-N-methylsulfamoyl)imidazo[1,2-a]pyridine-3-carboxamide;

N—(N-ethyl-N-methylsulfamoyl)-6-(4-fluoro-2-(5-fluoro-2-(2-fluoroethoxy)phenyl)pyrrolidin-1-yl)imidazo[1,2-a]pyridine-3-carboxamide;

N-(tert-butylsulfonyl)-6-(4-fluoro-2-(5-fluoro-2-(2-fluoroethoxy)phenyl)pyrrolidin-1-yl)imidazo[1,2-a]pyridine-3-carboxamide;

N-(tert-butylsulfonyl)-6-(4-fluoro-2-(5-fluoro-2-((tetrahydrofuran-3-yl)oxy)phenyl)pyrrolidin-1-yl)imidazo[1,2-a]pyridine-3-carboxamide;

N—(N-ethyl-N-methylsulfamoyl)-6-(4-fluoro-2-(5-fluoro-2-((tetrahydrofuran-3-yl)oxy)phenyl)pyrrolidin-1-yl)imidazo[1,2-a]pyridine-3-carboxamide;

6-(4-fluoro-2-(5-fluoro-2-((tetrahydrofuran-3-yl)oxy)phenyl)pyrrolidin-1-yl)-N-((1-methylcyclopropyl)sulfonyl)imidazo[1,2-a]pyridine-3-carboxamide;

6-(4-fluoro-2-(5-fluoro-2-((tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

N—(N-ethyl-N-methylsulfamoyl)-6-(2-(5-fluoro-2-((tetrahydrofuran-3-yl)oxy)phenyl)pyrrolidin-1-yl)imidazo[1,2-a]pyridine-3-carboxamide;

N—(N-ethyl-N-methylsulfamoyl)-6-(2-(5-fluoro-2-((tetrahydrofuran-3-yl)oxy)phenyl)pyrrolidin-1-yl)imidazo[1,2-a]pyridine-3-carboxamide;

N-(tert-butylsulfonyl)-6-(2-(5-fluoro-2-((tetrahydrofuran-3-yl)oxy)phenyl)pyrrolidin-1-yl)imidazo[1,2-a]pyridine-3-carboxamide;

N-(tert-butylsulfonyl)-6-(2-(5-fluoro-2-((tetrahydrofuran-3-yl)oxy)phenyl)pyrrolidin-1-yl)imidazo[1,2-a]pyridine-3-carboxamide;

N—(N-ethyl-N-methylsulfamoyl)-6-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N-ethyl-N-methylsulfamoyl)-6-(2R)-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N-ethyl-N-methylsulfamoyl)-6-((2S)-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N-ethyl-N-methylsulfamoyl)-6-(4-fluoro-2-(7-fluoro-2,3-dihydrobenzo[b][1,4]dioxin-5-yl)pyrrolidin-1-yl)imidazo[1,2-a]pyridine-3-carboxamide;

6-(2-(2,5-difluorophenyl)piperidin-1-yl)-N-((1-methylcyclopropyl)sulfonyl)imidazo[1,2-a]pyridine-3-carboxamide;

6-(2-(2,5-difluorophenyl)piperidin-1-yl)-N—(N-ethyl-N-methylsulfamoyl)imidazo[1,2-a]pyridine-3-carboxamide;

6-(2-(7-fluoro-2,3-dihydrobenzo[b][1,4]dioxin-5-yl)pyrrolidin-1-yl)-N—(N-(2-fluoroethyl)-N-methylsulfamoyl)imidazo[1,2-a]pyridine-3-carboxamide;

N—(N-ethyl-N-methylsulfamoyl)-6-(2-(7-fluoro-2,3-dihydrobenzo[b][1,4]dioxin-5-yl)pyrrolidin-1-yl)imidazo[1,2-a]pyridine-3-carboxamide;

6-(2-(5-fluoro-2-(((R)-tetrahydrofuran-3-yl)oxy)phenyl)pyrrolidin-1-yl)-N-((1-methylcyclopropyl)sulfonyl)imidazo[1,2-a]pyridine-3-carboxamide;

6-(2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

6-(2-(5-fluoro-2-((tetrahydrofuran-3-yl)oxy)phenyl)pyrrolidin-1-yl)-N—(N-methyl-N-propylsulfamoyl)imidazo[1,2-a]pyridine-3-carboxamide;

6-(2-(5-fluoro-2-((tetrahydrofuran-3-yl)oxy)phenyl)pyrrolidin-1-yl)-N—(N-(2-fluoro-2-methylpropyl)-N-methylsulfamoyl)imidazo[1,2-a]pyridine-3-carboxamide;

N—(N-ethyl-N-methylsulfamoyl)-6-(2-(5-fluoro-2-(2-fluoroethoxy)phenyl)pyrrolidin-1-yl)imidazo[1,2-a]pyridine-3-carboxamide;

6-(2-(5-fluoro-2-(2-fluoroethoxy)phenyl)pyrrolidin-1-yl)-N—(N-(2-fluoroethyl)-N-methylsulfamoyl)imidazo[1,2-a]pyridine-3-carboxamide;

6-(2-(5-fluoro-2-(2-fluoroethoxy)phenyl)pyrrolidin-1-yl)-N—(N-methyl-N-propylsulfamoyl)imidazo[1,2-a]pyridine-3-carboxamide;

6-(2-(5-fluoro-2-(2-fluoroethoxy)phenyl)pyrrolidin-1-yl)-N—(N-(2-fluoro-2-methylpropyl)-N-methylsulfamoyl)imidazo[1,2-a]pyridine-3-carboxamide;

N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-(2-fluoroethyl)-N-methylsulfamoyl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-(2-fluoro-2-methylpropyl)-N-methylsulfamoyl)imidazo[1,2-a]pyridine-3-carboxamide;

1-(6-(4-fluoro-2-(5-fluoro-2-((tetrahydro-2H-pyran-4-yl)oxy)phenyl)pyrrolidin-1-yl)imidazo[1,2-a]pyridin-3-yl)-N-(2-fluoroethyl)-N-methyl-1-oxomethanesulfonamide;

(tert-butylsulfonyl)(6-(4-fluoro-2-(5-fluoro-2-((tetrahydro-2H-pyran-4-yl)oxy)phenyl)pyrrolidin-1-yl)imidazo[1,2-a]pyridin-3-yl)methanone;

6-(2-(2,5-difluorophenyl)pyrrolidin-1-yl)-N—(N-methyl-N-(pyrazin-2-yl)sulfamoyl)imidazo[1,2-a]pyridine-3-carboxamide;

N-((6-(1H-imidazol-1-yl)pyridin-3-yl)sulfonyl)-6-(2-(2,5-difluorophenyl)pyrrolidin-1-yl)imidazo[1,2-a]pyridine-3-carboxamide;

N—(N,N-diethylsulfamoyl)-6-(4-fluoro-2-(5-fluoro-2-((tetrahydrofuran-3-yl)oxy)phenyl)pyrrolidin-1-yl)imidazo[1,2-a]pyridine-3-carboxamide;

N—(N-ethyl-N-(2-fluoroethyl)sulfamoyl)-6-(4-fluoro-2-(5-fluoro-2-(((R)-tetrahydrofuran-3-yl)oxy)phenyl)pyrrolidin-1-yl)imidazo[1,2-a]pyridine-3-carboxamide;

6-(4-fluoro-2-(5-fluoro-2-((tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide;

6-(4-fluoro-2-(5-fluoro-2-((tetrahydrofuran-3-yl)oxy)phenyl)pyrrolidin-1-yl)-N—(N-methyl-N-(thiazol-2-yl)sulfamoyl)imidazo[1,2-a]pyridine-3-carboxamide;

6-(4-fluoro-2-(5-fluoro-2-((tetrahydrofuran-3-yl)oxy)phenyl)pyrrolidin-1-yl)-N—(N-methyl-N-(6-methylpyridazin-3-yl)sulfamoyl)imidazo[1,2-a]pyridine-3-carboxamide N-(tert-butylsulfonyl)-6-(2-(5-fluoro-2-((tetrahydro-2H-pyran-4-yl)oxy)phenyl)pyrrolidin-1-yl)imidazo[1,2-a]pyridine-3-carboxamide;

N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide;

N—(N-(2-ethoxyethyl)-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-methyl-N-(6-methylpyridazin-3-yl)sulfamoyl)imidazo[1,2-a]pyridine-3-carboxamide;

6-(4-fluoro-2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide;

6-(4-fluoro-2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide;

6-(2-(2,5-difluorophenyl)pyrrolidin-1-yl)-N—(N-methyl-N-(1-methyl-1H-pyrazol-3-yl)sulfamoyl)imidazo[1,2-a]pyridine-3-carboxamide;

6-(2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-(4-fluoro-2-(5-fluoro-2-((tetrahydrofuran-3-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-(4-fluoro-2-(5-fluoro-2-((tetrahydrofuran-3-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;

N-(tert-butylsulfonyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N,N-diethylsulfamoyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;

6-(4-fluoro-2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-(4-fluoro-2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide;

6-(4-fluoro-2-(5-fluoro-2-((tetrahydro-2H-pyran-4-yl)oxy) phenyl)pyrrolidin-1-yl)-N—(N-methyl-N-(5-methyl-1,3, 4-thiadiazol-2-yl)sulfamoyl)imidazo[1,2-a]pyridine-3-carboxamide;
6-(4-fluoro-2-(5-fluoro-2-((tetrahydro-2H-pyran-4-yl)oxy) phenyl)pyrrolidin-1-yl)-N—(N-(2-fluoroethyl)-N-methylsulfamoyl)imidazo[1,2-a]pyridine-3-carboxamide;
6-(4-fluoro-2-(5-fluoro-2-((tetrahydro-2H-pyran-4-yl)oxy) phenyl)pyrrolidin-1-yl)-N—(N-methyl-N-(thiazol-2-yl) sulfamoyl)imidazo[1,2-a]pyridine-3-carboxamide;
6-(4-fluoro-2-(5-fluoro-2-((tetrahydrofuran-3-yl)oxy)phenyl)pyrrolidin-1-yl)-N—(N-methyl-N-propylsulfamoyl) imidazo[1,2-a]pyridine-3-carboxamide;
N—(N-ethyl-N-(2-fluoroethyl)sulfamoyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;
6-((2R,4S)-4-fluoro-2-(5-fluoro-2-((tetrahydrofuran-3-yl) oxy)phenyl)pyrrolidin-1-yl)-N—(N-methyl-N-(pyridin-2-yl)sulfamoyl)imidazo[1,2-a]pyridine-3-carboxamide;
6-(4-fluoro-2-(5-fluoro-2-((tetrahydro-2H-pyran-4-yl)oxy) phenyl)pyrrolidin-1-yl)-N—(N-methyl-N-(pyridin-2-yl) sulfamoyl)imidazo[1,2-a]pyridine-3-carboxamide;
6-(2-(5-fluoro-2-((tetrahydrofuran-3-yl)oxy)phenyl)pyrrolidin-1-yl)-N—(N-(2-methoxyethyl)-N-methylsulfamoyl) imidazo[1,2-a]pyridine-3-carboxamide;
N—(N,N-dimethylsulfamoyl)-6-(2-(5-fluoro-2-((tetrahydrofuran-3-yl)oxy)phenyl)pyrrolidin-1-yl)imidazo[1,2-a] pyridine-3-carboxamide;
6-(2-(5-fluoro-2-((tetrahydrofuran-3-yl)oxy)phenyl)pyrrolidin-1-yl)-N—(N-methyl-N-propylsulfamoyl)imidazo[1, 2-a]pyridine-3-carboxamide;
N—(N-cyclopropyl-N-methylsulfamoyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;
N—(N-(2,2-difluoroethyl)-N-methylsulfamoyl)-6-(4-fluoro-2-(5-fluoro-2-((tetrahydro-2H-pyran-4-yl)oxy) phenyl)pyrrolidin-1-yl)imidazo[1,2-a]pyridine-3-carboxamide;
6-(4-fluoro-2-(5-fluoro-2-((tetrahydro-2H-pyran-4-yl)oxy) phenyl)pyrrolidin-1-yl)-N—(N-(2-fluoro-2-methylpropyl)-N-methylsulfamoyl)imidazo[1,2-a]pyridine-3-carboxamide;
6-(2-(5-fluoro-2-((tetrahydrofuran-3-yl)oxy)phenyl)pyrrolidin-1-yl)-N—(N-(2-fluoroethyl)-N-methylsulfamoyl) imidazo[1,2-a]pyridine-3-carboxamide;
N—(N,N-diethylsulfamoyl)-6-(2-(5-fluoro-2-((tetrahydrofuran-3-yl)oxy)phenyl)pyrrolidin-1-yl)imidazo[1,2-a]pyridine-3-carboxamide;
or a pharmaceutically acceptable salt thereof, or a pharmaceutically acceptable solvate thereof or a stereoisomer thereof.

Another embodiment of this invention includes specific compounds of formula (I) enumerated below in List-2, or pharmaceutically acceptable salts thereof, pharmaceutically acceptable solvates thereof.

In another embodiment, specific compounds of formula (I) are represented by List-2 below:

In another embodiment, compounds of formula (I) are represented as the compound present in List-2:

List-2

(R)-6-(2-(2,5-difluorophenyl)pyrrolidin-1-yl)-N-(2-hydroxyethyl)imidazo[1,2-a]pyridine-3-carboxamide;
(S)-6-(2-(2,5-difluorophenyl)pyrrolidin-1-yl)-N-(2-hydroxyethyl)imidazo[1,2-a]pyridine-3-carboxamide;
(3S)—N-(6-(2-(2,5-difluorophenyl)pyrrolidin-1-yl)imidazo [1,2-a]pyridin-3-yl)-3-hydroxypyrrolidine-1-carboxamide;
(6-(2-(2,5-difluorophenyl)pyrrolidin-1-yl)imidazo[1,2-a] pyridin-3-yl)((S)-3-hydroxypyrrolidin-1-yl)methanone;
(6-((S)-2-(2,5-difluorophenyl)pyrrolidin-1-yl)imidazo[1,2-a]pyridin-3-yl)((S)-3-hydroxypyrrolidin-1-yl)methanone;
(6-((R)-2-(2,5-difluorophenyl)pyrrolidin-1-yl)imidazo[1,2-a]pyridin-3-yl)((S)-3-hydroxypyrrolidin-1-yl)methanone;
(Z/E)(6-(2-(2,5-difluorophenyl)pyrrolidin-1-yl)imidazo[1, 2-a]pyridin-3-yl)(4-fluorophenyl)methanone oxime;
(E/Z)-(6-(2-(2,5-difluorophenyl)pyrrolidin-1-yl)imidazo[1, 2-a]pyridin-3-yl)(4-fluorophenyl)methanone oxime;
(R)-6-(2-(2,5-difluorophenyl)pyrrolidin-1-yl)-N-(4-fluorophenyl)-N-methylimidazo[1,2-a]pyridine-3-carboxamide;
(S)-6-(2-(2,5-difluorophenyl)pyrrolidin-1-yl)-N-(4-fluorophenyl)-N-methylimidazo[1,2-a]pyridine-3-carboxamide;
6-((S)-2-(2,5-difluorophenyl)pyrrolidin-1-yl)-N-((1r,4S)-4-hydroxycyclohexyl)imidazo[1,2-a]pyridine-3-carboxamide;
6-((R)-2-(2,5-difluorophenyl)pyrrolidin-1-yl)-N-((1r,4R)-4-hydroxycyclohexyl)imidazo[1,2-a]pyridine-3-carboxamide;
(S)-(6-(2-(2,5-difluorophenyl)pyrrolidin-1-yl)imidazo[1,2-a]pyridin-3-yl)(4-hydroxypiperidin-1-yl)methanone;
(R)-(6-(2-(2,5-difluorophenyl)pyrrolidin-1-yl)imidazo[1,2-a]pyridin-3-yl)(4-hydroxypiperidin-1-yl)methanone;
(S)-6-(2-(2,5-difluorophenyl)pyrrolidin-1-yl)-N-(3-ethoxy-2-oxopropyl)imidazo[1,2-a]pyridine-3-carboxamide;
Ethyl(S)-2-(6-(2-(2,5-difluorophenyl)pyrrolidin-1-yl)imidazo[1,2-a]pyridine-3-carboxamido)acetate;
(R)-6-(2-(2,5-difluorophenyl)pyrrolidin-1-yl)-N-(3-ethoxy-2-oxopropyl)imidazo[1,2-a]pyridine-3-carboxamide;
Ethyl(R)-2-(6-(2-(2,5-difluorophenyl)pyrrolidin-1-yl)imidazo[1,2-a]pyridine-3-carboxamido)acetate;
(S)-(6-(2-(2,5-difluorophenyl)pyrrolidin-1-yl)imidazo[1,2-a]pyridine-3-carbonyl)glycine;
(S)-2-(6-(2-(2,5-difluorophenyl)pyrrolidin-1-yl)imidazo[1, 2-a]pyridine-3-carboxamido)acetic acid;
(R)-(6-(2-(2,5-difluorophenyl)pyrrolidin-1-yl)imidazo[1,2-a]pyridine-3-carbonyl)glycine;
(R)-2-(6-(2-(2,5-difluorophenyl)pyrrolidin-1-yl)imidazo[1, 2-a]pyridine-3-carboxamido)acetic acid;
((S)-3-aminopyrrolidin-1-yl)(6-((S)-2-(2,5-difluorophenyl) pyrrolidin-1-yl)imidazo[1,2-a]pyridin-3-yl)methanone;
((S)-3-aminopyrrolidin-1-yl)(6-((R)-2-(2,5-difluorophenyl) pyrrolidin-1-yl)imidazo[1,2-a]pyridin-3-yl)methanone;
(R)-6-(2-(2,5-difluorophenyl)pyrrolidin-1-yl)-N-(2-hydroxyethyl)imidazo[1,2-a]pyridine-3-carboxamide;
(S)-6-(2-(2,5-difluorophenyl)pyrrolidin-1-yl)-N-(2-hydroxyethyl)imidazo[1,2-a]pyridine-3-carboxamide;
(6-((R)-2-(2,5-difluorophenyl)pyrrolidin-1-yl)imidazo[1,2-a]pyridin-3-yl)(4-hydroxyazepan-1-yl)methanone;
6-((R)-2-(2,5-difluorophenyl)pyrrolidin-1-yl)-N-((1r,3S,5R, 7S)-3-hydroxyadamantan-1-yl)imidazo[1,2-a]pyridine-3-carboxamide;
(R)-6-(2-(2,5-difluorophenyl)pyrrolidin-1-yl)-N-(1,3-dihydroxy-2-methylpropan-2-yl)imidazo[1,2-a]pyridine-3-carboxamide;
6-((R)-2-(2,5-difluorophenyl)pyrrolidin-1-yl)-N—((S)-2,3-dihydroxypropyl)imidazo[1,2-a]pyridine-3-carboxamide;
(R)-(6-(2-(2,5-difluorophenyl)pyrrolidin-1-yl)imidazo[1,2-a]pyridin-3-yl)(3-hydroxy-3-methylazetidin-1-yl)methanone;

(R)-6-(2-(2,5-difluorophenyl)pyrrolidin-1-yl)-N-(piperidin-1-yl)imidazo[1,2-a]pyridine-3-carboxamide;

6-((R)-2-(2,5-difluorophenyl)pyrrolidin-1-yl)-N—((S)-1-hydroxypropan-2-yl)imidazo[1,2-a]pyridine-3-carboxamide;

(R)-6-(2-(2,5-difluorophenyl)pyrrolidin-1-yl)-N-(1-hydroxy-2-methylpropan-2-yl)imidazo[1,2-a]pyridine-3-carboxamide;

(R)-6-(2-(2,5-difluorophenyl)pyrrolidin-1-yl)-N-(tetrahydro-2H-pyran-4-yl)imidazo[1,2-a]pyridine-3-carboxamide;

(R)—N-(tert-butylsulfonyl)-6-(2-(2,5-difluorophenyl)pyrrolidin-1-yl)imidazo[1,2-a]pyridine-3-carboxamide;

(R)-6-(2-(2,5-difluorophenyl)pyrrolidin-1-yl)-N-((1-methylcyclopropyl)sulfonyl)imidazo[1,2-a]pyridine-3-carboxamide;

6-((R)-2-(2,5-difluorophenyl)pyrrolidin-1-yl)-N-((6-((S)-3-hydroxypyrrolidin-1-yl)pyridin-3-yl)sulfonyl)imidazo[1,2-a]pyridine-3-carboxamide;

(R)-6-(2-(2,5-difluorophenyl)pyrrolidin-1-yl)-N—(N-ethyl-N-methylsulfamoyl)imidazo[1,2-a]pyridine-3-carboxamide;

(R)—N-((4-(1H-1,2,4-triazol-1-yl)phenyl)sulfonyl)-6-(2-(2,5-difluorophenyl)pyrrolidin-1-yl)imidazo[1,2-a]pyridine-3-carboxamide;

6-((R)-2-(2,5-difluorophenyl)pyrrolidin-1-yl)-N-((4-((S)-3-hydroxypyrrolidin-1-yl)phenyl)sulfonyl)imidazo[1,2-a]pyridine-3-carboxamide;

(R)-6-(2-(2,5-difluorophenyl)pyrrolidin-1-yl)-N—(N-methyl-N-propylsulfamoyl)imidazo[1,2-a]pyridine-3-carboxamide;

(R)-6-(2-(2,5-difluorophenyl)pyrrolidin-1-yl)-N—(N-(2-fluoroethyl)-N-methylsulfamoyl)imidazo[1,2-a]pyridine-3-carboxamide;

(R)-6-(2-(2,5-difluorophenyl)pyrrolidin-1-yl)-N—(N-(2-methoxyethyl)-N-methylsulfamoyl)imidazo[1,2-a]pyridine-3-carboxamide;

(R)-6-(2-(2,5-difluorophenyl)pyrrolidin-1-yl)-N—(N-ethyl-N-(2-fluoroethyl)sulfamoyl)imidazo[1,2-a]pyridine-3-carboxamide;

(R)-6-(2-(2,5-difluorophenyl)pyrrolidin-1-yl)-N—(N-methyl-N-(2,2,2-trifluoroethyl)sulfamoyl)imidazo[1,2-a]pyridine-3-carboxamide;

(R)-6-(2-(2,5-difluorophenyl)pyrrolidin-1-yl)-N—(N-(2-fluoro-2-methylpropyl)-N-methylsulfamoyl)imidazo[1,2-a]pyridine-3-carboxamide;

(R)-6-(2-(2,5-difluorophenyl)pyrrolidin-1-yl)-N—(N-methyl-N-(pyridin-3-yl)sulfamoyl)imidazo[1,2-a]pyridine-3-carboxamide;

(R)—N—(N-(cyclopropylmethyl)-N-(pyridin-3-yl)sulfamoyl)-6-(2-(2,5-difluorophenyl)pyrrolidin-1-yl)imidazo[1,2-a]pyridine-3-carboxamide;

(R)-6-(2-(2,5-difluorophenyl)pyrrolidin-1-yl)-N—(N-methyl-N-(pyrazin-2-yl)sulfamoyl)imidazo[1,2-a]pyridine-3-carboxamide;

(R)—N-((6-(1H-imidazol-1-yl)pyridin-3-yl)sulfonyl)-6-(2-(2,5-difluorophenyl)pyrrolidin-1-yl)imidazo[1,2-a]pyridine-3-carboxamide;

(R)-6-(2-(2,5-difluorophenyl)pyrrolidin-1-yl)-N—(N-methyl-N-(pyridin-2-yl)sulfamoyl)imidazo[1,2-a]pyridine-3-carboxamide;

(R)-6-(2-(2,5-difluorophenyl)pyrrolidin-1-yl)-N—(N-methyl-N-(thiazol-2-yl)sulfamoyl)imidazo[1,2-a]pyridine-3-carboxamide;

6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide;

6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide;

6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide;

6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide;

6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide;

6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide;

6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide;

6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide;

(R)-6-(2-(5-fluoro-2-methoxyphenyl)pyrrolidin-1-yl)-N—(N-methyl-N-propylsulfamoyl)imidazo[1,2-a]pyridine-3-carboxamide;

(R)-6-(2-(5-fluoro-2-methoxyphenyl)pyrrolidin-1-yl)-N—(N-(2-fluoro-2-methylpropyl)-N-methylsulfamoyl)imidazo[1,2-a]pyridine-3-carboxamide;

(R)—N—(N-ethyl-N-methylsulfamoyl)-6-(2-(5-fluoro-2-methoxyphenyl)pyrrolidin-1-yl)imidazo[1,2-a]pyridine-3-carboxamide;

(R)-6-(2-(5-fluoro-2-methoxyphenyl)pyrrolidin-1-yl)-N—(N-(2-fluoroethyl)-N-methylsulfamoyl)imidazo[1,2-a]pyridine-3-carboxamide;

N—(N-ethyl-N-methylsulfamoyl)-6-((2R,4S)-4-fluoro-2-(5-fluoro-2-(2-fluoroethoxy)phenyl)pyrrolidin-1-yl)imidazo[1,2-a]pyridine-3-carboxamide;

N-(tert-butylsulfonyl)-6-((2R,4S)-4-fluoro-2-(5-fluoro-2-(2-fluoroethoxy)phenyl)pyrrolidin-1-yl)imidazo[1,2-a]pyridine-3-carboxamide;

N-(tert-butylsulfonyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-methylsulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N-((1-methylcyclopropyl)sulfonyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

N—(N-ethyl-N-methylsulfamoyl)-6-(2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-methylsulfamoyl)-6-(2-(5-fluoro-2-(((R)-tetrahydrofuran-3-yl)oxy)phenyl)pyrrolidin-1-yl)imidazo[1,2-a]pyridine-3-carboxamide;

N-(tert-butylsulfonyl)-6-(2-(5-fluoro-2-(((R)-tetrahydrofuran-3-yl)oxy)phenyl)pyrrolidin-1-yl)imidazo[1,2-a]pyridine-3-carboxamide;

N-(tert-butylsulfonyl)-6-(2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N-ethyl-N-methylsulfamoyl)-6-((2R,4S)-4-fluoro-2-(7-fluoro-2,3-dihydrobenzo[b][1,4]dioxin-5-yl)pyrrolidin-1-yl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—((1-methylcyclopropyl)sulfonyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-methyl-N-propylsulfamoyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-(2-fluoro-2-methylpropyl)-N-methylsulfamoyl)imidazo[1,2-a]pyridine-3-carboxamide;

(R)—N—(N-ethyl-N-methylsulfamoyl)-6-(2-(5-fluoro-2-(2-fluoroethoxy)phenyl)pyrrolidin-1-yl)imidazo[1,2-a]pyridine-3-carboxamide;

(R)-6-(2-(5-fluoro-2-(2-fluoroethoxy)phenyl)pyrrolidin-1-yl)-N—(N-(2-fluoroethyl)-N-methylsulfamoyl)imidazo[1,2-a]pyridine-3-carboxamide;

(R)-6-(2-(5-fluoro-2-(2-fluoroethoxy)phenyl)pyrrolidin-1-yl)-N—(N-methyl-N-propylsulfamoyl)imidazo[1,2-a]pyridine-3-carboxamide;

(R)-6-(2-(5-fluoro-2-(2-fluoroethoxy)phenyl)pyrrolidin-1-yl)-N—(N-(2-fluoro-2-methylpropyl)-N-methylsulfamoyl)imidazo[1,2-a]pyridine-3-carboxamide;

(R)—N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-(2-fluoroethyl)-N-methylsulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-(2-fluoro-2-methylpropyl)-N-methylsulfamoyl)imidazo[1,2-a]pyridine-3-carboxamide;

1-(6-((2S,4R)-4-fluoro-2-(5-fluoro-2-((tetrahydro-2H-pyran-4-yl)oxy)phenyl)pyrrolidin-1-yl)imidazo[1,2-a]pyridin-3-yl)-N-(2-fluoroethyl)-N-methyl-1-oxomethanesulfonamide;

(tert-butylsulfonyl)(6-((2S,4R)-4-fluoro-2-(5-fluoro-2-((tetrahydro-2H-pyran-4-yl)oxy)phenyl)pyrrolidin-1-yl)imidazo[1,2-a]pyridin-3-yl)methanone;

(S)-(6-(2-(2,5-difluorophenyl)pyrrolidin-1-yl)imidazo[1,2-a]pyridin-3-yl)(3-hydroxyazetidin-1-yl)methanone;

(R)-(6-(2-(2,5-difluorophenyl)pyrrolidin-1-yl)imidazo[1,2-a]pyridin-3-yl)(3-hydroxyazetidin-1-yl)methanone;

(R)-6-(2-(2,5-difluorophenyl)pyrrolidin-1-yl)-N—(N-methyl-N-(pyrazin-2-yl)sulfamoyl)imidazo[1,2-a]pyridine-3-carboxamide;

(R)—N—((6-(1H-imidazol-1-yl)pyridin-3-yl)sulfonyl)-6-(2-(2,5-difluorophenyl)pyrrolidin-1-yl)imidazo[1,2-a]pyridine-3-carboxamide;

N—(N,N-diethylsulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-(2-fluoroethyl)sulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(thiazol-2-yl)sulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(6-methylpyridazin-3-yl)sulfamoyl)imidazo[1,2-a]pyridine-3-carboxamide (R)—N-(tert-butylsulfonyl)-6-(2-(5-fluoro-2-((tetrahydro-2H-pyran-4-yl)oxy)phenyl)pyrrolidin-1-yl)imidazo[1,2-a]pyridine-3-carboxamide;

(R)—N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide;

(R)—N—(N-(2-ethoxyethyl)-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(6-methylpyridazin-3-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide;

(R)-6-(2-(2,5-difluorophenyl)pyrrolidin-1-yl)-N—(N-methyl-N-(1-methyl-1H-pyrazol-3-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;

N-(tert-butylsulfonyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N,N-diethylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-(2-fluoroethyl)-N-methylsulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-propylsulfamoyl)imidazo[1,2-a]pyridine-3-carboxamide;

N—(N-ethyl-N-(2-fluoroethyl)sulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(pyridin-2-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide;

N—(N,N-dimethylsulfamoyl)-6-((R)-2-(5-fluoro-2-(((R)-tetrahydrofuran-3-yl)oxy)phenyl)pyrrolidin-1-yl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-methyl-N-propylsulfamoyl)imidazo[1,2-a]pyridine-3-carboxamide;

N—(N-cyclopropyl-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N-(2,2-difluoroethyl)-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-(2-fluoro-2-methylpropyl)-N-methylsulfamoyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

N—(N,N-diethylsulfamoyl)-6-((R)-2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-methylsulfamoyl)-6-((2S,4R)-4-fluoro-2-(5-fluoro-2-(((R)-tetrahydrofuran-3-yl)oxy)phenyl)pyrrolidin-1-yl)imidazo[1,2-a]pyridine-3-carboxamide;

6-((2S,4R)-4-fluoro-2-(5-fluoro-2-(((R)-tetrahydrofuran-3-yl)oxy)phenyl)pyrrolidin-1-yl)-N-((1-methylcyclopropyl)sulfonyl)imidazo[1,2-a]pyridine-3-carboxamide;

N—(N-ethyl-N-methylsulfamoyl)-6-((2S,4R)-4-fluoro-2-(5-fluoro-2-((tetrahydro-2H-pyran-4-yl)oxy)phenyl)pyrrolidin-1-yl)imidazo[1,2-a]pyridine-3-carboxamide;

(R)-6-(2-(2,5-difluorophenyl)pyrrolidin-1-yl)-N—(N-methyl-N-propylsulfamoyl)imidazo[1,2-a]pyridine-3-carboxamide;

or a pharmaceutically acceptable salt thereof, or a pharmaceutically acceptable solvate thereof or a stereoisomer thereof.

In another embodiment, there is provided a method of treating or preventing pain or pain disorder in a patient in need of such a treatment comprising the administration of a therapeutically effective amount of the compound of formula (I) enlisted in List-1, or a stereoisomer thereof or a pharmaceutically acceptable salt thereof to said patient.

In another embodiment, there is provided a method of treating or preventing pain or pain disorder in a patient in need of such a treatment comprising the administration of a therapeutically effective amount of the compound of formula (I) enlisted in List-2, or a stereoisomer thereof or a pharmaceutically acceptable salt thereof to said patient.

The present application further relates to methods of treating a patient for diseases or disorders in which the nerve growth factor (NGF) receptor are involved, in particular TrkA, such as such as pain, cancer, restenosis, atherosclerosis, psoriasis, thrombosis, or a disease, disorder, or injury relating to dysmyelination or demyelination, by administering a therapeutically effective amount of compound of formula (I), as enlisted in List-1 or List-2, to said patient.

In another embodiment, there is provided a method of treating or preventing pain or pain disorder in a patient in need of such a treatment comprising the administration of a therapeutically effective amount of the compound of formula (I), as enlisted in List-1 or List-2, to said patient.

In another embodiment, pain includes chronic and acute pain but is not limited to, pain related to cancer, surgery and bone fracture, skeletal pain caused by tumor metastasis, osteoarthritis, visceral pain, inflammatory pain and neuropathic pain.

In one embodiment, there is provided a method of binding NGF receptor TrkA protein in a patient in need of such a treatment comprising the administration of a therapeutically effective amount of the compound of formula (I), as enlisted in List-1 or List-2, to said patient.

The present application further relates to use of compound of formulation (I) for treating a patient for diseases or disorders in which the NGF receptor are involved, in particular TrkA, such as pain, cancer, restenosis, atherosclerosis, psoriasis, thrombosis, or a disease, disorder, or injury relating to dysmyelination or demyelination, by administering a therapeutically effective amount of compound of formula (I), as enlisted in List-1 or List 2, to said patient.

In another embodiment, there is provided an use of the compound for formula (I) for treating or preventing pain or pain disorder in a patient in need of such a treatment, comprising the administration of a therapeutically effective amount of the compound of formula (I), as enlisted in List-1 or List-2, to said patient.

In another embodiment, pain includes chronic and acute pain but is not limited to, pain related to cancer, surgery and bone fracture, skeletal pain caused by tumor metastasis, osteoarthritis, visceral pain, inflammatory pain and neuropathic pain.

In another embodiment of the above aspect, there is provided a method of treating or preventing pain which comprises administering to said subject a pharmaceutical composition comprising an effective amount of a compound of formula (I), as enlisted in List-1 or List-2.

Another embodiment of the application provides the use of such compositions in the treatment or prevention of diseases associated with inhibiting NGF receptor TrkA, such as pain, cancer, restenosis, atherosclerosis, psoriasis, thrombosis, or a disease, disorder, or injury relating to dysmyelination or demyelination.

The pharmaceutical composition of a compound of formula (I) may be administered enterally and/or parenterally. Parenteral administration includes subcutaneous, intramuscular, intradermal, intramammary, intravenous, and other administrative methods known in the art. Enteral administration includes solution, tablets, sustained release capsules, enteric coated capsules, syrups, beverages, foods, and other nutritional supplements. When administered, the present pharmaceutical compositions may be at or near body temperature. In some embodiments, the present pharmaceutical compositions may be below body temperatures. In other embodiments, the present pharmaceutical compositions may be above body temperatures.

The compounds of the present invention may be administered in a wide variety of different dosage forms. For example, they may be combined with various pharmaceutically acceptable inert carriers in the form of, but not limited to, tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers may include solid diluents or fillers, sterile aqueous media, and various nontoxic organic solvents, etc. Moreover, oral pharmaceutical compositions may be sweetened and/or flavored. In general, the compounds of the invention may be present in such dosage forms at concentration levels ranging from about 0.1% to about 90% by weight.

In general, compounds of the present invention for treatment may be administered to a subject in a suitable effective dose in the range of from about 0.01 to about 100 mg per kilogram of body weight of recipient per day, in some embodiments, in the range of from about 0.5 to about 50 mg per kilogram body weight of recipient per day, in still other embodiments, in the range of from about 0.1 to about 20 mg per kilogram body weight of recipient per day. The exemplary dose may be suitably administered once daily, or several sub-doses, e.g. 2 to 5 sub-doses, may be administered at appropriate intervals through the day, or on other appropriate schedules.

An embodiment of the present invention provides the preparation of compounds of formula (I) according to the procedures of the following examples, using appropriate materials. Those skilled in the art will understand that known variations of the conditions and processes of the following preparative procedures and general schemes can be used to prepare these compounds. Moreover, by utilizing the procedures described in detail, one of ordinary skill in the art can prepare additional compounds of the present invention claimed herein. All temperatures are in degrees Celsius (° C.) unless otherwise noted.

The following acronyms, abbreviations, terms and definitions have been used throughout the reaction scheme and experimental section.
ACN (Acetonitrile), $(Ac)_2O$ (Acetic anhydride), Boc(tert-butoxycarbonyl), $(BOC)_2O$ (Di-tert-butyl dicarbonate), n-BuLi (n-butyl Lithium), $CDCl_3$ (Deuterated chloroform), $CD_3OD$ (Deuterated methanol), DCM (Dichloromethane), DME (Dimethyl ether), DIPEA [(N,N-diisopropylethylamine) (Hünig's base)], DMF (N,N-dimethylformamide), DMF-DMA (N,N-Dimethylformamide dimethyl acetal), DMSO (Dimethyl sulfoxide), DMAP (Dimethyl amino pyridine), Diphenylphosphorylazide (DPPA), EDC (1-Ethyl-3-(3-dimethylaminopropyl)carbodiimide), EtOH (Ethanol), EtOAc (Ethyl acetate), HATU [O-(-7-azabenzotriazol-1-yl)-N,N,N',N'-tetramethyluroniumhexafluorophosphate], MeOH (Methanol), LiHMDS (Lithium bis(trimethylsilyl)amide), LiOH (Lithium hydroxide), $NH_4OAc$ (Ammonium acetate), i-PrMgCl (Isopropylmagnesium chloride), (PCC) Pyridinium chlorochromate, TEA (Triethanolamine), TFA (Trifluoroacetic acid), THF (Tetrahydrofuran), $H_2O$ (Water), RT (Room temperature).

Another embodiment of the present invention provides a process for the preparation of compounds of formulae (2a)-(2f) which represent respectively a sub-group of a compound of formula (I), wherein all symbols/variables are as defined earlier unless otherwise stated. The process is represented by the following general scheme-1.

General Scheme 1:

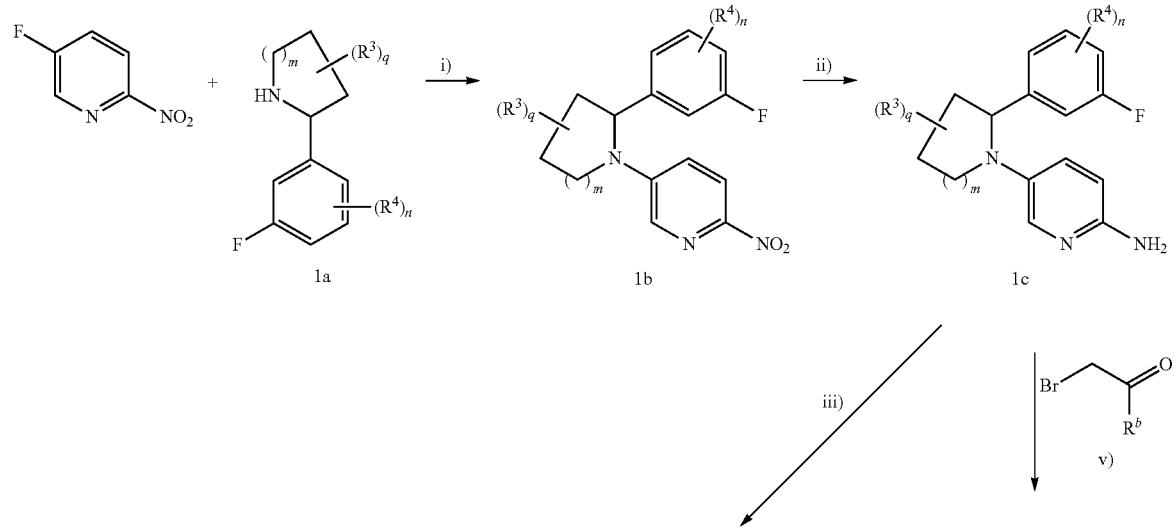

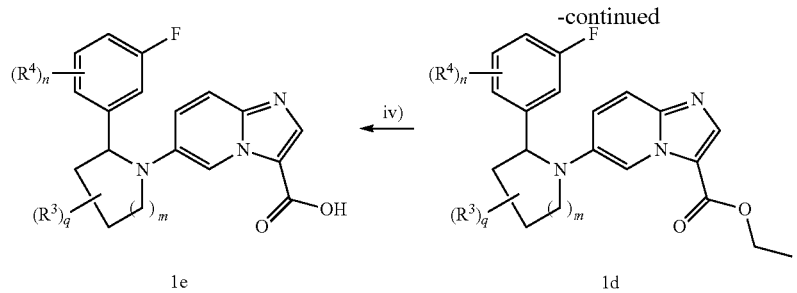
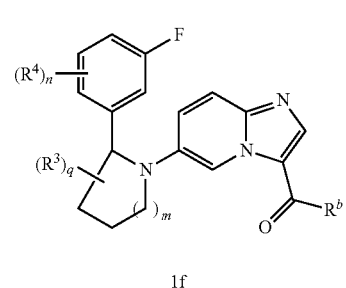
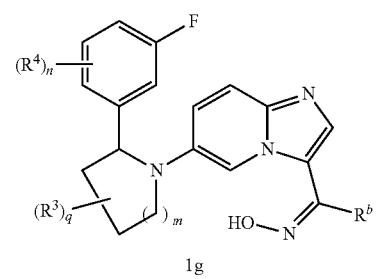

m = 1, 2
Reagent and condition:
i) K$_2$CO$_3$, DMF, RT, 16 h;
ii) N$_2$H$_4$•2H$_2$O, Raney Ni, Ethanol, 10° C. to RT;
iii) DMF DMA, Ethylbromoacetate, Toluene, 120° C.;
iv) 1M LiOH, EtOH, 85° C., 6 h;
v) DMF DMA, Toluene, 120° C.;
vi) NaOAc, NH$_2$OH•HCl, Ethanol, Reflux, 16 h An amine 1a reacts with 5-fluoro-2-nitropyridine in presence of DMF/K$_2$CO$_3$ or similar reagents/solvent condition undergo S$_N$Ar reaction to afford compound 1b. Reduction of compound 1b with a suitable reducing agent, followed by cyclization with DMF-DMA and Ethylbromoacetate afforded compound 1d. Base hydrolysis of 1d in Ethanol afforded the acid 1e which is a common intermediate for most of the final products. Compound 1c can also be cyclized to compound 1f in presence of DMF-DMA and a suitable bromoalkanone. Reaction of 1f with Hydroxylamine in presence of a base afforded 1g.

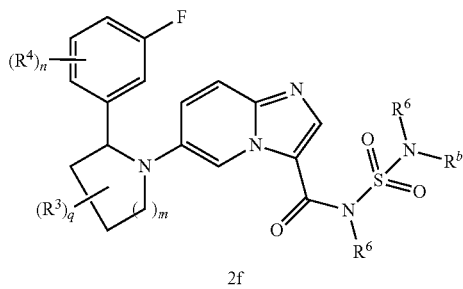
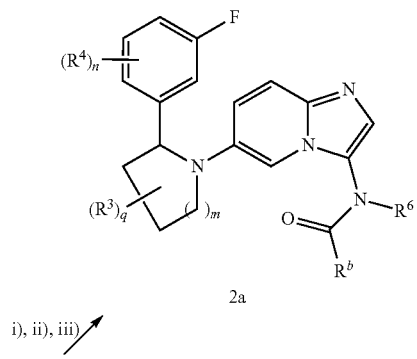

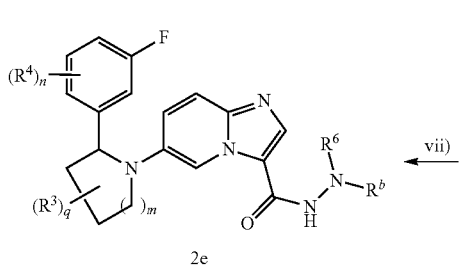

2e

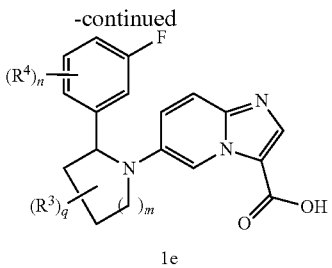

1e

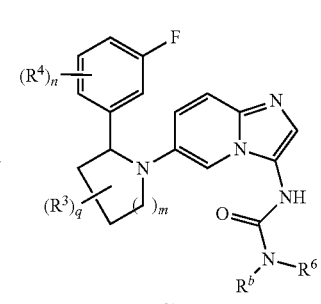

2b

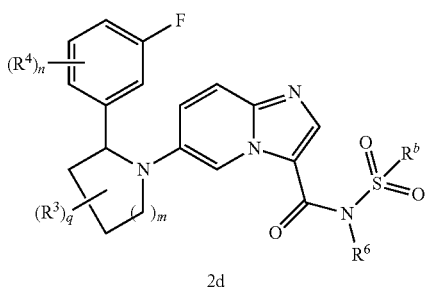

2d

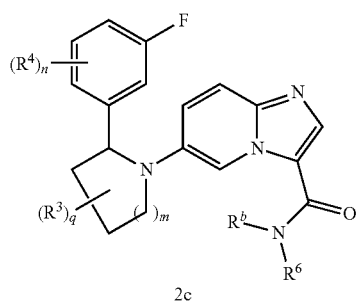

2c m = 1, 2
Reagent and condition:
i) DPPA, TEA, t-BuOH;
ii) Dioxane, HCl;
iii) Ac$_2$O, Pyridine, DCM
iv) R$^6$R$^b$NH, DPPA, TEA, Toluene, 120° C. 16 h;
v) R$^b$R$^6$NH, HATU, DIPEA, DMF, RT, 16 h;
vi) R$^b$SO$_2$NHR$^6$, EDC•HCl DMAP, DCM, RT 48 h.
vii) R$^b$R$^6$NHNH$_2$, HATU, DIPEA, DMF, RT.
viii) R$^b$R$^6$NSO$_2$NH$_2$, EDC•HCl DMAP, DCM, RT, 48 h Carboxylic acid derivative 1e can undergo rearrangement with Diphenylphosphorylazide (DPPA) in presence of t-Butanol to form a Boc protected amine, which on deprotection and amide coupling renders product 2a. Compound 2b is synthesized similar to 2a by quenching the intermediate isocyanide of DPPA reaction with a suitable amine. Compound 2c is synthesized from 1e, employing standard amide coupling reagents known in the literature. Acylsulfonamide derivative 2d is synthesized by reaction of 1e with a suitable sulfonamides in presence of a coupling reagent like EDC/DMAP. Acylhydrazide derivative 2e was synthesized employing a suitable amide coupling reagents and a hydrazine derivatives, Finally acylsulfamides 2f was synthesized by coupling a suitable sulfamide derivative with 1e in presence of EDC/DMAP.

As used in the examples, preparations that follow and any other place, the terms used therein shall have the meanings indicated: "g" or "gm" refers to grams, "mg" refers to milligrams, "μg" refers to micrograms, "mol" refers to moles, "mmol" refers to millimoles, "L" refers to liters, "mL" or "ml" refers to milliliters, "μL" refers to microliters, "mp" or "m.p." refers to melting point, "mm of Hg" refers to pressure in millimeters of mercury, "cm" refers to centimeters, "nm" refers to nanometers, "conc." refers to concentrated, "M" refers to molar, "mM" refers to millimolar, "μM" refers to micromolar, "nM" refers to nanomolar, "TLC" refers to thin layer chromatography, "HPLC" refers to high performance liquid chromatography, "anhyd" refers to anhydrous; "aq" refers to aqueous; "min" refers to minute; "mins" refers to minutes; "h" or "hr" refers to hour; "d" refers to day; "atm" refers to atmosphere; "sat." refers to saturated; "s" refers to singlet, "d" refers to doublet; "t" refers to triplet; "q" refers to quartet; "m" refers to multiplet; "dd" refers to "doublet of doublets"; "br" refers to broad; "bs" refers to broad singlet, "LC" refers to liquid chromatograph; "MS" refers to mass spectroscopy; "ES" refers to electrospray; "ESI" refers to electrospray ionization; "CI" refers to chemical ionization; "i,e" refers to that is, "e.g." refers to for example, "RT" refers to retention time; "M" refers to molecular ion; "NMR" refers to nuclear magnetic resonance spectroscopy; "MHz" refers to megahertz.

EXAMPLES

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

Synthesis of Intermediates

Synthesis of (R)-2-(2,5-difluorophenyl)pyrrolidine hydrochloride (Int-6)

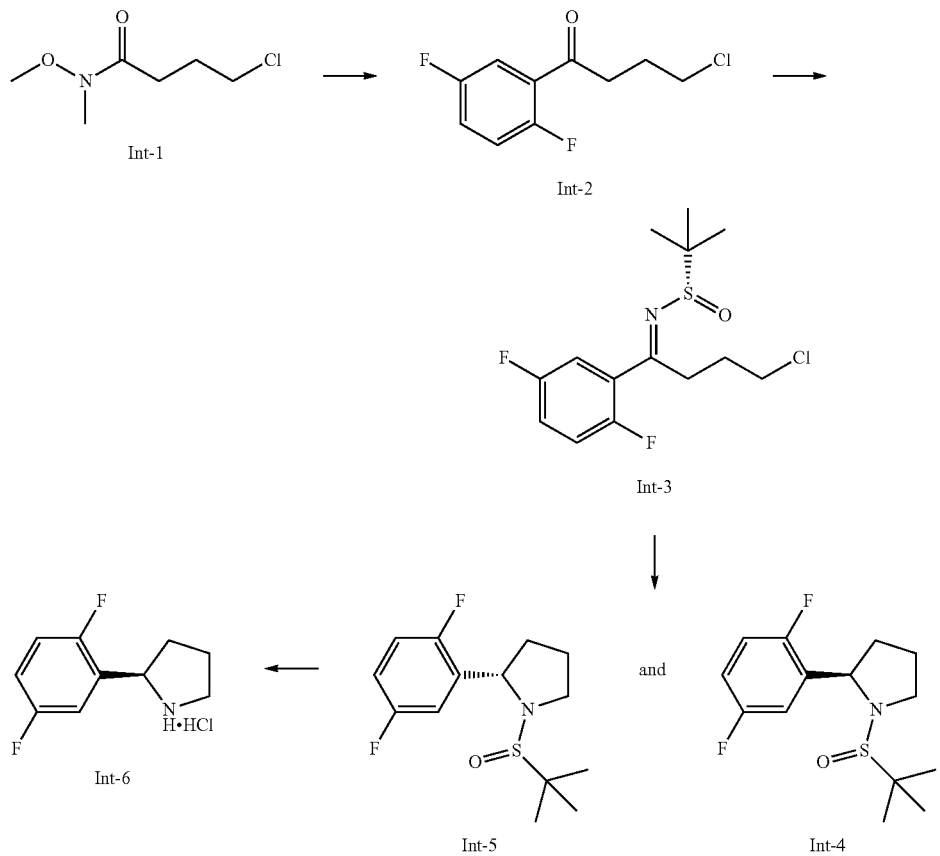

Int-1: 4-chloro-N-methoxy-N-methylbutanamide

Pyridine (101.28 g, 106.6 mL, 1281.79 mmol) was added to a solution of N,O-dimethylhydroxylamine hydrochloride (50 g, 512.72 mmol) in DCM (800 mL) at 0° C. and stirring was continued for 15 min. Chlorobutyrylchloride (72.29 g, 512.72 mmol) was then added to this mixture and was stirred continuously at 0° C. for 2 h. The reaction mixture was diluted with DCM and the organic layer was washed with water followed by brine. The organic layer was separated, dried over anhydrous sodium sulphate and concentrated under reduced pressure to afford 79 g of the title compound as a pale brown liquid. MS (ESI): m/z 166.1 (M+H).

Int-2: 4-chloro-1-(2,5-difluorophenyl)butan-1-one

2-Bromo-1,4-difluorobenzene (53.6 g, 277.74 mmol) in THF (50 ml) was cooled to −50° C., to it was added isopropyl magnesium chloride (2M in THF) (133 mL, 266 mmol). The reaction mixture thus obtained was warmed to 0° C. and stirred for 1 h. The reaction mixture was cooled again to −50° C. 4-chloro-N-methoxy-N-methylbutanamide (40 g, 241.52 mmol) in THF (200 mL) was added drop wise to this reaction mixture with stirring and the stirring was continued at 0° C. for 1 h. The reaction mixture was quenched with saturated aqueous NH$_4$Cl solution, extracted with ethylacetate. The organic layer collected was washed with water (500 mL) and then with brine solution, dried over anhydrous sodium sulfate and concentrated under reduced pressure to afford a crude liquid residue. The residue thus obtained was purified by column chromatography (using 60-120 silica gel and 5% EtOAc in Hexane as eluent) to afford 35 g of the title compound as a colorless liquid. $^1$H NMR (300 MHz, CDCl$_3$) δ 7.60-7.53 (1H, m), 7.26-7.09 (2H, m), 3.70 (2H, t), 3.22-3.14 (2H, m), 2.28-2.16 (2H, m).

Int-3: (S,E)-N-(4-chloro-1-(2,5-difluorophenyl)butylidene)-2-methylpropane-2-sulfinamide Titanium (IV) ethoxide (54.77 g, 240.13 mmol) was added to a solution of 4-chloro-1-(2,5-difluorophenyl)butan-1-one (35 g, 160.09 mmol) and (S)-2-methylpropane-2-sulfinamide (29.1 g, 240.13 mmol) in THF (400 mL) with stirring. The mixture was stirred continuously at 70° C. for 16 h. Reaction mixture was then cooled to a temperature of 20-35° C., quenched with saturated aqueous NH$_4$Cl solution, diluted with ethylacetate and filtered. The filtrate was washed with water followed by brine solution. The organic layer was separated, dried over anhydrous sodium sulfate and concentrated under reduced pressure to afford 44.5 g of the title compound as a colorless liquid. MS (ESI): m/z 322.3 (M+H).

Int-4: (R)-1-((S)-tert-butylsulfinyl)-2-(2,5-difluorophenyl)pyrrolidine and Int-5: (S)-1-((S)-tert-butylsulfinyl)-2-(2,5-difluorophenyl)pyrrolidine (S,E)-N-(4-chloro-1-(2,5-difluorophenyl)butylidene)-2-methylpropane-2-sulfinamide (44 g, 136.72 mmol) in THF (500 mL) was cooled to −78° C. and to which was added cold (−78° C.) Lithium triethylborohydride (1M in THF) (17.38 g, 165 mL, and 134.67 mmol) drop wise and stirring was continued at −78° C. for 3 h. LiHMDS (1M in THF) (25.26 g, 150 mL, 150 mmol) was then added and stirring was continued at −78° C. to 0° C. for 2 h. The resultant reaction mixture was quenched with saturated NH₄Cl solution, diluted with ethylacetate. The ethylacetate layer separated was washed with water followed by brine solution, dried over anhydrous sodium sulphate and concentrated under reduce pressure to afford the crude residue. The residue thus obtained was purified by column chromatography with 230-400 silicagel and 12-14% EtOAc in Hexane as eluent to afford 14.5 g of the title compound (R)-1-((S)-tert-butylsulfinyl)-2-(2,5-difluorophenyl)pyrrolidine as a pale brown liquid. $^1$H NMR (300 MHz, CDCl$_3$) δ 7.1-6.85 (3H, m), 5.0 (1H, t) 3.93-3.85 (1H, m), 3.02-2.94 (1H, m), 2.32-2.2 (1H, m), 2.0-1.72 (3H, m), 1.16 (9H, s) ppm and 4 g of the title compound (S)-1-((S)-tert-butylsulfinyl)-2-(2,5-difluorophenyl)pyrrolidine. $^1$H NMR (300 MHz, CDCl$_3$) δ 7.1-6.8 (3H, m), 5.42-5.2 (1H, d, J=7.5 Hz), 2.3-2.05 (1H, m), 2.0-1.65 (4H, m), 1.1 (9H, s) ppm.

Int-6: (R)-2-(2,5-difluorophenyl)pyrrolidine hydrochloride

4M HCl solution (in Dioxane) (75 mL) was added to stirred solution of (R)-1-((S)-tert-butylsulfinyl)-2-(2,5-difluorophenyl)pyrrolidine (15 g, 52.19 mmol) in Dioxane (25 mL) and stirring was continued at 20-35° C. for 4 h. After which the reaction mixture was concentrated under reduced pressure to afford the crude product. The crude product was purified by washing with diethyl ether to afford 7.5 g of the title compound as a white solid. MS (ESI): m/z 184 (M+H).

Synthesis of 2-(2,5-difluorophenyl)pyrrolidine (Int-10)

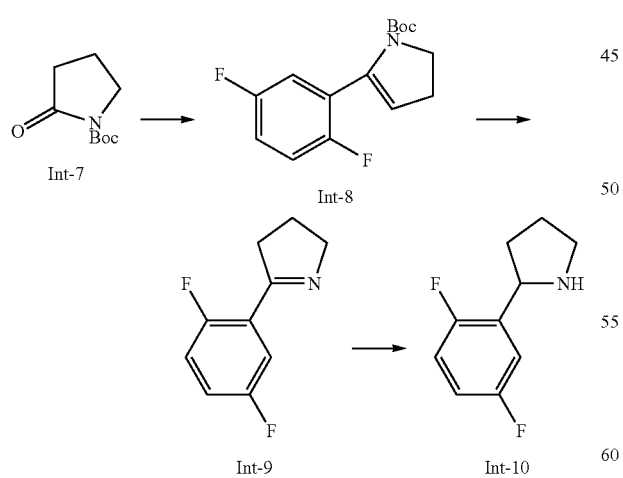

Int-7: tert-butyl 2-oxopyrrolidine-1-carboxylate

Di-tert-butyldicarbonate (154 g, 154 mL, 704 mmol) was added to solution of 2-Pyrrolidinone (50 g, 587 mmol) and DMAP (36 g, 293.7 mmol) in acetonitrile (500 mL) at 0-5° C. and stirring was continued at 20-35° C. for 2 h. Reaction mixture was concentrated under reduced pressure to afford the residue, which was diluted with EtOAc, washed it with water, dried over anhydrous sodium sulphate and concentrated under reduced pressure to afford 73 g of the title compound.

Int-8: tert-butyl 5-(2,5-difluorophenyl)-2,3-dihydro-1H-pyrrole-1-carboxylate 2.0 M Isopropyl magnesium chloride solution in THF (163 mL, 324.3 mmol) was added to a solution of 2-bromo-1,4-difluorobenzene (62.5 g, 324.3 mmol) in THF (350 mL) at −40° C. and stirring was continued at 5° C. for 1 h. tert-Butyl 2-oxopyrrolidine-1-carboxylate (Step-1) (73 g, 392 mmol) in THF (150 mL) was added dropwise to above reaction mixture at −40° C. and stirring was continued at 10° C. for 2 h. Reaction mixture was quenched with saturated NH₄Cl solution, extracted with EtOAc, dried over anhydrous sodium sulphate and concentrated under reduced pressure to afford 76 g of the title compound.

Int-9: 5-(2,5-difluorophenyl)-3,4-dihydro-2H-pyrrole

TFA (108 g, 940 mmol) was added to a solution of tert-butyl 5-(2,5-difluorophenyl)-2,3-dihydro-1H-pyrrole-1-carboxylate (53 g, 188 mmol) in DCM (300 mL) at 0° C. and stirring was continued at 20-35° C. for 2 h. The reaction mixture was concentrated under reduced pressure to afford the crude, which was diluted with EtOAc, washed with saturated NaHCO₃ solution, dried over anhydrous sodium sulphate to afford 28.5 g of the title compound. MS (ESI): m/z 181.9 (M+H).

Int-10: 2-(2,5-difluorophenyl)pyrrolidine

NaBH₄ (12 g, 314.9 mmol) was added to a solution of 5-(2,5-difluorophenyl)-3,4-dihydro-2H-pyrrole (28.5 g, 157.4 mmol) in a mixture of MeOH:H₂O (4:1, 250 mL) and stirring was continued at 25-35° C. for 2 h. The reaction mixture was quenched with 1N aqueous HCl solution and basified with 2N aqueous NaOH solution, extracted with DCM, dried over anhydrous sodium sulphate and concentrated under reduced pressure to afford 23 g of the title compound. MS (ESI): m/z 184 (M+H).

Synthesis of (R)-6-(2-(2,5-difluorophenyl)pyrrolidin-1-yl)imidazo[1,2-a]pyridine-3-carboxylic acid (Int 14)

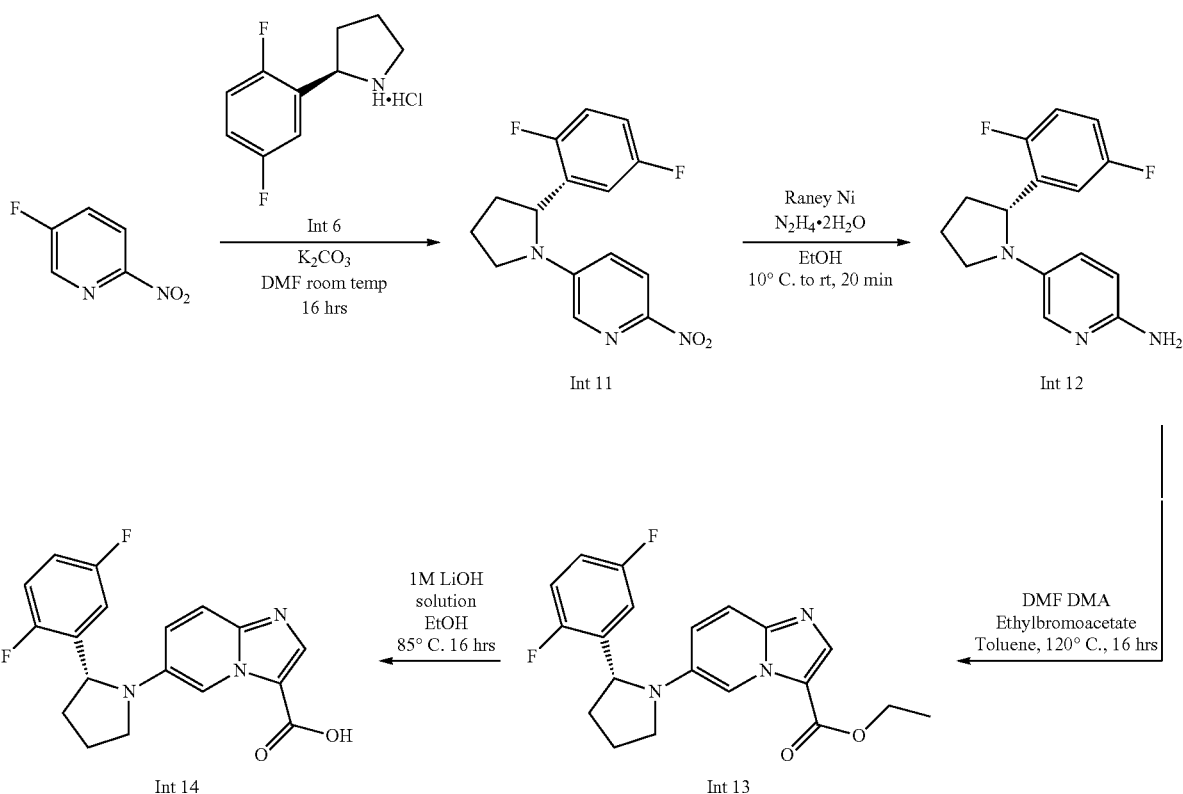

Int 11: (R)-5-(2-(2,5-difluorophenyl)pyrrolidin-1-yl)-2-nitropyridine

A solution of Int 6 (4.44 g, 20.4 mmol) in dry DMF (25 ml) was added $K_2CO_3$ (7.0 g, 51 mmol) and stirred for 5 min at room temperature then added 5-fluoro-2-nitropyridine (2.5 g, 17 mmol) under $N_2$ atmosphere and stirred for 16 h at room temperature. After completion of reaction, reaction mixture was poured in to ice and stirred for 10 min then solid was collected by filtration. Solid was dried under high vacuum to afford (R)-5-(2-(2,5-difluorophenyl)pyrrolidin-1-yl)-2-nitropyridine (Int-11) as yellow solid (3.2 g, 62.7% Yield) MS (ESI): m/z 306.1 (M+H).

Int 12: (R)-5-(2-(2,5-difluorophenyl)pyrrolidin-1-yl)pyridin-2-amine

To a stirred solution of (R)-5-(2-(2,5-difluorophenyl)pyrrolidin-1-yl)-2-nitropyridine (3.2 g, 10.46 mmol) in Ethanol (32 ml) was cooled to 10° C. and added Raney Ni (640 mg, 20% w/w) portion wise and stirred for 5 min, then added $N_2H_4.2H_2O$ (1.05 g, 20.98 mmol) drop wise for the period of 5 min, then stirred for 20 min at room temperature. After completion of reaction, reaction mixture was filter through celite bed under $N_2$ atmosphere and filtrate was concentration under reduced pressure, the residue was re-dissolved in DCM and washed with water, brine and dried over $Na_2SO_4$ and concentration to get desired product as brown solid (2.7 g, 93% yield), MS (ESI): m/z 276.1 (M+H).

Int 13: —(R)-ethyl 6-(2-(2,5-difluorophenyl)pyrrolidin 1-yl)imidazo[1,2-a]pyridine-3-carboxylate To stirred solution of (R)-5-(2-(2,5-difluorophenyl)pyrrolidin-1-yl)pyridin-2-amine (2.7 g, 9.8 mmol) in dry toluene (27 ml, 10 v) was added DMF-DMA (2.45 g, 20.61 mmol) under $N_2$ atm and stirred for 2 h at 120° C. during which complete consumption of Int-12 was observed by TLC, cool it to 10° C. then added Ethylbromoacetate (3.6 g, 21.59 mmol) drop wise and methanol (2 ml) was added under $N_2$ atm then stirred for 16 h at 120° C. Reaction mixture was cooled to room temperature and solvent was removed in vacuo and residue was dissolved in DCM (200 ml), washed with water and brine, dried over anhydrous $Na_2SO_4$ and concentrated under vacuum to get crude product. Crude was purified by column chromatography (eluted with 30-40% ethyl acetate/Hexane) to afford pale green solid (2.25 g, 61.8% yield), MS (ESI): m/z 372.1 (M+H); $^1$H NMR (400 MHz, $CDCl_3$) δ 8.57-8.56 (1H, m), 8.17 (1H, s), 7.51-7.49 (1H, dd), 7.08-7.04 (1H, m), 6.92-6.91 (1H, m), 6.84-6.80 (2H, m), 5.02-5.00 (1H, m), 4.40-4.35 (2H, q), 3.74-3.72 (1H, m), 3.43-3.42 (1H, m), 2.48-2.46 (1H, m), 2.12-2.02 (3H, m), 1.43-1.37 (3H, t) ppm.

Int 14: (R)-6-(2-(2,5-difluorophenyl)pyrrolidin-1-yl)imidazo[1,2-a]pyridine-3-carboxylic acid To stirred solution of (R)-ethyl 6-(2-(2,5-difluorophenyl)pyrrolidin 1-yl)imidazo[1,2-a]pyridine-3-carboxylate (4.5 g, 12.12 mmol) in Ethanol was added 1M LiOH (0.87 g, 36.3 mmol) solution and stirred for 5 h at 85° C. Solvent was removed under reduced pressure and residue was dissolved in water, extracted unwanted impurities with Diethyl ether and water layer was acidified with 2N HCl and solid was collected by filtration. Solid was dried under high vacuum to afford (R)-6-(2-(2,5-difluorophenyl)pyrrolidin-1-yl)imidazo[1,2-a]pyridine-3-carboxylic acid (Int-14) as pale yellow solid (3.5 g, 84.1% yield), MS (ESI): m/z 344.2 (M+H).

Synthesis of 6-(2-(2,5-difluorophenyl)pyrrolidin-1-yl)imidazo[1,2-a]pyridine-3-carboxylic acid (Int 15)

Int 15 was synthesized by employing a procedure substantially similar to Int-14 except that in step-1 of the synthesis Int-10 (an enantiomeric mixture) was used in place of Int-6 to afford R&S mixture of 6-(2-(2,5-difluorophenyl)pyrrolidin-1-yl)imidazo[1,2-a]pyridine-3-carboxylic acid as solid. MS (ESI): m/z 344.2 (M+H).

Synthesis of 2-(2,5-difluorophenyl)piperidine (Int 19)

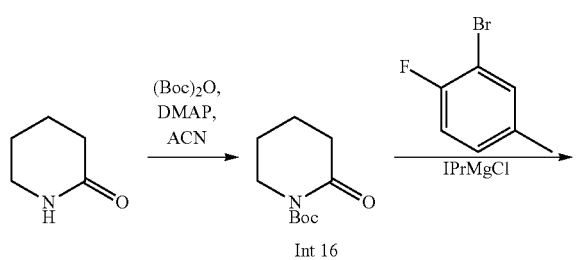

Int 16

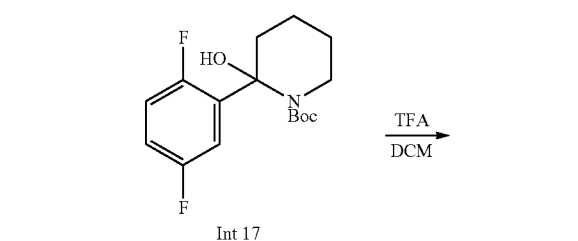

Int 17

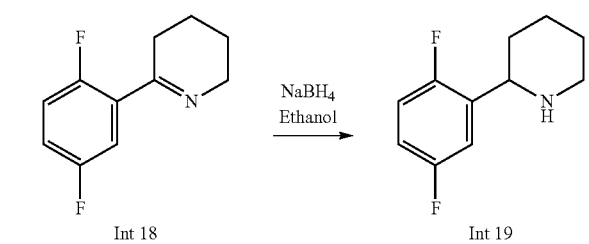

Int 18            Int 19

Int 16: tert-butyl 2-oxopiperidine-1-carboxylate

A solution of piperidin-2-one (25 g, 252.2 mmol) in acetonitrile (250 ml) was cooled to 0° C. and added DMAP (6.1 g, 50.4 mmol) and triethyl amine (25.5 g, 252.2 mmol) and stirred for 10 min at same temperature then added (BOC)$_2$O (66 g, 302.6 mmol) and continue stirring for 2 h at room temperature. After completion of starting material, solvent was removed and residue was re-dissolved in ethyl acetate and washed with water, brine and dried over Na$_2$SO$_4$ and concentration to afford crude product as brown liquid (31.8 g) which was used directly for the next step. $^1$H NMR (300 MHz, CDCl$_3$) δ 3.66-3.62 (2H, m), 2.52-2.47 (2H, m), 1.83-1.79 (4H, m), 1.52 (9H, s) ppm.

Int 17: tert-butyl 2-(2,5-difluorophenyl)-2-hydroxypiperidine-1-carboxylate

To a stirred solution of 2-bromo-1,4-difluorobenzene (5.15 g, 25.9 mmol) in dry THF (77 ml, 15 v) at −78° C. was added i-PrMgCl (2M, 19.5 ml, 38.8 mmol) drop wise and stirred for 1 h at room temperature then cooled again to −78° C. and added tert-butyl 2-oxopiperidine-1-carboxylate (dissolved in dry THF) (6.0 g, 31.0 mmol) drop wise and reaction mixture was stirred for 2 h at room temperature. After completion of reaction, quenched with sat.NH$_4$Cl solution and diluted with ethyl acetate. Organic layer was separated and water layer was extracted with ethyl acetate. Combined organic layer were washed with water, brine and dried over anhydrous Na$_2$SO$_4$ and concentrated under reduced pressure to afford crude Int-17 (9.4 g) which was directly used for the next step.

Int 18: 6-(2,5-difluorophenyl)-2,3,4,5-tetrahydropyridine

To a stifled solution of tert-butyl 2-(2,5-difluorophenyl)-2-hydroxypiperidine-1-carboxylate (9.4 g, 30 mmol) in DCM was added TFA (34.2 g, 300 mmol) and stifled at room temperature for 2 h. After completion of reaction, solvent was removed under vacuum and residue was quenched with sat.NaHCO$_3$ and extracted with DCM. Organic layer was washed with water, brine and dried over anhydrous Na$_2$SO$_4$ and concentration to afford crude product as brown liquid (5.5 g), this crude was directly used for next step without any purification.

Int 19: 2-(2,5-difluorophenyl)piperidine

To stirred solution of 6-(2,5-difluorophenyl)-2,3,4,5-tetrahydropyridine (5.5 g, 28.2 mmol) in mixture of methanol/water (4:1, 10v) in an ice bath was added NaBH$_4$ (2.14 g, 56.4 mmol) portion wise then stirred for 30 min at ambient temperature. After completion of reaction, solvent was removed under vacuum and residue was acidified with 2N HCl and washed with diethyl ether (2×50 ml) and aq. layer was basified with 5N NaOH solution (pH~10) and product was extracted with ethyl acetate, organic layer was washed with brine and dried over Na$_2$SO$_4$ and concentration under vacuum to afford brown color liquid. (3.4 g, 61.3% Yield)$^1$H NMR (300 MHz, CDCl$_3$) δ 7.26-7.19 (1H, m), 6.99-6.84 (2H, m), 3.94-3.91 (1H, m), 3.21-3.17 (1H, m), 2.86-2.77 (1H, m), 2.04-1.81 (2H, m), 1.62-1.40 (3H, m) ppm.

Above enantiomeric mixture was directly used for next step without any separation.

Synthesis of 6-(2-(2,5-difluorophenyl)piperidin-1-yl)imidazo[1,2-a]pyridine-3-carboxylic acid (Int 23)

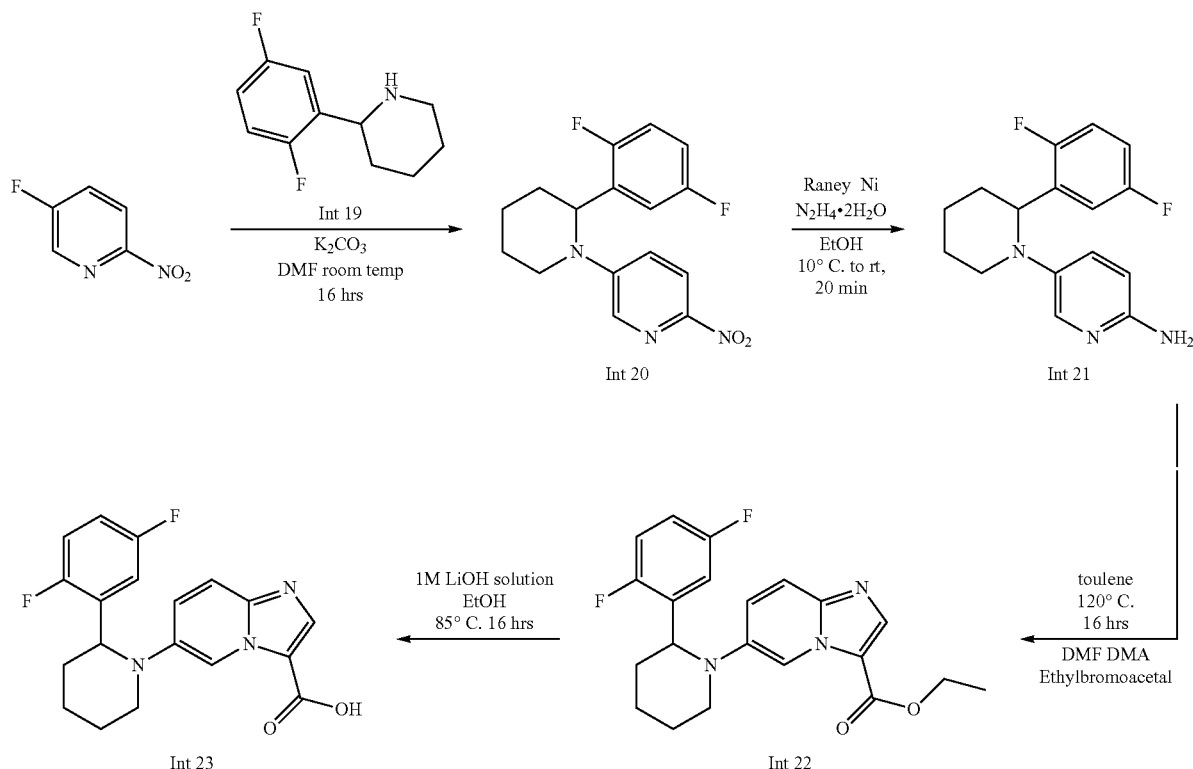 [SMILES: O=[N+]([O-])c1ccc(F)cn1 ; Fc1ccc(F)c(C2CCCCN2)c1 ; O=[N+]([O-])c1ccc(N2CCCCC2c2cc(F)ccc2F)cn1 ; Nc1ccc(N2CCCCC2c2cc(F)ccc2F)cn1 ; O=C(O)c1cnc2ccc(N3CCCCC3c3cc(F)ccc3F)cn12 ; CCOC(=O)c1cnc2ccc(N3CCCCC3c3cc(F)ccc3F)cn12]

Int 20: 5-(2-(2,5-difluorophenyl)piperidin-1-yl)-2-nitropyridine

Int-20 was prepared by the method similar to that of Int-11 employing Int-19 to afford 5-(2-(2,5-difluorophenyl)piperidin-1-yl)-2-nitropyridine (2.85 g, 42.5% yield) as yellow solid. MS (ESI): m/z 320.2 (M+H).

Int 21: 5-(2-(2,5-difluorophenyl)piperidin-1-yl)pyridin-2-amine

Int-21 was prepared by the method similar to that of Int-12 employing Int-20 to afford 5-(2-(2,5-difluorophenyl)piperidin-1-yl)pyridin-2-amine (2.6 g, 89.9% yield) as brown liquid. MS (ESI): m/z 290.1 (M+H).

Int 22: ethyl 6-(2-(2,5-difluorophenyl)piperidin-1-yl)imidazo[1,2-a]pyridine-3-carboxylate The title compound was prepared by the method similar to that of Int-13 employing Int-21 to afford ethyl 6-(2-(2,5-difluorophenyl)piperidin-1-yl)imidazo[1,2-a]pyridine-3-carboxylate (1.6 g, 47% yield) as brown liquid. MS (ESI): m/z 386.4 (M+H).

Int 23: 6-(2-(2,5-difluorophenyl)piperidin-1-yl)imidazo[1,2-a]pyridine-3-carboxylic acid The title compound was prepared by the method similar to that of Int-14 employing Int-22 to afford R&S mixture of 6-(2-(2,5-difluorophenyl)piperidin-1-yl)imidazo[1,2-a]pyridine-3-carboxylic acid (0.95 g, 64.1% yield) as off white solid. MS (ESI): m/z 358.25 (M+H).

Synthesis of 2-(7-fluoro-2,3-dihydrobenzo[b][1,4]dioxin-5-yl)pyrrolidine (Int-31)

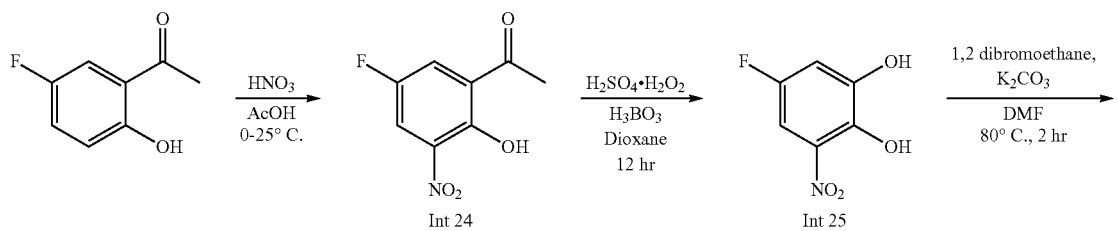

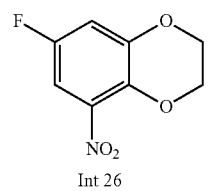
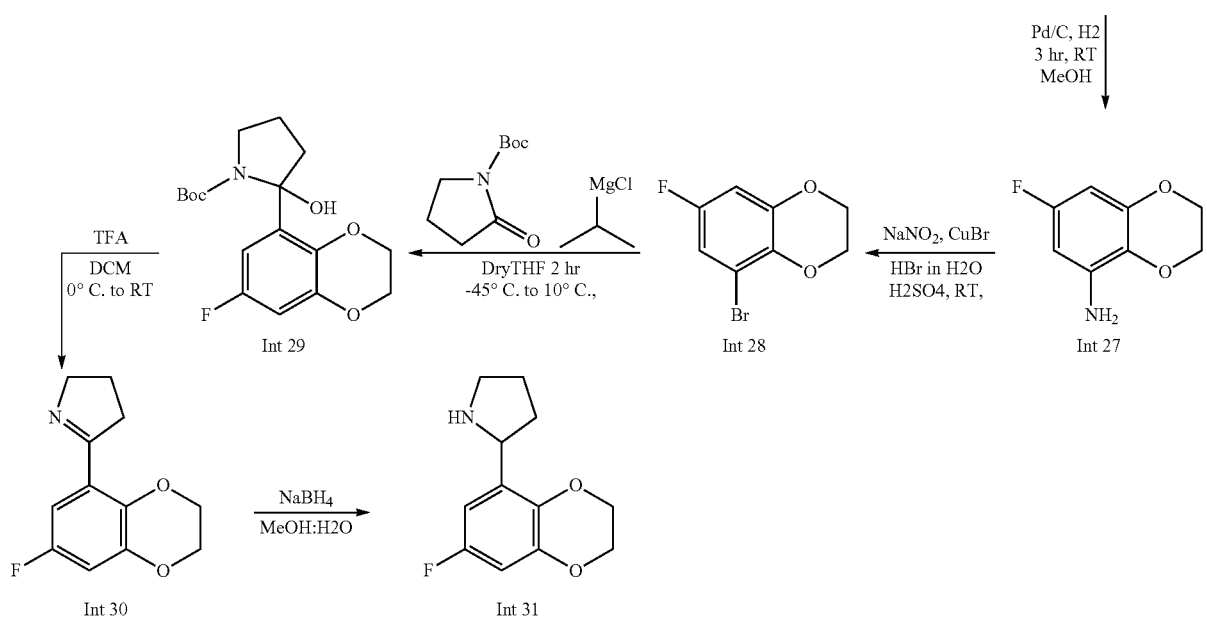

Int-24:
1-(5-Fluoro-2-hydroxy-3-nitrophenyl)ethanone

Conc. HNO$_3$ (22.49 g, 357 mmol) was added to a solution 1-(5-fluoro-2-hydroxyphenyl)ethanone (50 g, 325 mmol) in acetic acid (300 mL) at 0° C. and stirring was continued at 20° C. for 3 h. The reaction mixture was quenched with ice cold water. The separated solid was filtered and washed with cold water and dried to afford 1-(5-fluoro-2-hydroxy-3-nitrophenyl)ethanone (Int-19) (65 g, 98.48% yield) as pale yellow solid. $^1$H NMR (400 MHz, DMSO-d$_6$) δ 12.6 (1H, s), 8.3-8.2 (1H, dd), 8.2-8.1 (1H, dd), 2.7 (3H, s) ppm.

Int-25: 5-Fluoro-3-nitrobenzene-1,2-diol

H$_2$SO$_4$ (50 mL) was added to a solution of H$_3$BO$_3$ (89.3 g, 1.4 mol) in 1,4-Dioxane (300 mL) at 0° C. and stirred at 28° C. for 1 h. 1-(5-fluoro-2-hydroxy-3-nitrophenyl)ethanone (50 g, 289 mmol) was added portion wise to the above solution over 1 h, maintaining the temperature at 0° C., after addition was complete, the reaction mixture was warmed to 25° C. and stirred for 16 h. Reaction mixture was quenched with cold water, solid separated was collected by filtration. The solid was suspended in diethyl ether (500 mL) and filtered to remove insoluble inorganic mass, ether layer was washed with cold water (2 to 3 times) followed by brine, dried over anhydrous sodium sulphate and concentrated under reduced pressure to afford the crude sticky solid. The crude solid was triturated over n-Hexane and filtered to afford 5-fluoro-3-nitrobenzene-1,2-diol (Int-25) (36 g, 86% yield) as pale yellow solid. MS (ESI): m/z 171.9 (M−1).

Int-26:
7-Fluoro-5-nitro-2,3-dihydrobenzo[b][1,4]dioxine

K$_2$CO$_3$ (15.27 g, 110.6 mmol) was added to a solution of 5-fluoro-3-nitrobenzene-1,2-diol (5 g, 28.9 mmol) in DMF (35 mL) followed by the addition of 1,2-Dibromoethane (13.63 g, 6.25 mL, 72.5 mmol) and stirring was continued at 80° C. for 2 h. Reaction mixture was diluted with ethyl acetate, washed with cold water, dried over anhydrous sodium sulphate and concentrated under reduced pressure to afford the crude, which was purified by MPLC (silica gel, Mobile Phase: ethyl acetate in n-Hexane 0 to 5% as eluant) to afford 7-fluoro-5-nitro-2,3-dihydrobenzo[b][1,4]dioxine (Int-26) (5.7 g, 85% yield) as pale yellow solid. $^1$H NMR (300 MHz, CDCl$_3$) δ 7.3-7.2 (1H, dd), 6.9-6.8 (1H, dd), 4.4 (4H, s) ppm.

Int-27:
7-Fluoro-2,3-dihydrobenzo[b][1,4]dioxin-5-amine

10% Pd/C (400 mg) was added to a solution of 7-fluoro-5-nitro-2,3-dihydrobenzo[b][1,4]dioxine (2.0 g, 10 mmol) in methanol (50 mL) and stirring was continued at 25° C. under H$_2$ atmosphere for 3 h. The reaction mixture was filtered over celite bed and washed with methanol. The filtrate and the washings were concentrated under reduced pressure to afford 7-fluoro-2,3-dihydrobenzo[b][1,4]dioxin-5-amine (Int-27) (1.6 g, 94% yield) as pale brown liquid. MS (ESI): m/z 170.1 (M+H).

Int-28:
5-Bromo-7-fluoro-2,3-dihydrobenzo[b][1,4]dioxine

NaNO$_2$ (2.69 g, 39.9 mmol) in water (20 mL) was added slowly at 0° C. to a solution of 7-fluoro-2,3-dihydrobenzo[b]

[1,4]dioxin-5-amine (4.5 g, 26 mmol) in aq. 47% HBr (20 mL) and continued stirring at same temperature for 30 min. The above diazonium salt solution was added slowly to a solution of CuBr (5.7 g, 39.9 mmol) in aq. 47% HBr (25 mL) at 0° C. and stirred at 25° C. for 30 min. Reaction mixture was quenched with ice water, extracted with ethyl acetate (3×50 mL), washed it with water followed by brine, dried over anhydrous sodium sulphate and concentrated under reduced pressure to afford crude. The crude was purified by column purification (using silica gel and 0-5% ethyl acetate in Hexane as eluent) to afford 5-bromo-7-fluoro-2,3-dihydrobenzo[b][1,4]dioxine (Int-28) (5.9 g). $^1$H NMR (300 MHz, CDCl$_3$) δ 6.9-6.84 (1H, dd), 6.6-6.5 (1H, dd), 4.3-4.3 (4H, m) ppm.

Int-29: Tert-butyl-2-(7-fluoro-2,3-dihydrobenzo[b][1,4]dioxin-5-yl)-2-hydroxypyrrolidine-1-carboxylate A solution of isopropyl magnesium chloride in Dry THF (2M, 5.39 mL, 10.78 mmol) was added to a solution of 5-bromo-7-fluoro-2,3-dihydrobenzo[b][1,4]dioxine (1 g, 4.31 mmol) in THF (10 mL) at −45° C. drop-wise and then allowed it to warm up to 5° C. over a period of 1 h. The reaction mixture was cooled again to −45° C. and a solution of tert-butyl 2-oxopyrrolidine-1-carboxylate (1.6 g, 8.62 mmol) in THF (10 mL) was added drop-wise maintaining the temperature at −45° C. The reaction mixture was warmed to 25° C. and stirred for 1 h and then quenched with saturated NH$_4$Cl solution (100 mL). The reaction mixture was extracted with ethyl acetate (3×30 mL) and the organic layer was dried over anhydrous sodium sulphate and concentrated under reduced pressure and purified by column chromatography (using silica gel and 20% ethyl acetate Hexane as eluent) to afford tert-butyl 5-(7-fluoro-2,3-dihydrobenzo[b][1,4]dioxin-5-yl)-2,3-dihydro-1H-pyrrole-1-carboxylate (Int-29) (0.9 g, 61% yield). MS (ESI): m/z 340 (M+H).

Int-30: 5-(7-Fluoro-2,3-dihydrobenzo[b][1,4]dioxin-5-yl)-3,4-dihydro-2H-pyrrole

TFA (0.09 mL, 1.18 mmol) was added to a solution of tert-butyl 5-(7-fluoro-2,3-dihydrobenzo[b][1,4]dioxin-5-yl)-2,3-dihydro-1H-pyrrole-1-carboxylate (0.04 g, 0.117 mmol) in DCM (5 mL) at 0° C. and stirring was continued at 25° C. for 3 h. Reaction mixture was concentrated under reduced pressure to afford the crude, which was diluted with ethyl acetate, washed with saturated NaHCO$_3$ solution, dried over anhydrous sodium sulphate to afford 5-(7-fluoro-2,3-dihydrobenzo[b][1,4]dioxin-5-yl)-3,4-dihydro-2H-pyrrole (Int-30) (0.02 g, 71% yield). MS (ESI): m/z 222 (M+H).

Int-31: 2-(7-Fluoro-2,3-dihydrobenzo[b][1,4]dioxin-5-yl)pyrrolidine

NaBH$_4$ (0.25 g, 6.69 mmol) was added to a solution of 5-(7-fluoro-2,3-dihydrobenzo[b][1,4]dioxin-5-yl)-3,4-dihydro-2H-pyrrole (0.8 g, 3.34 mmol) in a mixture of MeOH and H$_2$O (3:1, 20 mL) and was stirred at 25° C. for 2 h. Reaction mixture was quenched with 1N aqueous HCl solution (50 mL) and basified with 2N aqueous NaOH solution to pH 8 and extracted with DCM (3×20 mL). The organic layer was dried over anhydrous sodium sulphate and concentrated under reduced pressure to afford 2-(7-fluoro-2,3-dihydrobenzo[b][1,4]dioxin-5-yl)pyrrolidine (Int-31). (0.7 g, 94% yield). MS (ESI): m/z 224.5 (M+H).
Above enantiomeric mixture was directly use for next step without any separation.

Synthesis of: 2-(7-fluoro-2,3-dihydrobenzo[b][1,4]dioxin-5-yl)piperidine (Int 34)

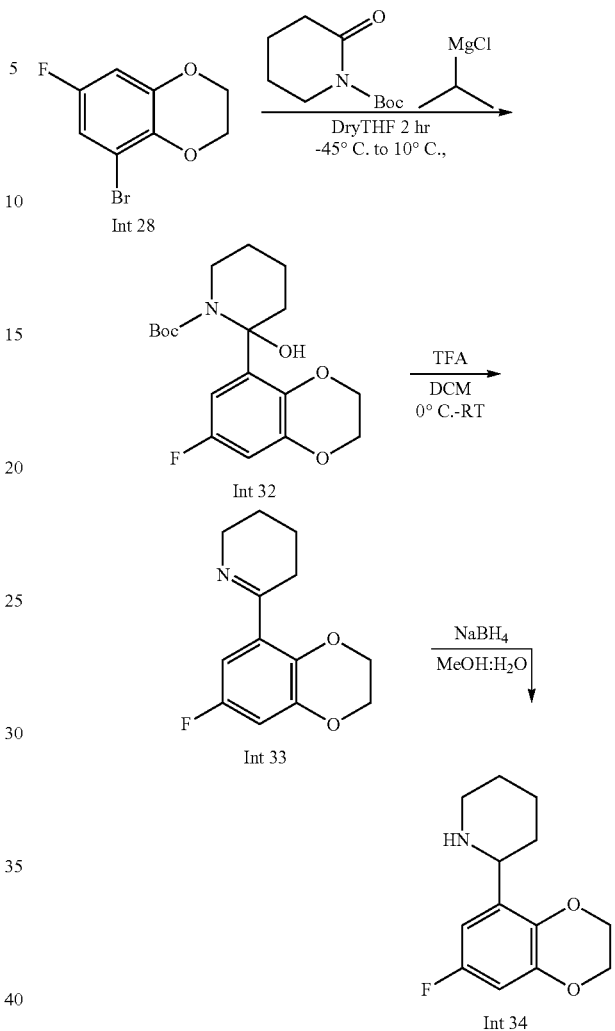

Int-32: tert-butyl 2-(7-fluoro-2,3-dihydrobenzo[b][1,4]dioxin-5-yl)-2-hydroxypiperidine-1-carboxylate The title compound (Int-32) was prepared by the method similar to that of Int-29 employing tert-butyl 2-oxopiperidine-1-carboxylate and Int-28 to afford tert-butyl 2-(7-fluoro-2,3-dihydrobenzo[b][1,4]dioxin-5-yl)-2-hydroxypiperidine-1-carboxylate (5.0 g, 65.78% yield) as brown color liquid. MS (ESI): m/z 354.2 (M+H).

Int-33: 6-(7-fluoro-2,3-dihydrobenzo[b][1,4]dioxin-5-yl)-2,3,4,5-tetrahydropyridine The title compound (Int-33) was prepared by the method similar to that of Int-30 employing Int-32 to afford 6-(7-fluoro-2,3-dihydrobenzo[b][1,4]dioxin-5-yl)-2,3,4,5-tetrahydropyridine (Int-33) (3.1 g, 92.53% yield). MS (ESI): m/z 236.2 (M+H).

Int-34: 2-(7-fluoro-2,3-dihydrobenzo[b][1,4]dioxin-5-yl)piperidine

The title compound (Int-34) was prepared by the method similar to that of Int-31 employing Int-33 to afford 2-(7-fluoro-2,3-dihydrobenzo[b][1,4]dioxin-5-yl)piperidine (2.0 g, 64.12% yield) as brown color liquid. MS (ESI): m/z 238.2 (M+H).

Synthesis of 6-(2-(7-fluoro-2,3-dihydrobenzo[b][1,4]dioxin-5-yl)pyrrolidin-1-yl)imidazo[1,2-a]pyridine-3-carboxylic acid (Int 38)

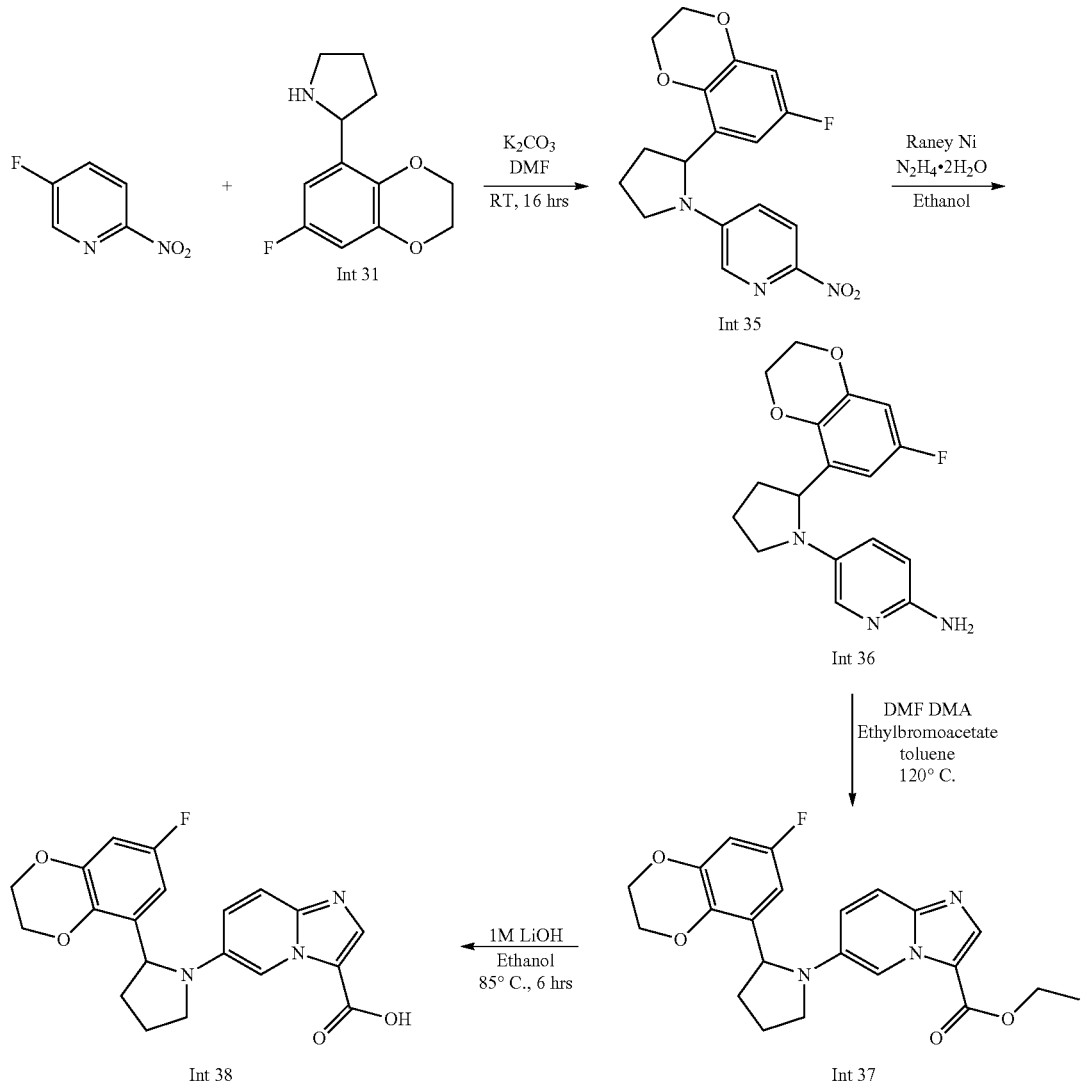

Int 35: 5-(2-(7-fluoro-2,3-dihydrobenzo[b][1,4]dioxin-5-yl)pyrrolidin-1-yl)-2-nitropyridine The title compound (Int-35) was prepared by the method similar to that of Int-11 employing Int-31 to afford 5-(2-(7-fluoro-2,3-dihydrobenzo[b][1,4]dioxin-5-yl)pyrrolidin-1-yl)-2-nitropyridine (Int 35) (3.1 g, 98.4% yield) as yellow solid. MS (ESI): m/z 346.1 (M+H).

Int 36: 5-(2-(7-fluoro-2,3-dihydrobenzo[b][1,4]dioxin-5-yl)pyrrolidin-1-yl)pyridin-2-amine The title compound (Int-36) was prepared by the method similar to that of Int-12 employing Int-35 to afford (2.6 g, 90.2% yield) as brown color liquid. MS (ESI): m/z 316.4 (M+H).

Int 37: ethyl 6-(2-(7-fluoro-2,3-dihydrobenzo[b][1,4]dioxin-5-yl)pyrrolidin-1-yl)imidazo[1,2-a]pyridine-3-carboxylate The title compound (Int-37) was prepared by the method similar to that of Int-13 employing Int-36 to afford ethyl 6-(2-(7-fluoro-2,3-dihydrobenzo[b][1,4]dioxin-5-yl)pyrrolidin-1-yl)imidazo[1,2-a]pyridine-3-carboxylate (1.6 g, 42.3% yield) as brown solid. MS (ESI): m/z 412.2 (M+H).

Int 38: 6-(2-(7-fluoro-2,3-dihydrobenzo[b][1,4]dioxin-5-yl)pyrrolidin-1-yl)imidazo[1,2-a]pyridine-3-carboxylic acid The title compound (Int-38) was prepared by the method similar to that of Int-14 employing Int-37 to afford (1.0 g, 67.1% yield) as off white solid. MS (ESI): m/z 384.25 (M+H).

Synthesis of 6-(2-(7-fluoro-2,3-dihydrobenzo[b][1,4]dioxin-5-yl)piperidin-1-yl)imidazo[1,2-a]pyridine-3-carboxylic acid (Int 42)

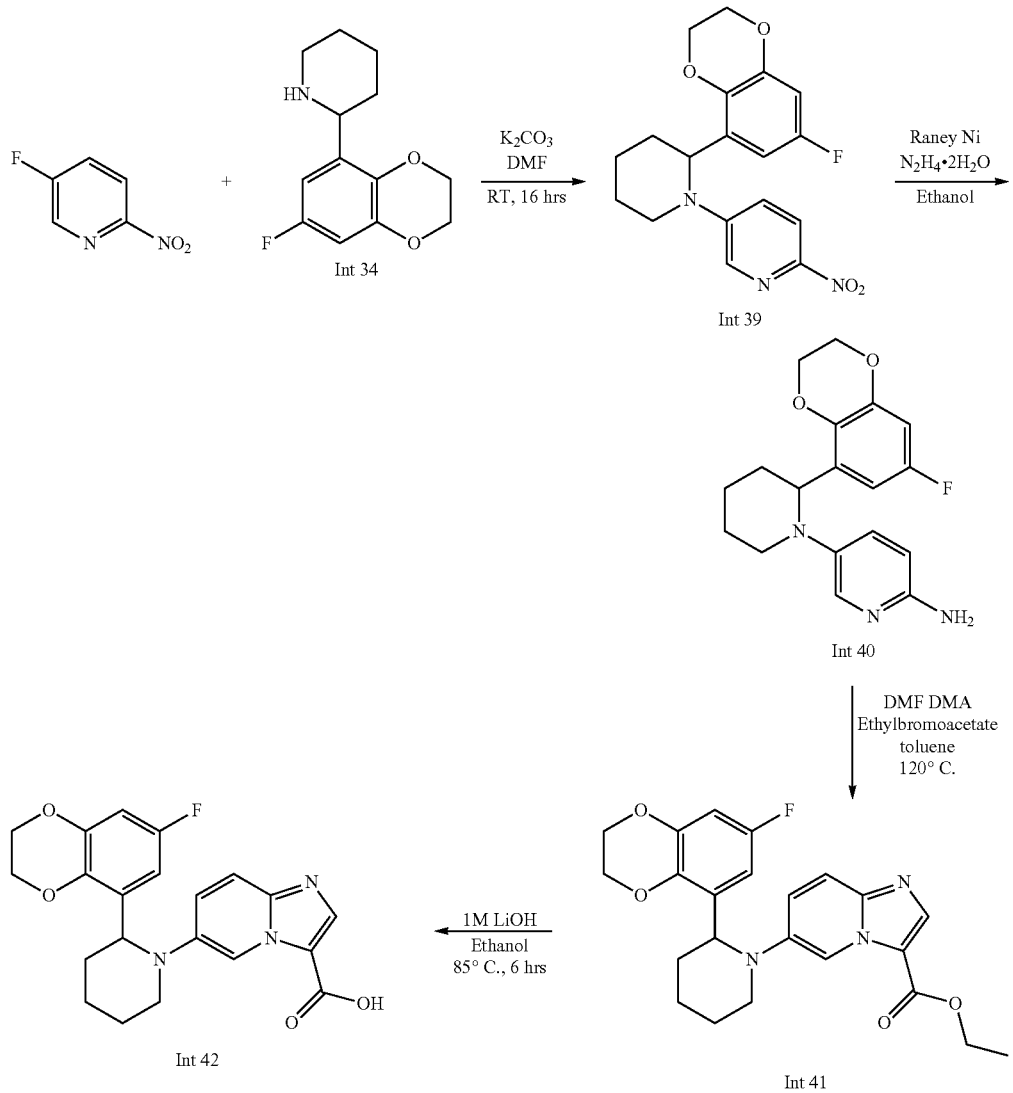

Int 39: 5-(2-(7-fluoro-2,3-dihydrobenzo[b][1,4]dioxin-5-yl)piperidin-1-yl)-2-nitropyridine The title compound (Int-39) was prepared by the method similar to that of Int-11 employing Int-34 to afford 5-(2-(7-fluoro-2,3-dihydrobenzo[b][1,4]dioxin-5-yl)piperidin-1-yl)-2-nitropyridine (Int 39) (1.9 g, 97.4% yield) as yellow solid. MS (ESI): m/z 360.5 (M+H).

Int 40: 5-(2-(7-fluoro-2,3-dihydrobenzo[b][1,4]dioxin-5-yl)piperidin-1-yl)pyridin-2-amine The title compound (Int-40) was prepared by the method similar to that of Int-12 employing Int-39 to afford 5-(2-(7-fluoro-2,3-dihydrobenzo[b][1,4]dioxin-5-yl)piperidin-1-yl)pyridin-2-amine (Int 40) (1.0 g, 58.8% yield) as brown color liquid. MS (ESI): m/z 330.1 (M+H).

Int 41: ethyl 6-(2-(7-fluoro-2,3-dihydrobenzo[b][1,4]dioxin-5-yl)piperidin-1-yl)imidazo[1,2-a]pyridine-3-carboxylate The title compound (Int-41) was prepared by the method similar to that of Int-13 employing Int-40 to afford ethyl 6-(2-(7-fluoro-2,3-dihydrobenzo[b][1,4]dioxin-5-yl)piperidin-1-yl)imidazo[1,2-a]pyridine-3-carboxylate (Int 41) (0.7 g, 54.2% yield) as brown solid. MS (ESI): m/z 426.15 (M+H).

Int 42: 6-(2-(7-fluoro-2,3-dihydrobenzo[b][1,4]dioxin-5-yl)piperidin-1-yl)imidazo[1,2-a]pyridine-3-carboxylic acid The title compound (Int-42) was prepared by the method similar to that of Int-14 employing Int-41 to afford 6-(2-(7-fluoro-2,3-dihydrobenzo[b][1,4]dioxin- 5-yl)piperidin-1-yl)

imidazo[1,2-a]pyridine-3-carboxylic acid (Int 42) (0.48 g, 73.5% yield) as off white solid. MS (ESI): m/z 398.1 (M+H).

Synthesis of tert-butyl 3-hydroxyazetidine-1-carboxylate (Int 43)

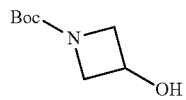

Cold aqueous NaOH (3.65 g, 91.25 mmol in 25 mL of water) was added to cold (0° C.) solution of azetidin-3-ol hydrochloride (4 g, 36.5 mmol) in water (15 mL) followed by addition of di-tert-butyl dicarbonate (8.4 mL, 38.33 mmol). The reaction mixture was stirred continuously at 20-35° C. for 12-14 h. The reaction mixture was diluted with ethyl acetate, the organic layer was separated, washed with water followed by brine solution, dried over anhydrous sodium sulphate and concentrated under reduce pressure to afford the crude compound, which was purified by column chromatography (using 60-120 silica gel and 30% EtOAc in Hexane as eluent) to afford 3.5 g of the title compound. $^1$H NMR (400 MHz, DMSO-$d_6$) δ 5.6 (1H, s), 4.4 (1H, bs), 4.0 (2H, t), 3.6-3.5 (2H, m), 1.4 (9H, s) ppm.

Synthesis of tert-butyl 3-oxoazetidine-1-carboxylate (Int 44)

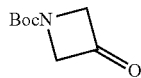

PCC (4.94 g, 22.8 mmol) was added portion wise to a stirred solution of tert-butyl-3-hydroxyazetidine-1-carboxylate (3.3 g, 19 mmol) in DCM (50 mL) at 20-35° C. and the reaction mixture was stirred continuously at the same temperature for 12-16 h. The reaction mixture was filtered and the filtrate was washed with water, dried over anhydrous sodium sulphate and concentrated under reduced pressure to afford the crude product, which was purified by column chromatography (using 60-120 silica gel and 10% EtOAc in Hexane as eluent) to afford 650 mg of the title compound. $^1$H NMR (400 MHz, DMSO-$d_6$) δ 4.66 (4H, s), 1.4 (9H, s) ppm.

Synthesis of tert-butyl 3-hydroxy-3-methylazetidine-1-carboxylate (Int 45)

Methyl magnesium bromide (3.0M in Diethyl ether) (1.5 mL, 4.5 mmol) was added to cold (−10° C.) solution of tert-butyl 3-oxoazetidine-1-carboxylate (650 mg, 3.8 mmol) in THF (10 mL) and stirring was continued at 20-35° C. for 1 h. After which the reaction mixture was quenched with saturated aqueous NH$_4$Cl solution and extracted with ethylacetate. The organic layer separated was washed with water, dried over anhydrous sodium sulphate and concentrated under reduced pressure to afford the residue. The residue was purified by column chromatography (using 60-120 silica gel and 50% EtOAc in Hexane as eluent) to afford 430 mg of the title compound. $^1$H NMR (400 MHz, DMSO-$d_6$) δ 5.56 (1H, s), 3.7-3.5 (4H, m), 1.4 (9H, s), 1.3 (3H, s) ppm.

Synthesis of 3-methylazetidin-3-ol hydrochloride (Int 46)

4M solution of HCl in EtOAc (3 mL) was added dropwise to a stirred cold (0° C.) solution of tert-butyl 3-hydroxy-3-methylazetidine-1-carboxylate (100 mg, 0.53 mmol) in EtOAc (1 mL) and stirring was continued at 20-35° C. for 2 h. The reaction mixture was concentrated under reduced pressure to afford 80 mg (crude), which was taken to the next step without purification.

Synthesis of Butylcyclopropanesulfonate (Int-47)

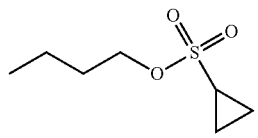

Cyclopropyl sulfonyl chloride (2 g, 14.2 mmol) was added drop-wise at 0° C. to a solution of Butylalcohol (2.1 g, 28.4 mmol) and Pyridine (2.35 g, 29.8 mmol) in DCM (20 mL) and continued stirring at 25° C. for 16 h. The reaction mixture was diluted with DCM (100 mL), washed with 1N aq.HCl solution followed by water and brine Organic layer collected was dried over anhydrous sodium sulphate and concentrated under reduced pressure to afford the Benzyl cyclopropanesulfonate (1.8 g, 72% yield). $^1$H NMR (300 MHz, CD$_3$OD) δ 4.3-4.1 (2H, t), 2.7-2.6 (1H, m), 1.8-1.6 (2H, m), 1.6-1.4 (2H, m), 1.2-1.1 (4H, m), 1.0-0.9 (3H, t) ppm.

Synthesis of Butyl 1-methylcyclopropane-1-sulfonate (Int-48)

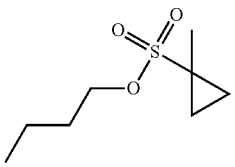

n-BuLi (0.78 g, 12.25 mmol) was added drop-wise at −78° C. to a solution of Butylcyclopropane sulfonate (2.0 g, 11.2 mmol) in THF (20 mL) and continued stirring at the same temperature for 10 min. CH$_3$I (3.98 g, 28.0 mmol) was added at −78° C., allowed the reaction to warm to 0° C. with stirring for 30 min. The reaction mixture was quenched with ice cold water, diluted with ethylacetate (100 mL), organic layer collected was dried over anhydrous sodium sulphate and concentrated under reduced pressure to afford the crude. The crude was purified by column chromatography (using silica gel and 4% ethyl acetate in Hexane as eluent) to afford benzyl 1-methylcyclopropane-1-sulfonate (Int-48) (2.0 g, 93% yield). $^1$H NMR (300 MHz, CD$_3$OD) δ 4.2-4.1 (2H, t), 1.7-1.6 (2H, m), 1.4 (3H, s), 1.5-1.3 (2H, m), 1.3-1.2 (2H, m), 1.0-0.9 (2H, m), 0.9 (3H, t) ppm.

Synthesis of Potassium 1-methylcyclopropane-1-sulfonate (Int-49)

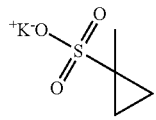

KSCN (2.48 g, 25.5 mmol) was added to a solution of Benzyl 1-methylcyclopropane-1-sulfonate (4.9 g, 25.5 mmol) in DME/H$_2$O (1:1, 120 mL) and continued stirring at 100° C. for 16 h. Reaction mixture was concentrated under reduced pressure and the residue was washed with n-pentane and dried to afford potassium 1-methylcyclopropane-1-sulfonate (Int-49) (4.44 g, 100% yield) which was used in the next step without further purification.

Synthesis of 1-Methylcyclopropane-1-sulfonamide (Int-50)

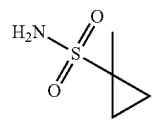

To a solution of potassium 1-methylcyclopropane-1-sulfonate (4.44 g, 25.5 mmol) in THF (50 mL) at 0° C. was added POCl$_3$ (11.7 g, 76.5 mmol) with stirring, maintaining the same temperature for 30 min. DIPEA (9.8 g, 76.5 mmol) was added to above mixture and continued stirring at 25° C. for 2 h. Reaction mixture was quenched with ice cold water, extracted into diethyl ether (3×100 mL), dried over anhydrous sodium sulphate to afford 1-methylcyclopropane-1-sulfonylchloride in diethyl ether. The above dried ethereal solution of 1-methylcyclopropane-1-sulfonylchloride was cooled to −78° C. and purged in with NH$_3$ gas for 30 min. and slowly allowed the reaction mixture to warm to 25° C. with stirring for 16 h. Reaction mixture was filtered through celite bed and the filtrate was concentrated under reduced pressure and the crude thus obtained was washed with n-pentane to afford 1-methylcyclopropane-1-sulfonamide (Int-50) (2.68 g, 77.9% yield) as pale brown solid. $^1$H NMR (300 MHz, DMSO-d$_6$) δ 6.7 (2H, s), 1.4 (3H, s), 1.1-1.0 (2H, m) 0.7-0.6 (2H, m) ppm.

Synthesis of 4-(3-hydroxypyrrolidin-1-yl)benzene sulfonamide (Int-51)

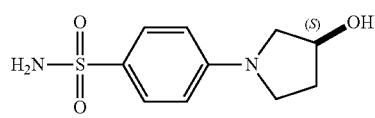

A solution of 4-fluorobenzene sulfonamide (0.39 g, 2.22 mmol) and S(−)-3-hydroxypyrrolidine (0.32 g, 2.67 mmol) in DMSO (2 mL) was heated to 100° C. for 20 h. Reaction was cooled to 25° C. and quenched with cold water. The separated solid was filtered and washed with water and dried to afford 4-(3-hydroxypyrrolidin-1-yl)benzene sulfonamide (Int-51) (0.4 g, 74% yield) as a white solid. MS (ESI): m/z 243.1 (M+H).

The intermediates Int-52 to Int-54 are synthesized following the procedure as mentioned in Int-51 using the appropriate aryl halides and amines.

| Intermediate | Structure | MS (ESI): (M + H) |
|---|---|---|
| Int-52 | ![structure] | m/z 244 |
| Int-53 | ![structure] | m/z 226 |
| Int-54 | ![structure] | m/z 225.1 |

Synthesis of N-Ethyl-N-methyl sulfamide (Int-55)

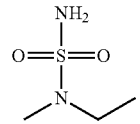

N-Ethyl-N-methyl amine (2.95 g, 50 mmol) was added to a solution of Sulfamide (4 g, 41.6 mmol) in 1,4-Dioxane (40 mL) and continued stirring at 110° C. for 16 h. Reaction mass was concentrated under reduced pressure to afford the crude, which was purified by column purification (using neutral alumina and 10-70% ethyl acetate in Hexane as eluent) to afford N-Ethyl-N-methyl sulfamide (Int-55) (1.2 g, 20.87% yield) as pale yellow oil. $^1$H NMR (300 MHz, DMSO-d$_6$) δ 6.7 (2H, s), 3.1-2.3 (2H, m), 2.6 (3H, s), 1.2-1.0 (3H, t) ppm.

Following intermediates Int-55 and Int-61 were made using above method except changing the amine

| Intermediate No. & Structure | MS (ESI) (M + H) |
|---|---|
| 56 | m/z 153.07 |

| Intermediate No. & Structure | MS (ESI) (M + H) |
|---|---|
| 57 — NH₂-S(=O)(=O)-N(CH₃)-CH₂CH₂F | m/z 157.2 |
| 58 — NH₂-S(=O)(=O)-N(CH₃)-CH₂CH₂OCH₃ | m/z 169.1 |
| 59 — NH₂-S(=O)(=O)-N(Et)-CH₂CH₂F | m/z 171.2 |
| 60 — NH₂-S(=O)(=O)-N(CH₃)-CH₂CF₃ | m/z 193.2 |
| 61 — NH₂-S(=O)(=O)-N(CH₃)-CH₂C(CH₃)₂F | m/z 185.2 |

Synthesis of N-methyl-N-(pyridin-2-yl)sulfamide (Int 63)

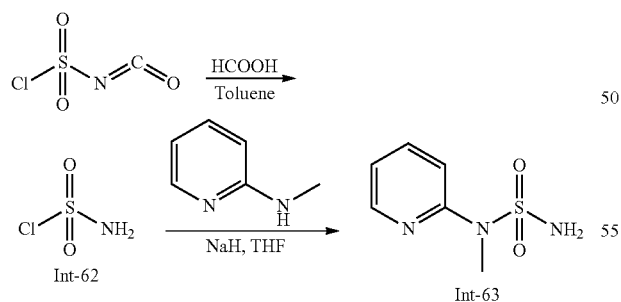

Int-62: Sulfamoyl chloride

Anhydrous formic acid (0.76 mL, 20.0 mmol) was added to chlorosulfonyl isocyanate (1.74 mL, 20.0 mmol) at ice cold condition. The solution solidified halfway through the addition of the formic acid. After complete addition reaction mass was brought to RT and added anhydrous toluene 5 ml. The resulting white light emulsion was kept stirring overnight and the toluene removed by vacuum pump to give a white color crystal of sulfamoyl chloride (2.05 g, 88%). ¹H NMR (300 MHz, CDCl₃) δ 6.1 (2H, bs) ppm.

Int-63: N-methyl-N-(pyridin-2-yl)sulfamide

To a stirred solution of NaH (60%) (0.112 g, 2.78 mmol) in THF (6 ml), N-methylpyridin-2-amine (prepared by N-methylation of 2-aminopyridine) (0.3 g, 2.78 mmol) in THF (2 ml) was added and stirred for 1 h. To this a solution of Sulfamoyl chloride (0.32 g, 2.78 mmol) in THF (1 ml) was added and stirred for 2 h at RT. Reaction mass was quenched with methanol (0.6 ml) at ice cold condition and concentrated to dryness to get crude which was purified using neutral alumina column, eluent ethyl acetate in n-Hexane 0 to 85% to afford N-methyl-N-(pyridin-2-yl)sulfamide as off white solid (0.12 g, 23% yield)

¹H NMR (600 MHz, DMSO-d₆): δ 7.98-7.97 (1H, t), 7.37-7.34 (1H, m), 6.47-6.41 (3H, m), 2.75-2.74 (3H, s).

Following intermediates Int-64 and Int-67 were made using method described above by changing the amine in 2$^{nd}$ step.

| S.N. | Structure | ¹H NMR |
|---|---|---|
| Int-64 | 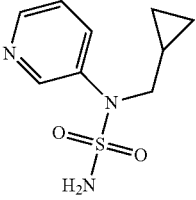 | ¹H NMR (300 MHz, DMSO-d₆): δ 8.8 (1H, s), 8.43-8.35 (2H, m), 7.54 (2H, s), 3.25 (3H, s) ppm. |
| Int-65 | 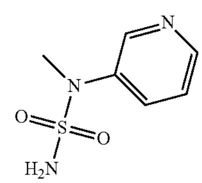 | ¹H NMR (300 MHz, DMSO-d₆): δ 8.56-8.55 (1H, d, J = 2.1 Hz), 8.43-8.42 (1H, d, J = 4.8 Hz), 7.77-7.74 (1H, m), 7.44-7.40 (1H, m), 7.19 (2H, bs), 3.15 (3H, s) ppm. |
| Int-66 | 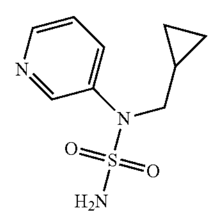 [SMILES: NS(=O)(=O)N(CC1CC1)c1cccnc1] | ¹H NMR (300 MHz, DMSO-d₆): δ 8.56-8.54 (1H, d, J = 2.1 Hz), 8.48-8.47 (1H, t), 7.82-7.78 (1H, m), 7.46-7.42 (1H, m), 7.12 (2H, bs), 3.44-3.42 (2H, m), 0.82 (1H, m), 0.37-0.33 (2H, m), 0.12 (2H, m). |
| Int-67 | 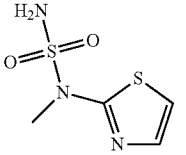 | ¹H NMR (300 MHz, CDCl₃): δ 7.44-7.42 (1H, d, J = 3.6), 7.02 (1H, m), 5.51 (2H, bs), 3.47 (3H, s) ppm. |

Synthesis of (2R,4S)-4-fluoro-2-(5-fluoro-2-((tetrahydrofuran-3-yl)oxy)phenyl)pyrrolidine hydrochloride (Int 80)
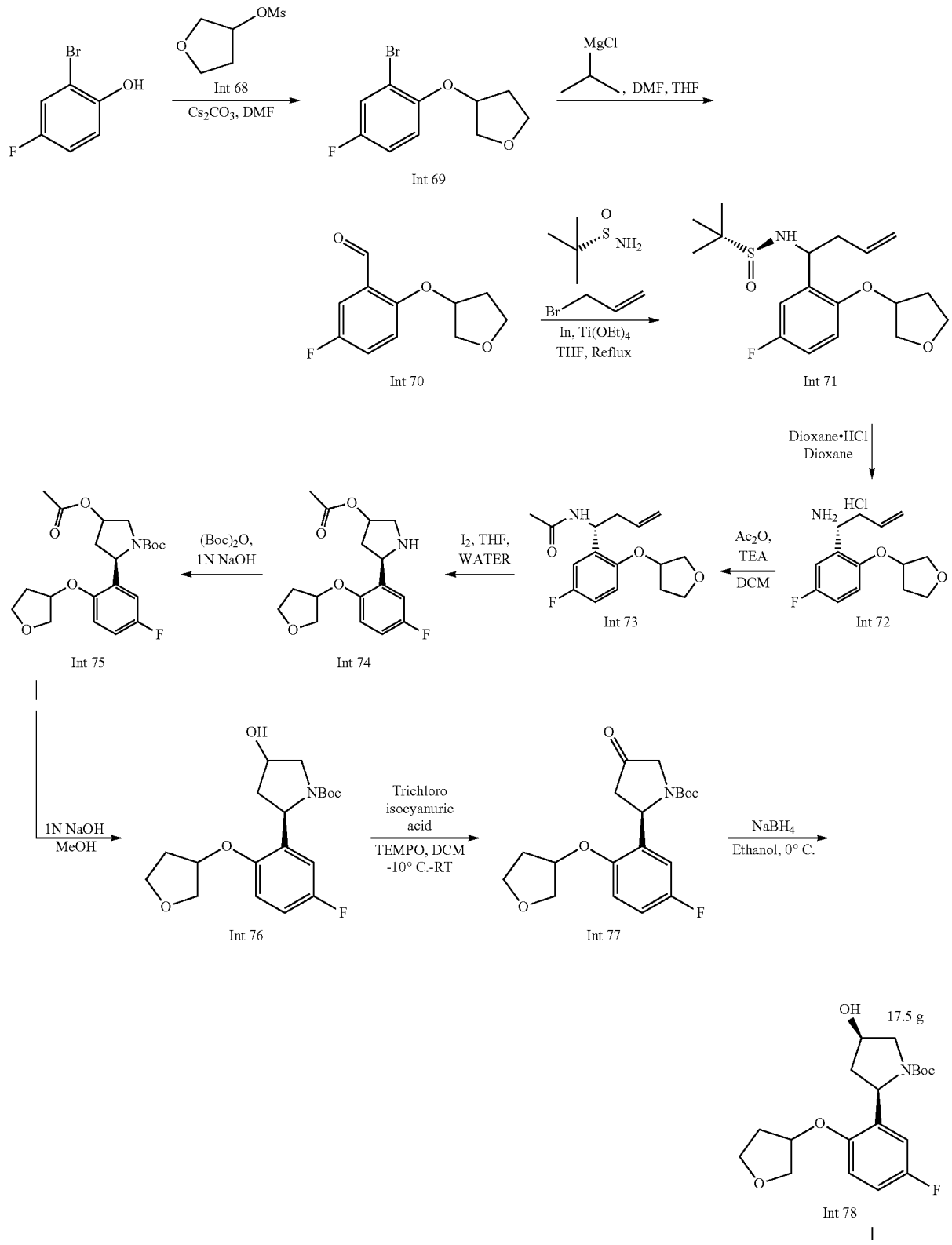

-continued

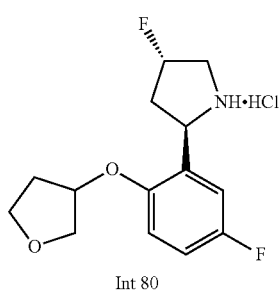  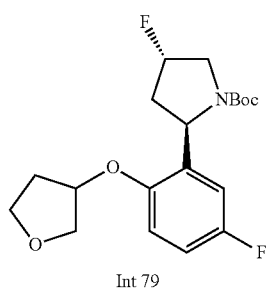

Int 80 ← Dioxane·HCl — Int 79 ← DAST DCM

Int-68: (S)-tetrahydrofuran-3-yl methanesulfonate

A solution of tetrahydrofuran-3-ol (25.0 g, 283 mmol) in 150 ml of DCM was cooled to 0° C., to this was added triethylamine (59 ml, 425 mmol) and mesylchloride (26.0 ml, 340 mmol), stirred the reaction mixture for 4 h at room temperature. TLC indicated reaction completion, it was diluted with DCM (100 ml), washed with water and brine solution, dried over anhydrous sodium sulfate, organic layer was evaporated to yields (44.0 g) of title product which was used as such for the next step.

Int-68a, Int-68b were synthesized by following procedure substantially similar to that of Int-68.

| S.N. | Structure | MS (ESI) (M + H) or $^1$H NMR |
|---|---|---|
| Int-68a | 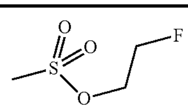 | $^1$H NMR (300 MHz, DMSO-$d_6$) δ ppm 4.76-4.74 (1H, m), 4.60-4.58 (1H, m), 4.58-4.39 (2H, m) 3.22 (3H, s) |
| Int-68b | 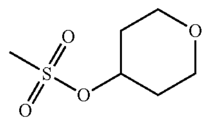 | m/z 181.05 (M + H) |

Int-69: 3-(2-bromo-4-fluorophenoxy)tetrahydrofuran

To a solution of 2-bromo-4-fluorophenol (50.0 g, 261 mmol) in 300 ml of DMF was added $Cs_2CO_3$ (213 g, 654 mmol) and heated the reaction mixture for 3 h at 80° C., after that tetrahydrofuran-3-yl methanesulfonate (Int-68) (43.5 g, 261 mmol) was added at room temperature, stirred the reaction mixture for 16 h at 80° C. filtered the base, filtrate was dissolved with EtOAc (1.2 L), washed with water and 1N NaOH solution (800 ml), water and brine solution, dried over sodium sulfate and concentrated to dryness to afford crude compound. This was purified over 60-120 mesh silica using 10-12% ethyl acetate and hexane as an eluent to get the pure product (50 g, yield 73%). $^1$H NMR (300 MHz, $CDCl_3$) δ 7.32-7.26 (m, 1H), 7.00-6.93 (m, 1H), 6.82-6.77 (m, 1H), 4.91-4.87 (m, 1H), 4.07-3.96 (m, 3H), 3.94-3.89 (m, 1H), 2.20-2.13 (m, 2H).

Int-70: 5-fluoro-2-((tetrahydrofuran-3-yl)oxy)benzaldehyde

To a solution of 3-(2-bromo-4-fluorophenoxy)tetrahydrofuran (50.0 g, 191 mmol) in 400 ml of dry THF at −78° C., isopropyl magnesium chloride (2M in THF) (240 ml, 479 mmol) was added drop wise, stirred the reaction mixture at room temperature for 4 h, again cooled the reaction mixture at −78° C., DMF (22.1 ml, 287 mmol) was added, stirred the reaction mixture at room temperature for 1 h, quenched with $NH_4Cl$ solution (400 ml), diluted with EtOAc (1.0 L), washed with water and brine solution, dried over sodium sulfate and concentrated to dryness to afford the title product 38.0 g (crude).

Int-71: (S)—N—((R)-1-(5-fluoro-2-((tetrahydrofuran-3-yl)oxy)phenyl)but-3-en-1-yl)-2-methylpropane-2-sulfinamide A mixture of Indium powder (27 g, 235 mmol), S-tert-butyl sulfinamide (26.3 g, 216 mmol), 5-fluoro-2-((tetrahydrofuran-3-yl)oxy)benzaldehyde (38.0 g, 181 mmol) and $Ti(OEt)_4$ (61.8 g, 271 mmol) in THF (380 mL) was refluxed for 2 h. Reaction mass was cooled to 0° C. and added 3-bromoprop-1-ene (28.4 g, 235 mmol) slowly for a period of 30 min. Reaction mass was heated to reflux for 16 h, cooled to room temperature and diluted with water (1.0 L), the hazy solution was filtered through celite bed and the solids were washed with ethyl acetate (1.0 L). The filtrate was extracted with ethyl acetate (600 ml). The combined organic phases were washed with water and brine which was dried over $Na_2SO_4$ and concentrated to get the desired product as viscous liquid. This was purified over 60-120 mesh silica using 50-60% ethyl acetate and hexane as an eluent to get the pure product (30 g, yield: 47%). MS (ESI): m/z 356.45 (M+H)

Int-72: (R)-1-(5-fluoro-2-((tetrahydrofuran-3-yl)oxy)phenyl)but-3-en-1-amine hydrochloride To a solution of (S)—N—((R)-1-(5-fluoro-2-((tetrahydrofuran-3-yl)oxy)phenyl)but-3-en-1-yl)-2-methylpropane-2-sulfinamide (30.0 g, 84 mmol) in Dioxane (60 ml) at 0° C. was added 4N solution of HCl in Dioxane (150 ml) and stirred the content for 16 h at room temperature. The solvent was evaporated completely and the crude was washed with diethyl ether to obtain title product 22.0 g (crude) as off white solid. MS m/z 252.05 (M+H).

Int-73: N—((R)-1-(5-fluoro-2-((tetrahydrofuran-3-yl)oxy)phenyl)but-3-en-1-yl)acetamide The above amine (22.0 g 76 mmol) was dissolved in DCM (300 ml), cooled to 0° C. and charged with triethylamine (16 ml, 115 mmol) and then acetic anhydride (8.7 ml, 92 mmol). After stirring for 2 h, the reaction mixture was diluted with DCM (300 ml) and washed successively with saturated aqueous $NaHCO_3$ (100 ml), water and brine, then dried over sodium sulfate and concentrated to dryness to afford N—((R)-1-(5-fluoro-2-((tetrahydrofuran-3-yl)oxy)phenyl) but-3-en-1-yl)acetamide as a crude compound. This was purified over 60-120 mesh silica using 50-60% ethyl acetate and hexane as an elute to get the pure product. 20.0 g (yield: 89%). MS (ESI): m/z: 294.2 (M+H).

Int-74: (5R)-5-(5-fluoro-2-((tetrahydrofuran-3-yl)oxy)phenyl)pyrrolidin-3-yl acetate To a solution of N—((R)-1-(5-fluoro-2-((tetrahydrofuran-3-yl)oxy)phenyl)but-3-en-1-yl)acetamide (20.0 g, 68 mmol) in THF (160 ml) was added water (40 ml) followed by iodine (52 g, 204 mmol). After stirring at room temperature for 16 h, the reaction mixture was poured into a mixture of saturated aqueous $NaHCO_3$ solution (200 mL) and saturated aqueous $Na_2S_2O_3$ solution (150 mL), extracted with EtOAc (2×200 mL), washed successively with saturated aqueous $Na_2S_2O_3$, water and brine, dried over anhydrous sodium sulfate and concentrated to dryness to give (5R)-5-(5-fluoro-2-((tetrahydro-2H-pyran-4-yl)oxy)phenyl)pyrrolidin-3-yl acetate as a pale amber oil, which was used without purification in the next step. MS (ESI): m/z: 310.4 (M+H).

Int-75: (2R)-tert-butyl-4-acetoxy-2-(5-fluoro-2-((tetrahydrofuran-3-yl)oxy)phenyl)pyrrolidine-1-carboxylate To a mixture of (5R)-5-(5-fluoro-2-((tetrahydrofuran-3-yl)oxy)phenyl) pyrrolidin-3-yl acetate (18.0 g, 58 mmol), THF (180 mL) and water (180 mL) was added a solution of di-tert-butyl dicarbonate (15.9 mL, 73 mmol). Added 1 N NaOH (25 ml), after 3 h the reaction mixture was partitioned into water (100 ml) and extracted with ethyl acetate (600 ml), the combined extracts were washed with brine, dried over sodium sulfate and concentrated to dryness to afford the corresponding carbamate yields 23.0 g (crude). MS (ESI): m/z 310.2 (de Boc) (M+H).

Int-76: (2R)-tert-butyl-2-(5-fluoro-2-((tetrahydrofuran-3-yl)oxy)phenyl)-4-hydroxypyrrolidine-1-carboxylate The above carbamate (23.0 g 56 mmol) was dissolved in MeOH (200 mL) and cooled to 0° C., and then charged drop wise with 1 N NaOH (56 mL, 56 mmol). After stirring 4 h at room temperature, solvent was completely evaporated, the reaction mixture was dissolved in ethyl acetate (600 ml), washed with water and brine, dried over anhydrous sodium sulfate and concentrated. The residue was purified by silica chromatography with EtOAc/Hexane (50-60%) as elute, to yield (2R)-tert-butyl 2-(5-fluoro-2-((tetrahydrofuran-3-yl)oxy)phenyl)-4-hydroxypyrrolidine-1-carboxylate 18.0 g (yield: 87%) as white solid. MS (ESI): m/z 368 (M+H).

Int-77: (2R)-tert-butyl-2-(5-fluoro-2-((tetrahydrofuran-3-yl)oxy)phenyl)-4-oxopyrrolidine-1-carboxylate To a solution of (2R)-tert-butyl 2-(5-fluoro-2-((tetrahydrofuran-3-yl)oxy)phenyl)-4-hydroxypyrrolidine-1-carboxylate (18.0 g, 49 mmol) in DCM (150 mL) at −40° C. was added trichloroisocyanuric acid (12.5 g, 54 mmol) followed by 2,2,6,6-tetramethylpiperidino-1-oxy (TEMPO) (0.76 g, 4.9 mmol). After stirring 1 h at −40° C. to −10° C., the reaction mixture was poured into cold saturated aqueous $NaHCO_3$ solution (200 ml), extracted with DCM (400 ml), combined extracts were washed with water and brine solution, dried over anhydrous sodium sulfate and concentrated to dryness to give the corresponding ketone (17.5 g, crude yield 98%) as pale yellow oil, which was used without purification in the next step. MS (ESI): m/z 266.2 (de-Boc), (M+H).

Int-78: (2R,4R)-tert-butyl-2-(5-fluoro-2-((tetrahydrofuran-3-yl)oxy)phenyl)-4-hydroxypyrrolidine-1-carboxylate To a clear solution of Int-77 (17.5 g, 48 mmol) in methanol (150 ml), $NaBH_4$ (2.72 g, 72 mmol) was added portion wise at −20° C. and allowed the reaction mass to warm to 0° C. and the reaction mass was stifled for 30 min at 0° C. The reaction mass was quenched with ice cold water and extracted with EtOAc (500 ml), combined extracts were washed with brine, dried over sodium sulphate and concentrated. The crude was purified over 60-120 silica chromatography using 50-60% EtOAc/Hexane as elute to yield the title product (15.0 g, yield 85%) as white solid. MS (ESI): m/z 268.1 (de-Boc) (M+H).

Int-79: (2R,4S)-tert-butyl 4-fluoro-2-(5-fluoro-2-((tetrahydrofuran-3-yl)oxy)phenyl)pyrrolidine-1-carboxylate To a solution of Int-78 (15.0 g, 40.8 mmol) in DCM (300 mL) in a plastic bottle at −78° C. was added DAST (14.5 g, 89.8 mmol). The mixture was stirred at −78° C. for 2 h and then warmed slowly to room temperature for 16 h. To it was added drop wise aqueous $NaHCO_3$ at 0° C. and was extracted with DCM (450 ml). The combined extracts were washed with brine, dried over sodium sulfate and concentrated. The two diastereomers were separated by 230-400 silica column chromatography using 20% EtOAc/hexane as eluent to yield title product (10.0 g, yield 66%) MS (ESI): m/z: 370.3 (M+H).

Int-80: (2R,4S)-4-fluoro-2-(5-fluoro-2-((tetrahydrofuran-3-yl)oxy)phenyl)pyrrolidine hydrochloride To a cooled solution of above product (10.0 g, 27 mmol) in dioxane (20 ml) at 0° C. was added 4N solution of HCl in Dioxane (50 ml) and stirred the reaction mixture for 2 h at room temperature. The solvent was evaporated completely and the crude was washed with diethyl ether to obtain title product (7.7 g, yield: 93%) as white solid. MS (ESI): m/z: 270.2 (M+H).

Synthesis of 6-((2R,4S)-4-fluoro-2-(5-fluoro-2-(((S)-tetrahydrofuran-3-yl)oxy)phenyl) pyrrolidin-1-yl) imidazo[1,2-a]pyridine-3-carboxylic acid (Int-84)

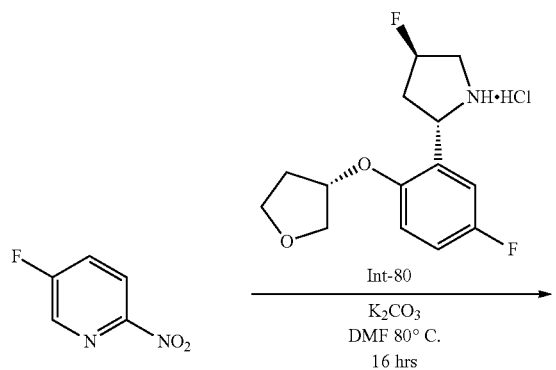
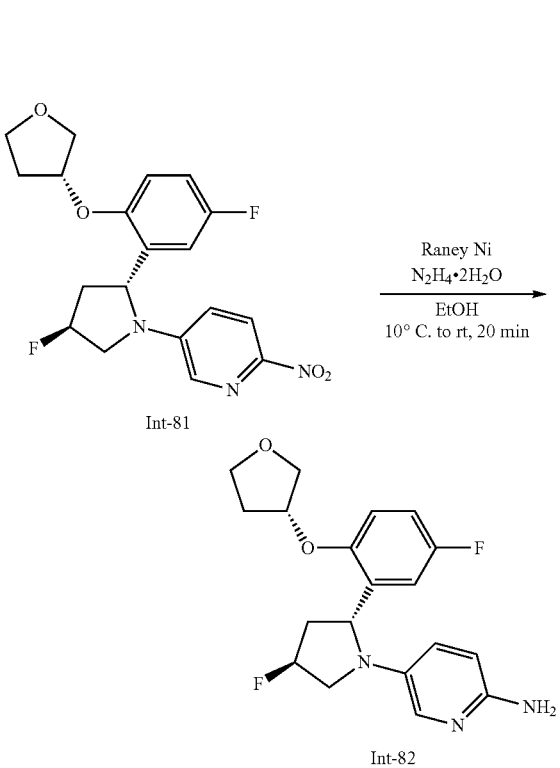
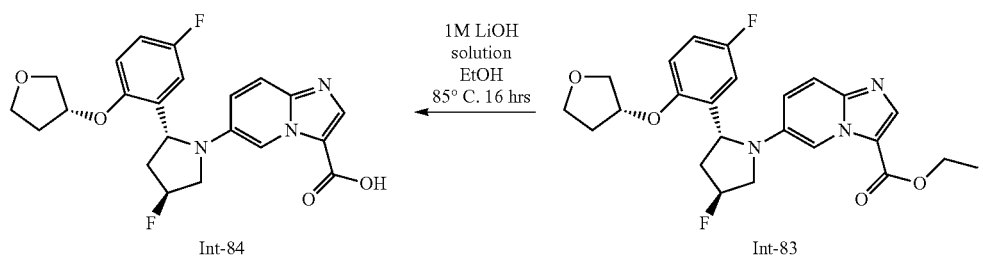
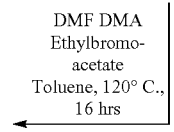

Int-81: 5-((2R,4S)-4-fluoro-2-(5-fluoro-2-(((S)-tetrahydrofuran-3-yl)oxy)phenyl)pyrrolidin-1-yl)-2-nitropyridine To a solution of (2R,4S)-4-fluoro-2-(5-fluoro-2-((tetrahydrofuran-3-yl)oxy)phenyl)pyrrolidine hydrochloride (4.74 g, 15.49 mmol) in dry DMF (20 ml), was added $K_2CO_3$ (4.85 g, 35.2 mmol) and stirred for 5 min at room temperature, then added 5-fluoro-2-nitropyridine (2.0 g, 14.08 mmol) under $N_2$ atmosphere and stirred for 16 h at 80° C. After completion of reaction, poured the reaction mixture in ice cooled water and stirred for 10 min, solid precipitated was collected by filtration. Solid was dried under high vacuum to afford 5-((2R,4S)-4-fluoro-2-(5-fluoro-2-(((S)-tetrahydrofuran-3-yl)oxy)phenyl)pyrrolidin-1-yl)-2-nitropyridine as yellow solid (5.1 g, yield: 93%) MS (ESI): 392.1 (M+H).

Int-82: 5-((2R,4S)-4-fluoro-2-(5-fluoro-2-(((S)-tetrahydrofuran-3-yl)oxy)phenyl)pyrrolidin-1-yl)pyridin-2-amine To a stirred solution of 5-((2R,4S)-4-fluoro-2-(5-fluoro-2-(((S)-tetrahydrofuran-3-yl)oxy)phenyl)pyrrolidin-1-yl)-2-nitropyridine (5.1 g, 3.26 mmol) in ethanol (50 ml) was cooled to 10° C. and added Raney Ni (1.02 g, 20% w/w) portion wise and stirred for 5 min, then added $N_2H_4.2H_2O$ (3 ml) drop wise for the period of 5 min, then stirred for 20 min at room temperature. After completion of reaction, reaction mixture was filter through celite bed under $N_2$ atmosphere and filtrate was concentration under reduced pressure, the residue was re-dissolved in DCM and washed with water, brine and dried over $Na_2SO_4$ and concentration to get desired product as brown solid (4.2 g, yield: 89%), MS (ESI): 362.1 (M+H).

Int-83: Ethyl-6-((2R,4S)-4-fluoro-2-(5-fluoro-2-(((S)-tetrahydrofuran-3-yl)oxy)phenyl) pyrrolidin-1-yl)imidazo[1,2-a]pyridine-3-carboxylate To a stirred solution of 5-((2R,4S)-4-fluoro-2-(5-fluoro-2-(((S)-tetrahydrofuran-3-yl)oxy)phenyl)pyrrolidin-1-yl)pyridin-2-amine (4.2 g, 11.63 mmol) in dry toluene (11 ml) was added DMF-DMA (2.9 g, 24.43 mmol) under N₂ atm and stirred for 2 h at 120° C. during which complete consumption of starting material was observed by TLC, cooled it to 10° C. then added Ethylbromoacetate (4.27 g, 25.59 mmol) drop wise and methanol (4 ml) was added under N₂ atm then stirred for 16 h at 120° C. Reaction mixture was cooled to room temperature and solvent was removed in vacuo and residue was dissolved in DCM (200 ml), washed with water and brine, dried over anhydrous $Na_2SO_4$ and concentrated under vacuum to get crude product. Crude was purified by column chromatography (eluted with 30-40% ethyl acetate/Hexane) to afford pale green solid (1.3 g, yield: 30%), MS (ESI): 458.2 (M+H)

Int-84: 6-((2R,4S)-4-fluoro-2-(5-fluoro-2-(((S)-tetrahydrofuran-3-yl)oxy)phenyl)pyrrolidin-1-yl)imidazo[1,2-a]pyridine-3-carboxylic acid To a stirred solution of Ethyl-6-((2R,4S)-4-fluoro-2-(5-fluoro-2-(((S)-tetrahydrofuran-3-yl)oxy)phenyl)pyrrolidin-1-yl)imidazo[1,2-a]pyridine-3-carboxylate (1.3 g, 28.43 mmol) in ethanol was added 1M LiOH (2.6 ml) solution and stirred for 5 h at 85° C. Solvent was removed under reduced pressure and residue was dissolved in water, extracted unwanted impurities with Diethyl ether and water was acidified with 2N HCl and solid was collected by filtration. Solid was dried under high vacuum to afford 6-((2R,4S)-4-fluoro-2-(5-fluoro-2-(((S)-tetrahydrofuran-3-yl)oxy)phenyl)pyrrolidin-1-yl)imidazo[1,2-a]pyridine-3-carboxylic acid (1.0 g, yield: 82%). MS (ESI): 430 (M+H).

Synthesis of 6-(2-(5-fluoro-2-(((R)-tetrahydrofuran-3-yl)oxy)phenyl)pyrrolidin-1-yl)imidazo[1,2-a]pyridine-3-carboxylic acid (Int-92)

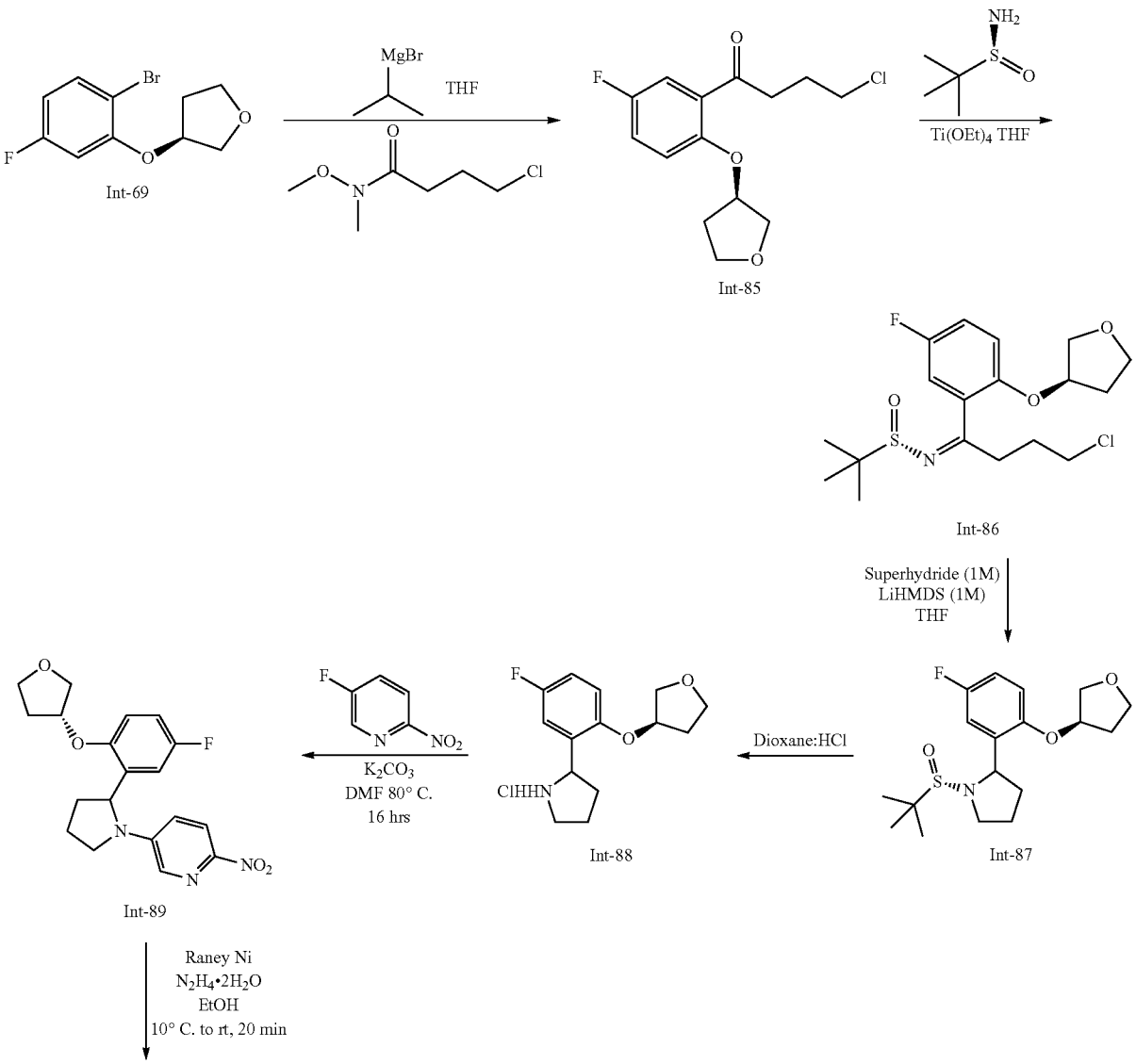

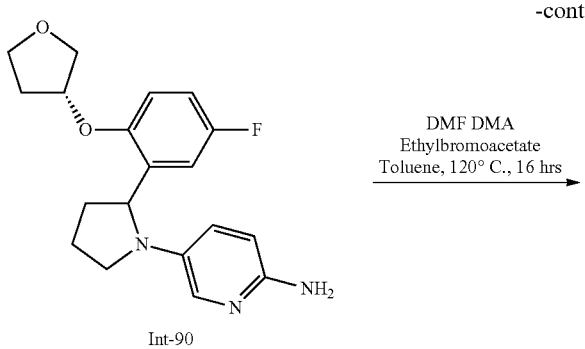

Int-90

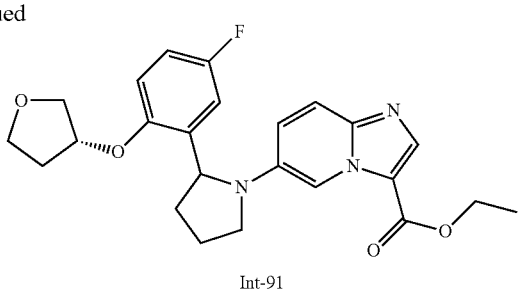

Int-91

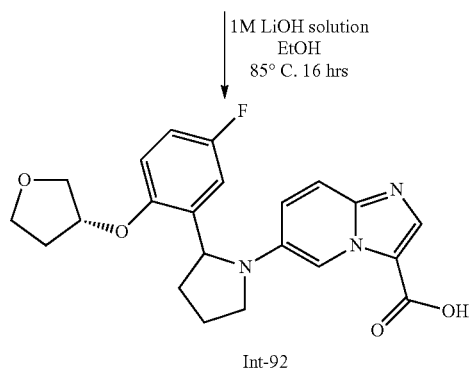

Int-92

Int-85: (S)-4-chloro-1-(5-fluoro-2-((tetrahydrofuran-3-yl)oxy)phenyl)butan-1-one (S)-3-(2-bromo-5-fluorophenoxy)tetrahydrofuran (Int 69) (13.8 g, 53.1 mmol) in THF (50 ml) was cooled to −50° C., to it was added isopropyl magnesium chloride (2M in THF) (133 mL, 132 mmol). The reaction mixture thus obtained was warmed to 0° C. and stirred for 1 h. The reaction mixture was cooled again to −50° C., 4-chloro-N-methoxy-N-methylbutanamide (10.51 g, 63.7 mmol) in THF (100 mL) was added drop wise to this reaction mixture with stirring and the stirring was continued at 0° C. for 1 h. The reaction mixture was quenched with saturated aqueous NH$_4$Cl solution, extracted with ethyl acetate. The organic layer collected was washed with water (500 mL) and then with brine solution, dried over anhydrous sodium sulfate and concentrated under reduced pressure to afford a crude liquid residue. The residue thus obtained was purified by column chromatography (using 60-120 silica gel and 5% EtOAc in Hexane as eluent) to afford 11.2 g of the title compound as a colorless liquid. MS (ESI): 287.1 (M+H).

Int-86: (S,Z)—N-(4-chloro-1-(5-fluoro-2-(((R)-tetrahydrofuran-3-yl)oxy)phenyl)butylidene)-2-methylpropane-2-sulfinamide Titanium (IV) ethoxide (17.5 g, 76.92 mmol) was added to a solution of (S)-4-chloro-1-(5-fluoro-2-((tetrahydrofuran-3-yl)oxy)phenyl)butan-1-one (11 g, 38.46 mmol) and (S)-2-methylpropane-2-sulfinamide (9.32 g, 76.92 mmol) in THF (170 mL) with stirring. The mixture was stirred continuously at 70° C. for 16 h. Reaction mixture was then cooled to a temperature of 20-35° C., quenched with saturated aqueous NH$_4$Cl solution, diluted with ethyl acetate and filtered. The filtrate was washed with water followed by brine solution. The organic layer was separated, dried over anhydrous sodium sulfate and concentrated under reduced pressure to afford 44.5 g of the title compound as a colorless liquid. MS (ESI): 390.2 (M+H).

Int-87: 1-((S)-tert-butylsulfinyl)-2-(5-fluoro-2-(((R)-tetrahydrofuran-3-yl)oxy)phenyl)pyrrolidine (S,Z)—N-(4-chloro-1-(5-fluoro-2-(((R)-tetrahydrofuran-3-yl)oxy)phenyl)butylidene)-2-methylpropane-2-sulfinamide (7.6 g, 19.5 mmol) in THF (100 mL) was cooled to −78° C. and to which was added cold (−78° C.) Lithium triethylborohydride (1M in THF) (21.48 ml, 21.5 mmol) drop wise and stirring was continued at −78° C. for 3 h. LiHMDS (1M in THF) (19.53 ml, 19.5 mmol) was then added and stirring was continued at −78° C. to 0° C. for 2 h. The resultant reaction mixture was quenched with saturated NH$_4$Cl solution, diluted with ethyl acetate. The ethyl acetate layer separated was washed with water followed by brine solution, dried over anhydrous sodium sulphate and concentrated under reduce pressure to afford the crude residue. The residue thus obtained was purified by column chromatography twice (using initially with 60-120 silica gel and 15% EtOAc in Hexane as elute and again with 230-400 silica gel and 12-14% EtOAc in Hexane as elute) to afford 4.1 g of the title compound as crude, which was used as such for the next step.

Int-88: 2-(5-fluoro-2-(((R)-tetrahydrofuran-3-yl)oxy)phenyl)pyrrolidine hydrochloride 4M HCl solution (in Dioxane) (20 mL) was added to stirred solution of 1-((S)-tert-butylsulfinyl)-2-(5-fluoro-2-(((R)-tetrahydrofuran-3-yl)oxy)phenyl)pyrrolidine (4.1 g, 11.54 mmol) in Dioxane (25 mL) and stirring was continued at 20-35° C. for 4 h. After which the reaction mixture was concentrated under reduced pressure to afford the crude product. The crude product was purified by washing with diethyl ether to afford 3.2 g of the title compound as a white solid. MS (ESI): 288.2 (M+H).

Int-89: 5-(2-(5-fluoro-2-(((R)-tetrahydrofuran-3-yl) oxy)phenyl)pyrrolidin-1-yl)-2-nitropyridine To a solution of 2-(5-fluoro-2-(((R)-tetrahydrofuran-3-yl) oxy)phenyl)pyrrolidine hydrochloride (3.15 g, 10.98 mmol) in dry DMF (10 ml) was added $K_2CO_3$ (3.15 g, 22.88 mmol) and stirred for 5 min at room temperature then added 5-fluoro-2-nitropyridine (1.3 g, 91.54 mmol) under $N_2$ atmosphere and stirred for 16 h at 80° C. After completion of reaction, reaction mixture was poured in to ice and stirred for 10 min then solid was collected by filtration. Solid was dried under high vacuum to afford 5-(2-(5-fluoro-2-(((R)-tetrahydrofuran-3-yl)oxy)phenyl)pyrrolidin-1-yl)-2-nitropyridine as yellow solid (2.8 g, Yield: 82.11%) MS (ESI): 374.3 (M+H).

Int-90: 5-(2-(5-fluoro-2-(((R)-tetrahydrofuran-3-yl) oxy)phenyl)pyrrolidin-1-yl)pyridin-2-amine To a stirred solution of 5-(2-(5-fluoro-2-(((R)-tetrahydrofuran-3-yl)oxy)phenyl)pyrrolidin-1-yl)-2-nitropyridine (2.8 g, 75.06 mmol) in ethanol (28 ml) was cooled to 10° C. and added Raney Ni (560 mg, 20% w/w) portion wise and stirred for 5 min, then added $N_2H_4.2H_2O$ drop wise for the period of 5 min, then stirred for 20 min at room temperature. After completion of reaction, reaction mixture was filter through celite bed under $N_2$ atmosphere and filtrate was concentration under reduced pressure, the residue was re-dissolved in DCM and washed with water, brine and dried over anhydrous $Na_2SO_4$ and concentrated in vacuo to get desired product as brown solid (2.4 g, yield: 93.3%), MS (ESI): 344.2 (M+H).

Int-91: Ethyl-6-(2-(5-fluoro-2-(((R)-tetrahydrofuran-3-yl)oxy)phenyl)pyrrolidin-1-yl)imidazo[1,2-a]pyridine-3-carboxylate To stirred solution of 5-(2-(5-fluoro-2-(((R)-tetrahydrofuran-3-yl)oxy)phenyl)pyrrolidin-1-yl)pyridin-2-amine (2.4 g, 69.97 mmol) in dry toluene (6 ml) was added DMF-DMA (1.87 ml, 13.99 mmol) under $N_2$ atm and stirred for 2 h at 120° C. during which complete consumption of starting material was observed by TLC, cool it to 10° C. then added Ethylbromoacetate (1.66 ml, 14.69 mmol) drop wise and methanol (2 ml) was added under $N_2$ atm then stirred for 16 h at 120° C. Reaction mixture was cooled to room temperature and solvent was removed in vacuo and residue was dissolved in DCM (200 ml), washed with water and brine, dried over anhydrous $Na_2SO_4$ and concentrated under vacuum to get crude product. Crude was purified by column chromatography (eluted with 30-40% ethyl acetate/Hexane) to afford pale green solid (1.15 g, yield: 38.3), MS (ESI): 440.2 (M+H).

Int-92: 6-(2-(5-fluoro-2-(((R)-tetrahydrofuran-3-yl) oxy)phenyl)pyrrolidin-1-yl)imidazo[1,2-a]pyridine-3-carboxylic acid To stirred solution of Ethyl-6-(2-(5-fluoro-2-(((R)-tetrahydrofuran-3-yl)oxy)phenyl)pyrrolidin-1-yl)imidazo[1,2-a] pyridine-3-carboxylate (1.15 g, 26.18 mmol) in ethanol was added 1M LiOH (2.3 ml) solution and stirred for 5 h at 85° C. Solvent was removed under reduced pressure and residue was dissolved in water, extracted unwanted impurities with diethyl ether and water was acidified with 2N HCl and solid was collected by filtration. Solid was dried under high vacuum to afford 6-(2-(5-fluoro-2-(((R)-tetrahydrofuran-3-yl)oxy)phenyl)pyrrolidin-1-yl)imidazo[1,2-a]pyridine-3-carboxylic acid as pale yellow solid (400 mg, yield: 37.7%), MS (ESI): 412.1 (M+H).

Int-93 and Int-94 was synthesized by a procedure substantially similar to Int-84, except in the first step alkylation was carried out with Int-68a and Int-68b respectively.

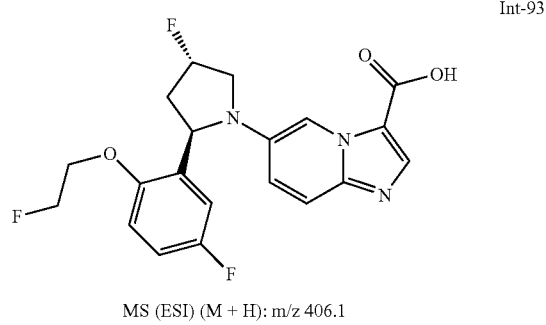

Int-93

MS (ESI) (M + H): m/z 406.1

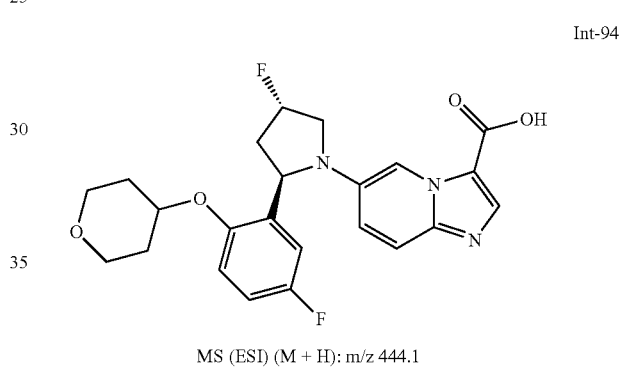

Int-94

MS (ESI) (M + H): m/z 444.1

Synthesis of 6-((2R,4S)-4-fluoro-2-(7-fluoro-2,3-dihydrobenzo[b][1,4]dioxin-5-yl)pyrrolidin-1-yl) imidazo[1,2-a]pyridine-3-carboxylic acid (Int-95)

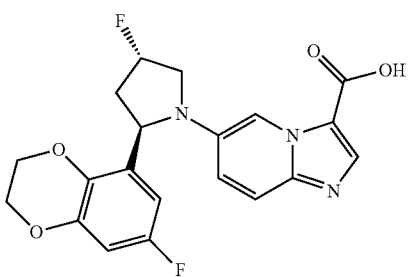 [SMILES: O=C(O)c1cnc2ccc(N3C[C@@H](F)C[C@@H]3c3cc(F)cc4c3OCCO4)cn12]

Title intermediate was synthesized using s procedure substantially similar to that of Int-84 except for the formylation step, Int-28 was used in place of Int-69 to afford 6-((2R,4S)-4-fluoro-2-(7-fluoro-2,3-dihydrobenzo[b][1,4]dioxin-5-yl) pyrrolidin-1-yl)imidazo[1,2-a]pyridine-3-carboxylic acid as pale yellow solid (60 mg, 84.1% yield), MS (ESI): 402.1 (M+H).

Synthesis of Compounds of Formula (I)

Example 1

6-(2-(2,5-difluorophenyl)pyrrolidin-1-yl)-N-(4-fluorophenyl)imidazo[1,2-a]pyridine-3-carboxamide

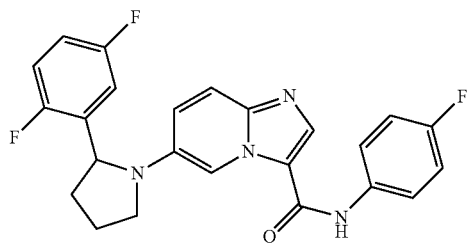 [SMILES: O=C(Nc1ccc(F)cc1)c1cnc2ccc(N3CCCC3c3cc(F)ccc3F)cn12]

To a stirred solution of 6-(2-(2,5-difluorophenyl)pyrrolidin-1-yl)imidazo[1,2-a]pyridine-3-carboxylic acid (Int-15) (0.15 g, 0.44 mmol) in dry DMF (1.5 ml) was added HATU (0.215 g, 0.57 mmol), DIPEA (0.084 g, 0.65 mmol) under $N_2$ atm at RT and stirred for 10 min, then added 4-fluoroaniline (0.053 g, 0.48 mmol) and stirred for 16 h at RT. After completion of reaction, quenched with ice water and solid was filter. Solid thus obtained was dried under high vacuum to afford 6-(2-(2,5-difluorophenyl)pyrrolidin-1-yl)-N-(4-fluorophenyl)imidazo[1,2-a]pyridine-3-carboxamide (0.018 g, 9.7% Yield) MS (ESI): m/z 437.1 (M+H); $^1$H NMR (300 MHz, CDCl$_3$) δ 10.07 (1H, s), 8.72-8.71 (1H, d J=3 Hz), 8.41 (1H, s), 7.74-7.71 (2H, m), 7.59-7.57 (1H, d J=6 Hz), 7.35-7.28 (1H, m), 7.23-7.12 (3H, m), 7.00-6.94 (2H, m), 5.02-5.00 (1H, d), 3.80-3.77 (1H, t), 2.05-1.89 (3H, m).

Example 2

(3 S)—N-(6-(2-(2,5-difluorophenyl)pyrrolidin-1-yl)imidazo[1,2-a]pyridin-3-yl)-3-hydroxypyrrolidine-1-carboxamide

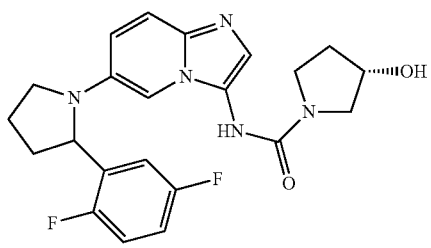 [SMILES: O=C(Nc1cnc2ccc(N3CCCC3c3cc(F)ccc3F)cn12)N1CC[C@H](O)C1]

To a stirred solution of 6-(2-(2,5-difluorophenyl)pyrrolidin-1-yl)imidazo[1,2-a]pyridine-3-carboxylic acid (Int-15) (0.25 g, 0.72 mmol) in anhydrous Toluene (2.5 ml) was added DPPA (0.3 g, 1.09 mmol) and TEA (0.22 g, 2.18 mmol) and stirred for 2 h at 120° C., then cooled to RT and then added (S)-pyrrolidin-3-ol (500 mg) again heated at 120° C. for 16 h, after completion of reaction solvent was remove under vacuum and residue was dissolved in DCM and washed with water, brine and dried over anhydrous sodium sulfate, concentration under vacuum to afford crude. Crude was purified on prep TLC plates (eluted with 10% MeOH:CHCl$_3$) to get pure product as green solid (0.042 g, 12.8% Yield). MS (ESI): m/z 428.2 (M+H); $^1$H NMR (400 MHz, DMSO-d$_6$) δ 8.18 (1H, s), 7.40-7.38 (1H, d J=8 Hz), 7.29-7.10 (4H, m), 5.03 (1H, s), 4.86-4.84 (1H, d J=8 Hz), 4.33 (1H, bs), 3.76 (1H, s), 2.02-1.84 (6H, m) ppm.

Example 3

(6-(2-(2,5-difluorophenyl)pyrrolidin-1-yl)imidazo[1,2-a]pyridin-3-yl)((S)-3-hydroxypyrrolidin-1-yl)methanone

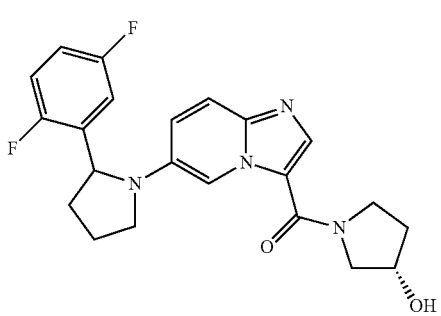 [SMILES: O=C(c1cnc2ccc(N3CCCC3c3cc(F)ccc3F)cn12)N1CC[C@H](O)C1]

The title compound (Example 3) was prepared by the method similar to that of Example 1 employing (S)-pyrrolidin-3-ol to afford (6-(2-(2,5-difluorophenyl)pyrrolidin-1-yl)imidazo[1,2-a]pyridin-3-yl)((S)-3-hydroxypyrrolidin-1-yl)methanone (0.04 g, 33.3% yield) as off white solid. MS (ESI): m/z 413.2 (M+H). $^1$H NMR (400 MHz, DMSO-d$_6$) δ 8.68 (1H, s), 8.05-7.99 (1H, bs), 7.54-7.52 (1H, d, J=8 Hz), 7.32-7.31 (1H, m), 7.13 (1H, m), 6.94-6.92 (1H, dd), 5.01-4.96 (1H, m), 4.32 (1H, s), 3.74 (2H, m), 3.69-3.42 (3H, m), 1.94-1.86 (5H, m) ppm.

Example 4

(6-(2-(2,5-difluorophenyl)pyrrolidin-1-yl)imidazo[1,2-a]pyridin-3-yl)(3-hydroxyazetidin-1-yl)methanone

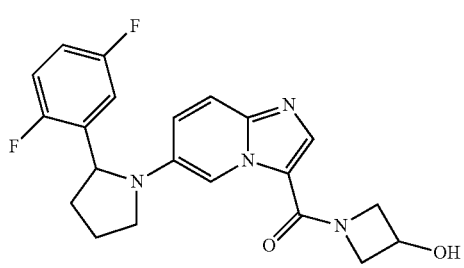 [SMILES: O=C(c1cnc2ccc(N3CCCC3c3cc(F)ccc3F)cn12)N1CC(O)C1]

The title compound was prepared by the method similar to that of Example 1 employing azetidin-3-ol to afford (6-(2-(2,5-difluorophenyl)pyrrolidin-1-yl)imidazo[1,2-a]pyridin-3-yl)(3-hydroxyazetidin-1-yl)methanone as off white solid.

MS (ESI): m/z 399.1 (M+H). $^1$H NMR (400 MHz, DMSO-d$_6$) δ 8.73-8.72 (1H, d, J=2.4 Hz), 7.90 (1H, s), 7.57-7.55 (1H, d, J=9.6 Hz), 7.35-7.29 (1H, m), 7.15-7.11 (1H, m), 7.00-6.94

(1H, dd), 5.80-5.79 (1H, d, J=3.2 Hz), 4.96-4.94 (1H, d), 4.54-4.51 (2H, m), 3.78-3.74 (2H, m), 2.04-1.87 (4H, m) ppm.

Example 5

6-(2-(2,5-difluorophenyl)pyrrolidin-1-yl)-N-(1,3-dihydroxypropan-2-yl)imidazo[1,2-a]pyridine-3-carboxamide

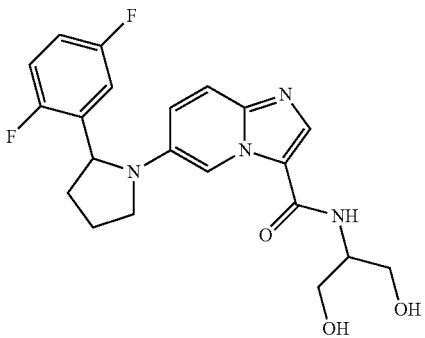 [SMILES: O=C(NC(CO)CO)c1cnc2ccc(N3CCCC3c3cc(F)ccc3F)cn12]

The title compound was prepared by the method similar to that of Example 1 employing 2-aminopropane-1,3-diol to afford 6-(2-(2,5-difluorophenyl)pyrrolidin-1-yl)-N-(1,3-dihydroxypropan-2-yl)imidazo[1,2-a]pyridine-3-carboxamide as white solid.

Chiral separation employing chiral Column: Lux Amylose-2 Axia, Mobile phase: 75:25 Hexane:Ethanol-isocratic Flow: 20 ml/min to afford (Isomer II), MS (ESI): m/z 417.1 (M+H). $^1$H NMR (400 MHz, DMSO-$d_6$) δ 8.74 (1H, s), 8.27 (1H, s), 8.17 (1H, s), 7.88-7.86 (1H, d, J=8.0 Hz), 7.59-7.52 (1H, m), 7.35-7.29 (1H, m), 7.16-7.14 (1H, m), 6.97-6.94 (2H, m), 4.99-4.97 (1H, d, J=7.6 Hz), 4.69 (2H, s), 3.98-3.96 (1H, m), 3.78-3.75 (1H, m), 3.64-3.62 (2H, m), 3.50 (4H, m), 3.15-3.13 (2H, m), 2.03-1.87 (4H, m), 1.27-1.24 (11H, s) ppm.

And (Isomer I), MS (ESI): m/z 417.1 (M+H). $^1$H NMR (400 MHz, DMSO-$d_6$) δ 8.42-8.40 (1H, d, J=8.0 Hz), 8.35 (1H, s), 7.39-7.30 (2H, m), 7.17-7.13 (1H, m), 6.95 (1H, s), 6.90-6.85 (1H, m), 6.38-6.36 (1H, d, J=6.4 Hz), 5.12-5.10 (1H, m), 4.65-4.61 (2H, m), 3.92-3.84 (2H, m), 3.49-3.39 (5H, m), 2.04 (1H, m), 1.91 (2H, m) ppm.

Example 6

(6-(2-(2,5-difluorophenyl)pyrrolidin-1-yl)imidazo[1,2-a]pyridin-3-yl)(morpholino)methanone

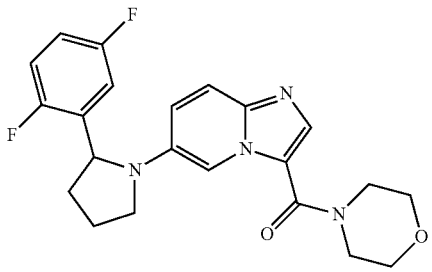 [SMILES: O=C(c1cnc2ccc(N3CCCC3c3cc(F)ccc3F)cn12)N1CCOCC1]

The title compound was prepared by the method similar to that of Example 1 employing morpholine to afford (6-(2-(2,5-difluorophenyl)pyrrolidin-1-yl)imidazo[1,2-a]pyridin-3-yl)(morpholino)methanone as off white solid (0.006 g) MS (ESI): m/z 413.1 (M+H); $^1$H NMR (400 MHz, DMSO-$d_6$) δ 8.29-8.28 (1H, d J=4 Hz), 7.73 (1H, s), 7.45-7.43 (1H, d, J=8 Hz), 7.09-7.03 (1H, m), 6.94-6.81 (2H, m), 6.76-6.73 (1H, dd), 5.02-5.00 (1H, d, J=8 Hz), 3.86-3.83 (4H, m), 3.79-3.76 (4H, m), 3.72-3.67 (2H, m), 3.43-3.37 (1H, m), 2.47-2.42 (1H, m), 2.10-1.99 (4H, m) ppm.

Example 7

N-(6-(2-(2,5-difluorophenyl)pyrrolidin-1-yl)imidazo[1,2-a]pyridin-3-yl)morpholine-4-carboxamide

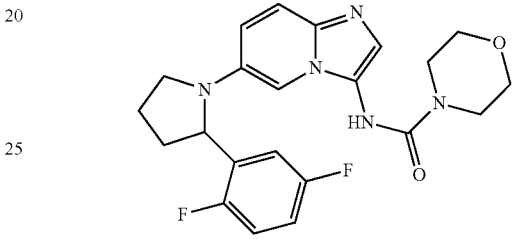

The title compound was prepared by the method similar to that of Example 2 employing morpholine to afford N-(6-(2-(2,5-difluorophenyl)pyrrolidin-1-yl)imidazo[1,2-a]pyridin-3-yl)morpholine-4-carboxamide as greenish solid (0.005 g) MS (ESI): m/z 428.2 (M+H); $^1$H NMR (400 MHz, CDCl$_3$) δ 7.35-7.32 (1H, bd), 7.28 (1H, s), 7.07-7.01 (1H, m), 6.92-6.87 (3H, m), 6.75-6.72 (1H, dd), 6.55 (1H, bs), 4.89-4.87 (1H, d J=8 Hz), 3.77-3.70 (5H, m), 3.54-3.48 (4H, m), 3.38-3.32 (1H, m), 2.47-2.42 (1H, m), 2.09-1.95 (3H, m) ppm.

Example 8

6-(2-(2,5-difluorophenyl)pyrrolidin-1-yl)-N,N-dimethylimidazo[1,2-a]pyridine-3-carboxamide

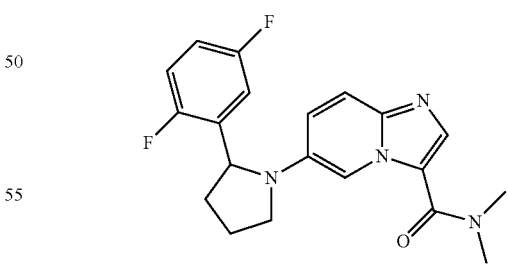

The title compound was prepared by the method similar to that of Example 1 employing dimethylamine hydrochloride to afford 6-(2-(2,5-difluorophenyl)pyrrolidin-1-yl)-N,N-dimethylimidazo[1,2-a]pyridine-3-carboxamide as off white solid (0.014 g) MS (ESI): m/z 371.1 (M+H); $^1$H NMR (400 MHz, CDCl$_3$) δ 8.57-8.47 (1H, d), 7.82 (1H, s), 7.44-7.42 (1H, d J=8 Hz), 7.08-7.02 (1H, m), 6.93-6.87 (1H, m), 6.84-6.80 (1H, m), 6.75-6.72 (1H, dd), 5.02-4.99 (1H, d J=12 Hz), 3.86-3.76 (1H, m), 3.69-3.68 (1H, m), 3.42-3.35 (1H, m), 3.25 (6H, s), 2.47-2.40 (1H, m), 2.08-1.99 (4H, m) ppm.

Example 9

(6-(2-(2,5-difluorophenyl)pyrrolidin-1-yl)imidazo[1,2-a]pyridin-3-yl)(4-methylpiperazin-1-yl)methanone

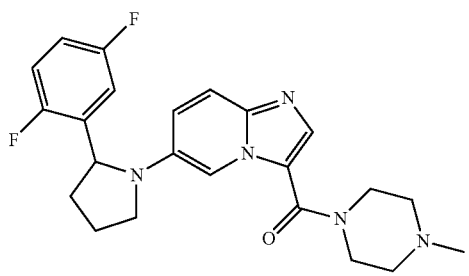 [SMILES: CN1CCN(C(=O)c2cnc3ccc(N4CCCC4c4cc(F)ccc4F)cn23)CC1]

The title compound was prepared by the method similar to that of Example 1 employing 1-methylpiperazine hydrochloride to afford (6-(2-(2,5-difluorophenyl)pyrrolidin-1-yl)imidazo[1,2-a]pyridin-3-yl)(4-methylpiperazin-1-yl)methanone as off white solid (0.014 g)

MS (ESI): m/z 426.2 (M+H). $^1$H NMR (400 MHz, CDCl$_3$) δ 8.288-8.280 (1H, d, J=2.0 Hz), 7.73 (1H, m), 7.43-7.41 (1H, d, J=9.6 Hz), 7.08-7.02 (1H, m), 6.93-6.87 (1H, m), 6.85-6.82 (1H, m), 6.73-6.70 (1H, m), 5.01-4.99 (1H, m), 3.87 (4H, m), 3.71-3.67 (1H, m), 2.59-2.41 (5H, m), 2.37 (3H, s), 2.08-2.00 (3H, m). ppm.

Example 10

(6-(2-(2,5-difluorophenyl)pyrrolidin-1-yl)imidazo[1,2-a]pyridin-3-yl)(4-fluorophenyl)methanone

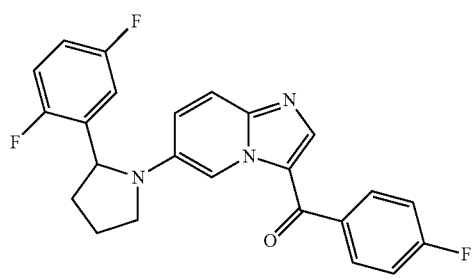 [SMILES: O=C(c1ccc(F)cc1)c1cnc2ccc(N3CCCC3c3cc(F)ccc3F)cn12]

To stirred solution of 5-(2-(2,5-difluorophenyl)pyrrolidin-1-yl)pyridin-2-amine (0.3 g, 1.0 mmol) (from Int-15) in dry toluene (3 ml, 10 v) was added DMF-DMA (0.14 g, 1.2 mmol) under N$_2$ atm and stirred for 2 h at 120° C., after completion of starting material; cooled it to 10° C. then added 2-bromo-1-(4-fluorophenyl)ethanone (0.3 g, 1.4 mmol) drop wise and methanol (1 ml) was added under N$_2$ atm then stirred for 16 h at 120° C. Reaction mixture was cooled to room temperature and solvent was removed under vacuum and residue was dissolved in DCM (100 ml), washed with water, brine and dried over Na$_2$SO$_4$ and concentrated under vacuum to get crude product. Crude was purified by column chromatography using 60-120 mesh silica gel product eluted with 30-40% ethyl acetate/Hexane to afford (6-(2-(2,5-difluorophenyl)pyrrolidin-1-yl)imidazo[1,2-a]pyridin-3-yl)(4-fluorophenyl)methanone as a off white solid (0.02 g, 4.3% Yield), MS (ESI): m/z 423.1 (M+H). $^1$H NMR (300 MHz, CDCl$_3$) δ 9.08 (1H, s), 8.04 (1H, s), 7.89-7.84 (2H, m), 7.59-7.56 (1H, d J=9 Hz), 7.23-7.17 (2H, m), 7.09-7.08 (1H, m), 6.96-6.92 (2H, m), 6.81 (1H, bs), 5.07-5.04 (1H, d J=9 Hz), 3.85-3.75 (1H, m), 3.49-3.47 (1H, m), 2.54-2.46 (1H, m), 2.14-2.08 (3H, m) ppm.

Example 11

3-(6-(2-(2,5-difluorophenyl)pyrrolidin-1-yl)imidazo[1,2-a]pyridin-3-yl)-1,1-dimethylurea

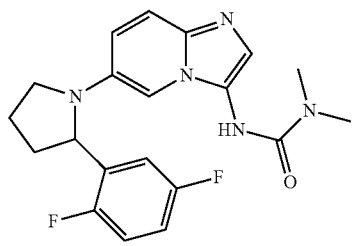 [SMILES: CN(C)C(=O)Nc1cnc2ccc(N3CCCC3c3cc(F)ccc3F)cn12]

The title compound was prepared by the method similar to that of Example 2 employing dimethylamine hydrochloride to afford 3-(6-(2-(2,5-difluorophenyl)pyrrolidin-1-yl)imidazo[1,2-a]pyridin-3-yl)-1,1-dimethylurea as white solid (0.006 g) MS (ESI): m/z 386.1 (M+H); $^1$H NMR (300 MHz, CDCl$_3$) δ 7.35-7.28 (2H, m), 7.03-6.97 (2H, m), 6.92-6.83 (2H, m), 6.71-6.68 (1H, d J=9 Hz), 6.60 (1H, bs), 4.91-4.88 (1H, d J=9 Hz), 3.69 (1H, bs), 3.35-3.33 (1H, m), 3.04 (6H, s), 2.44-2.41 (1H, m), 2.37-2.18 (2H, m), 2.08-1.99 (5H, m) ppm.

Example 12

(6-((S)-2-(2,5-difluorophenyl)pyrrolidin-1-yl)imidazo[1,2-a]pyridin-3-yl)((S)-3-hydroxypyrrolidin-1-yl)methanone (Isomer-II) and (6-((R)-2-(2,5-difluorophenyl)pyrrolidin-1-yl)imidazo[1,2-a]pyridin-3-yl)((S)-3-hydroxypyrrolidin-1-yl)methanone (Isomer-I)

The title compounds were prepared by chiral chromatographic separation of Example-3 (0.3 g) employing chiral Column: Lux Amylose-2 Axia, Mobile phase: 75:25 Hexane:Ethanol-isocratic Flow: 20 ml/min to afford Ex-12 (Isomer-II)

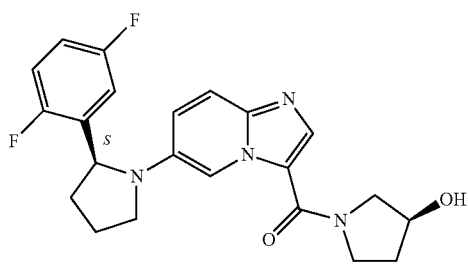

Ex-12 (Isomer-I)

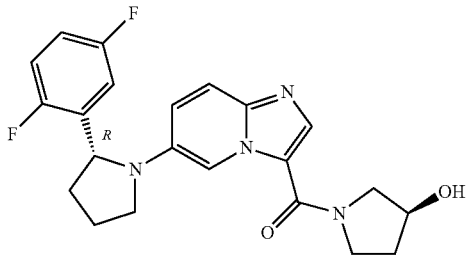

(6-((S)-2-(2,5-difluorophenyl)pyrrolidin-1-yl)imidazo[1,2-a]pyridin-3-yl)((S)-3-hydroxypyrrolidin-1-yl)methanone (Isomer-II))(0.11 g) MS (ESI): m/z 413.2 (M+H); $^1$H NMR (300 MHz, CDCl$_3$) δ 8.87 (1H, s), 7.92 (1H, s), 7.44-7.41 (1H, d J=9 Hz), 7.05-7.02 (1H, m), 6.91-6.71 (3H, m), 5.02-4.99 (1H, d J=9 Hz), 4.61 (1H, bs), 3.91-3.66 (5H, m), 3.42-3.39 (1H, m), 2.44-2.42 (1H, m), 2.09-1.98 (6H, m) ppm.

and (6-((R)-2-(2,5-difluorophenyl)pyrrolidin-1-yl)imidazo[1,2-a]pyridin-3-yl)((S)-3-hydroxypyrrolidin-1-yl)methanone (Isomer-I) (0.124 g) MS (ESI): m/z 413.2 (M+H); $^1$H NMR (300 MHz, CDCl$_3$) δ 8.86 (1H, s), 7.93 (1H, s), 7.45-7.42 (1H, d J=9 Hz), 7.10-7.00 (1H, m), 6.91-6.71 (3H, m), 5.02-4.99 (1H, d J=9 Hz), 4.62 (1H, bs), 3.89-3.72 (5H, m), 3.42-3.39 (1H, m), 2.49-2.44 (1H, m), 2.10-1.99 (6H, m) ppm.

Example 13

N-(6-(2-(2,5-difluorophenyl)pyrrolidin-1-yl)imidazo[1,2-a]pyridin-3-yl)acetamide

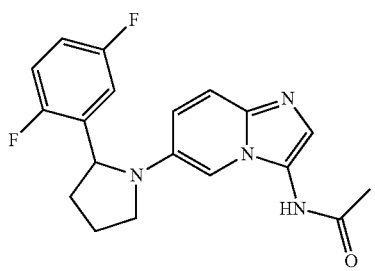 [SMILES: CC(=O)Nc1cnc2ccc(N3CCCC3c3cc(F)ccc3F)cn12]

To stirred solution of 6-(2-(2,5-difluorophenyl)pyrrolidin-1-yl)imidazo[1,2-a]pyridin-3-amine (0.25 g, 0.71 mmol) (prepared treating Int-15, with DPPA in t-BuOH, followed by Boc-deprotection in Dioxane HCL) in DCM was added pyridine (0.28 g, 1.4 mmol), at 0-5° C. Then added (Ac)$_2$O and stirred for 4 h at 25° C. under N$_2$ atm. After completion of reaction solvent was remove under vacuum and quenched with ice water and solid was filter. Solid was washed with hexane and dried under high vacuum to get crude product. Crude was purified by Prep HPLC using following method. Column: ZORBAX, XDB, C-18, Flow: 20 ml/min, 0.01% TFA: ACN to afford N-(6-(2-(2,5-difluorophenyl)pyrrolidin-1-yl)imidazo[1,2-a]pyridin-3-yl)acetamide as brown solid (0.007 g) MS (ESI): m/z 357.1 (M+H). $^1$H NMR (300 MHz, CD$_3$OD) δ 7.31 (1H, bs), 7.22-7.10 (1H, m), 4.98-4.93 (1H, m), 3.88-3.76 (1H, m), 3.48-3.38 (1H, m), 2.59-2.42 (1H, m), 2.18 (3H, s), 2.17-1.90 (3H, m) ppm.

Example 14

(Z/E)(6-(2-(2,5-difluorophenyl)pyrrolidin-1-yl)imidazo[1,2-a]pyridin-3-yl)(4-fluorophenyl)methanone oxime (Isomer-I) and (E/Z)-(6-(2-(2,5-difluorophenyl)pyrrolidin-1-yl)imidazo[1,2-a]pyridin-3-yl)(4-fluorophenyl)methanone oxime (Isomer-II)

Isomer-I

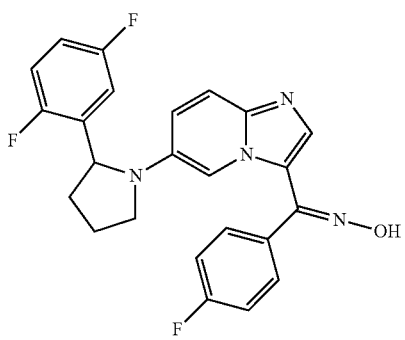

Isomer-II

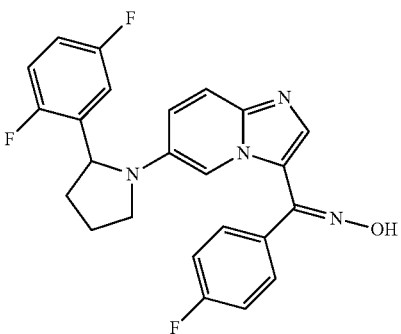

To a stirred solution of (6-(2-(2,5-difluorophenyl)pyrrolidin-1-yl)imidazo[1,2-a]pyridin-3-yl)(4-fluorophenyl)methanone (0.07 g, 0.16 mmol) in EtOH was added NaOAc (0.068 g, 0.83 mmol) at 10-15° C. under N$_2$ atm, stirred for 5 min then added NH$_2$OH.HCl (0.068 g, 0.99 mmol) and stirred for 16 h at 75° C. After completion of reaction solvent was removed under vacuum and residue was dissolved in DCM and washed with water, brine and dried over Na$_2$SO$_4$ and concentration under vacuum to get crude product. Crude was purified by prep HPLC. (Method: column: AG/PP/C18-15/028, flow rate: 20 ml/min, mobile phase: NH$_4$OAC:ACN) after concentration to afford pure (Z/E)(6-(2-(2,5-difluorophenyl)pyrrolidin-1-yl)imidazo[1,2-a]pyridin-3-yl)(4-fluorophenyl)methanone oxime (Isomer-I) (0.004 g) MS (ESI): m/z 437.1 (M+H); $^1$H NMR (300 MHz, DMSO-d$_6$) δ 8.68 (1H, s), 7.81 (1H, s), 7.77 (1H, s), 7.54-7.54 (2H, m), 7.37-7.31 (3H, m), 7.26-7.10 (1H, m), 6.98-6.90 (1H, m), 5.16-5.09 (1H, m), 3.82-3.72 (1H, m), 3.42-3.32 (1H, m), 3.12 (1H, s), 2.29-1.90 (3H, m) ppm. and (E/Z)-(6-(2-(2,5-difluorophenyl)pyrrolidin-1-yl)imidazo[1,2-a]pyridin-3-yl)(4-fluorophenyl)methanone oxime (Isomer-II) (0.010 g) MS (ESI): m/z 437.1 (M+H); $^1$H NMR (300 MHz, CD$_3$OD) δ 7.60 (1H, s), 7.49-7.40 (2H, m), 7.13-7.03 (3H, m), 6.98-6.94 (1H, m), 6.08-6.76 (1H, m), 4.79-4.76 (1H, d J=9 Hz), 3.72-3.64 (1H, m), 2.49-2.39 (1H, m), 2.05-1.93 (3H, m) ppm.

Example 15

6-(2-(2,5-difluorophenyl)pyrrolidin-1-yl)-N-(4-fluorophenyl)-N-methylimidazo[1,2-a]pyridine-3-carboxamide (Isomer-II) and (Isomer-I)

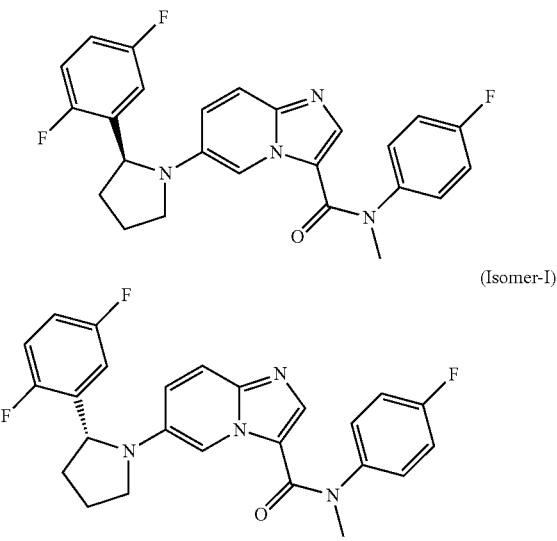

The title compound was prepared by the method similar to that of Example-1, employing 4-fluorophenyl methyl amine to afford 6-(2-(2,5-difluorophenyl)pyrrolidin-1-yl)-N-(4-fluorophenyl)-N-methylimidazo[1,2-a]pyridine-3-carboxamide as enantiomeric mixture. It was separated by chiral chromatography using LUXAMYLOSE-2 column and 70:30 Heptane:Ethanol-isocratic solution as eluent to afford (Isomer-II) MS (ESI): m/z 451.1 (M+H); $^1$H NMR (300 MHz, CDCl$_3$) δ 8.903 (1H, bs), 7.36-7.33 (1H, d J=9.6 Hz), 7.23-7.22 (2H, m) 6.93-6.82 (2H, m), 6.73-6.7 (1H, m), 6.52 (1H, s) 5.035-5.00 (1H, d, J=8.7 Hz), 3.74 (1H, m), 3.46-3.39 (4H, m), 2.47-2.44 (1H, t), 2.10-2.011 (3H, m) ppm.

And (Isomer-I) MS (ESI): m/z 451.1 (M+H)$^1$H NMR (300 MHz, CDCl$_3$) δ 8.70-8.69 (1H, bs), 7.38-7.34 (3H, m), 7.22-7.17 (3H, m), 7.05-7.01 (2H, m), 6.8 (1H, m), 6.48 (1H, s) 5.07-5.04 (1H, d, J=7.5 Hz), 3.84-3.79 (1H, m), 3.50-3.47 (4H, m), 2.14-1.99 (1H, t), 1.47-1.30 (3H, m) ppm.

Example 16

6-(2-(2,5-difluorophenyl)pyrrolidin-1-yl)-N-((1r,4r)-4-hydroxycyclohexyl)imidazo[1,2-a]pyridine-3-carboxamide (Isomer-II) and Isomer (I)

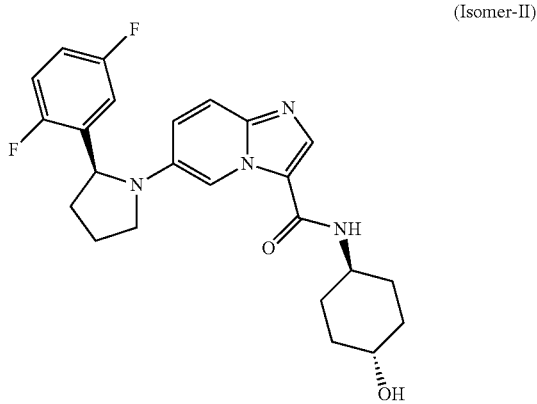

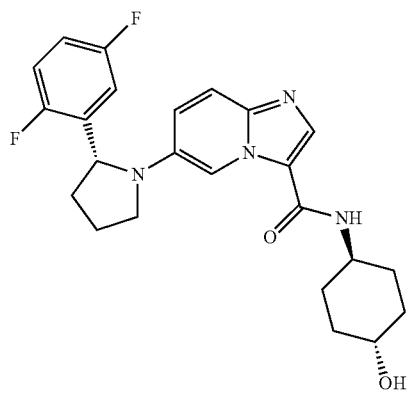

The title compound was prepared by the method similar to that of Example-1, employing (1r,4r)-4-aminocyclohexanol to afford 6-(2-(2,5-difluorophenyl)pyrrolidin-1-yl)-N-((1r,4r)-4-hydroxycyclohexyl)imidazo[1,2-a]pyridine-3-carboxamide as enantiomeric mixture. The above enantiomeric mixture was separated by chiral HPLC method using Chiral pak ADH column and 60:40 Heptane:Ethanol-isocratic solution as eluent (Isomer-II): MS (ESI): m/z 440.1 (M+H); $^1$H NMR (300 MHz, CD$_3$OD) δ 8.74-8.74 (1H, d, J=1.8 Hz), 8.12 (1H, s), 7.48-7.45 (1H, d, J=9 Hz), 7.21-7.14 (1H, m), 7.08-6.97 (2H, m), 6.9-6.85 (1H, m), 5.05-5.02 (1H, d, J=7.8 Hz), 3.85-3.77 (2H, m), 3.6-3.55 (3H, m), 2.56-2.47 (1H, m), 2.18-2.0 (7H, m) 1.52-1.29 (4H, m) ppm.

(Isomer-I): MS (ESI): m/z 440.1; (M+H)$^1$H NMR (300 MHz, CD$_3$OD) δ ppm 8.73-8.73 (1H, d, J=2.1 Hz), 8.10 (1H, s), 7.47-7.44 (1H, d, J=9.6 Hz), 7.22-7.14 (1H, m), 7.06-6.98 (2H, m), 6.9-6.85 (1H, m), 5.05-5.02 (1H, d, J=8.7 Hz), 3.85-3.77 (2H, m), 3.57-3.45 (3H, m), 2.56-2.50 (1H, m), 2.14-1.99 (7H, m), 1.52-1.29 (3H, m) ppm.

Example 17

(6-(2-(2,5-difluorophenyl)pyrrolidin-1-yl)imidazo[1,2-a]pyridin-3-yl)(4-hydroxypiperidin-1-yl)methanone (Isomer-II) and (Isomer-I)

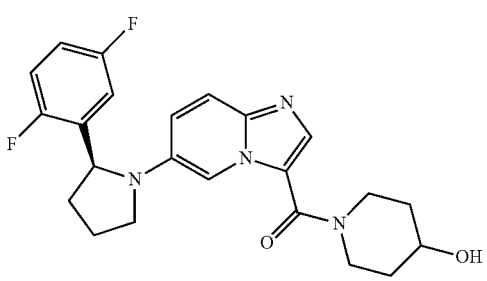

-continued (Isomer-I)

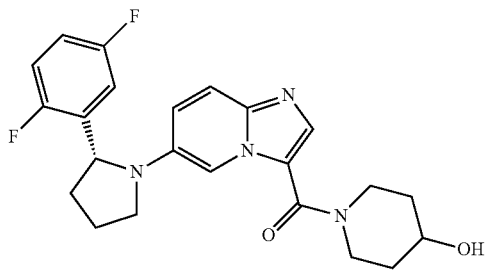

The title compound was prepared by the method similar to that of Example-1 employing piperidin-4-ol to afford (6-(2-(2,5-difluorophenyl)pyrrolidin-1-yl)imidazo[1,2-a]pyridin-3-yl)(4-hydroxypiperidin-1-yl)methanone as enantiomeric mixture. This enantiomeric mixture was separated by chiral HPLC method using Chiral pak ADH column and 25:75 Heptane:Ethanol-isocratic solution as eluent to afford (Isomer-II): MS (ESI): m/z 427.1 (M+H); $^1$H NMR (300 MHz, CD$_3$OD) δ 8.03-8.02 (1H, d, J=1.8 Hz), 7.88 (1H, s), 7.53-7.50 (1H, d, J=9.6 Hz), 7.22-7.13 (2H, m), 7.05-6.86 (2H, m), 5.07-5.04 (1H, d, J=7.2 Hz), 4.15-4.10 (2H, m), 3.96-3.80 (2H, m), 3.48-3.41 (3H, m), 2.57-2.51 (1H, m), 2.13-1.92 (5H, m), 1.61-1.55 (2H, m) ppm.

(Isomer-I): MS (ESI): m/z 427.1 (M+H)$^1$H NMR (300 MHz, CD$_3$OD) δ 8.03-8.02 (1H, d, J=1.8 Hz), 7.85 (1H, s), 7.52-7.48 (1H, d, J=10.2 Hz), 7.22-7.09 (2H, m), 7.06-6.99 (2H, m), 5.06-5.04 (1H, d, J=6.9 Hz), 4.15-4.11 (2H, m), 3.96-3.82 (2H, m), 348-3.45 (3H, m), 2.56-2.51 (1H, m), 2.14-1.92 (5H, m), 1.61-1.54 (2H, m) ppm.

Example 18

Ethyl 2-(6-(2-(2,5-difluorophenyl)pyrrolidin-1-yl)imidazo[1,2-a]pyridine-3-carboxamido)acetate (Isomer-II) and (Isomer-I)

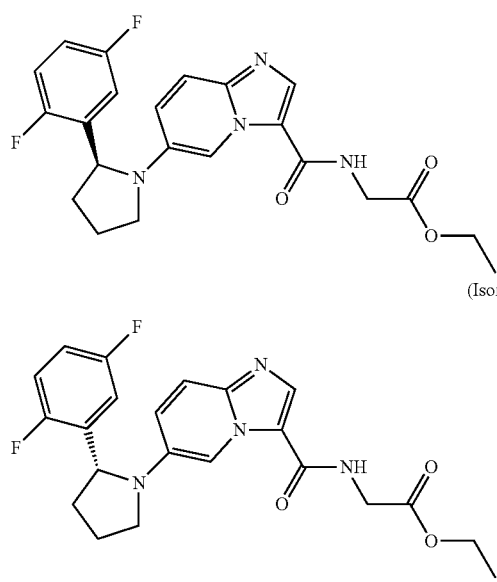

The title compound was prepared by the method similar to that of Example-1 employing ethyl 2-aminoacetate hydrochloride to afford ethyl 2-(6-(2-(2,5-difluorophenyl)pyrrolidin-1-yl)imidazo[1,2-a]pyridine-3-carboxamido)acetate (0.39 g) as enantiomeric mixture. The above enantiomeric mixture was separated by chiral HPLC method.

(Chiral method: column: LUXAMYLOSE-2, eluent 40:60 Heptane:Ethanol-isocratic) to afford isomer-II: (S)-ethyl 2-(6-(2-(2,5-difluorophenyl)pyrrolidin-1-yl)imidazo[1,2-a]pyridine-3-carboxamido)acetate as white solid (100 mg). MS (ESI): m/z 429.1 (M+H); $^1$H NMR (300 MHz, CDCl$_3$) δ 8.80-8.79 (1H, d J=3 Hz), 7.99 (1H, s), 7.47-7.44 (1H, d J=9 Hz), 7.06-7.02 (1H, m), 6.93-6.90 (1H, m), 6.81-6.74 (2H, m), 6.42-6.38 (1H, m), 5.02-5.00 (1H, d J=6 Hz), 4.31-4.23 (3H, m), 3.76-3.69 (1H, m), 3.47-3.37 (1H, m), 2.46-2.44 (1H, m), 2.11-2.00 (3H, m), 1.35-1.30 (2H, t) ppm and Isomer-I: (R)-ethyl 2-(6-(2-(2,5-difluorophenyl)pyrrolidin-1-yl)imidazo[1,2-a]pyridine-3-carboxamido)acetate (110 mg). MS (ESI): m/z 429.1 (M+H); $^1$H NMR (300 MHz, CDCl$_3$) δ 8.81-8.80 (1H, d J=3 Hz), 7.99 (1H, s), 7.48-7.45 (1H, d J=9 Hz), 7.10-7.03 (1H, m), 6.94-6.91 (1H, m), 6.84-6.75 (2H, m), 6.42-6.38 (1H, m), 5.03-5.02 (1H, d J=3 Hz), 4.32-4.23 (3H, m), 3.76-3.69 (1H, m), 3.42-3.37 (1H, m), 2.50-2.45 (1H, m), 2.10-2.01 (3H, m), 1.36-1.31 (2H, t) ppm.

Example-19

2-(6-(2-(2,5-difluorophenyl)pyrrolidin-1-yl)imidazo[1,2-a]pyridine-3-carboxamido)acetic acid (Isomer-II) and (Isomer-I)

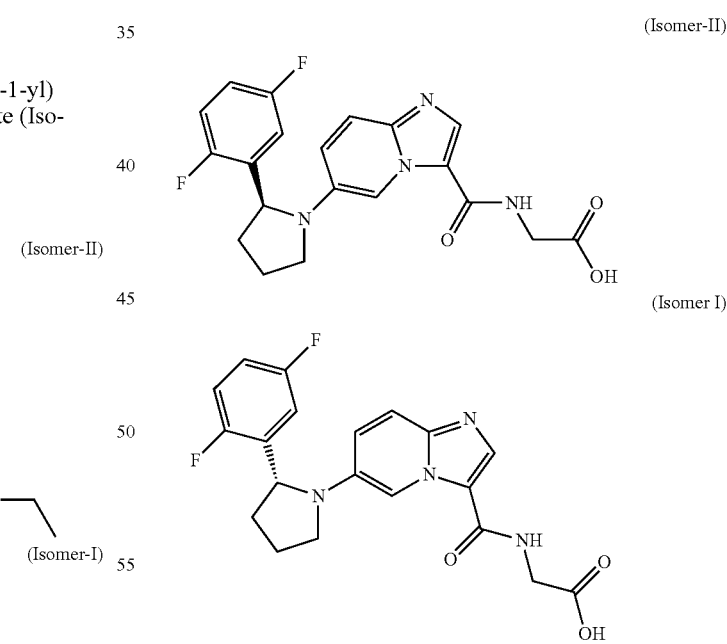

Isomer II

To a stirred solution of (S)-ethyl 2-(6-(2-(2,5-difluorophenyl)pyrrolidin-1-yl)imidazo[1,2-a]pyridine-3-carboxamido)acetate (Example-18; Isomer-II) (0.08 g, 0.18 mmol) in ethanol (10 mL) was added 1M LiOH solution at 20° C. then stirred for 1 h RT. After completion of reaction solvent was remove under reduced pressure then residue was dissolved in water and washed with diethylether and water layer was acidified with 2N HCl (pH~2) and solid was filter to afford pure (S)-2-(6(2(2,5difluorophenyl)pyrrolidin-1-yl)imidazo[1,2-a]pyridine-3-carboxamido)acetic acid (Isomer-II) (0.035 g, 47.29% Yield). MS (ESI): m/z 401.3 (M+H); $^1$H NMR (300 MHz, DMSO-$d_6$) δ 12.66-12.60 (1H, bs), 8.75-8.72 (2H, m), 8.27 (1H, s), 7.59-7.55 (1H, d J=12 Hz), 7.35-7.28 (1H, m), 7.16-7.10 (1H, m), 7.00-6.93 (2H, m), 5.00-4.98 (1H, d J=6 Hz), 3.93-3.91 (2H, d J=6 Hz), 3.79-3.74 (1H, m), 2.03-1.87 (3H, m) ppm.

Isomer I

The title compound (19) was prepared by the method similar to that of Example-20 by LiOH mediated hydrolysis of Isomer-I of Example-18 to afford (R)-2-(6-(2-(2,5-difluorophenyl)pyrrolidin-1-yl)imidazo[1,2-a]pyridine-3-carboxamido)acetic acid (Isomer-I) (0.030 g, 40.45% Yield). MS (ESI): m/z 401.1 (M+H); $^1$H NMR (300 MHz, CDCl$_3$) δ 8.71 (1H, s), 8.51 (1H, bs), 8.19 (1H, s), 7.54-7.51 (1H, d J=9 Hz), 7.35-7.27 (1H, m), 7.15-7.13 (1H, m), 6.93-6.90 (2H, m), 4.99-4.96 (1H, d J=9 Hz), 3.85-3.83 (2H, d J=6 Hz), 3.75-3.73 (2H, m), 2.02-1.86 (3H, m) ppm.

Example 20

(S)-3-aminopyrrolidin-1-yl)(6-((S)-2-(2,5-difluorophenyl)pyrrolidin-1-yl)imidazo[1,2-a]pyridin-3-yl)methanone (Isomer-II And ((S)-3-aminopyrrolidin-1-yl)(6-((R)-2-(2,5-difluorophenyl)pyrrolidin-1-yl)imidazo[1,2-a]pyridin-3-yl)methanone (Isomer-I)

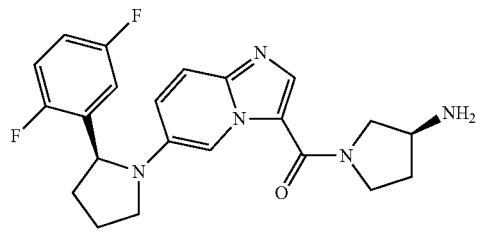 [SMILES: N[C@H]1CCN(C(=O)c2cnc3ccc(N4CCC[C@H]4c4cc(F)ccc4F)cn23)C1]

To a stirred solution of tert-butyl((S)-1-(6-((S)-2-(2,5-difluorophenyl)pyrrolidin-1-yl)imidazo[1,2-a]pyridine-3-carbonyl)pyrrolidin-3-yl)carbamate (Isomer-II) (prepared by method similar to Example-1, employing (S)-tert-butyl pyrrolidin-3-ylcarbamate as amine followed by chiral separation in LUXAMYLOSE-2 column with eluent 1:1 Hexane:Ethanol isocratic solution) (0.16 g, 0.31 mmol), in Dioxane (2 mL), cooled to 5-10° C. was added Dioxane HCl (4 Molar) (2 mL) and stirred for 2 h at room temperature, after completion of reaction solvent was remove under vacuum and residue was dissolved in water and washed with diethylether and water was basified with sat.NaHCO$_3$ (pH~9) and solid was filter and dried to afford ((S)-3-aminopyrrolidin-1-yl)(6-((S)-2-(2,5-difluorophenyl)pyrrolidin-1-yl)imidazo[1,2-a]pyridin-3-yl)methanone (0.07 g, 54.68% yield). MS (ESI): m/z 412.2 (M+H); $^1$H NMR (300 MHz, CDCl$_3$) δ 8.66 (1H, bs), 7.98 (1H, bs), 7.54-7.51 (1H, d J=9 Hz), 7.31-7.29 (1H, m), 7.20-7.09 (1H, m), 6.94-6.91 (2H, m), 4.99-4.96 (1H, d J=9 Hz), 3.95-3.50 (4H, m), 2.19-1.80 (5H, m), 1.99 (1H, bs) ppm.

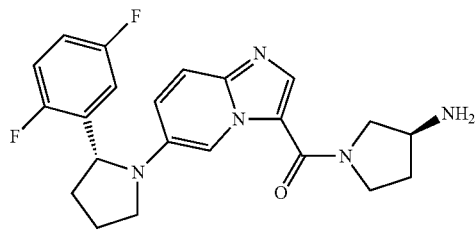 [SMILES: N[C@H]1CCN(C(=O)c2cnc3ccc(N4CCC[C@@H]4c4cc(F)ccc4F)cn23)C1]

The title compound (Example-20) was prepared by the method similar to that of Example-20 Isomer-II employing tert-butyl((S)-1-(6-((R)-2-(2,5-difluorophenyl)pyrrolidin-1-yl)imidazo[1,2-a]pyridine-3-carbonyl)pyrrolidin-3-yl)carbamate (Isomer-I) to afford ((S)-3-aminopyrrolidin-1-yl)(6-((R)-2-(2,5-difluorophenyl)pyrrolidin-1-yl)imidazo[1,2-a]pyridin-3-yl)methanone (Isomer-I) (0.055 g, 46.87% yield). MS (ESI): m/z 412.1 (M+H); $^1$H NMR (300 MHz, CDCl$_3$) δ 8.66 (1H, s), 7.99 (1H, bs), 7.54-7.51 (1H, d J=9 Hz), 7.35-7.27 (1H, m), 7.17-7.10 (1H, m), 6.95-6.91 (2H, m), 4.99-4.96 (1H, d J=9 Hz), 3.95-3.71 (3H, m), 3.59-3.49 (2H, m), 2.20-1.86 (4H, m), 1.80-1.65 (1H, bs) ppm.

Example 21

(S)-6-(2-(2,5-difluorophenyl)pyrrolidin-1-yl)-N-(2-hydroxyethyl)imidazo[1,2-a]pyridine-3-carboxamide (Isomer-I)

And (R)-6-(2-(2,5-difluorophenyl)pyrrolidin-1-yl)-N-(2-hydroxyethyl)imidazo[1,2-a]pyridine-3-carboxamide (Isomer-II)

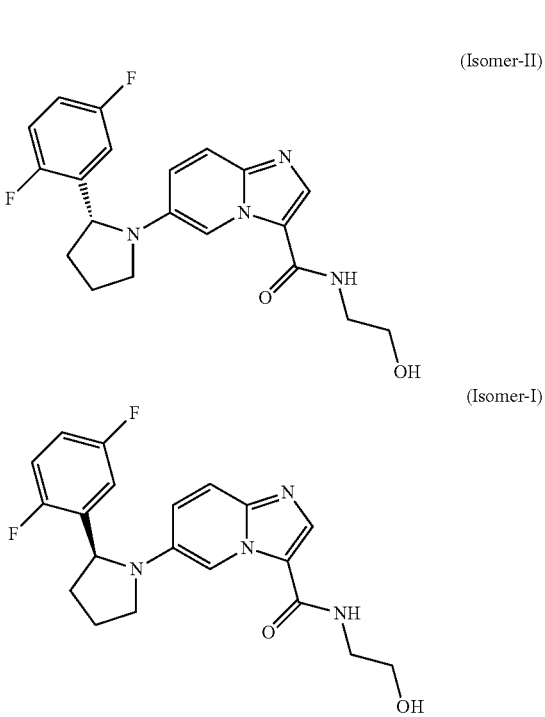

The title compounds (Example-21) were prepared by the method similar to that of Example-1 employing ethyl 2-aminoethanol to afford an enantiomeric mixture which was separated by chiral column employing Chiral pak ADH column and 60:40 Hexane:Ethanol isocratic solution as eluent to afford (R)-6-(2-(2,5-difluorophenyl)pyrrolidin-1-yl)-N-(2-hydroxyethyl)imidazo[1,2-a]pyridine-3-carboxamide (Isomer-II) MS (ESI): m/z 387.2 (M+H); $^1$H NMR (300 MHz, CD$_3$OD) δ 8.75-8.74 (1H, d, J=1.8 Hz), 8.09 (1H, s), 7.48-7.44 (1H, d, J=9.6 Hz), 7.21-7.13 (1H, m), 7.07-6.96 (2H, m), 6.91-6.85 (1H, m), 5.05-5.03 (1H, d, J=6.6 Hz), 3.83-3.77 (1H, m), 3.7-3.69 (2H, m), 3.51-3.44 (3H, m), 2.56-2.47 (1H, m), 2.14-2.03 (3H, m) ppm.

And (S)-6-(2-(2,5-difluorophenyl)pyrrolidin-1-yl)-N-(2-hydroxyethyl)imidazo[1,2-a]pyridine-3-carboxamide (Isomer I) MS (ESI): m/z 387.2 (M+H); $^1$H NMR (300 MHz, CD$_3$OD) δ 8.75-8.74 (1H, d, J=1.8 Hz), 8.09 (1H, s), 7.48-7.44 (1H, d, J=9.6 Hz), 7.21-7.13 (1H, m), 7.07-6.96 (2H, m), 6.91-6.85 (1H, m), 5.05-5.03 (1H, d, J=6.6 Hz), 3.83-3.77 (1H, m), 3.7-3.69 (2H, m), 3.51-3.44 (3H, m), 2.56-2.47 (1H, m), 2.14-2.03 (3H, m) ppm.

Example-22

(6-((R)-2-(2,5-difluorophenyl)pyrrolidin-1-yl)imidazo[1,2-a]pyridin-3-yl)(4-hydroxyazepan-1-yl)methanone

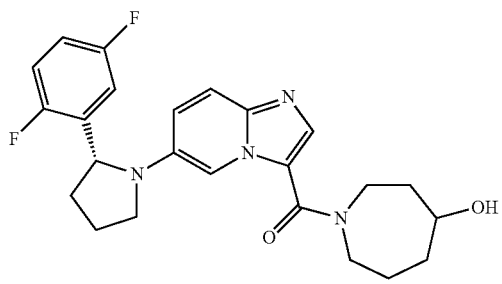 [SMILES: O=C(c1cnc2ccc(N3CCC[C@@H]3c3cc(F)ccc3F)cn12)N1CCCC(O)CC1]

The title compound was prepared by the method similar to that of Example-1 employing ethyl azepan-4-ol hydrochloride and Int-14 to afford (6-((R)-2-(2,5-difluorophenyl)pyrrolidin-1-yl)imidazo[1,2-a]pyridin-3-yl)(4-hydroxyazepan-1-yl)methanone. MS (ESI): m/z 441.2 (M+H); $^1$H NMR (300 MHz, DMSO-d$_6$) δ 8.22 (1H, bs), 7.79 (1H, s), 7.48 (1H, m), 7.3 (1H, m), 7.17 (1H, m), 6.99-6.85 (2H, m), 5.95-5.91 (1H, m), 4.57-4.56 (1H, d, J=3.6 Hz), 4.81-4.30 (6H, m), 2.45-2.22 (1H, m), 2.11-1.85 (5H, m), 1.80-1.45 (4H, m) ppm.

Example 23

6-((R)-2-(2,5-difluorophenyl)pyrrolidin-1-yl)-N-((1r,3S,5R,7S)-3-hydroxyadamantan-1-yl)imidazo[1,2-a]pyridine-3-carboxamide

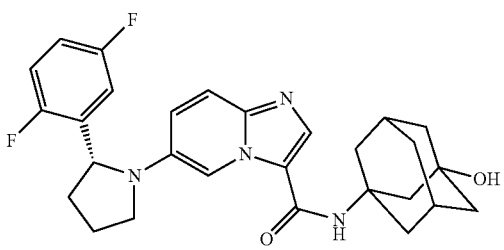 [SMILES: O=C(NC12CC3CC(CC(O)(C3)C1)C2)c1cnc2ccc(N3CCC[C@@H]3c3cc(F)ccc3F)cn12]

The title compound was prepared by the method similar to that of Example-22 employing (1s,3r,5R,7S)-3-aminoadamantan-1-ol to afford 6-((R)-2-(2,5-difluorophenyl)pyrrolidin-1-yl)-N-((1r,3S,5R,7S)-3-hydroxyadamantan-1-yl)imidazo[1,2-a]pyridine-3-carboxamide (0.04 g, 32% yield) MS (ESI): m/z 492.6 (M+H); $^1$H NMR (300 MHz, DMSO-d$_6$) δ 8.71-8.70 (1H, bs), 8.19 (1H, s), 7.45-7.42 (2H, m), 7.28-7.24 (1H, m), 7.13-7.09 (1H, m), 6.93-6.90 (1H, m), 6.81-6.77 (1H, m), 5.00-4.97 (1H, d, J=7.8 Hz), 4.49 (1H, s), 3.75-3.65 (1H, m), 2.44-2.40 (2H, m), 2.16 (2H, bs), 1.99-1.89 (9H, m), 1.55-1.46 (6H, m) ppm.

Example 24

(R)-6-(2-(2,5-difluorophenyl)pyrrolidin-1-yl)-N-(1,3-dihydroxy-2-methylpropan-2-yl)imidazo[1,2-a]pyridine-3-carboxamide

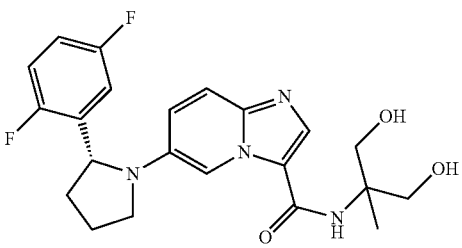 [SMILES: CC(CO)(CO)NC(=O)c1cnc2ccc(N3CCC[C@@H]3c3cc(F)ccc3F)cn12]

The title compound was prepared by the method similar to that of Example-22 by employing 2-amino-2-methylpropane-1,3-diol to afford (R)-6-(2-(2,5-difluorophenyl)pyrrolidin-1-yl)-N-(1,3-dihydroxy-2-methylpropan-2-yl)imidazo[1,2-a]pyridine-3-carboxamide (0.018 g, 14.4% yield). MS (ESI): m/z 430.6 (M+H); $^1$H NMR (300 MHz, DMSO-d$_6$) δ 8.73 (1H, bs), 8.38 (1H, s), 7.62-7.59 (1H, d J=9.9 Hz), 7.40-7.30 (2H, m), 7.20-7.05 (2H, m), 6.99-6.91 (1H, m), 5.08-5.01 (1H, d, J=2.1 Hz), 3.82-3.74 (2H, m), 3.65-3.54 (5H, m), 2.12-1.85 (4H, m), 1.28-1.23 (4H, m) ppm.

Example 25

6-((R)-2-(2,5-difluorophenyl)pyrrolidin-1-yl)-N—((S)-2,3-dihydroxypropyl)imidazo[1,2-a]pyridine-3-carboxamide

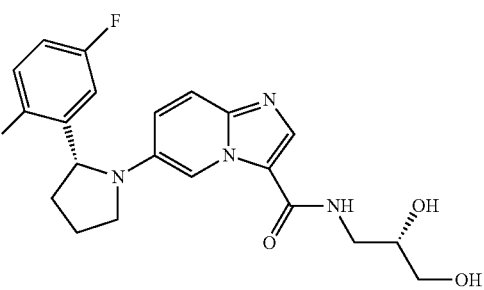

The title compound was prepared by the method similar to that of Example-22, employing (S)-3-aminopropane-1,2-diol to afford 6-((R)-2-(2,5-difluorophenyl)pyrrolidin-1-yl)-N—((S)-2,3-dihydroxypropyl)imidazo[1,2-a]pyridine-3-carboxamide (0.048 g, 39.66% yield) MS (ESI): m/z 416.6

(M+H); ¹H NMR (300 MHz, DMSO-d₆) δ 8.70 (1H, bs), 8.23-8.17 (2H, m), 7.50-7.47 (1H, d J=9.6 Hz), 7.29-7.26 (1H, m), 7.13-7.11 (1H, m), 6.91-6.88 (2H, m), 4.98-4.93 (1H, d J=13.8 Hz), 4.91 (1H, bs), 4.54 (1H, bs), 3.76-3.71 (1H, m), 3.59-3.49 (1H, m), 3.19-3.12 (2H, m), 2.44-2.41 (2H, m), 2.01-1.84 (3H, m) ppm.

Example 26

(R)-(6-(2-(2,5-difluorophenyl)pyrrolidin-1-yl)imidazo[1,2-a]pyridin-3-yl)(3-hydroxy-3-methylazetidin-1-yl)methanone

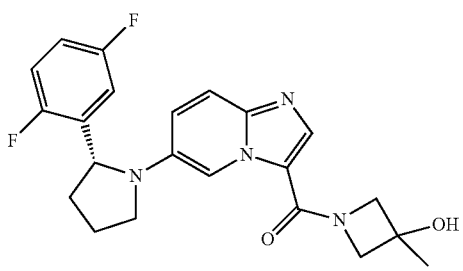 [SMILES: CC1(O)CN(C(=O)c2cnc3ccc(N4CCC[C@@H]4c4cc(F)ccc4F)cn23)C1]

The title compound was prepared by the method similar to that of Example-22 employing 3-methylazetidin-3-ol hydrochloride (int-46) to afford (R)-(6-(2-(2,5-difluorophenyl)pyrrolidin-1-yl)imidazo[1,2-a]pyridin-3-yl)(3-hydroxy-3-methylazetidin-1-yl)methanone (0.03 g, 25% yield). MS (ESI): m/z 412.6 (M+H); ¹H NMR (400 MHz, CDCl₃) δ 8.94-8.94 (1H, d J=2 Hz), 7.76 (1H, s), 7.45-7.43 (1H, d J=9.6 Hz), 7.07-7.02 (1H, m), 6.93-6.88 (1H, m), 6.82-6.75 (2H, m), 5.02-4.99 (1H, d J=8.4 Hz), 4.25 (3H, bs), 3.72-3.69 (1H, m), 3.42-3.36 (1H, m), 2.47-2.42 (1H, m), 2.09-2.02 (4H, m), 1.62 (3H, s) ppm.

Example 27

(R)-6-(2-(2,5-difluorophenyl)pyrrolidin-1-yl)-N-(piperidin-1-yl)imidazo[1,2-a]pyridine-3-carboxamide

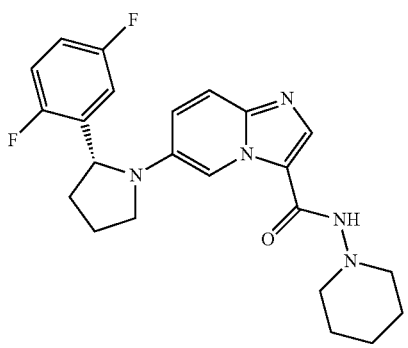 [SMILES: O=C(NN1CCCCC1)c1cnc2ccc(N3CCC[C@@H]3c3cc(F)ccc3F)cn12]

The title compound was prepared by the method similar to that of Example 22 employing 1-aminopiperidine hydrochloride to afford (R)-6-(2-(2,5-difluorophenyl)pyrrolidin-1-yl)-N-(piperidin-1-yl)imidazo[1,2-a]pyridine-3-carboxamide. MS (ESI): m/z 426.9 (M+H); ¹H NMR (400 MHz, DMSO-d₆) δ 9.19 (1H, bs), 8.67 (1H, bs), 8.13 (1H, bs), 7.53-7.51 (1H, d, J=10 Hz), 7.34-7.28 (1H, m), 7.16-7.10 (1H, m), 6.96-6.92 (1H, m), 4.97-4.95 (1H, d, J=8.0 Hz), 3.78-3.75 (1H, m), 2.82-2.67 (3H, m), 2.51-2.50 (1H, m), 2.07-1.96 (2H, m), 1.90-1.87 (1H, m), 1.60 (1H, bs), 1.35 (2H, bs) ppm.

Example 28

6-((R)-2-(2,5-difluorophenyl)pyrrolidin-1-yl)-N—((S)-1-hydroxypropan-2-yl)imidazo[1,2-a]pyridine-3-carboxamide

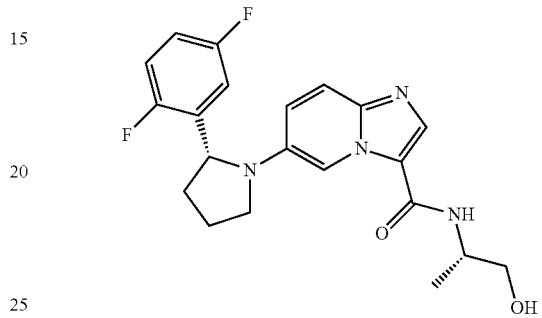

The title compound was prepared by the method similar to that of Example 22 employing (S)-2-amino-1-propanol to afford 6-((R)-2-(2,5-difluorophenyl)pyrrolidin-1-yl)-N—((S)-1-hydroxypropan-2-yl)imidazo[1,2-a]pyridine-3-carboxamide (0.04 g, 43% yield). MS (ESI): m/z 401.3 (M+H); ¹H NMR (300 MHz, CDCl₃) δ 8.79-8.78 (1H, d J=2.4 Hz), 7.89 (1H, m), 7.45-7.41 (1H, dd), 7.07-7.05 (1H, m), 6.96-6.85 (1H, m), 6.81-6.74 (2H, m), 5.02-4.99 (1H, d J=6.9 Hz), 4.39-4.32 (1H, m), 3.82-3.63 (3H, m), 3.41-3.39 (1H, m), 2.51-2.48 (1H, m), 2.10-2.04 (3H, m), 1.33-1.26 (3H, m) ppm.

Example 29

(R)-6-(2-(2,5-difluorophenyl)pyrrolidin-1-yl)-N-(1-hydroxy-2-methylpropan-2-yl)imidazo[1,2-a]pyridine-3-carboxamide

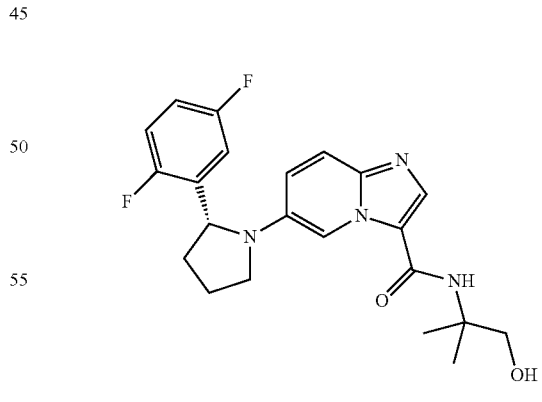

The title compound was prepared by the method similar to that of Example 22 employing 2-amino-2-methyl-1-propanol to afford (R)-6-(2-(2,5-difluorophenyl)pyrrolidin-1-yl)-N-(1-hydroxy-2-methylpropan-2-yl)imidazo[1,2-a]pyridine-3-carboxamide (0.034 g, 35.4% yield) MS (ESI): m/z 415.1 (M+H); ¹H NMR (300 MHz, CDCl₃) δ 8.73-8.73 (1H, d, J=2.4 Hz), 7.84 (1H, s), 7.45-7.42 (1H, d J=9.6 Hz), 7.10-7.02

(1H, m), 6.85-80 (1H, m), 6.79-6.75 (2H, m), 5.92 (1H, s), 5.01-4.99 (2H, d J=7.2 Hz), 3.70-3.69 (3H, m), 3.48-3.41 (1H, m), 2.52-2.48 (1H, m), 2.09-2.08 (3H, m), 1.43-1.42 (6H, 2s) ppm.

Example 30

(R)-6-(2-(2,5-difluorophenyl)pyrrolidin-1-yl)-N-(tetrahydro-2H-pyran-4-yl)imidazo[1,2-a]pyridine-3-carboxamide

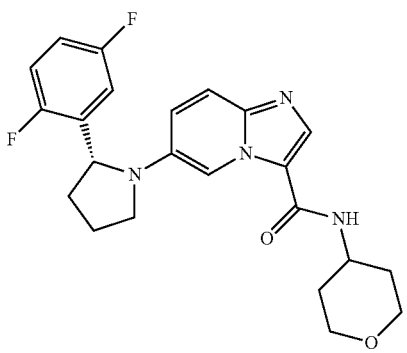 [SMILES: O=C(NC1CCOCC1)c1cnc2ccc(N3CCC[C@@H]3c3cc(F)ccc3F)cn12]

The title compound was prepared by the method similar to that of Example-22 employing tetrahydro-2H-pyran-4-amine to afford (R)-6-(2-(2,5-difluorophenyl)pyrrolidin-1-yl)-N-(tetrahydro-2H-pyran-4-yl)imidazo[1,2-a]pyridine-3-carboxamide.

MS (ESI): m/z 426.9 (M+H); $^1$H NMR (400 MHz, DMSO-$d_6$) δ 8.72-8.1 (1H, d, J=2.4 Hz), 8.20 (1H, s), 8.11-8.09 (1H, d, J=8.0 Hz), 7.52-7.50 (1H, d, J=9.6 Hz), 7.32-7.31 (1H, m), 7.13 (1H, m), 6.95-6.92 (2H, m), 4.97-4.95 (1H, d, J=8.0 Hz), 4.01 (1H, bs), 4.89-4.87 (1H, m), 3.75 (1H, t), 2.08-1.85 (3H, m), 1.75-1.72 (2H, m), 1.56-1.53 (2H, m) ppm.

Example 31

(R)—N-(tert-butylsulfonyl)-6-(2-(2,5-difluorophenyl)pyrrolidin-1-yl)imidazo[1,2-a]pyridine-3-carboxamide

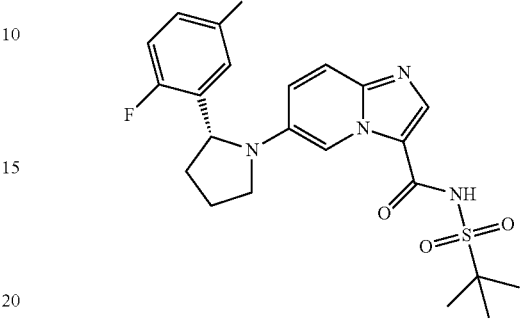

To a stirred solution of (R)-6-(2-(2,5-difluorophenyl)pyrrolidin-1-yl)imidazo[1,2-a]pyridine-3-carboxylic acid (Int-14) (0.2 g, 0.58 mmol) in dry DCM (10 mL) was added EDC.HCl (0.221 g, 1.16 mmol) and DMAP (0.14 g, 1.16 mmol) and stirred for 5 min, then added 2-methylpropane-2-sulfonamide (0.095 g, 0.69 mmol) and stirred for 48 h, after completion of reaction diluted with DCM and quenched with sat.KHSO4 solution and separate the organic layer. DCM was washed with water, brine and dried over $Na_2SO_4$ and concentration under vacuum to get crude. Crude was purified by prep HPLC method: column: 21.2*150*5 mm ZORBAX XDB D-18, mobile phase: A: $NH_4OAC$, B: CAN, Flow: 20 ml/min to afford title compound (R)—N-(tert-butylsulfonyl)-6-(2-(2,5-difluorophenyl)pyrrolidin-1-yl)imidazo[1,2-a]pyridine-3-carboxamide (0.054 g, 20.7% yield). MS (ESI): m/z 462.2 (M+H); $^1$H NMR (400 MHz, DMSO-$d_6$) δ 8.62 (1H, bs), 8.46 (1H, bs), 7.61-7.59 (1H, d J=9.6 Hz), 7.32-7.27 (1H, m), 7.15-7.10 (1H, m), 7.05-7.02 (1H, dd), 6.97-6.93 (1H, m), 5.02-5.00 (1H, d J=7.6 Hz), 3.79-3.76 (1H, m), 2.06-1.89 (3H, m), 1.39 (9H, s) ppm.

Following examples, Example 32 to Example 48 in table 2, were prepared by a method substantially similar to Example 31 using an appropriate amine in place of 2-methylpropane-2-sulfonamide.

TABLE 2

| Example No. and Structure | Name and Characteristics data |
|---|---|
| Example 32 | (R)-6-(2-(2,5-difluorophenyl)pyrrolidin-1-yl)-N-((1-methylcyclopropyl)sulfonyl)imidazo[1,2-a]pyridine-3-carboxamide; MS (ESI): m/z 461.2 (M + H); $^1$H NMR (400 MHz, DMSO-$d_6$) δ 8.6 (1H, bs), 8.45 (1H, s), 7.6 (1H, bs), 7.6 (1H, m), 7.2 (1H, m), 7.15 (1H, m), 6.91 (1H, m), 5.05 (1H, m), 3.6 (1H, m), 3.45 (1H, m), 3.8 (1H, m), 3.65 (2H, m), 2.8 (3H, s), 2.1-1.8 (3H, m) ppm. |

TABLE 2-continued

| Example No. and Structure | Name and Characteristics data |
|---|---|
| Example 33 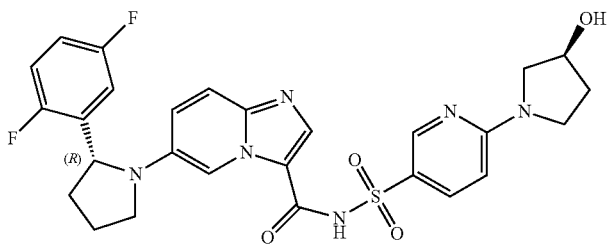 | 6-((R)-2-(2,5-difluorophenyl)pyrrolidin-1-yl)-N-((6-((S)-3-hydroxypyrrolidin-1-yl)pyridin-3-yl)sulfonyl)imidazo[1,2-a]pyridine-3-carboxamide; MS (ESI): m/z 569.2 (M + H); $^1$H NMR (400 MHz, DMSO-d$_6$) δ 12.1 (1H, bs), 8.56-8.41 (2H, m), 7.89-7.87 (1H, d, J = 8.8 Hz), 7.580-7.555 (2H, d, J = 10 Hz), 7.32-7.25 (1H, m), 7.10-7.05 (1H, m), 7.01-6.95 (1H, m), 6.95-6.85 (1H, m), 6.553-6.531 (1H, d, J = 8.8 Hz), 4.973-4.952 (1H, d, J = 8.4 Hz), 4.38 (1H, s), 3.75-3.65 (1H, m), 3.62-3.45 (3H, m), 2.06-1.87 (7H, m) ppm. |
| Example 34 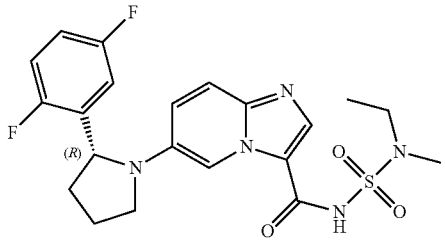 | (R)-6-(2-(2,5-difluorophenyl)pyrrolidin-1-yl)-N-(N-ethyl-N-methylsulfamoyl)imidazo[1,2-a]pyridine-3-carboxamide; MS (ESI): m/z 464.2 (M + H); $^1$H NMR (400 MHz, DMSO-d$_6$) δ 11.75 (1H, bs), 8.56-8.50 (2H, d), 7.68-7.65 (1H. D, J = 12 Hz), 7.32-7.27 (1H, m), 7.16-7.10 (2H, m), 6.98-6.93 (1H, m), 5.00-4.98 (1H, d, J = 7.2 Hz), 3.39-3.21 (4H, m), 2.87 (3H, s), 2.10-1.85 (3H, m), 1.09-1.06 (3H, t) ppm. |
| Example 35 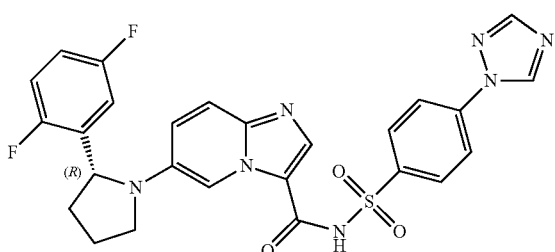 | (R)-N-((4-(1H-1,2,4-triazol-1-yl)phenyl)sulfonyl)-6-(2-(2,5-difluorophenyl)pyrrolidin-1-yl)imidazo[1,2-a]pyridine-3-carboxamide; MS (ESI): m/z 549.75 (M + H); $^1$H NMR (400 MHz, DMSO-d$_6$) δ 9.39 (1H, s), 8.85-8.65 (1H, bs), 8.38 (1H, s), 8.29 (1H, s), 8.05-8.02 (3H, m), 7.62-7.60 (1H, d, J = 9.6 Hz), 7.32-7.28 (1H, m), 7.17-7.03 (2H, m), 6.92-6.87 (1H, m), 5.01-4.99 (1H, d, J = 8 Hz), 3.74-3.68 (1H, m), 2.08-1.85 (3H, m) ppm. |
| Example 36 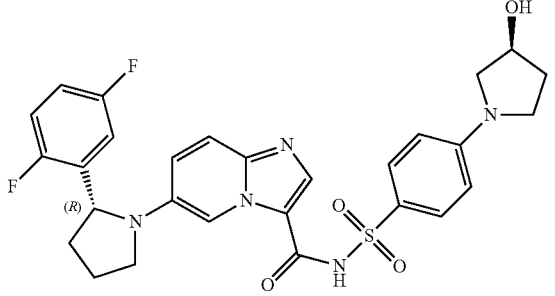 | 6-((R)-2-(2,5-difluorophenyl)pyrrolidin-1-yl)-N-((4-((S)-3-hydroxypyrrolidin-1-yl)phenyl)sulfonyl)imidazo[1,2-a]pyridine-3-carboxamide; MS (ESI): m/z 568.3 (M + H); $^1$H NMR (400 MHz, DMSO-d$_6$) δ 11.95 (1H, bs), 8.47-8.44 (2H, d, J = 12 Hz), 7.75-7.72 (2H, m), 7.54-7.58 (1H, m), 7.34-7.25 (1H, m), 7.13-7.07 (1H, m), 6.97-6.87 (2H, m), 6.62-6.58 (2H, d), 5.00-4.98 (1H, d, J = 7.2 Hz), 4.40 (1H, s), 3.75-3.72 (1H, m), 3.18-3.15 (2H, m), 2.08-1.73 (5H, m) ppm |

TABLE 2-continued

| Example No. and Structure | Name and Characteristics data |
|---|---|
| Example 37 | (R)-6-(2-(2,5-difluorophenyl)pyrrolidin-1-yl)-N-(N-methyl-N-propylsulfamoyl)imidazo[1,2-a]pyridine-3-carboxamide; MS (ESI): m/z 478.5 (M + H); $^1$H NMR (400 MHz, DMSO-d$_6$) δ 11.63 (1H, bs), 8.57 (1H, s), 8.42 (1H, s), 7.615-7.590 (1H, d J = 10 Hz), 7.30-7.25 (1H, m), 7.15-7.13 (1H, m), 7.07-6.96 (2H, m), 4.98-4.96 (1H, d, J = 7.6 Hz), 3.78 (1H, s), 3.18-3.15 (3H, m), 2.85 (3H, s), 2.04-1.88 (3H, m), 1.56-1.50 (2H, q), 0.88-0.84 (3H, t) ppm. |
| Example 38 | (R)-6-(2-(2,5-difluorophenyl)pyrrolidin-1-yl)-N-(N-(2-fluoroethyl)-N-methylsulfamoyl)imidazo[1,2-a]pyridine-3-carboxamide; MS (ESI): m/z 515.2 (M + H); $^1$H NMR (600 MHz, DMSO-d$_6$) δ 11.88 (1H, s), 8.74 (1H, s), 8.56 (1H, s), 7.65-7.64 (1H, d, J = 9.6 Hz), 7.52-7.51 (1H, d, J = 9.6 Hz), 6.51-6.45 (2H, m), 4.44-4.42 (3H, m), 4.30-4.22 (2H, m), 3.64-3.62 (1H, d, J = 11.4 Hz), 2.79-2.76 (1H, m), 1.90-1.78 (4H, m), 1.56-1.50 (8H, m), 1.28-1.27 (2H, m), 1.23-1.02 (2H, m) ppm. |
| Example 39 | (R)-6-(2-(2,5-difluorophenyl)pyrrolidin-1-yl)-N-(N-(2-methoxyethyl)-N-methylsulfamoyl)imidazo[1,2-a]pyridine-3-carboxamide; MS (ESI): m/z 494.4 (M + H); $^1$H NMR (600 MHz, DMSO-d$_6$) δ 11.70 (1H, s), 8.60 (1H, s), 8.47 (1H, s), 7.64-7.62 (1H, d, J = 9.6 Hz), 7.33-7.30 (1H, m), 7.17-7.14 (1H, m), 7.09-7.07 (1H m), 7.00-6.97 (1H, m), 5.00-4.99 (1H, d, J = 5.3 Hz), 3.82-3.79 (1H, m), 3.50-3.46 (2H, m), 3.22 (3H, s), 2.91 (1H, s), 2.08-1.98 (2H, m), 1.90-1.88 (1H, m) ppm. |
| Example 40 | (R)-6-(2-(2,5-difluorophenyl)pyrrolidin-1-yl)-N-(N-ethyl-N-(2-fluoroethyl)sulfamoyl)imidazo[1,2-a]pyridine-3-carboxamide; MS (ESI): m/z 496.5 (M + H); $^1$H NMR (400 MHz, DMSO-d$_6$) δ 11.80 (1H, s), 8.61 (1H, s), 8.39 (1H, s), 7.61-7.59 (1H, d, J = 10 Hz), 7.31-7.30 (1H, m), 7.14 (1H, m), 7.05-7.03 (1H, m), 6.98 (2H, m), 5.00-4.99 (1H, m), 3.79 (1H, m), 3.67-3.61 (3H, m), 2.05-2.03 (2H, m), 1.10-1.06 (3H, t) ppm. |

TABLE 2-continued

| Example No. and Structure | Name and Characteristics data |
|---|---|
| Example 41 | (R)-6-(2-(2,5-difluorophenyl)pyrrolidin-1-yl)-N-(N-methyl-N-(2,2,2-trifluoroethyl)sulfamoyl)imidazo[1,2-a]pyridine-3-carboxamide; MS (ESI): m/z 518.4 (M + H); $^1$H NMR (400 MHz, DMSO-d$_6$) δ 12.15 (1H, bs), 8.69 (1H, bs), 8.45 (1H, s), 7.66-7.63 (1H, d, J = 9.6 Hz), 7.28-7.12 (2H, m), 6.99 (1H, m), 5.00-4.99 (1H, m), 4.14-4.09 (2H, m), 3.79 (1H, m), 2.89 (3H, s), 2.05-1.90 (3H, m) ppm. |
| Example 42 | (R)-6-(2-(2,5-difluorophenyl)pyrrolidin-1-yl)-N-(N-(2-fluoro-2-methylpropyl)-N-methylsulfamoyl)imidazo[1,2-a]pyridine-3-carboxamide; MS (ESI): m/z 510.3 (M + H); $^1$H NMR (400 MHz, DMSO-d$_6$) δ 11.80 (1H, bs), 8.57 (1H, bs), 8.47 (1H, s), 7.64-7.62 (1H, d, J = 9.6 Hz), 7.32-7.28 (2H, m), 7.11-7.08 (2H, m), 6.99 (1H, m), 5.00-4.99 (1H, m), 3.82 (1H, m), 3.52-3.42 (3H, m), 2.88 (3H, s), 2.10-1.89 (3H, m), 1.41 (3H, s), 1.36 (3H, s) ppm. |
| Example 43 | (R)-6-(2-(2,5-difluorophenyl)pyrrolidin-1-yl)-N-(N-methyl-N-(pyridin-3-yl)sulfamoyl)imidazo[1,2-a]pyridine-3-carboxamide; MS (ESI): m/z 513.4 (M + H); $^1$H NMR (400 MHz, DMSO-d$_6$) δ 8.77 (1H, bs), 8.63 (1H, s), 8.36 (1H, s), 7.82 (1H, m), 7.67-7.65 (1H, d, J = 9.6 Hz), 7.45-7.42 (1H, m), 7.33-7.31 (1H, m), 7.21-7.14 (2H, m), 6.97-6.96 (1H, m), 5.02-5.00 (1H, m), 3.81-3.78 (1H, m), 3.40-3.35 (3H, m), 2.06-1.97 (2H, m), 1.93-1.90 (1H, m) ppm. |
| Example 44 | (R)-N-(N-(cyclopropylmethyl)-N-(pyridin-3-yl)sulfamoyl)-6-(2-(2,5-difluorophenyl)pyrrolidin-1-yl)imidazo[1,2-a]pyridine-3-carboxamide; MS (ESI): m/z 553.2 (M + H); $^1$H NMR (400 MHz, DMSO-d$_6$) δ 8.69 (1H, bs), 8.54 (1H, s), 8.50 (1H, s), 8.34 (1H, m), 7.75-7.73 (1H, dd), 7.65-7.63 (1H, d, J = 9.6 Hz), 7.46-7.43 (1H, m), 7.30-7.28 (1H, m), 7.15-7.13 (2H, m), 7.00 (1H, m), 5.01-5.09 (1H, m), 3.82-3.72 (3H, m), 2.10-1.90 (3H, m), 0.88 (1H, m), 0.40-0.36 (2H, m) ppm. |
| Example 45 | (R)-6-(2-(2,5-difluorophenyl)pyrrolidin-1-yl)-N-(N-methyl-N-(pyrazin-2-yl)sulfamoyl)imidazo[1,2-a]pyridine-3-carboxamide; MS (ESI): m/z 514.1 (M + H); $^1$H NMR (400 MHz, DMSO-d$_6$): δ 9.01-9.00 (2H, m J = 1.6 Hz), 8.33 (1H, s), 8.24 (1H, s), 8.05 (1H, s), 7.66-7.64 (1H, d j = 8 Hz), 7.29-7.12 (3H, m), 5.04-5.01 (1H, d, J = 12 Hz), 3.74 (1H, t), 3.40 (3H, s), 2.52-2.46 (1H, m), 1.91 (3H, m) ppm. |

TABLE 2-continued

| Example No. and Structure | Name and Characteristics data |
|---|---|
| Example 46 | (R)-N-((6-(1H-imidazol-1-yl)pyridin-3-yl)sulfonyl)-6-(2-(2,5-difluorophenyl)pyrrolidin-1-yl)imidazo[1,2-a]pyridine-3-carboxamide: MS (ESI): m/z 548.00 (M + H); $^1$H NMR (400 MHz, DMSO-$d_6$) δ 8.93 (1H, s), 8.88-8.87 (1H, s), 8.65 (1H, s), 8.38-8.35 (1H, dd), 8.22 (1H, s), 8.04 (1H, s), 7.92-7.90 (1H, d, J = 8.8 Hz) 7.61-7.59 (1H, d, J = 10 Hz), 7.31-7.30 (1H, m), 7.18 (1H, s), 7.13-7.11 (1H, d, J = 9.2 Hz), 7.05 (1H, m), 6.91 (1H, m), 5.02-5.00 (1H, d), 3.74 (1H, t), 3.09 (1H, s), 2.50-2.46 (1H, m), 2.10-2.00 (1H, m), 2.0-1.9 (1H, m), 1.90 (1H, m) ppm. |
| Example 47 | (R)-6-(2-(2,5-difluorophenyl)pyrrolidin-1-yl)-N-(N-methyl-N-(pyridin-2-yl)sulfamoyl)imidazo[1,2-a]pyridine-3-carboxamide; MS (ESI): m/z 513.45 (M + H); $^1$H NMR (400 MHz, DMSO-$d_6$) δ 8.8 (1H, bs), 8.34 (1H, s), 8.26 (1H, bs), 7.65-7.60 (2H, m), 7.27 (1H, m), 7.13-7.11 (2H, d, J = 8.4 Hz), 6.92 (2H, m), 5.01-4.99 (1H, d), 3.73 (1H, m), 3.47 (3H, s), 2.03-1.99 (4H, m) ppm. |
| Example 48 | (R)-6-(2-(2,5-difluorophenyl)pyrrolidin-1-yl)-N-(N-methyl-N-(thiazol-2-yl)sulfamoyl)imidazo[1,2-a]pyridine-3-carboxamide; MS (ESI): m/z 519.2 (M + H); $^1$H NMR (400 MHz, DMSO-$d_6$) δ 8.95 (1H, s), 8.21 (1H, s), 7.62-7.58 (1H, m), 7.26 (2H, m), 7.15 (2H, m), 7.01 (1H, m), 6.95 (1H, m), 5.10 (1H, d), 3.73 (1H, t), 2.18-1.82 (3H, m) ppm. |

Example 49

6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide (isomer II) and 6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide (isomer I)

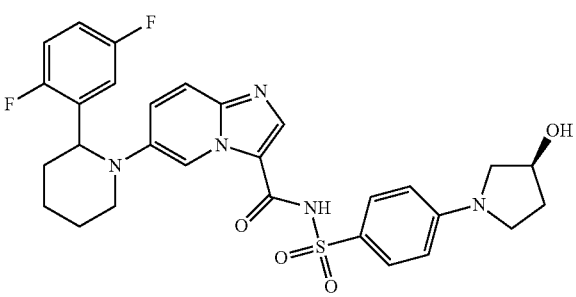 [SMILES: O=C(NS(=O)(=O)c1ccc(N2CC[C@H](O)C2)cc1)c1cnc2ccc(N3CCCCC3c3cc(F)ccc3F)cn12]

The title compound was prepared by the method similar to that of Example 31 employing 4-(3-hydroxypyrrolidin-1-yl)benzene sulfonamide (Int-51) and 6-(2-(2,5-difluorophenyl)piperidin-1-yl)imidazo[1,2-a]pyridine-3-carboxylic acid (Int 23) to afford an enantiomeric mixture which was purified by column chromatography using CHIRALPAK AD-H column and n-HEXANE:ETHANOL, 80:20 isocratic solution as eluent to afford 6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide (0.012 g) (Isomer-II) MS (ESI): m/z 582.2 (M+H); $^1$H NMR (400 MHz, DMSO-$d_6$) δ 12.00 (1H, S), 8.83 (1H, s), 8.4 (1H, s), 7.76-7.74 (2H, m), 7.58-7.56 (1H, m), 7.46-7.43 (1H, m), 7.07-6.99 (2H, m), 6.91-6.90 (1H, m), 6.65-6.62 (1H, m), 5.04-5.03 (1H, d), 4.42 (2H, bs), 3.50-3.38 (4H, m), 3.28-3.20 (1H, m), 2.90-2.85 (1H, m), 2.06-2.03 (1H, m), 1.91-1.88 (3H, m), 1.76-1.67 (1H, m), 1.64-1.53 (1H, m) ppm.

And 6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide (Isomer-I)

MS (ESI): m/z 582.2 (M+H); $^1$H NMR (400 MHz, DMSO-$d_6$) δ 12.00 (1H, S), 8.80 (1H, s), 8.4 (1H, s), 7.77-7.74 (2H, m), 7.59-7.57 (1H, m), 7.47-7.45 (1H, m), 7.07-7.05 (2H, m), 7.04-7.01 (1H, m), 6.66-6.63 (2H, m), 5.04-5.03 (1H, d), 4.44-4.42 (2H, bs), 3.49-3.38 (4H, m), 3.28-3.18 (1H, m), 2.90-2.85 (1H, m), 2.06-2.03 (1H, m), 2.02-1.95 (2H, m), 1.88-1.64 (3H, m), 1.60-1.53 (1H, m), 1.40-1.35 (1H, m) ppm.

Example 50

6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide

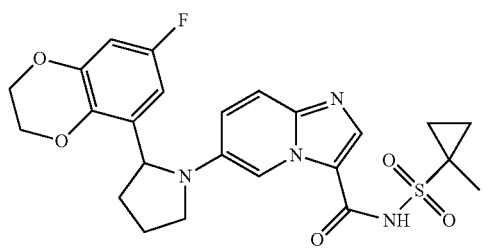 [SMILES: CC1(S(=O)(=O)NC(=O)c2cnc3ccc(N4CCCC4c4cc(F)cc5c4OCCO5)cn23)CC1]

The title compound was prepared by the method similar to that of Example 31 employing 1-Methylcyclopropane-1-sulfonamide (int-50) and 6-(2-(7-fluoro-2,3-dihydrobenzo[b][1,4]dioxin-5-yl)pyrrolidin-1-yl)imidazo[1,2-a]pyridine-3-carboxylic acid (Int 38) to afford an enantiomeric mixture which was separated by chiral chromatography using CHIRALPAK AD-H column and n-HEXANE:ETHANOL, 60:40 Isocratic solution as eluent to afford 6-(2-(7-fluoro-2,3-dihydrobenzo[b][1,4]dioxin-5-yl)pyrrolidin-1-yl)-N-((l-methylcyclopropyl)sulfonyl)imidazo[1,2-a]pyridine-3-carboxamide (Isomer-I)

MS (ESI): m/z 501.1 (M+H); $^1$H NMR (400 MHz, DMSO-d$_6$) δ 11.70 (1H, s), 8.54-8.45 (2H, d, J=9.6 Hz), 7.62-7.60 (1H, d), 7.06-7.03 (1H, m), 6.65-6.62 (1H, m), 6.41-6.38 (1H, m), 4.93-4.91 (1H, m), 4.45-4.37 (4H, m), 3.79 (1H, bs), 2.41-2.33 (1H, m), 2.02-2.01 (2H, m), m), 1.85 (1H, m), 1.47-1.35 (5H, m), 1.34-1.32 (1H, m), 1.28-1.23 (3H, m), 0.94-0.85 (2H, m).

And 6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide. (Isomer-I)

MS (ESI): m/z 501.1 (M+H); $^1$H NMR (400 MHz, DMSO-d$_6$) δ 11.70 (1H, s), 8.56 (1H, s), 8.42 (1H, s), 7.62-7.59 (1H, d), 7.05-7.02 (1H, m), 6.65-6.62 (1H, m), 6.41-6.38 (1H, m), 4.93-4.91 (1H, m), 4.45-4.39 (5H, m), 3.80-3.77 (1H, m), 2.44-2.33 (2H, m), 2.01-1.87 (2H, m), 1.8-1.83 (1H, m), 1.52-1.40 (5H, m), 1.35-1.34 (1H, m), 1.28-1.23 (4H, m), 0.93-0.84 (2H, m) ppm.

Example 51

6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide. (Isomer II) and 6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide. (Isomer-I)

(Isomer-II)

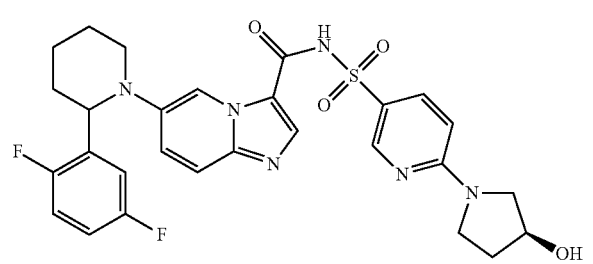

(Isomer-I)

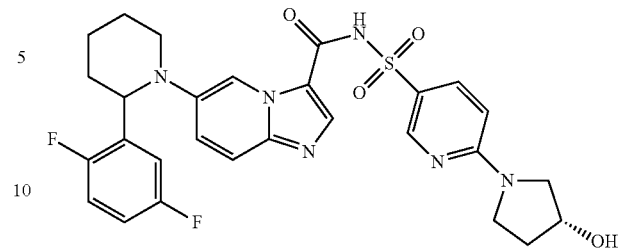

The title compounds was prepared by the method similar to that of Example 31 employing (S)-6-(3-hydroxypyrrolidin-1-yl)pyridine-3-sulfonamide (int-52) and 6-(2-(2,5-difluorophenyl)piperidin-1-yl)imidazo[1,2-a]pyridine-3-carboxylic acid (Int-23) to afford an enantiomeric mixture, which was purified by chiral chromatography employing CHIRALPAK AD-H column with n-HEXANE:ETHANOL, 80:20 Isocratic solution as eluent.

(Isomer II) MS (ESI): m/z 583.2 (M+H); $^1$H NMR (600 MHz, DMSO-d$_6$) δ 12.30 (1H, s), 8.87 (1H, s), 8.62 (1H, s), 8.39 (1H, s), 7.94-7.92 (1H, m), 7.59-7.58 (1H, m), 7.48-7.46 (1H, d, J=10 Hz), 7.06-7.02 (2H, m), 6.92-6.89 (1H, m), 6.59-6.58 (1H, d, J=8.0 Hz), 5.06 (1H, s), 4.44-4.42 (2H, d, J=9.6 Hz), 3.56-3.55 (2H, m), 3.46-3.42 (1H, m), 2.89-2.86 (1H, t), 2.03 (2H, m), 1.91-1.89 (3H, m), 1.79-1.76 (4H, m), 1.68-1.36 (2H, m) ppm.

And (Isomer-I) MS (ESI): m/z 583.2 (M+H); $^1$H NMR (600 MHz, DMSO-d$_6$) δ 12.30 (1H, s), 8.82 (1H, s), 8.63 (1H, s), 8.45 (1H, s), 7.94-7.92 (1H, d, J=9.6 Hz), 7.61-7.60 (1H, d, J=12 Hz), 7.51-7.49 (1H, d, J=10 Hz), 7.06-7.01 (2H, m), 6.91-6.88 (1H, m), 6.61-6.60 (1H, d, J=10 Hz), 5.06 (1H, s), 4.44-4.43 (2H, d, J=2.6 Hz), 3.55-3.38 (4H, m), 2.89-2.86 (1H, t), 2.03 (1H, s), 1.94-1.89 (2H, m), 1.81-1.76 (4H, m), 1.68-1.64 (1H, m), 1.55-1.51 (1H, m) ppm.

Example 52

6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide. (Isomer-II)

6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide (Isomer I)

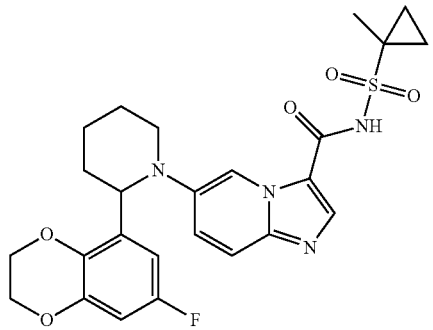 [SMILES: CC1(S(=O)(=O)NC(=O)c2cnc3ccc(N4CCCCC4c4cc(F)cc5c4OCCO5)cn23)CC1]

The title compound was prepared by the method similar to that of Example 31 employing 6-(2-(7-fluoro-2,3-dihydrobenzo[b][1,4]dioxin-5-yl)piperidin-1-yl)imidazo[1,2-a]pyridine-3-carboxylic acid (Int 42) and 1-Methylcyclopropane-1-sulfonamide (int-50) to afford an enantiomeric mixture, which was purified by chiral chromatography employing CHIRALPAK AD-H column with n-HEXANE:ETHANOL, 60:40 Isocratic solution as eluent. MS (ESI): m/z 515.2 (M+H); $^1$H NMR (600 MHz, DMSO-d$_6$) δ 11.88 (1H, s), 8.74 (1H, s), 8.55 (1H, s), 7.65-7.64 (1H, d, J=10.4 Hz), 7.52-7.50 (1H, d, J=10.4 Hz), 6.51-6.45 (2H, m), 4.45-4.42 (3H, m), 4.30-4.22 (2H, m), 3.64-3.62 (1H, d), 2.79-2.73 (1H, m), 1.90-1.78 (4H, m), 1.57-1.53 (8H, m), 1.23-1.03 (2H, m) ppm.

Isomer-I

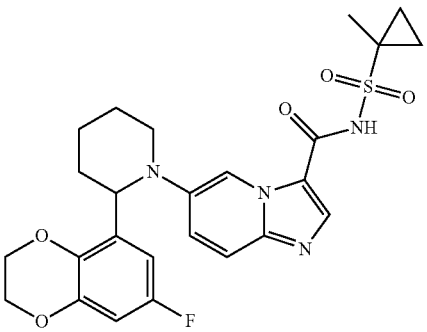 [SMILES: CC1(S(=O)(=O)NC(=O)c2cnc3ccc(N4CCCCC4c4cc(F)cc5c4OCCO5)cn23)CC1]

MS (ESI): m/z 515.2 (M+H); $^1$H NMR (600 MHz, DMSO-d$_6$) δ 11.88 (1H, s), 8.74 (1H, s), 8.56 (1H, s), 7.65-7.64 (1H, d, J=9.6 Hz), 7.52-7.51 (1H, d, J=9.6 Hz), 6.51-6.45 (2H, m), 4.44-4.42 (3H, m), 4.30-4.22 (2H, m), 3.64-3.62 (1H, d, J=11.4 Hz), 2.79-2.76 (1H, m), 1.90-1.78 (4H, m), 1.56-1.50 (8H, m), 1.28-1.27 (2H, m), 1.23-1.02 (2H, m) ppm.

The following Examples 53 to 68, in table 3 were prepared by the method substantially similar to that of Example 31 by employing appropriate carboxylic acid and sulfonamide or sulfamide.

TABLE 3

| Example No. and Structure | Name & Characteristics data |
|---|---|
| Example 53 | (R)-6-(2-(5-methoxyphenyl)pyrrolidin-1-yl)-N-(N-methyl-N-propylsulfamoyl)imidazo[1,2-a]pyridine-3-carboxamide; MS (ESI): m/z 490.4 (M + H); $^1$H NMR (400 MHz, DMSO-d$_6$): δ 8.58 (1H, s), 8.52 (1H, s), 7.71-7.69 (1H, d J = 8 Hz), 7.16-7.05 (3H, m), 6.81-6.79 (1H, d), 4.98-4.96 (1H, d J = 8 Hz), 3.90 (3H, s), 3.82 (2H, m), 3.40-3.16 (4H, m), 2.86 (3H, s), 2.09-1.98 (3H, m), 1.57-1.52 (2H, q), 0.88-0.85 (3H, t). |
| Example 54 | (R)-6-(2-(5-fluoro-2-methoxyphenyl)pyrrolidin-1-yl)-N-(N-(2-fluoro-2-methylpropyl)-N-methylsulfamoyl)imidazo[1,2-a]pyridine-2-carboxamide; MS (ESI): m/z 522.1 (M + H); $^1$H NMR (400 MHz, DMSO-d$_6$) δ 8.58 (1H, s), 8.51 (1H, s), 7.71-7.68 (1H, d J = 9.6 Hz), 7.16-7.15 (1H, d, J = 9.6 Hz), 7.08-7.05 (1H, m), 6.82-6.79 (1H, d, J = 9.2 Hz), 4.98-4.96 (1H, d, J = 7.6 Hz), 3.91 (3H, s), 3.84-3.77 (1H, m), 3.55-3.44 (5H, m), 2.89 (3H, s) 2.50-2.40 (1H, m), 2.03-1.99 (2H, m), 1.83 (1H, m), 1.41-1.35 (6H, m). |

TABLE 3-continued

| Example No. and Structure | Name & Characteristics data |
|---|---|
| Example 55 | (R)-N-(N-ethyl-N-methylsulfamoyl)-6-(2-(5-fluoro-2-methoxyphenyl)pyrrolidin-1-yl)imidazo[1,2-a]pyridine-3-carboxamide; MS (ESI): m/z 476.1 (M + H); $^1$H NMR (400 MHz, DMSO-d$_6$) δ 11.8 (1H, bs), 8.57-8.53 (2H, d J = 14.4 Hz 7.70-7.67 (1H, d J = 10 Hz), 7.08-7.07 (3H, m), 6.80 (1H, m), 4.95 (1H, m), 3.90 (3H, s), 3.81 (2H, m), 3.39-3.35 (2H, m), 3.31-3.27 (3H, m), 2.89 (3H, s) 2.88 (3H, s), 2.4 (1H, m), 2.05 (2H, m), 1.83 (1H, m), 1.12-1.09 (3H, m). |
| Example 56 | (R)-6-(2-(5-fluoro-2-methoxyphenyl)pyrrolidin-1-yl)-N-(N-(2-fluoroethyl)-N-methylsulfamoyl)imidazo[1,2-a]pyridine-3-carboxamide; MS (ESI): m/z 494.1 (M + H); $^1$H NMR (400 MHz, DMSO-d$_6$): δ 11.7 (1H, bs), 8.53 (1H, s), 8.84 (1H, s), 7.61-7.59 (1H, d J = 9.6 Hz), 7.08-7.03 (2H, m), 6.99-6.96 (1H, m), 6.81-6.78 (1H, m), 4.96-4.94 (1H, d), 4.66-4.64 (1H, t), 4.54-4.52 (1H, t), 3.90 (3H, s), 3.79 (1H, t), 3.63-3.62 (1H, d), 3.56-3.55 (1H, d), 2.90 (3H, s), 2.39 (1H, m), 2.01-2.00 (2H, m), 2.80 (1H, m). |
| Example 57 | N-(N-ethyl-N-methylsulfamoyl)-6-((2R,4S)-4-fluoro-2-(5-fluoro-2-(2-fluoroethoxy)phenyl)pyrrolidin-1-yl)imidazo[1,2-a]pyridine-3-carboxamide; MS (ESI): m/z 526.3 (M + H). $^1$H NMR (400 MHz, DMSO-d$_6$): δ 11.6 (1H, s), 8.47-8.42 (2H, d J = 18.8 Hz), 7.6-7.59 (1H, d J = 10 Hz), 7.17-7.15 (1H, d J = 8.8 Hz), 7.10-7.02 (3H, m), 5.55-5.42 (1H, m), 5.24-5.10 (1H, t), 4.90-4.86 (1H, m), 4.74 (1H, m), 4.39-4.31 (2H, m), 4.23-4.11 (1H, m), 3.75-3.66 (1H, m), 3.29-3.23 (2H, m), 2.86-2.79 (2H, m), 2.78-2.69 (1H, m), 2.20-1.99 (2H, m), 1.23-1.08 (3H, s). |
| Example 58 | N-(tert-butylsulfonyl)-6-((2R,4S)-4-fluoro-2-(5-fluoro-2-(2-fluoroethoxy)phenyl)pyrrolidin-1-yl)imidazo[1,2-a]pyridine-3-carboxamide; MS (ESI): m/z 525.3 (M + H). $^1$H NMR (400 MHz, DMSO-d$_6$) δ 11.3 (1H, s), 8.53-8.45 (2H, d J = 2 Hz), 7.61-7.59 (1H, d J = 6), 7.16-7.13 (1H, d, J = 6.2 Hz), 7.07-7.00 (3H, m), 5.55 (1H, s), 5.42 (1H, s), 5.17-5.03 (1H, t), 4.92-4.86 (1H, m), 4.83-4.71 (1H, m), 4.71 (1H, s), 4.41 (1H, s), 4.33-4.13 (1H, m), 3.73-3.64 (1H, m), 2.78-2.67 (2H, m), 2.33-2.05 (2H, m), 1.39 (9H, s). |

TABLE 3-continued

| Example No. and Structure | Name & Characteristics data |
| --- | --- |
| Example 59 | N-(tert-butylsulfonyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide; MS (ESI): m/z 550.0 (M + H); $^1$H NMR (400 MHz, DMSO-d$_6$) δ 11.3 (1H, bs), 8.50-8.43 (1H, d J = 2.6 Hz), 7.66-7.63 (1H, d, J = 9.6 Hz), 7.20-7.18 (1H, d, J = 9.2 Hz), 7.02 (3H, m), 5.62-5.49 (1H, m), 5.15-5.06 (2H, m), 3.93-3.90 (1H, m), 3.80-3.78 (2H, m), 3.72-3.69 (3H, m), 2.67 (1H, m) 2.29-2.22 (2H, m), 2.21-1.96 (1H, m), 1.38 (9H, s). |
| Example 60 | N-(N-ethyl-N-methylsulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide; MS (ESI): m/z 476.1 (M + H); $^1$H NMR (400 MHz, DMSO-d$_6$) δ 11.7 (1H, bs), 8.52 (1H, s), 8.45-8.44 (1H, d J = 2.0), 7.70-7.68 (1H, d, J = 8 Hz), 7.29-7.85 (1H, m), 7.05-7.00 (3H, m), 5.49-5.47 (1H, m), 5.15 (1H, m), 5.09-5.04 (1H, m), 4.25-4.09 (1H, m), 3.90-3.88 (2H, m), 3.81-3.76 (4H, m), 3.30-3.24 (3H, m), 2.87 (3H, s) 2.86-2.69 (1H, m), 2.32-1.95 (3H, m), 1.11-1.07 (3H, t). |
| Example 61 | 6-((2R,4S)-4-fluoro-2-(5-fluoro-2-(((R)-tetrahydrofuran-3-yl)oxy)phenyl)pyrrolidin-1-yl)-N-((1-methylcyclopropyl)sulfonyl)imidazo[1,2-a]pyridine-3-carboxamide; MS (ESI): m/z 529.2 (M + H); $^1$H NMR (400 MHz, DMSO-d$_6$) δ 11.7 (1H, bs), 8.62 (1H, bs), 8.32 (1H, bs), 7.577-7.553 (1H, d J = 9.6 Hz), 7.06-7.02 (2H, m), 6.95-6.78 (3H, m), 5.17 (1H, m), 4.907-4.887 (1H, d J = 8 Hz), 3.96-3.90 (2H, m), 3.84-3.77 (3H, m), 3.09 (1H, m), 2.29-2.23 (2H, m), 2.18-2.00 (3H, m), 1.45-1.39 (3H, s), 1.23 (2H, s), 0.85-0.83 (2H, bs). |
| Example 62 | 6-((2R,4S)-4-fluoro-2-(5-fluoro-2-(((R)-tetrahydrofuran-3-yl)oxy)phenyl)pyrrolidin-1-yl)-N-(N-(2-fluoroethyl)-N-methylsulfamoyl)imidazo[1,2-a]pyridine-3-carboxamide; MS (ESI): m/z 568.3 (M + H); $^1$H NMR (400 MHz, DMSO-d$_6$) δ 11.8 (1H, bs), 8.50 (1H, s), 8.44 (1H), 7.69-7.66 (1H, d J = 10 Hz), 7.25-7.22 (1H, d J = 11.2 Hz), 7.04-7.00 (3H, m), 5.54-5.41 (1H, m), 5.14-5.06 (1H, bs), 5.04-5.02 (1H, t), 4.66-4.63 (1H, t), 4.54-4.52 (1H, t), 4.18-4.08 (1H, m), 3.92-3.88 (2H, m), 3.83-3.81 (3H, m), 3.71-3.57 (2H, m), 2.89 (3H, s) 2.75-2.67 (1H, m), 2.33-2.02 (4H, m). |

TABLE 3-continued

| Example No. and Structure | Name & Characteristics data |
| --- | --- |
| Example 63 | N-(N-ethyl-N-methylsulfamoyl)-6-(2-(5-fluoro-2-(((R)-tetrahydrofuran-3-yl)oxy)phenyl)pyrrolidin-1-yl)imidazo[1,2-a]pyridine-3-carboxamide; (Peak-I): MS (ESI): m/z 533.0 (M + H); $^1$H NMR (400 MHz, DMSO-$d_6$) δ 11.8 (1H, bs), 8.56 (1H, s), 8.47 (1H, s), 7.70-7.68 (1H, d J = 9.6 Hz), 7.16-7.13 (1H, d J = 9.2 Hz), 7.07-7.03 (2H, m), 6.80-6.78 (1H, d J = 8.4 Hz), 5.16 (1H, s), 4.90-4.88 (1H, d), 3.96-3.91 (3H, m), 3.89-3.81 (4H, m), 3.37-3.35 (2H, m), 3.27-3.25 (3H, m), 2.85 (3H, s), 2.42-2.40 (1H. m), 2.23-2.21 (2H, m), 2.00 (2H, m), 1.81 (1H, m), 1.11-1.07 (3H, t). |
| Example 64 | N-(N-ethyl-N-methylsulfamoyl)-6-(2-(5-fluoro-2-(((R)-tetrahydrofuran-3-yl)oxy)phenyl)pyrrolidin-1-yl)imidazo[1,2-a]pyridine-3-carboxamide; (Peak-II): MS (ESI): m/z 532.6 (M + H); $^1$H NMR (400 MHz, DMSO-$d_6$) δ 11.75 (1H, bs), 8.56 (1H, s), 8.52 (1H, s), 7.69-7.67 (1H, d J = 10 Hz), 7.12-7.03 (3H, m), 6.81-6.79 (1H, d J = 9.6 Hz), 5.14 (1H, s), 4.93-4.91 (1H, d), 3.97-3.79 (9H, m), 3.39-3.35 (4H, m), 3.30-3.27 (3H, m), 2.87 (3H, s), 2.27-2.22 (1H. m), 2.02-1.99 (3H, m), 1.82 (1H, m), 1.12-1.08 (3H, t). |
| Example 65 | N-(tert-butylsulfamoyl)-6-(2-(5-fluoro-2-(((R)-tetrahydrofuran-3-yl)oxy)phenyl)pyrrolidin-1-yl)imidazo[1,2-a]pyridine-3-carboxamide; (Peak-I): MS (ESI): m/z 532.00 (M + H); $^1$H NMR (400 MHz, DMSO-$d_6$) δ 11.38 (1H, bs), 8.52-8.49 (2H, m), 7.66-7.64 (1H, d J = 10.0 Hz), 7.07-7.02 (3H, m), 6.80-6.78 (1H, d J = 4.0 Hz), 5.17 (1H, s), 4.91-4.89 (1H, d), 3.92-3.81 (6H, m), 2.22-2.19 (2H, m), 2.00-1.80 (3H, m), 1.39 (9H, s). |
| Example 66 | N-(tert-butylsulfonyl)-6-(2-(5-fluoro-2-(((R)-tetrahydrofuran-3-yl)oxy)phenyl)pyrrolidin-1-yl)imidazo[1,2-a]pyridine-3-carboxamide; (Peak-II): MS (ESI): m/z 531.55 (M + H); $^1$H NMR (400 MHz, DMSO-$d_6$) δ 11.4 (1H, bs), 8.72 (1H, bs) 8.16 (H, bs), 7.51-7.49 (1H, d J = 8.4 Hz), 7.04 (2H, bs), 6.77 (2H, m), 5.14 (1H, s), 4.93 (1H, bs), 3.95-3.70 (6H, m), 2.33-2.24 (2H, m), 2.00-1.82 (5H, m), 1.36 (9H, s). |

TABLE 3-continued

| Example No. and Structure | Name & Characteristics data |
| --- | --- |
| Example 67 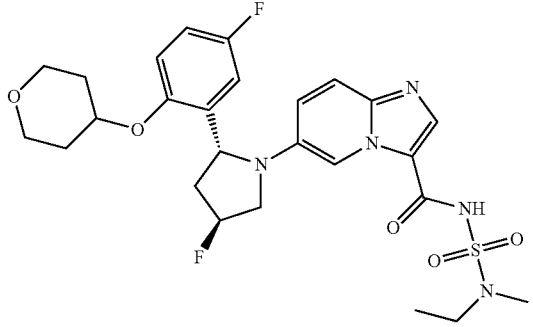 | N-(N-ethyl-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide; MS (ESI): m/z 564.3 (M + H); $^1$H NMR (400 MHz, DMSO-$d_6$): δ 11.75 (1H, bs), 8.52-8.45 (2H, m), 7.71-7.68 (1H, d, J = 10.4 Hz), 7.30-7.28 (1H, d, J = 9.6 Hz), 7.11 (1H, bs), 7.00-6.98 (2H, d, J = 8.4 Hz), 5.56-5.42 (1H, m), 5.12-5.08 (1H, t), 4.67 (1H, bs), 4.24-4.11 (2H, m), 3.85-3.69 (5H, m), 3.29-3.19 (4H, m), 2.85 (3H, s), 2.80-2.74 (3H, s), 2.15-1.96 (3H, m), 1.77-1.75 (1H, m), 1.64 (1H, m), 1.10-1.07 (3H, t). |
| Example 68 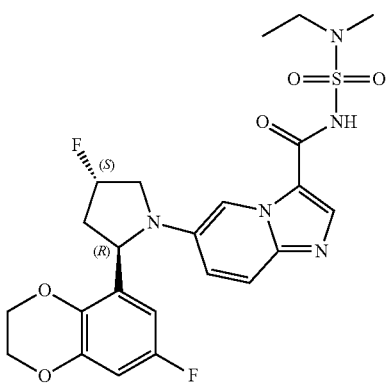 | N-(N-ethyl-N-methylsulfamoyl)-6-((2R,4S)-4-fluoro-2-(7-fluoro-2,3-dihydrobenzo[b][1,4]dioxin-5-yl)pyrrolidin-1-yl)imidazo[1,2-a]pyridine-3-carboxamide; MS (ESI): m/z 522.1 (M + H); $^1$H NMR (400 MHz, DMSO-$d_6$) δ 11.61 (1H, bs), 8.43 (2H, s), 7.65-7.62 (1H, d J = 9.6 Hz), 7.23-7.21 (1H, dd), 6.63-6.56 (2H, m), 5.55-5.42 (1H, m), 5.04-5.00 (1H, t), 4.52-4.48 (1H, m), 4.40-4.36 (2H, m), 4.35-4.26 (1H, m), 4.23-4.14 (1H, m), 3.73-3.63 (1H, m), 3.34-3.19 (1H, m), 2.85 (3H, s), 2.74-2.65 (2H, m), 2.15-2.05 (2H, m), 1.11-1.07 (3H, t). |
| Example 69 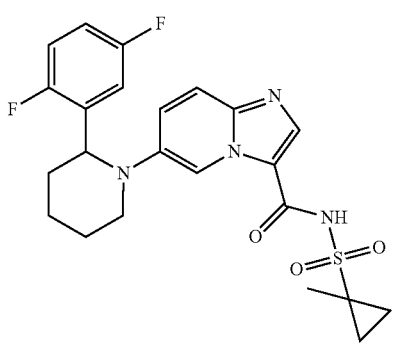 | 6-(2-(2,5-difluorophenyl)piperidin-1-yl)-N-((1-methylcyclopropyl)sulfonyl)imidazo[1,2-a]pyridine-3-carboxamide; (Isomer-II) MS (ESI): m/z 475.5 (M + H); $^1$H NMR (400 MHz, DMSO-$d_6$) δ 11.76 (1H, bs), 8.90 (1H, s), 8.41 (1H, s), 7.604-7.581 (1H, d, J = 9.2 Hz), 7.494-7.469 (1H, d J = 10 Hz), 7.10-7.05 (2H, m), 6.96-6.91 (1H, m), 4.440-4.423 (1H, d J = 6.8 Hz), 3.49-3.41 (1H, m), 2.91-2.86 (1H, m), 1.88-1.76 (1H, m), 1.76-1.70 (3H, m), 1.67-1.61 (1H, m), 1.53-1.50 (2H, m), 1.44 (3H, s), 1.28-1.26 (1H, m), 1.11-0.85 (2H, m). <br>(Isomer-I) MS (ESI) m/z 475.5 (M + H); $^1$H NMR (400 MHz, DMSO-$d_6$) δ 11.79 (1H, bs), 8.90 (1H, s), 8.46 (1H, s), 7.63-7.61 (1H, d J = 9.6 Hz), 7.50-7.50 (1H, d, J = 1.6 Hz), 7.12-7.08 (2H, m), 6.98-6.92 (1H, m), 4.46-4.44 (1H, d J = 7.2 Hz), 3.52-3.43 (1H, m), 2.94-2.88 (1H, m), 1.91-1.79 (1H, m), 1.79-1.72 (3H, s), 1.64-1.54 (1H, m), 1.42-1.37 (2H, m), 1.37-1.36 (5H, m), 1.04-1.02 (2H, s). |

TABLE 3-continued

| Example No. and Structure | Name & Characteristics data |
| --- | --- |
| Example 70 | 6-(2-(2,5-difluorophenyl)piperidin-1-yl)-N-(N-ethyl-N-methyl-sulfamoyl)imidazo[1,2-a]pyridine-3-carboxamide;<br>(Isomer-II) MS (ESI) m/z 478.6 (M + H) $^1$H NMR (400 MHz, DMSO-$d_6$) δ 11.72 (1H, bs), 8.90 (1H, s), 8.39 (1H, s), 7.58-7.47 (1H, m), 7.068-7.062 (2H, m), 6.92 (1H, s), 4.41-4.39 (1H, d J = 8.8 Hz), 3.36-3.36 (1H, m), 3.26-3.23 (2H, m), 2.85 (4H, s), 1.95-1.1.72 (4H, m), 1.68-1.52 (2H, m), 1.20-1.06 (5H, m).<br>(Isomer-I) MS (ESI) m/z 478.6 (M + H) $^1$H NMR (400 MHz, DMSO-$d_6$) δ 11.92 (1H, bs), 8.84 (1H, s), 8.52 (1H, s), 7.67-7.59 (2H, m), 7.12-7.05 (2H, m), 6.97-6.93 (1H, m), 4.486-4.368 (1H, d J = 7.2 Hz), 3.33-3.22 (3H, m), 2.96-2.89 (4H, m), 1.92-1.89 (1H, m), 1.81-1.74 (3H, m), 1.62-1.50 (2H, m), 1.11-1.08 (3H, t). |
| Example 71 | 6-(2-(7-fluoro-2,3-dihydrobenzo[b][1,4]dioxin-5-yl)pyrrolidin-1-yl)-N-(N-(2-fluoroethyl)-N-methylsulfamoyl)imidazo[1,2-a]pyridine-3-carboxamide;<br>(Isomer II) MS (ESI) mz/ 521.7 (M + H) $^1$H NMR (400 MHz, DMSO-$d_6$) δ 11.8 (1H, s), 8.51-8.43 (2H, d), 7.62-7.60 (1H, d), 7.02 (1H, d), 6.6 (1H, d), 4.91-4.89 (1H, d), 4.84-4.29 (5H, m), 3.77-3.65 (2H, m), 2.89 (2H, s), 2.36-1.83 (3H, m).<br>(Isomer I) MS (ESI) m/z 521.7 (M + H) $^1$H NMR (400 MHz, DMSO-$d_6$) δ 11.8 (1H, s), 8.50-8.43 (2H, d), 7.62-7.59 (1H, d), 7.06 (1H, d), 6.64-6.37 (1H, d), 4.65-4.63 (1H, t), 4.53-4.51 (1H, t), 4.38-4.32 (3H, m), 3.78 (1H, t), 2.89 (2H, s), 2.02-1.86 (3H, m). |
| Example 72 | N-(N-ethyl-N-methylsulfamoyl)-6-(2-(7-fluoro-2,3-dihydrobenzo[b][1,4]dioxin-5-yl)pyrrolidin-1-yl)imidazo[1,2-a]pyridine-3-carboxamide;<br>(Isomer II): MS m/z 504.2 (M + H) $^1$H NMR (400 MHz, DMSO-$d_6$) δ 11.61 (1H, s), 8.49-8.43 (2H, d), 7.62-7.59 (1H, d), 7.03 (1H, d), 6.65-6.62 (1H, dd), 6.4-6.37 (1H, dd), 4.91-4.88 (1H, d), 4.41-4.43 (4H, m), 3.78-3.77 (1H, t), 2.86 (3H, s), 2.02-1.82 (3H, m), 1.11-1.08 (3H, t).<br>(Isomer I): MS m/z 504.2 (M + H) $^1$H NMR (400 MHz, DMSO-$d_6$) δ 11.61 (1H, s), 8.47-8.41 (2H, d), 7.60-7.57 (1H, d), 7.03 (1H, d), 6.63-6.6 (1H, dd), 6.38-6.35 (1H, dd), 4.98-4.86 (1H, d), 4.39-4.3 (4H, m), 3.78-3.77 (1H, t), 2.84 (3H, s), 2.0-1.99 (3H, m), 1.09-1.06 (3H, t). |
| Example 73 | (6-(2-(2,5-difluorophenyl)pyrrolidin-1-yl)imidazo[1,2-a]pyridine-3 yl)(3-hydroxyazetidin-1-yl)methanone;<br>(Isomer II): MS (ESI) m/z 399.1 (M + H) $^1$H NMR (300 MHz, CDCl$_3$) δ 8.93-8.92 (1H, d, J = 3.6 Hz), 7.77 (1H, s,), 7.46-7.43 (1H, d, J = 9.9 Hz), 7.06-7.02 (1H, m), 6.93-6.75 (3H, m), 5.02-4.99 (1H, d, J = 9 Hz), 4.80-4.78 (1H, t), 4.57 (2H, bs), 4.21 (2H, m), 3.71-3.69 (1H, m), 3.4-3.38 (1H, t), 2.48-2.43 (1H, m), 2.08-2.00 (3H, m).<br>(Isomer I): MS (ESI) m/z 399.1 (M + H) $^1$H NMR (300 MHz, CDCl$_3$) δ 8.93-8.92 (1H, d, J = 3.6 Hz), 7.77 (1H, s), 7.45-7.42 (1H, d, J = 8.1 Hz), 7.06-7.04 (1H, m), 6.99-6.74 (3H, m), 5.01-4.98 (1H, d, J = 8.1 Hz), 4.79 (1H, t), 4.57 (2H, bs), 4.21 (2H, m), 3.71 (1H, m), 3.4-3.37 (1H, t), 2.49 (1H, m), 2.07-1.99 (3H, m). |

The following Examples 74 to 112 were prepared by the method substantially similar to that of Example 31 by employing appropriate carboxylic acid and sulfonamide or sulfamide.

Example 74

N—(N,N-diethylsulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide

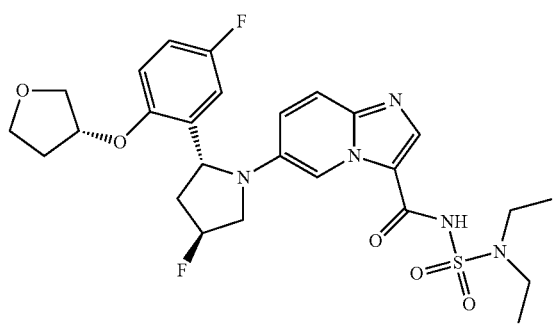 [SMILES: CCN(CC)S(=O)(=O)NC(=O)c1cnc2ccc(N3C[C@@H](F)C[C@@H]3c3cc(F)ccc3O[C@@H]3CCOC3)cn12]

$^1$H NMR: (400 MHz, DMSO-d$_6$): δ 11.56 (s, 1H), 8.46-8.38 (m, 2H), 7.63 (d, 1H, J=9.6 Hz), 7.18 (d, 1H, J=9.6 Hz), 7.10-6.95 (m, 3H), 5.47 (mm, 1H, J=52.8 Hz), 5.18-5.11 (m, 1H), 5.05-5.00 (m, 1H), 4.22-4.04 (m, 1H), 3.94-3.62 (m, 5H), 2.80-2.62 (m, 1H), 2.30-1.92 (m, 3H), 1.08 (t, 6H). MS (ESI): m/z 564.0 (M+H).

Example 75

N—(N-ethyl-N-(2-fluoroethyl)sulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide

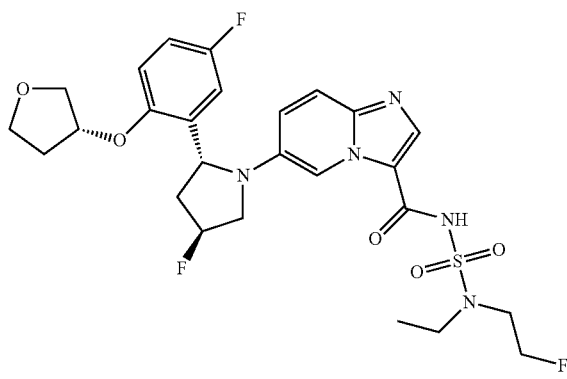 [SMILES: CCN(CCF)S(=O)(=O)NC(=O)c1cnc2ccc(N3C[C@@H](F)C[C@@H]3c3cc(F)ccc3O[C@@H]3CCOC3)cn12]

$^1$H NMR: (400 MHz, DMSO-d$_6$): δ 11.70 (s, 1H), 8.46-8.38 (m, 2H), 7.63 (d, 1H, J=9.6 Hz), 7.18 (d, 1H, J=9.6 Hz), 7.10-6.98 (m, 3H), 5.47 (mm, 1H, J=52.8 Hz), 5.18-5.11 (m, 1H), 5.05-5.00 (m, 1H), 4.62-4.50 (m, 2H), 4.22-4.04 (m, 1H), 3.94-3.51 (m, 5H), 2.80-2.62 (m, 1H), 2.30-1.92 (m, 3H), 1.08 (t, 3H). MS (ESI): m/z 582.2 (M+H).

Example 76

6-((2R,4S)-4-fluoro-2-(5-fluoro-2-(((R)-tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide

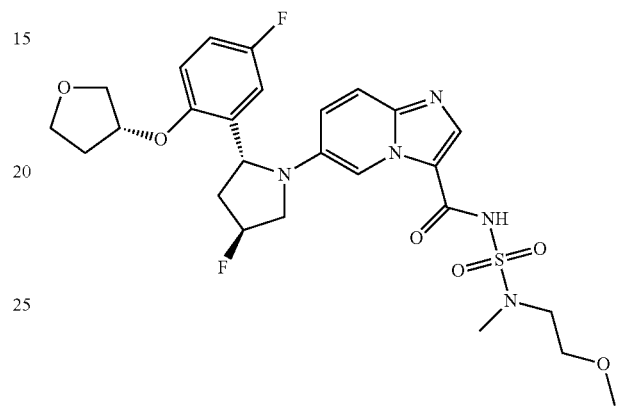

$^1$H NMR: (400 MHz, DMSO-d$_6$): δ 11.60 (s, 1H), 8.46-8.38 (m, 2H), 7.63 (d, 1H, J=10.0 Hz), 7.18 (d, 1H, J=9.6 Hz), 7.08-6.97 (m, 3H), 5.47 (mm, 1H, J=52.8 Hz), 5.18-5.11 (m, 1H), 5.05-5.00 (m, 1H), 4.22-4.04 (m, 1H), 3.94-3.51 (m, 5H), 3.50-3.35 (m, 4H), 3.20 (s, 3H), 2.88 (s, 3H), 2.80-2.62 (m, 1H), 2.30-1.92 (m, 3H). MS (ESI): m/z 580.3 (M+H).

Example 77

6-((2R,4S)-4-fluoro-2-(5-fluoro-2-(((R)-tetrahydrofuran-3-yl)oxy)phenyl)pyrrolidin-1-yl)-N—(N-methyl-N-(thiazol-2-yl)sulfamoyl)imidazo[1,2-a]pyridine-3-carboxamide

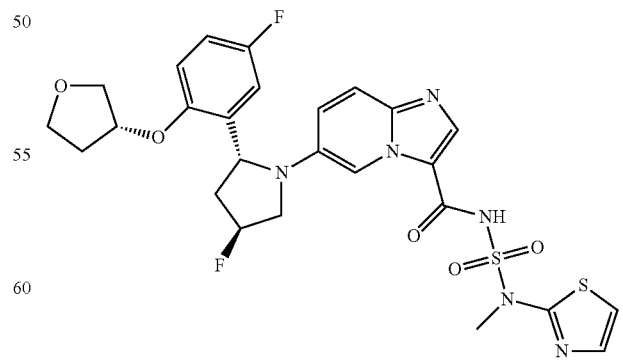

$^1$H NMR: (400 MHz, DMSO-d$_6$): δ 8.85 (s, 1H), 8.30 (s, 1H), 7.67 (d, 1H, J=10.0 Hz), 7.32-7.22 (m, 2H), 7.05-6.95 (m, 4H), 5.47 (mm, 1H, J=52.4 Hz), 5.16-5.04 (m, 2H), 4.20-4.01 (m, 1H), 3.92-3.53 (m, 5H), 3.48-3.35 (m, 6H), 2.80-2.62 (m, 1H), 2.30-1.92 (m, 3H). MS (ESI): m/z 605.1 (M+H).

Example 78

6-((2R,4S)-4-fluoro-2-(5-fluoro-2-(((R)-tetrahydro-furan-3-yl)oxy)phenyl)pyrrolidin-1-yl)-N—(N-methyl-N-(6-methylpyridazin-3-yl)sulfamoyl)imidazo[1,2-a]pyridine-3-carboxamide

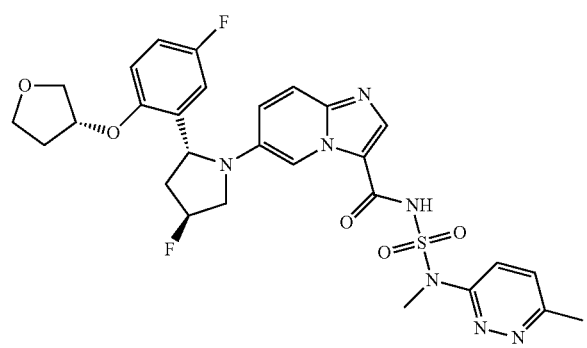 [SMILES: Cc1ccc(N(C)S(=O)(=O)NC(=O)c2cnc3ccc(N4C[C@@H](F)C[C@@H]4c4cc(F)ccc4O[C@@H]4CCOC4)cn23)nn1]

$^1$H NMR: (400 MHz, DMSO-d$_6$): δ 8.75 (s, 1H), 8.26 (s, 1H), 7.93 (d, 1H, J=9.2 Hz), 7.64 (d, 1H, J=9.6 Hz), 7.37 (d, 1H, J=9.6 Hz), 7.24 (d, 1H, J=10.0 Hz), 7.03-6.95 (m, 3H), 5.55-5.38 (mm, 1H, J=52.8 Hz), 5.15-5.10 (m, 1H), 5.07-5.01 (3, 1H), 4.20-4.14 (m, 1H), 3.91-3.84 (m, 2H), 3.80-3.73 (m, 2H), 3.70-3.68 (m, 2H), 3.49 (s, 3H), 2.82-2.69 (m, 1H), 2.47 (s, 3H), 2.26-1.96 (m, 3H). MS (ESI): m/z 614.2 (M+H).

Example 79

(R)—N-(tert-butylsulfonyl)-6-(2-(5-fluoro-2-((tetrahydro-2H-pyran-4-yl)oxy)phenyl) pyrrolidin-1-yl)imidazo[1,2-a]pyridine-3-carboxamide

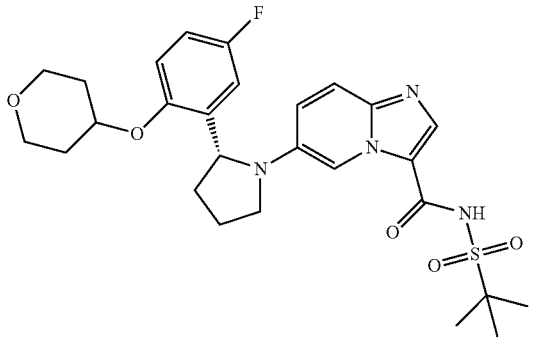 [SMILES: CC(C)(C)S(=O)(=O)NC(=O)c1cnc2ccc(N3CCC[C@@H]3c3cc(F)ccc3OC3CCOCC3)cn12]

$^1$H NMR: (400 MHz, DMSO-d$_6$): δ 11.16 (s, 1H), 8.51 (bs, 2H), 7.65 (d, 1H, J=10.0 Hz), 7.16-7.10 (m, 1H), 7.09-6.95 (m, 2H), 6.78 (d, 1H, J=9.2 Hz), 6.61 (s, 1H), 4.99-4.94 (m, 1H), 4.74-4.68 (m, 1H), 3.92-3.76 (m, 3H), 3.60-3.50 (m, 2H), 2.10-1.89 (m, 4H), 1.89-1.62 (m, 4H), 1.38 (s, 9H). MS (ESI): m/z 545.1 (M+H).

Example 80

(R)—N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide

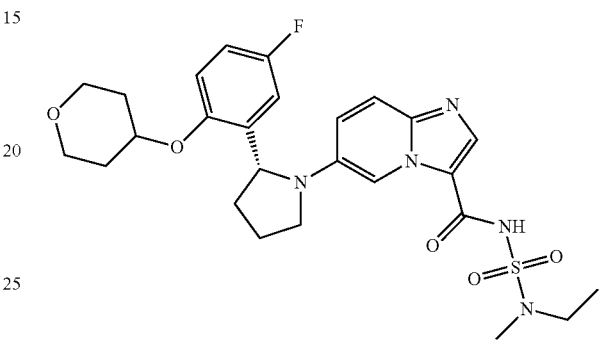

$^1$H NMR: (400 MHz, DMSO-d$_6$): δ 11.31 (s, 1H), 8.48 (bs, 2H), 7.65 (d, 1H, J=10.0 Hz), 7.16-7.10 (m, 1H), 7.09-6.96 (m, 2H), 6.78 (d, 1H, J=9.2 Hz), 6.63 (s, 1H), 4.99-4.94 (m, 1H), 4.74-4.68 (m, 1H), 3.91-3.78 (m, 3H), 3.60-3.50 (m, 2H), 3.30-3.20 (m, 3H), 2.96 (q, 2H), 2.85 (s, 3H), 2.60 (s, 2H), 2.48-2.36 (m, 1H), 2.10-1.89 (m, 4H), 1.89-1.62 (m, 3H), 1.08 (t, 3H). MS (ESI): m/z 546.2 (M+H).

Example 81

(R)-6-(2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide

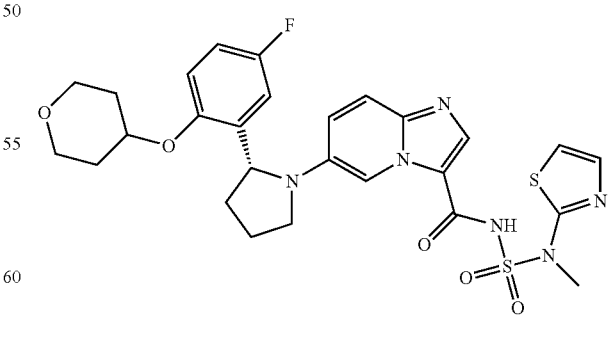

$^1$H NMR: (400 MHz, DMSO-d$_6$): δ 8.89 (s, 1H), 8.22 (s, 1H), 7.63 (d, 1H, J=9.6 Hz), 7.26-7.09 (m, 2H), 7.08-6.97 (m, 3H), 6.74 (d, 1H, J=9.6 Hz), 5.01-4.94 (m, 1H), 4.72-4.64 (m, 1H), 3.90-3.80 (m, 2H), 3.73-3.50 (m, 3H), 3.39 (s, 3H), 3.35-3.20 (m, 3H), 2.45-2.38 (m, 1H), 2.10-1.98 (m, 3H), 1.98-1.60 (m, 4H). MS (ESI): m/z 601.2 (M+H).

Example 82

(R)-6-(2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide

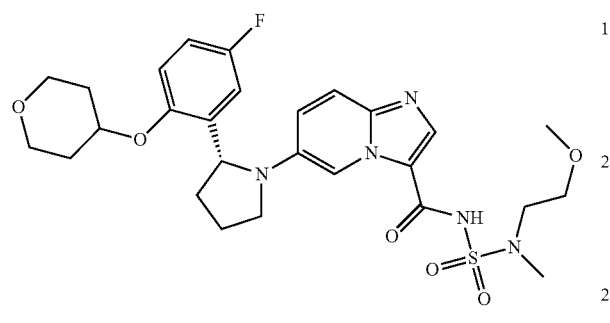

¹H NMR: (400 MHz, DMSO-d₆): δ 11.58 (s, 1H), 8.50-8.40 (m, 2H), 7.61 (d, 1H, J=9.6 Hz), 7.14-7.08 (m, 1H), 7.04-6.93 (m, 2H), 6.80-6.74 (m, 1H), 4.99-4.94 (m, 1H), 4.72-4.65 (m, 1H), 3.90-3.75 (m, 3H), 3.55-3.35 (m, 5H), 3.18 (s, 3H), 2.85 (s, 3H), 2.45-2.36 (m, 2H), 2.08-1.78 (m, 5H), 1.78-1.60 (m, 2H). MS (ESI): m/z 576.5 (M+H).

Example 83

(R)—N—(N-(2-ethoxyethyl)-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide

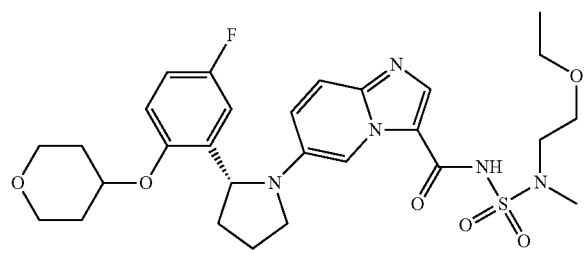 [SMILES: CCOCCN(C)S(=O)(=O)NC(=O)c1cnc2ccc(N3CCC[C@@H]3c3cc(F)ccc3OC3CCOCC3)cn12]

¹H NMR: (400 MHz, DMSO-d₆): δ 11.58 (s, 1H), 8.50-8.44 (m, 2H), 7.62 (d, 1H, J=9.6 Hz), 7.16-6.98 (m, 3H), 6.82-6.76 (m, 1H), 4.99-4.94 (m, 1H), 4.72-4.65 (m, 1H), 3.91-3.79 (m, 3H), 3.60-3.45 (m, 4H), 2.88 (s, 3H), 2.10-1.90 (m, 4H), 1.90-1.62 (m, 3H), 1.02 (t, 3H). MS (ESI): m/z 590.2 (M+H).

Example 84

(R)-6-(2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide

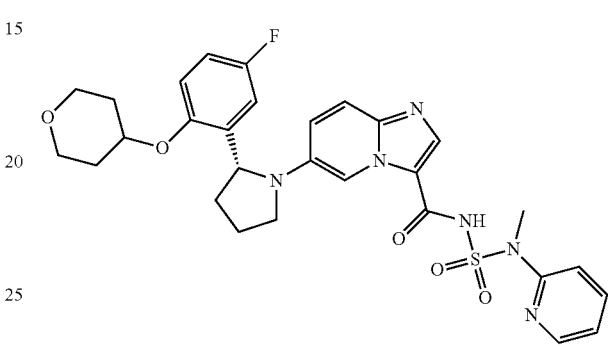

¹H NMR: (400 MHz, DMSO-d₆): δ 8.70 (bs, 1H), 8.38 (s, 1H), 8.28-8.24 (m, 1H), 7.68-7.60 (m, 3H), 7.16-7.08 (m, 2H), 7.07-6.92 (m, 2H), 6.75 (d, 1H, J=9.2 Hz), 4.99-4.94 (m, 1H), 4.72-4.65 (m, 1H), 3.90-3.70 (m, 3H), 3.60-3.45 (m, 4H), 3.45 (s, 3H), 2.45-2.38 (m, 1H), 2.08-1.98 (m, 3H), 1.98-1.62 (m, 4H). MS (ESI): m/z 595.3 (M+H).

Example 85

(R)-6-(2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide

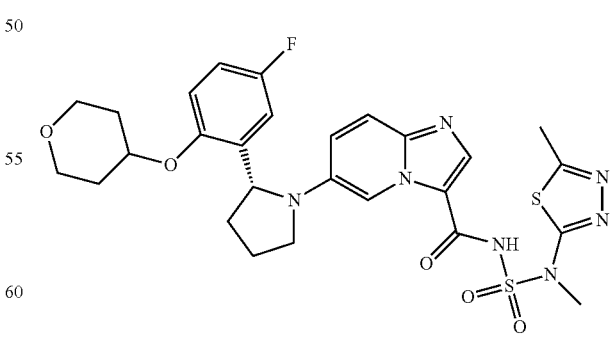

¹H NMR: (400 MHz, DMSO-d₆): δ 14.0 (bs, 1H), 8.89 (s, 1H), 8.33 (s, 1H), 7.69 (d, 1H, J=9.6 Hz), 7.19-7.08 (m, 2H), 7.04-6.97 (m, 1H), 6.78-6.74 (m, 1H), 5.02-4.96 (m, 1H), 4.72-4.65 (m, 1H), 3.90-3.80 (m, 2H), 3.78-3.71 (m, 1H), 3.60-3.50 (m, 2H), 3.27 (s, 3H), 2.47 (s, 3H), 2.47-2.38 (m, 1H), 2.10-1.98 (m, 3H), 1.98-1.61 (m, 4H). MS (ESI): m/z 616.1 (M+H).

Example 86

(R)-6-(2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide

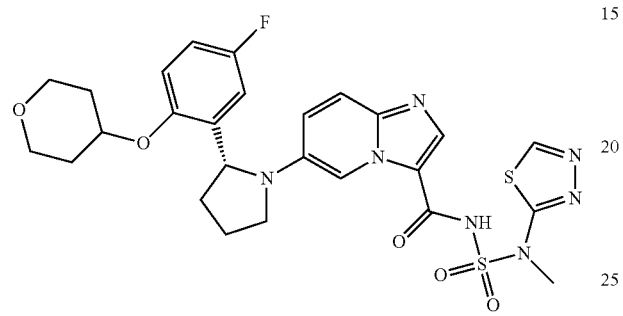

$^1$H NMR: (400 MHz, DMSO-$d_6$): δ 8.93 (s, 1H), 8.84 (s, 1H), 8.30 (s, 1H), 7.67 (d, 1H, J=10.0 Hz), 7.14-7.07 (m, 1H), 7.02-6.92 (m, 1H), 6.75-6.72 (m, 1H), 5.02-4.96 (m, 1H), 4.69-4.62 (m, 1H), 3.83-3.81 (m, 2H), 3.77-3.71 (m, 1H), 3.58-3.49 (m, 2H), 3.38 (s, 3H), 2.48-2.32 (m, 1H), 2.00-1.99 (m, 3H), 1.95-1.80 (m, 2H), 1.75-1.61 (m, 2H). MS (ESI): m/z 602.1 (M+H).

Example 87

(R)-6-(2-(5-fluoro-2-((tetrahydro-2H-pyran-4-yl)oxy)phenyl)pyrrolidin-1-yl)-N—(N-methyl-N-(6-methylpyridazin-3-yl)sulfamoyl)imidazo[1,2-a]pyridine-3-carboxamide

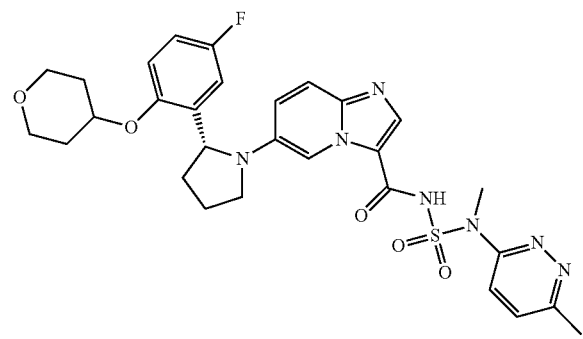 [SMILES: Cc1ccc(N(C)S(=O)(=O)NC(=O)c2cnc3ccc(N4CCC[C@@H]4c4cc(F)ccc4OC4CCOCC4)cn23)nn1]

$^1$H NMR: (400 MHz, DMSO-$d_6$): δ 8.81 (s, 1H), 8.25 (s, 1H), 7.90 (d, 1H, J=5.4 Hz), 7.62 (d, 1H, J=9.6 Hz), 7.33 (d, 1H, J=9.2 Hz), 7.09-7.07 (m, 2H), 7.00-6.98 (m, 1H), 6.73 (d, 1H, J=6.4 Hz), 4.96-4.94 (m, 1H), 4.66 (bs, 1H), 3.88-3.79 (m, 2H), 3.76-3.70 (m, 1H), 3.54-3.50 (m, 2H), 3.46 (s, 3H), 2.05-1.95 (m, 3H), 1.91-1.82 (m, 2H), 1.72-1.65 (m, 2H). MS (ESI): m/z 610.4 (M+H).

Example 88

6-((2R,4S)-4-fluoro-2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide

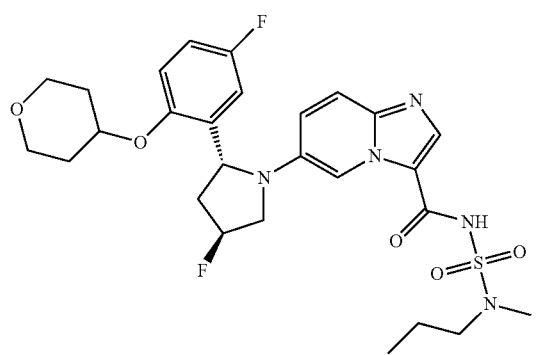 [SMILES: CCCN(C)S(=O)(=O)NC(=O)c1cnc2ccc(N3C[C@@H](F)C[C@@H]3c3cc(F)ccc3OC3CCOCC3)cn12]

$^1$H NMR: (400 MHz, DMSO-$d_6$): δ 11.58 (s, 1H), 8.42 (s, 1H), 7.63 (d, 1H, J=9.6 Hz), 7.19 (d, 1H, J=10.8 Hz), 7.13-7.10 (m, 1H), 7.02-6.97 (m, 2H), 5.55-5.42 (m, 1H), 5.11-5.07 (m, 1H), 4.68 (m, 1H), 4.23-4.06 (m, 1H), 3.88-3.82 (m, 2H), 3.76-3.67 (m, 1H), 3.56-3.51 (m, 2H), 3.44-3.00 (m, 2H), 2.83 (s, 3H), 2.77-2.67 (m, 1H), 2.16-1.97 (m, 3H), 1.78-1.75 (m, 1H), 1.75-1.63 (m, 1H), 1.55-1.49 (m, 2H), 1.29-1.25 (m, 2H), 0.84 (t, 3H). MS (ESI): m/z 577.7 (M+H).

Example 89

6-((2R,4S)-4-fluoro-2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide

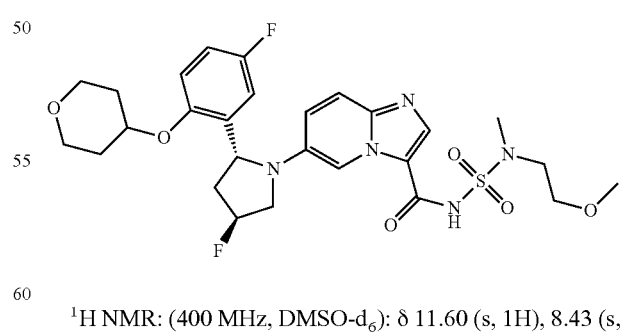

$^1$H NMR: (400 MHz, DMSO-$d_6$): δ 11.60 (s, 1H), 8.43 (s, 2H), 7.63 (d, 1H, J=10.0 Hz), 7.21-7.10 (m, 2H), 7.03-6.95 (m, 2H), 5.55-5.38 (mm, 1H, J=53.2 Hz), 5.11-5.06 (m, 1H), 4.71-4.64 (m, 1H), 4.26-4.10 (m, 1H), 3.90-3.64 (m, 3H), 3.60-3.40 (m, 5H), 3.20 (s, 3H), 2.86 (s, 3H), 2.85-2.70 (m, 1H), 2.18-1.94 (m, 3H), 1.80-1.58 (m, 2H). MS (ESI): m/z 593.7 (M+H).

Example 90

(R)-6-(2-(2,5-difluorophenyl)pyrrolidin-1-yl)-N—(N-methyl-N-(1-methyl-1H-pyrazol-3-yl)sulfamoyl)imidazo[1,2-a]pyridine-3-carboxamide

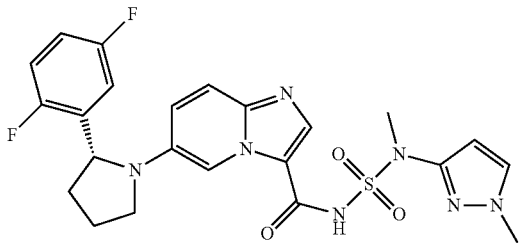 [SMILES: CN(c1ccn(C)n1)S(=O)(=O)NC(=O)c1cnc2ccc(N3CCC[C@@H]3c3cc(F)ccc3F)cn12]

$^1$H NMR: (400 MHz, DMSO-d$_6$): δ 12.10 (bs, 1H), 8.62 (bs, 1H), 8.42 (s, 1H), 7.61 (d, 1H, J=9.6 Hz), 7.56 (s, 1H), 7.35-7.26 (m, 2H), 7.18-7.02 (m, 2H), 6.99-6.91 (m, 1H), 6.16 (s, 1H), 5.02-4.97 (m, 1H), 3.80-3.75 (m, 1H), 3.70 (s, 3H), 3.40 (s, 3H), 2.55-2.40 (m, 1H), 2.10-1.85 (m, 3H). MS (ESI): m/z 516.1 (M+H).

Example 91

(R)-6-(2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide

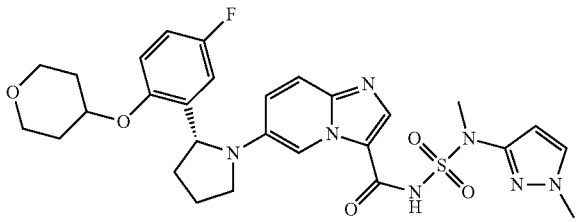 [SMILES: CN(c1ccn(C)n1)S(=O)(=O)NC(=O)c1cnc2ccc(N3CCC[C@@H]3c3cc(F)ccc3OC3CCOCC3)cn12]

$^1$H NMR: (400 MHz, DMSO-d$_6$): δ 12.20 (bs, 1H), 8.56 (s, 1H), 8.30 (s, 1H), 7.59 (d, 1H, J=9.6 Hz), 7.52 (s, 1H), 7.17-7.11 (m, 1H), 7.04-6.94 (m, 1H), 6.78 (d, 1H, J=6.4 Hz), 6.15 (s, 1H), 5.00-4.95 (m, 1H), 4.74-4.68 (m, 1H), 3.90-3.72 (m, 3H), 3.69 (s, 3H), 3.59-3.52 (m, 2H), 2.50-2.38 (m, 1H), 2.10-1.65 (m, 6H). MS (ESI): m/z 597.7 (M+H).

Example 92

6-((2R,4S)-4-fluoro-2-(5-fluoro-2-(((R)-tetrahydrofuran-3-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide

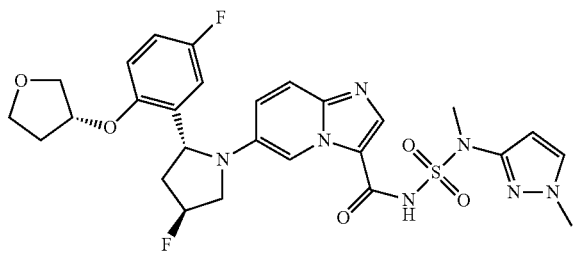 [SMILES: CN(c1ccn(C)n1)S(=O)(=O)NC(=O)c1cnc2ccc(N3C[C@@H](F)C[C@@H]3c3cc(F)ccc3O[C@@H]3CCOC3)cn12]

$^1$H NMR: (400 MHz, DMSO-d$_6$): δ 12.10 (bs, 1H), 8.47 (bs, 1H), 8.33 (bs, 1H), 7.59 (d, 1H, J=10.0 Hz), 7.54 (s, 1H), 7.13 (d, 1H, J=9.6 Hz), 7.08-6.96 (m, 3H), 6.15 (s, 1H), 5.55-5.38 (mm, 1H, J=53.2 Hz), 5.18-5.11 (m, 1H), 5.07-5.02 (m, 1H), 4.21-4.14 (m, 1H), 3.94-3.76 (m, 4H), 3.76-3.61 (m, 4H), 2.81-2.64 (m, 1H), 2.80-1.93 (m, 4H). MS (ESI): m/z 602.3 (M+H).

Example 93

6-((2R,4S)-4-fluoro-2-(5-fluoro-2-(((R)-tetrahydrofuran-3-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide

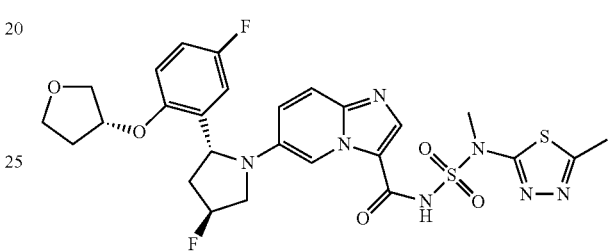

$^1$H NMR: (400 MHz, DMSO-d$_6$): δ 8.77 (s, 1H), 8.09 (s, 1H), 7.57 (d, 1H, J=9.6 Hz), 7.12 (d, 1H, J=10.0 Hz), 7.06-6.94 (m, 3H), 5.55-5.38 (mm, 1H, J=53.2 Hz), 5.12-5.03 (m, 2H), 4.18-4.02 (m, 1H), 3.93-3.72 (m, 4H), 3.68-3.54 (m, 1H), 2.70-2.58 (m, 1H), 2.8-1.96 (m, 3H). MS (ESI): m/z 619.6 (M+H).

Example 94

N-(tert-butylsulfonyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide

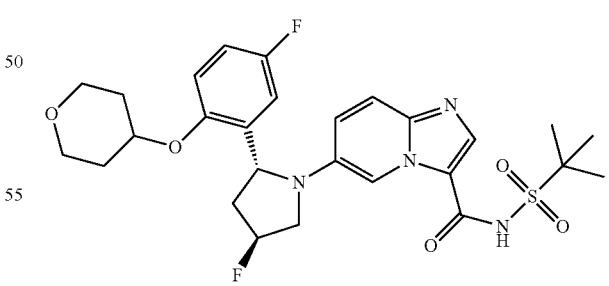

$^1$H NMR: (400 MHz, DMSO-d$_6$): δ 11.30 (bs, 1H), 8.56-8.44 (m, 2H), 7.67 (d, 1H, J=8.0 Hz), 7.23 (d, 1H, J=9.2 Hz), 7.14-7.06 (m, 1H), 7.02-6.92 (m, 2H), 5.58-5.41 (mm, 1H, J=53.2 Hz), 5.16-5.11 (m, 1H), 4.73-4.65 (m, 1H), 4.28-4.10 (m, 1H), 3.92-3.80 (m, 2H), 3.80-3.65 (m, 1H), 3.60-3.45 (m, 2H), 2.85-2.71 (m, 1H), 2.20-1.95 (m, 3H), 1.85-1.60 (m, 2H), 1.39 (s, 9H). MS (ESI): m/z 563.3 (M+H).

Example 95

N—(N,N-diethylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide

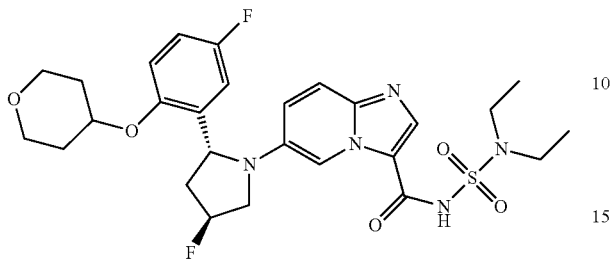

$^1$H NMR: (400 MHz, DMSO-d$_6$): δ 11.61 (s, 1H), 8.42 (s, 2H), 7.64 (d, 1H, J=9.6 Hz), 7.20 (d, 1H, J=9.2 Hz), 7.16-7.10 (m, 1H), 7.04-6.93 (m, 2H), 5.58-5.41 (mm, 1H, J=53.2 Hz), 5.11-5.03 (m, 1H), 4.72-4.64 (m, 1H), 4.27-4.10 (m, 1H), 3.90-3.81 (m, 2H), 3.78-3.64 (m, 1H), 3.60-3.50 (m, 2H), 3.40-3.20 (m, 3H), 2.85-2.72 (m, 1H), 2.18-1.96 (m, 3H), 1.84-1.60 (m, 2H), 1.07 (t, 6H). MS (ESI): m/z 578.5 (M+H).

Example 96

6-((2R,4S)-4-fluoro-2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide

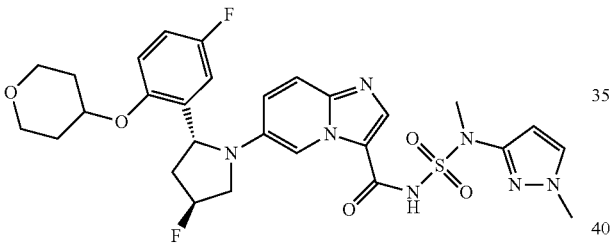

$^1$H NMR: (400 MHz, DMSO-d$_6$): δ 8.77 (bs, 1H), 7.86 (bs, 1H), 7.42 (d, 1H, J=9.6 Hz), 5.58-5.41 (mm, 1H, J=53.2 Hz), 5.16-5.11 (m, 1H), 4.72-4.64 (m, 1H), 4.18-4.10 (m, 1H), 3.91-3.81 (m, 2H), 3.66 (s, 3H), 3.60-3.50 (m, 3H), 3.26 (s, 3H), 2.83-2.72 (m, 1H), 2.18-1.94 (m, 3H), 1.80-1.60 (m, 2H). MS (ESI): m/z 615.6 (M+H).

Example 97

6-((2R,4S)-4-fluoro-2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide

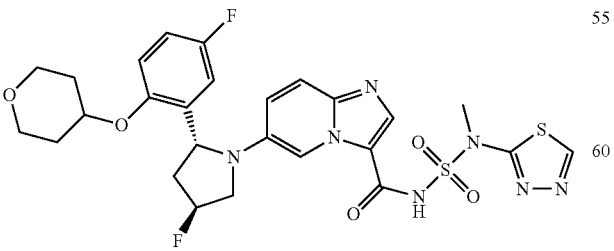

$^1$H NMR: (400 MHz, DMSO-d$_6$): δ 8.97 (s, 1H), 8.83 (s, 1H), 8.35 (s, 1H), 7.70 (d, 1H, J=9.6 Hz), 7.35 (d, 1H, J=9.2 Hz), 7.10-6.96 (m, 3H), 5.59-5.41 (mm, 1H, J=54.0 Hz), 5.17-5.11 (m, 1H), 4.68-4.59 (m, 1H), 4.21-4.05 (m, 1H), 3.89-3.79 (m, 2H), 3.71-3.60 (m, 1H), 3.60-3.49 (m, 2H), 3.40 (s, 3H), 2.83-2.72 (m, 1H), 2.21-1.92 (m, 3H), 1.78-1.56 (m, 2H). MS (ESI): m/z 620.2 (M+H).

Example 98

6-((2R,4S)-4-fluoro-2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide

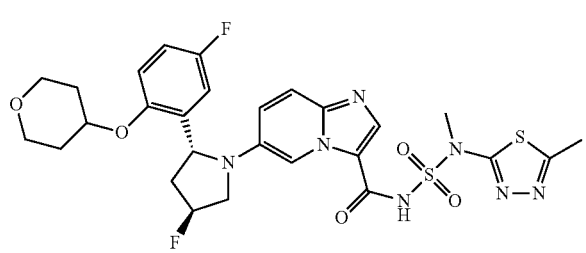 [SMILES: Cc1nnc(N(C)S(=O)(=O)NC(=O)c2cnc3ccc(N4C[C@@H](F)C[C@@H]4c4cc(F)ccc4OC4CCOCC4)cn23)s1]

$^1$H NMR: (400 MHz, DMSO-d$_6$): δ 8.87 (s, 1H), 8.33 (s, 1H), 7.71 (d, 1H, J=10.0 Hz), 7.34 (d, 1H, J=10.0 Hz), 7.10-6.96 (m, 3H), 5.59-5.41 (mm, 1H, J=53.2 Hz), 5.19-5.12 (m, 1H), 4.68-4.60 (m, 1H), 4.21-4.05 (m, 1H), 3.90-3.79 (m, 2H), 3.71-3.60 (m, 1H), 3.60-3.49 (m, 2H), 2.83-2.72 (m, 1H), 2.21-1.92 (m, 3H), 1.78-1.56 (m, 2H). MS (ESI): m/z 634.4 (M+H).

Example 99

6-((2R,4S)-4-fluoro-2-(5-fluoro-2-((tetrahydro-2H-pyran-4-yl)oxy)phenyl)pyrrolidin-1-yl)-N—(N-(2-fluoroethyl)-N-methylsulfamoyl)imidazo[1,2-a]pyridine-3-carboxamide

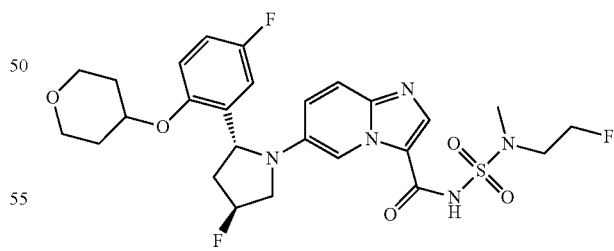

$^1$H NMR: (400 MHz, DMSO-d$_6$): δ 12.40 (bs, 1H), 8.61 (bs, 1H), 8.19 (bs, 1H), 7.54 (d, 1H, J=10.0 Hz), 7.15-6.94 (m, 4H), 5.59-5.41 (mm, 1H, J=52.8 Hz), 5.15-5.10 (m, 1H), 4.71-4.60 (m, 2H), 4.52-4.48 (m, 1H), 4.22-4.06 (m, 1H), 3.91-3.80 (m, 2H), 3.72-3.60 (m, 1H), 3.60-3.44 (m, 4H), 2.83-2.72 (m, 4H), 2.20-1.92 (m, 3H), 1.80-1.60 (m, 2H). MS (ESI): m/z 582.4 (M+H).

Example 100

6-((2R,4S)-4-fluoro-2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide

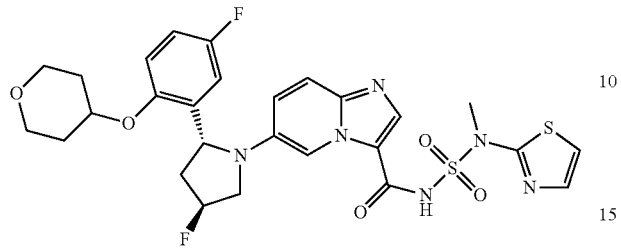

$^1$H NMR: (400 MHz, DMSO-$d_6$): δ 8.78 (s, 1H), 7.92 (s, 1H), 7.48 (d, 1H, J=9.6 Hz), 7.24 (s, 1H), 7.10-7.03 (m, 1H), 7.02-6.90 (m, 4H), 5.56-5.39 (mm, 1H, J=53.2 Hz), 5.16-5.11 (m, 1H), 4.69-4.60 (m, 1H), 4.18-4.02 (m, 1H), 3.90-3.79 (m, 2H), 3.62-3.48 (m, 3H), 2.83-2.65 (m, 1H), 2.18-1.92 (m, 3H), 1.78-1.59 (m, 2H). MS (ESI): m/z 618.6 (M+H).

Example 101

6-((2R,4S)-4-fluoro-2-(5-fluoro-2-(((R)-tetrahydrofuran-3-yl)oxy)phenyl)pyrrolidin-1-yl)-N—(N-methyl-N-propylsulfamoyl)imidazo[1,2-a]pyridine-3-carboxamide

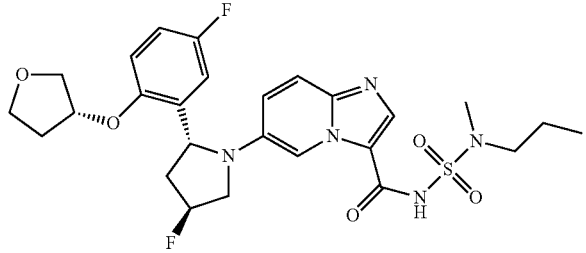 [SMILES: CCCN(C)S(=O)(=O)NC(=O)c1cnc2ccc(N3C[C@@H](F)C[C@@H]3c3cc(F)ccc3O[C@@H]3CCOC3)cn12]

$^1$H NMR: (400 MHz, CDCl$_3$): δ 8.63 (s, 1H), 8.03 (s, 1H), 7.51 (d, 1H, J=10.0 Hz), 6.92-6.74 (m, 3H), 5.45-5.30 (mm, 1H, J=53.2 Hz), 5.25-5.20 (m, 1H), 5.04 (s, 1H), 4.15-3.92 (m, 4H), 3.88-3.72 (m, 1H), 3.49 (s, 2H), 3.38-3.24 (m, 2H), 2.99 (s, 2H), 2.38-2.25 (m, 2H), 0.96 (t, 3H). MS (ESI): m/z 564.1 (M+H).

Example 102

N—(N-ethyl-N-(2-fluoroethyl)sulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide

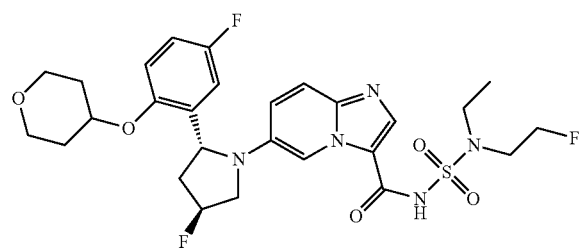 [SMILES: CCN(CCF)S(=O)(=O)NC(=O)c1cnc2ccc(N3C[C@@H](F)C[C@@H]3c3cc(F)ccc3OC3CCOCC3)cn12]

$^1$H NMR: (400 MHz, DMSO-$d_6$): δ 11.71 (bs, 1H), 8.46-8.38 (m, 2H), 7.64 (d, 1H, J=8.0 Hz), 7.22-7.10 (m, 2H), 7.04-6.96 (m, 2H), 5.59-5.41 (mm, 1H, J=52.8 Hz), 5.12-5.08 (m, 1H), 4.71-4.60 (m, 2H), 4.52-4.48 (m, 1H), 4.26-4.10 (m, 1H), 3.90-3.80 (m, 2H), 3.80-3.50 (m, 6H), 2.83-2.72 (m, 1H), 2.20-1.92 (m, 3H), 1.81-1.59 (m, 2H), 1.06 (t, 3H). MS (ESI): m/z 596.1 (M+H).

Example 103

6-((2R,4S)-4-fluoro-2-(5-fluoro-2-(((R)-tetrahydrofuran-3-yl)oxy)phenyl)pyrrolidin-1-yl)-N—(N-methyl-N-(pyridin-2-yl)sulfamoyl)imidazo[1,2-a]pyridine-3-carboxamide

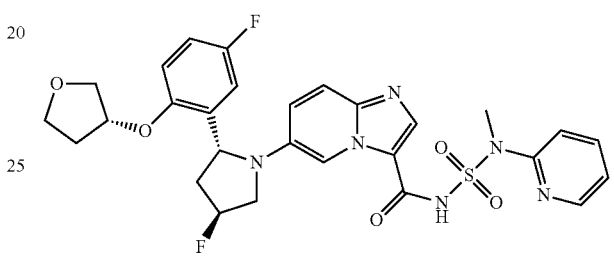

$^1$H NMR: (400 MHz, DMSO-$d_6$): δ 8.63 (bs, 1H), 8.29-8.24 (m, 2H), 7.66-7.58 (m, 3H), 7.20-7.13 (m, 1H), 7.05-6.95 (m, 4H), 5.55-5.39 (m, 1H), 5.12 (bs, 1H), 5.08-5.01 (m, 1H), 3.90-3.81 (m, 2H), 3.80-3.74 (m, 2H), 3.70-3.60 (m, 1H), 3.45 (s, 3H), 2.80-2.65 (m, 1H), 2.26-1.95 (m, 4H). MS (ESI): m/z 599.1 (M+H).

Example 104

6-((2R,4S)-4-fluoro-2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide

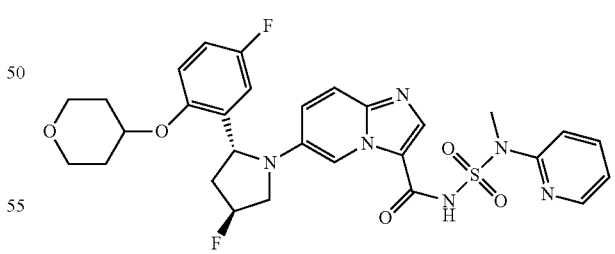

$^1$H NMR: (400 MHz, DMSO-$d_6$): δ 8.62 (bs, 1H), 8.30-8.25 (m, 2H), 7.70-7.59 (m, 3H), 7.20-7.08 (m, 2H), 7.05-6.92 (m, 2H), 5.56-5.40 (m, 1H), 5.15-5.10 (m, 1H), 4.70-62 (m, 1H), 4.20-4.05 (m, 1H), 3.86-3.76 (m, 2H), 3.70-3.60 (m, 1H), 3.58-3.48 (m, 2H), 3.46 (s, 3H), 2.85-2.70 (m, 1H), 2.15-1.92 (m, 4H), 1.80-1.55 (m, 3H). MS (ESI): m/z 613.1 (M+H).

Example 105

6-((R)-2-(5-fluoro-2-(((R)-tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide

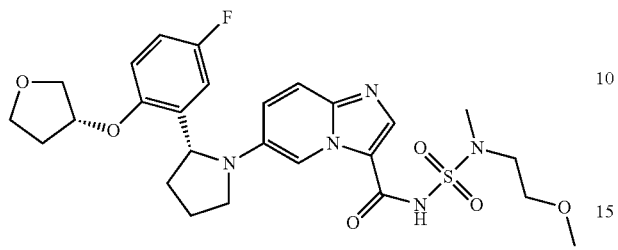

$^1$H NMR: (400 MHz, DMSO-d$_6$): δ 11.62 (bs, 1H), 8.54-8.36 (m, 2H), 7.61 (d, 1H, J=9.2 Hz), 7.10-6.96 (m, 3H), 6.79 (d, 1H, J=9.2 Hz), 5.16 (s, 1H), 4.90-4.84 (m, 1H), 3.96-3.72 (m, 5H), 3.50-3.45 (m, 2H), 2.45-2.10 (m, 4H), 2.08-1.75 (m, 3H). MS (ESI): m/z 562.2 (M+H).

Example 106

N—(N,N-dimethylsulfamoyl)-6-((R)-2-(5-fluoro-2-(((R)-tetrahydrofuran-3-yl)oxy)phenyl)pyrrolidin-1-yl)imidazo[1,2-a]pyridine-3-carboxamide

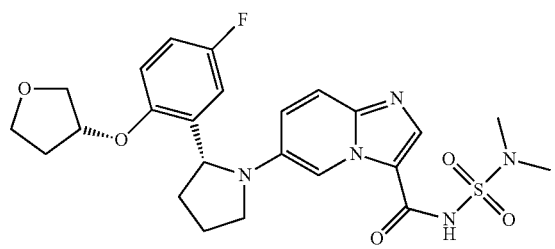

$^1$H NMR: (400 MHz, DMSO-d$_6$): δ 11.60 (bs, 1H), 8.52-8.46 (m, 2H), 7.65 (d, 1H, J=9.2 Hz), 7.10-6.98 (m, 3H), 6.80 (d, 1H, J=9.2 Hz), 5.16 (bs, 1H), 4.90-4.84 (m, 1H), 3.97-3.76 (m, 4H), 2.84 (s, 6H), 2.48-2.10 (m, 5H), 2.08-1.76 (m, 4H). MS (ESI): m/z 518.2 (M+H).

Example 107

6-((R)-2-(5-fluoro-2-(((R)-tetrahydrofuran-3-yl)oxy)phenyl)pyrrolidin-1-yl)-N—(N-methyl-N-propylsulfamoyl)imidazo[1,2-a]pyridine-3-carboxamide

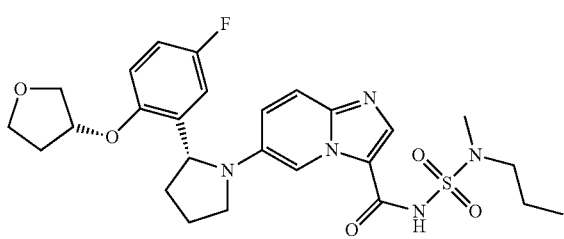

$^1$H NMR: (400 MHz, DMSO-d$_6$): δ 11.06 (bs, 1H), 8.46 (bs, 2H), 7.62 (d, 1H, J=9.2 Hz), 7.10-6.98 (m, 3H), 6.80 (d, 1H, J=9.2 Hz), 5.16 (bs, 1H), 4.90-4.84 (m, 1H), 3.97-3.76 (m, 5H), 3.22-3.08 (m, 2H), 2.84 (s, 3H), 2.48-2.10 (m, 3H), 2.08-1.76 (m, 3H), 1.60-1.48 (m, 2H), 0.85 (t, 3H). MS (ESI): m/z 546.2 (M+H).

Example 108

N—(N-cyclopropyl-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide

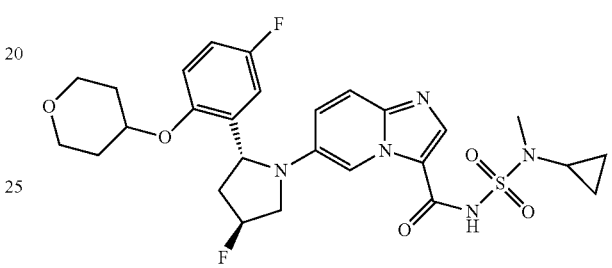

$^1$H NMR: (400 MHz, DMSO-d$_6$): δ 11.75 (s, 1H), 8.50-8.44 (m, 2H), 7.64 (d, 1H, J=10.0 Hz), 7.21-7.15 (m, 1H), 7.14-7.08 (m, 1H), 7.02-6.96 (m, 2H), 5.58-5.39 (mm, 1H, J=53.2 Hz), 5.14-5.08 (m, 1H), 4.70-4.62 (m, 1H), 4.25-4.10 (m, 1H), 3.90-3.65 (m, 3H), 3.58-3.48 (m, 2H), 2.90 (s, 3H), 2.84-2.70 (m, 1H), 2.18-1.92 (m, 3H), 1.80-1.58 (m, 2H). MS (ESI): m/z 576.1 (M+H).

Example 109

N—(N-(2,2-difluoroethyl)-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide

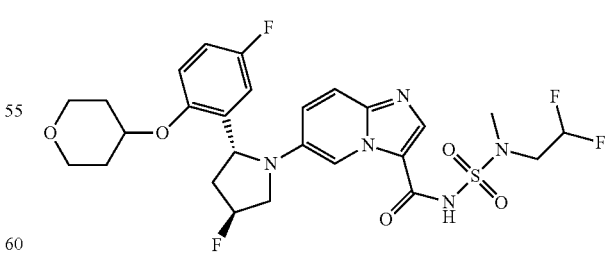

$^1$H NMR: (400 MHz, DMSO-d$_6$): δ 11.90 (bs, 1H), 8.50-8.40 (m, 2H), 7.65 (d, 1H, J=10.0 Hz), 7.21 (d, 1H, J=9.6 Hz), 7.14-7.08 (m, 1H), 7.04-6.96 (m, 2H), 6.38-6.08 (mm, 1H, J=55.6 Hz), 5.58-5.39 (mm, 1H, J=53.2 Hz), 5.13-5.06 (m, 1H), 4.70-4.60 (m, 1H), 4.24-4.09 (m, 1H), 3.90-3.65 (m,

4H), 3.65-3.45 (m, 3H), 2.86 (s, 3H), 2.84-2.70 (m, 1H), 2.20-1.92 (m, 3H), 1.80-1.59 (m, 2H). MS (ESI): m/z 600.2 (M+H).

Example 110

6-((2R,4S)-4-fluoro-2-(5-fluoro-2-((tetrahydro-2H-pyran-4-yl)oxy)phenyl)pyrrolidin-1-yl)-N—(N-(2-fluoro-2-methylpropyl)-N-methylsulfamoyl)imidazo[1,2-a]pyridine-3-carboxamide

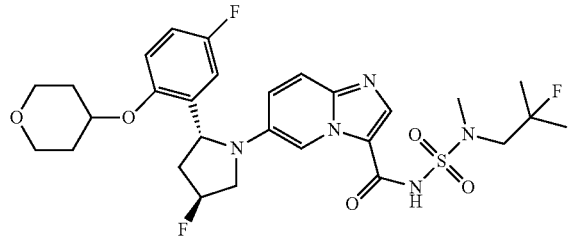 [SMILES: CN(CC(C)(C)F)S(=O)(=O)NC(=O)c1cnc2ccc(N3C[C@@H](F)C[C@@H]3c3cc(F)ccc3OC3CCOCC3)cn12]

$^1$H NMR: (400 MHz, DMSO-d$_6$): δ 11.90 (bs, 1H), 8.57 (s, 1H), 8.45 (s, 1H), 7.73 (d, 1H, J=9.6 Hz), 7.36-7.32 (m, 1H), 7.14-6.98 (m, 3H), 5.58-5.39 (mm, 1H, J=53.2 Hz), 5.13-5.06 (m, 1H), 4.70-4.60 (m, 1H), 4.24-4.09 (m, 1H), 3.90-3.65 (m, 4H), 2.87 (s, 3H), 2.84-2.70 (m, 1H), 2.20-1.92 (m, 3H), 1.80-1.59 (m, 2H), 1.42-1.32 (m, 6H). MS (ESI): m/z 610.2 (M+H).

Example 111

6-((R)-2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide

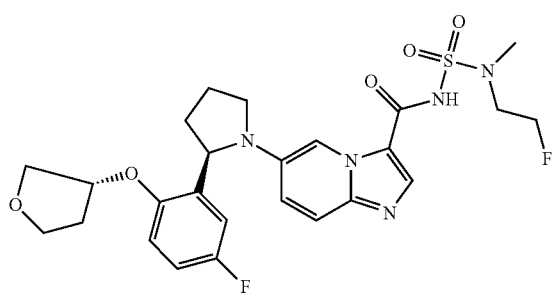 [SMILES: CN(CCF)S(=O)(=O)NC(=O)c1cnc2ccc(N3CCC[C@@H]3c3cc(F)ccc3O[C@@H]3CCOC3)cn12]

$^1$H NMR: (400 MHz, DMSO-d$_6$): δ 11.75 (s, 1H), 8.57 (s, 1H), 8.30 (s, 1H), 7.58-7.56 (d, 1H, J=9.6 Hz), 7.08-6.99 (m, 2H), 6.94-6.92 (d, 1H, J=9.2 Hz), 6.81-6.78 (m, 1H), 5.16 (s, 1H), 4.89-4.87 (m, 1H), 4.65-4.61 (m, 1H), 4.55-4.49 (m, 1H), 4.03-3.87 (m, 2H), 3.83-3.75 (m, 3H), 3.56-3.43 (m, 2H), 2.84 (s, 3H), 2.43-2.36 (m, 1H), 2.24-2.09 (m, 2H), 1.99-1.97 (m, 1H), 1.95-1.88 (m, 1H), 1.82-1.79 (m, 1H). MS (ESI): m/z 550.3 (M+H).

Example 112

N—(N,N-diethylsulfamoyl)-6-((R)-2-(5-fluoro-2-(((R)-tetrahydrofuran-3-yl)oxy)phenyl)pyrrolidin-1-yl)imidazo[1,2-a]pyridine-3-carboxamide

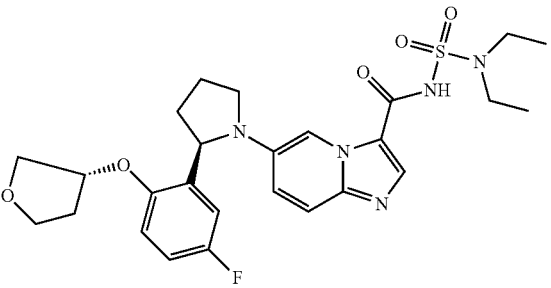 [SMILES: CCN(CC)S(=O)(=O)NC(=O)c1cnc2ccc(N3CCC[C@@H]3c3cc(F)ccc3O[C@@H]3CCOC3)cn12]

$^1$H NMR: (400 MHz, CDCl$_3$): δ 8.89 (s, 1H), 8.82 (s, 1H), 7.83-7.80 (d, 1H, J=9.6 Hz), 7.15-7.12 (d, 1H, J=9.6 Hz), 6.75-6.89 (m, 1H), 6.81-6.78 (m, 1H), 6.65-6.62 (m, 1H), 5.06-5.04 (m, 1H), 4.06-3.95 (m, 1H), 3.77-3.73 (m, 2H), 3.49-3.44 (m, 4H), 2.55-2.41 (m, 1H), 2.31-2.28 (m, 2H), 2.15-2.00 (m, 3H), 1.22 (t, 6H). MS (ESI): m/z 546.25 (M+H).

Example 113

Determination of In Vitro TrkA Inhibitory Activity Using TR-FRET Assay

Compounds were screened in the TR-FRET assay with TrkA kinase. 5 ng of TrkA [Upstate, USA] kinase was used for assay. The compound was incubated with the kinase for 30 minutes at 20-35° C. After the incubation, substrate mix [40 nM Ultra light poly GT (Perkin Elmer, USA) and 500 μM ATP] was added. The above reaction was stopped by the addition of 40 mM EDTA after 30 minutes. The Eu-labelled antiphospho-tyrosine antibody [Perkin Elmer, USA] was added at 0.5 nM and the fluorescence emission at 615 nm/665 nm [excitation at 340 nm] was measured. The compounds were initially screened at 100 nM, 1 μM and 10 μM concentrations. The potent compounds with >25% inhibition at 1 μM of TrkA were taken for the full dose response studies. The final DMSO concentration in the assay was 1%. For IC$_{50}$ determination, ⅓$^{rd}$ serial dilution was made from the 20 mM DMSO stock solution. 2 μl of these were transferred to the test wells containing 20 μl reaction mixture [Total reaction volume 22 μl]. The fluorescence was measured in Perkin Elmer Wallac 1420 Multilabel Counter Victor 3. The IC$_{50}$ was determined by fitting the dose response data to a sigmoidal curve fitting equation using GraphPad Prism software version 5.

Using this protocol, various compounds as described herein and further as exemplified above, were found to exhibit inhibitory effect on TrkA.

Example 1, 3, 4, 5, 34, 37, 38, 39, 41, 42, 43, 45, 47, 48, 55, 56, 57, 58, 59, 60, 62, 63, 69, 73, 74, 75, 76, 77, 78, 81, 83, 84, 85, 86, 87, 88, 89, 90, 92, 93, 95, 96, 97, 99, 100, 101, 102, 103, 104, 105, 106, 107, 108 or 110, as described herein, exhibited a TrkA inhibition in-vitro IC$_{50}$ values less than or equal to about 50 nM;

Example 10, 12, 25, 32, 35, 40, 44, 46, 53, 68, 80, 82, 91, 94 or 98 as described herein, exhibited a TrkA inhibitory activity in-vitro IC$_{50}$ values between about 50 nM and about 100 nM;

Example 2, 8, 16, 18, 19, 21, 24, 28, 30, 31, 33, 36, 50, 54, 61, 65, 71, 72 or 79, as described herein, exhibited a TrkA inhibitory activity in-vitro IC$_{50}$ values between about 100 nM to about 500 nM;

Example 23, 26 or 27 as described herein, exhibited a TrkA inhibitory activity in-vitro IC$_{50}$ values between about 500 nM to about 1 μM;

Example 6, 9, 11, 49, 51, 52, 64, 66 or 70 as described herein, exhibited a TrkA inhibitory activity in-vitro IC$_{50}$ values between about 1 μM to about 10 μM.

Although the present application has been illustrated by certain of the preceding examples, it is not to be construed as being limited thereby but rather, the present application encompasses the generic area as hereinbefore disclosed.

What is claimed is:

1. A compound having the formula (I),

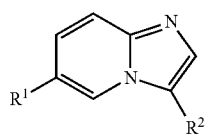

(I)

or pharmaceutically acceptable salts thereof, or pharmaceutically acceptable solvates thereof
or stereoisomers thereof,
wherein,
$R^1$ is —$X^a$—$R^a$;
$R^2$ is —$X^b$—$R^b$;
$X^a$ is a 3-7 membered heterocyclyl selected from aziridinyl, azetidinyl, pyrrolidinyl, piperidinyl, piperazinyl, azepanyl, thiomorpholinyl, 1,1-dioxo-thiomorphonyl and morpholinyl, any of which is optionally substituted with 1-3 times with $R^3$;
$R^3$, in each occurrence is selected independently from halogen, hydroxy, —(C$_1$-C$_6$)alkyl, —(C$_1$-C$_6$)alkoxy and halo(C$_1$-C$_6$)alkoxy;
$R^a$ is a phenyl ring optionally substituted 1-3 times with $R^4$;
$R^4$, in each occurrence is selected independently from halogen, —(C$_1$-C$_6$)alkyl and —O—$R^5$;
Alternatively, two $R^4$, on adjacent carbon atoms, together with the carbon atoms to which they are attached may form a 5-6 membered heterocyclyl or a 5-6 membered heteroaryl ring;
$R^5$ is selected from —(C$_1$-C$_6$)alkyl, halo(C$_1$-C$_6$)alkyl and 5-6 membered heterocyclyl;
$X^b$ is selected from —CO—, —CONR$^6$—, —NR$^6$CO—, —C(=N—OR$^6$)—, —CONR$^6$—SO$_2$—, —CONR$^6$—SO$_2$—NR$^6$—, and —R$^6$N—CO—NR$^6$;
$R^b$ is selected from
(i) alkyl, optionally substituted with 1-3 substituents selected independently from halogen, —(C$_1$-C$_6$)alkoxy, hydroxyl and —CO—(CR$^7$R$^8$)$_p$—OR$^9$;
(ii) aryl, heteroaryl or cycloalkyl, any of which is optionally substituted with 1-3 substituents selected independently from halogen, halo(C$_1$-C$_6$)alkyl, halo(C$_1$-C$_6$)alkoxy, —(C$_1$-C$_6$)alkoxy, hydroxyl, —(C$_1$-C$_6$)alkyl and —R$^{10}$;
(iii) heterocyclyl, optionally substituted with 1-3 substituents selected independently from halogen, halo(C$_1$-C$_6$)alkyl, halo(C$_1$-C$_6$)alkoxy, —(C$_1$-C$_6$)alkoxy, hydroxyl, —(C$_1$-C$_6$)alkyl, and N(R$^i$)$_2$, wherein R$^i$, in each occurrence, independently selected from hydrogen, —(C$_1$-C$_6$)alkyl or —(C$_3$-C$_6$)alkyl;
Alternatively, R$^6$ and R$^b$ together with Nitrogen atom to which they are attached, may form a 3-10 membered heterocyclic ring optionally substituted 1-3 times with R$^{11}$;
R$^6$, in each occurrence, is independently selected from hydrogen, —(C$_1$-C$_6$)alkyl and —(C$_1$-C$_6$)alkyl-(C$_3$-C$_6$)cycloalkyl;
R$^7$, R$^8$ or R$^9$, in each occurrence, is independently selected from hydrogen and —(C$_1$-C$_6$)alkyl;
R$^{10}$ is a 5-6 membered heterocyclyl or a 5-6 membered heteroaryl, any of which is optionally substituted with 1-2 substituents selected independently from —(C$_1$-C$_6$)alkyl, halogen, halo(C$_1$-C$_6$)alkyl, halo(C$_1$-C$_6$)alkoxy, —(C$_1$-C$_6$)alkoxy and hydroxyl;
R$^{11}$ is selected from halogen, hydroxyl, alkyl and —NH$_2$; and
p is 0, 1, 2 or 3.

2. The compound according to claim 1, having the formula (Ia):

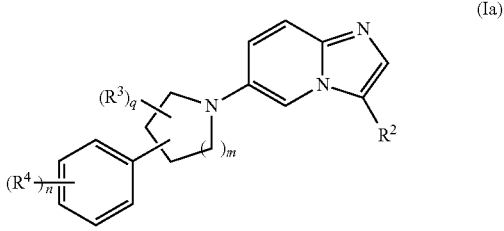

(Ia)

or pharmaceutically acceptable salts thereof, or pharmaceutically acceptable solvates thereof or stereoisomers thereof,
wherein
'n' is 1, 2 or 3;
'm' is 1, 2 or 3;
'q' is 0, 1, 2 or 3;
$R^2$, $R^3$, and $R^4$ are as described in claim 1.

3. The compound according to claim 1, having the formula (Id):

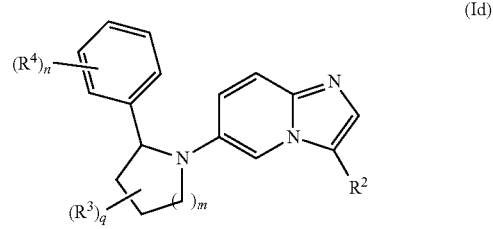

(Id)

or pharmaceutically acceptable salts thereof, or pharmaceutically acceptable solvates thereof or stereoisomers thereof,
wherein
'm' is 1 or 2;
'n' is 1, 2 or 3;
'q' is 0 or 1;
$R^2$, $R^3$, and $R^4$ are as described in claim 1.

4. The compound according to claim 1, having the formula (Ie):

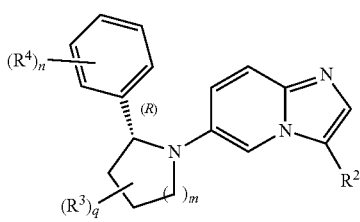

or pharmaceutically acceptable salts thereof, or pharmaceutically acceptable solvates thereof or stereoisomers thereof,
wherein
'm' is 1 or 2;
'n' is 1, 2 or 3;
'q' is 0 or 1;
$R^2$, $R^3$, and $R^4$ are as described in claim 1.

5. The compound according to claim 1, having the formula (Ig):

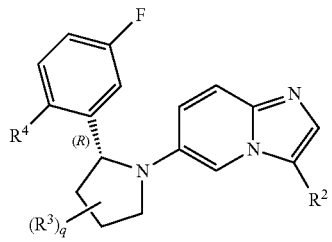

or pharmaceutically acceptable salts thereof, or pharmaceutically acceptable solvates thereof or stereoisomers thereof,
wherein
$R^3$ is halogen;
'q' is 0 or 1;
$R^2$ and $R^4$ are as described in claim 1.

6. The compound according to claim 1, having the formula (Ij):

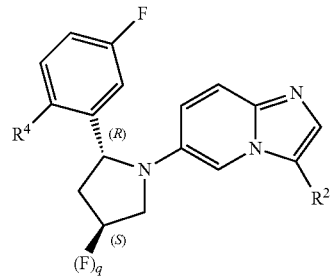

or pharmaceutically acceptable salts thereof, or pharmaceutically acceptable solvates thereof or stereoisomers thereof,
wherein
'q' is 0 or 1;
$R^2$ and $R^4$ are as described in claim 1.

7. The compound according to claim 1, having the formula (Ik):

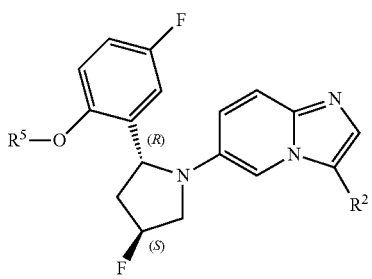

or pharmaceutically acceptable salts thereof, or pharmaceutically acceptable solvates thereof or stereoisomers thereof,
wherein
$R^2$ and $R^5$ are as described in claim 1.

8. The compound according to claim 1, having the formula (Il):

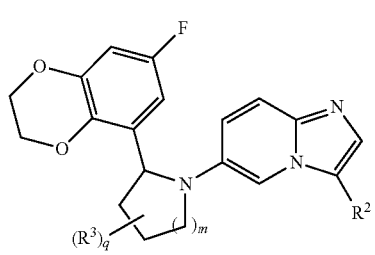

or pharmaceutically acceptable salts thereof, or pharmaceutically acceptable solvates thereof or stereoisomers thereof,
wherein
$R^3$ is halogen;
'm' is 1 or 2;
'q' is 0 or 1;
$R^2$ is as described in claim 1.

9. The compound according to claim 1, wherein $R^2$ is —CO—$R^b$, —CONH—$R^b$, —CONCH$_3$—$R^b$, —NHCO—$R^b$, —C(=N—OH)—$R^b$, —CONH—SO$_2$—$R^b$, —CON(CH$_3$)—SO$_2$—$R^b$, —CONH—SO$_2$—NH—$R^b$, —CONH—SO$_2$—N(CH$_3$)—$R^b$, —CONH—SO$_2$—N(CH$_2$CH$_3$)—$R^b$, —CONH—SO$_2$—N(CH$_2$CH$_2$CH$_3$)—$R^b$, —CONH—SO$_2$—N(cyclopropylmethyl)-$R^b$ or —NH—CO—NH—$R^b$.

10. The compound according to claim 1, wherein $R^b$ is
(i) methyl, ethyl, propyl, tert-butyl, isobutyl, propan-2-yl or 2-methylpropan-2-yl, any of which is optionally substituted with 1-3 substituents independently selected from fluorine, methoxy, hydroxyl, —COOCH$_2$CH$_3$ and —COOH;
(ii) phenyl, pyridin-2-yl, pyridin-3-yl, pyrazin-2-yl, pyridazin-3-yl, thiazol-2-yl, 1,3,4-thiadiazol-2-yl, 1H-pyrazol-3-yl, cyclopropyl, cyclohexyl or amantan-1-yl, any of which is optionally substituted with 1-3 substituents independently selected from fluorine, fluoromethyl, difluoromethyl, trifluoromethyl, fluoromethoxy, methoxy, ethoxy, hydroxyl, methyl, 3-hydroxypyrrolidin-1-yl, piperidin-1-yl, 1,2,4-triazol-1-yl and 1H-imidazol-1-yl; or
(iii) pyrrolidin-1-yl, azetidin-1-yl, piperidin-1-yl, morpholino, piperazin-1-yl, azepan-1-yl or tetrahydro-2H-pyran-4-yl, optionally substituted with 1-3 substituents independently selected from fluorine, fluoromethyl, difluoromethyl, trifluoromethyl, fluoromethoxy, methoxy, hydroxyl, —NH$_2$ and methyl.

11. The compound according to claim 1, wherein R$^4$ is independently selected from fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy or (R)-(tetrahydrofuran-3-yl)oxy; or R$^4$ on two carbon adjacent atoms, together with the carbon atoms to which they are attached form a 1,4-dioxine ring.

12. The compound according to claim 1, wherein
R$^1$ is —X$^a$—R$^a$;
R$^2$ is —CO—R$^b$, —CONH—R$^b$, —CONCH$_3$—R$^b$, —NHCO—R$^b$, —C(=N—OH)—R$^b$, —CONH—SO$_2$—R$^b$, —CON(CH$_3$)—SO$_2$—R$^b$, —CONH—SO$_2$—NH—R$^b$, —CONH—SO$_2$—N(CH$_3$)—R$^b$, —CONH—SO$_2$—N(CH$_2$CH$_3$)—R$^b$, —CONH—SO$_2$—N(CH$_2$CH$_2$CH$_3$)—R$^b$, —CONH—SO$_2$—N(cyclopropylmethyl)-R$^b$ or —NH—CO—NH—R$^b$;
X$^a$ is pyrrolidinyl or piperidinyl ring, optionally substituted with fluorine;
R$^a$ is a phenyl ring optionally substituted 2-3 times with R$^4$;
R$^4$ is independently selected from fluorine, methoxy, 2-fluoroethoxy, (tetrahydrofuranyl)oxy, (tetrahydropyranyl)oxy, (tetrahydrofuran-3-yl)oxy, (tetrahydro-2H-pyran-4-yl)oxy or (R)-(tetrahydrofuran-3-yl)oxy; or
R$^4$ on two adjacent carbon atoms, together with the carbon atoms to which they are attached form a 1,4-dioxine ring;
R$^b$ is methyl, ethyl, propyl, tert-butyl, —CH$_2$C(O)OCH$_2$CH$_3$, —CH$_2$C(O)OH, 2-hydroxyethyl, 1,3-dihydroxypropan-2-yl, 1,3-dihydroxy-2-methylpropan-2-yl, 1-hydroxy-2-methylpropan-2-yl, (S)-2,3-dihydroxypropyl, (S)-1-hydroxypropan-2-yl, 2-fluoroethyl, 2,2-difluoroethyl, 2-fluoro-2-methylpropyl, 2,2,2-trifluoroethyl, 2-methoxyethyl, 2-ethoxyethyl, cyclopropyl, 1-methylcyclopropyl, (1r,4r)-4-hydroxycyclohexyl, 3-hydroxyadamantan-1-yl, 3-hydroxyazetidin-1-yl, 3-hydroxy-3-methylazetidin-1-yl, (S)-3-aminopyrrolidin-1-yl), (S)-3-hydroxypyrrolidin-1-yl, piperidin-1-yl, 4-hydroxypiperidin-1-yl, morpholinyl, 4-methylpiperazinyl, tetrahydro-2H-pyran-4-yl, 4-hydroxyazepan-1-yl, thiazol-2-yl, 5-methyl-1,3,4-thiadiazol-2-yl, 1,3,4-thiadiazol-2-yl, 1H-1,2,4-triazol-1-yl, (1-methyl-1H-pyrazol-3-yl), 1H-imidazol-1-yl, 6-methylpyridazin-3-yl, pyridin-2-yl, pyridin-3-yl, pyrazin-2-yl, 4-fluorophenyl, ((S)-3-hydroxypyrrolidin-1-yl)phenyl or ((S)-3-hydroxypyrrolidin-1-yl)pyridin-3-yl.

13. The compound according to claim 1, selected from
6-(2-(2,5-difluorophenyl)pyrrolidin-1-yl)-N-(4-fluorophenyl)imidazo[1,2-a]pyridine-3-carboxamide;
N-(6-(2-(2,5-difluorophenyl)pyrrolidin-1-yl)imidazo[1,2-a]pyridin-3-yl)-3-hydroxypyrrolidine-1-carboxamide;
(6-(2-(2,5-difluorophenyl)pyrrolidin-1-yl)imidazo[1,2-a]pyridin-3-yl)(3-hydroxypyrrolidin-1-yl)methanone;
(6-(2-(2,5-difluorophenyl)pyrrolidin-1-yl)imidazo[1,2-a]pyridin-3-yl)(3-hydroxyazetidin-1-yl)methanone;
6-(2-(2,5-difluorophenyl)pyrrolidin-1-yl)-N-(1,3-dihydroxypropan-2-yl)imidazo[1,2-a]pyridine-3-carboxamide;
(6-(2-(2,5-difluorophenyl)pyrrolidin-1-yl)imidazo[1,2-a]pyridin-3-yl)(morpholino)methanone;
N-(6-(2-(2,5-difluorophenyl)pyrrolidin-1-yl)imidazo[1,2-a]pyridin-3-yl)morpholine-4-carboxamide;
6-(2-(2,5-difluorophenyl)pyrrolidin-1-yl)-N,N-dimethylimidazo[1,2-a]pyridine-3-carboxamide;
(6-(2-(2,5-difluorophenyl)pyrrolidin-1-yl)imidazo[1,2-a]pyridin-3-yl)(4-methylpiperazin-1-yl)methanone;
(6-(2-(2,5-difluorophenyl)pyrrolidin-1-yl)imidazo[1,2-a]pyridin-3-yl)(4-fluorophenyl)methanone;
3-(6-(2-(2,5-difluorophenyl)pyrrolidin-1-yl)imidazo[1,2-a]pyridin-3-yl)-1,1-dimethylurea;
(6-(2-(2,5-difluorophenyl)pyrrolidin-1-yl)imidazo[1,2-a]pyridin-3-yl)(3-hydroxypyrrolidin-1-yl)methanone;
N-(6-(2-(2,5-difluorophenyl)pyrrolidin-1-yl)imidazo[1,2-a]pyridin-3-yl)acetamide;
(6-(2-(2,5-difluorophenyl)pyrrolidin-1-yl)imidazo[1,2-a]pyridin-3-yl)(4-fluorophenyl)methanone oxime;
6-(2-(2,5-difluorophenyl)pyrrolidin-1-yl)-N-(4-fluorophenyl)-N-methylimidazo[1,2-a]pyridine-3-carboxamide;
6-(2-(2,5-difluorophenyl)pyrrolidin-1-yl)-N-(4-hydroxycyclohexyl)imidazo[1,2-a]pyridine-3-carboxamide;
(6-(2-(2,5-difluorophenyl)pyrrolidin-1-yl)imidazo[1,2-a]pyridin-3-yl)(4-hydroxypiperidin-1-yl)methanone;
6-(2-(2,5-difluorophenyl)pyrrolidin-1-yl)-N-(3-ethoxy-2-oxopropyl)imidazo[1,2-a]pyridine-3-carboxamide;
(6-(2-(2,5-difluorophenyl)pyrrolidin-1-yl)imidazo[1,2-a]pyridine-3-carbonyl)glycine;
2-(6-(2-(2,5-difluorophenyl)pyrrolidin-1-yl)imidazo[1,2-a]pyridine-3-carboxamido)acetic acid;
(3-aminopyrrolidin-1-yl)(6-(2-(2,5-difluorophenyl)pyrrolidin-1-yl)imidazo[1,2-a]pyridin-3-yl)methanone;
6-(2-(2,5-difluorophenyl)pyrrolidin-1-yl)-N-(2-hydroxyethyl)imidazo[1,2-a]pyridine-3-carboxamide;
6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide;
6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide;
6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide;
6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide;
N-(tert-butylsulfonyl)-6-(2-(5-fluoro-2-((tetrahydrofuran-3-yl)oxy)phenyl)pyrrolidin-1-yl)imidazo[1,2-a]pyridine-3-carboxamide;
N—(N-ethyl-N-methylsulfamoyl)-6-(2-(5-fluoro-2-((tetrahydrofuran-3-yl)oxy)phenyl)pyrrolidin-1-yl)imidazo[1,2-a]pyridine-3-carboxamide;
6-(2-(2,5-difluorophenyl)pyrrolidin-1-yl)-N-(2-hydroxyethyl)imidazo[1,2-a]pyridine-3-carboxamide;
(6-(2-(2,5-difluorophenyl)pyrrolidin-1-yl)imidazo[1,2-a]pyridin-3-yl)((S)-3-hydroxypyrrolidin-1-yl)methanone;
(6-(2-(2,5-difluorophenyl)pyrrolidin-1-yl)imidazo[1,2-a]pyridin-3-yl)(4-fluorophenyl)methanone oxime;
6-(2-(2,5-difluorophenyl)pyrrolidin-1-yl)-N-(4-fluorophenyl)-N-methylimidazo[1,2-a]pyridine-3-carboxamide;
6-(2-(2,5-difluorophenyl)pyrrolidin-1-yl)-N-((1r,4R)-4-hydroxycyclohexyl)imidazo[1,2-a]pyridine-3-carboxamide;

(6-(2-(2,5-difluorophenyl)pyrrolidin-1-yl)imidazo[1,2-a]pyridin-3-yl)(4-hydroxypiperidin-1-yl)methanone;
6-(2-(2,5-difluorophenyl)pyrrolidin-1-yl)-N-(3-ethoxy-2-oxopropyl)imidazo[1,2-a]pyridine-3-carboxamide;
Ethyl 2-(6-(2-(2,5-difluorophenyl)pyrrolidin-1-yl)imidazo[1,2-a]pyridine-3-carboxamido)acetate;
(6-(2-(2,5-difluorophenyl)pyrrolidin-1-yl)imidazo[1,2-a]pyridine-3-carbonyl)glycine;
2-(6-(2-(2,5-difluorophenyl)pyrrolidin-1-yl)imidazo[1,2-a]pyridine-3-carboxamido)acetic acid;
6-(2-(2,5-difluorophenyl)pyrrolidin-1-yl)-N-(2-hydroxyethyl)imidazo[1,2-a]pyridine-3-carboxamide;
(6-(2-(2,5-difluorophenyl)pyrrolidin-1-yl)imidazo[1,2-a]pyridin-3-yl)(4-hydroxyazepan-1-yl)methanone;
6-(2-(2,5-difluorophenyl)pyrrolidin-1-yl)-N-((1r,3S,5R,7S)-3-hydroxyadamantan-1-yl)imidazo[1,2-a]pyridine-3-carboxamide;
6-(2-(2,5-difluorophenyl)pyrrolidin-1-yl)-N-(1,3-dihydroxy-2-methylpropan-2-yl)imidazo[1,2-a]pyridine-3-carboxamide;
6-(2-(2,5-difluorophenyl)pyrrolidin-1-yl)-N—((S)-2,3-dihydroxypropyl)imidazo[1,2-a]pyridine-3-carboxamide;
(6-(2-(2,5-difluorophenyl)pyrrolidin-1-yl)imidazo[1,2-a]pyridin-3-yl)(3-hydroxy-3-methylazetidin-1-yl)methanone;
6-(2-(2,5-difluorophenyl)pyrrolidin-1-yl)-N-(piperidin-1-yl)imidazo[1,2-a]pyridine-3-carboxamide;
6-(2-(2,5-difluorophenyl)pyrrolidin-1-yl)-N—((S)-1-hydroxypropan-2-yl)imidazo[1,2-a]pyridine-3-carboxamide;
6-(2-(2,5-difluorophenyl)pyrrolidin-1-yl)-N-(1-hydroxy-2-methylpropan-2-yl)imidazo[1,2-a]pyridine-3-carboxamide;
6-(2-(2,5-difluorophenyl)pyrrolidin-1-yl)-N-(tetrahydro-2H-pyran-4-yl)imidazo[1,2-a]pyridine-3-carboxamide;
N-(tert-butylsulfonyl)-6-(2-(2,5-difluorophenyl)pyrrolidin-1-yl)imidazo[1,2-a]pyridine-3-carboxamide;
6-(2-(2,5-difluorophenyl)pyrrolidin-1-yl)-N-((1-methylcyclopropyl)sulfonyl)imidazo[1,2-a]pyridine-3-carboxamide;
6-(2-(2,5-difluorophenyl)pyrrolidin-1-yl)-N-((6-((S)-3-hydroxypyrrolidin-1-yl)pyridin-3-yl)sulfonyl)imidazo[1,2-a]pyridine-3-carboxamide;
6-(2-(2,5-difluorophenyl)pyrrolidin-1-yl)-N—(N-ethyl-N-methylsulfamoyl)imidazo[1,2-a]pyridine-3-carboxamide;
N-((4-(1H-1,2,4-triazol-1-yl)phenyl)sulfonyl)-6-(2-(2,5-difluorophenyl)pyrrolidin-1-yl)imidazo[1,2-a]pyridine-3-carboxamide;
6-(2-(2,5-difluorophenyl)pyrrolidin-1-yl)-N-((4-((S)-3-hydroxypyrrolidin-1-yl)phenyl)sulfonyl)imidazo[1,2-a]pyridine-3-carboxamide;
6-(2-(2,5-difluorophenyl)pyrrolidin-1-yl)-N—(N-methyl-N-propylsulfamoyl)imidazo[1,2-a]pyridine-3-carboxamide;
6-(2-(2,5-difluorophenyl)pyrrolidin-1-yl)-N—(N-(2-fluoroethyl)-N-methylsulfamoyl)imidazo[1,2-a]pyridine-3-carboxamide;
6-(2-(2,5-difluorophenyl)pyrrolidin-1-yl)-N—(N-(2-methoxyethyl)-N-methylsulfamoyl)imidazo[1,2-a]pyridine-3-carboxamide;
6-(2-(2,5-difluorophenyl)pyrrolidin-1-yl)-N—(N-ethyl-N-(2-fluoroethyl)sulfamoyl)imidazo[1,2-a]pyridine-3-carboxamide;
6-(2-(2,5-difluorophenyl)pyrrolidin-1-yl)-N—(N-methyl-N-(2,2,2-trifluoroethyl)sulfamoyl)imidazo[1,2-a]pyridine-3-carboxamide;
6-(2-(2,5-difluorophenyl)pyrrolidin-1-yl)-N—(N-(2-fluoro-2-methylpropyl)-N-methylsulfamoyl)imidazo[1,2-a]pyridine-3-carboxamide;
6-(2-(2,5-difluorophenyl)pyrrolidin-1-yl)-N—(N-methyl-N-(pyridin-3-yl)sulfamoyl)imidazo[1,2-a]pyridine-3-carboxamide;
N—(N-(cyclopropylmethyl)-N-(pyridin-3-yl)sulfamoyl)-6-(2-(2,5-difluorophenyl)pyrrolidin-1-yl)imidazo[1,2-a]pyridine-3-carboxamide;
6-(2-(2,5-difluorophenyl)pyrrolidin-1-yl)-N—(N-methyl-N-(pyrazin-2-yl)sulfamoyl)imidazo[1,2-a]pyridine-3-carboxamide;
N-((6-(1H-imidazol-1-yl)pyridin-3-yl)sulfonyl)-6-(2-(2,5-difluorophenyl)pyrrolidin-1-yl)imidazo[1,2-a]pyridine-3-carboxamide;
6-(2-(2,5-difluorophenyl)pyrrolidin-1-yl)-N—(N-methyl-N-(pyridin-2-yl)sulfamoyl)imidazo[1,2-a]pyridine-3-carboxamide;
6-(2-(2,5-difluorophenyl)pyrrolidin-1-yl)-N—(N-methyl-N-(thiazol-2-yl)sulfamoyl)imidazo[1,2-a]pyridine-3-carboxamide;
6-(2-(2,5-difluorophenyl)piperidin-1-yl)-N-((4-(3-hydroxypyrrolidin-1-yl)phenyl)sulfonyl)imidazo[1,2-a]pyridine-3-carboxamide;
6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide;
6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide;
6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide;
6-(2-(5-fluoro-2-methoxyphenyl)pyrrolidin-1-yl)-N—(N-methyl-N-propylsulfamoyl)imidazo[1,2-a]pyridine-3-carboxamide;
6-(2-(5-fluoro-2-methoxyphenyl)pyrrolidin-1-yl)-N—(N-(2-fluoro-2-methylpropyl)-N-methylsulfamoyl)imidazo[1,2-a]pyridine-3-carboxamide;
N—(N-ethyl-N-methylsulfamoyl)-6-(2-(5-fluoro-2-methoxyphenyl)pyrrolidin-1-yl)imidazo[1,2-a]pyridine-3-carboxamide;
6-(2-(5-fluoro-2-methoxyphenyl)pyrrolidin-1-yl)-N—(N-(2-fluoroethyl)-N-methylsulfamoyl)imidazo[1,2-a]pyridine-3-carboxamide;
N—(N-ethyl-N-methylsulfamoyl)-6-(4-fluoro-2-(5-fluoro-2-(2-fluoroethoxy)phenyl)pyrrolidin-1-yl)imidazo[1,2-a]pyridine-3-carboxamide;
N-(tert-butylsulfonyl)-6-(4-fluoro-2-(5-fluoro-2-(2-fluoroethoxy)phenyl)pyrrolidin-1-yl)imidazo[1,2-a]pyridine-3-carboxamide;
N-(tert-butylsulfonyl)-6-(4-fluoro-2-(5-fluoro-2-((tetrahydrofuran-3-yl)oxy)phenyl)pyrrolidin-1-yl)imidazo[1,2-a]pyridine-3-carboxamide;
N—(N-ethyl-N-methylsulfamoyl)-6-(4-fluoro-2-(5-fluoro-2-((tetrahydrofuran-3-yl)oxy)phenyl)pyrrolidin-1-yl)imidazo[1,2-a]pyridine-3-carboxamide;
6-(4-fluoro-2-(5-fluoro-2-((tetrahydrofuran-3-yl)oxy)phenyl)pyrrolidin-1-yl)-N-((1-methylcyclopropyl)sulfonyl)imidazo[1,2-a]pyridine-3-carboxamide;
6-(4-fluoro-2-(5-fluoro-2-((tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

N—(N-ethyl-N-methylsulfamoyl)-6-(2-(5-fluoro-2-((tetrahydrofuran-3-yl)oxy)phenyl)pyrrolidin-1-yl)imidazo[1,2-a]pyridine-3-carboxamide;
N—(N-ethyl-N-methylsulfamoyl)-6-(2-(5-fluoro-2-((tetrahydrofuran-3-yl)oxy)phenyl)pyrrolidin-1-yl)imidazo[1,2-a]pyridine-3-carboxamide;
N-(tert-butylsulfonyl)-6-(2-(5-fluoro-2-((tetrahydrofuran-3-yl)oxy)phenyl)pyrrolidin-1-yl)imidazo[1,2-a]pyridine-3-carboxamide;
N-(tert-butylsulfonyl)-6-(2-(5-fluoro-2-((tetrahydrofuran-3-yl)oxy)phenyl)pyrrolidin-1-yl)imidazo[1,2-a]pyridine-3-carboxamide;
N—(N-ethyl-N-methylsulfamoyl)-6-4-fluoro-2-(5-fluoro-2-((tetrahydro-2H-pyran-4-yl)oxy)phenyl)pyrrolidin-1-yl)imidazo[1,2-a]pyridine-3-carboxamide;
N—(N-ethyl-N-methylsulfamoyl)-6-((2R)-4-fluoro-2-(5-fluoro-2-((tetrahydro-2H-pyran-4-yl)oxy)phenyl)pyrrolidin-1-yl)imidazo[1,2-a]pyridine-3-carboxamide;
N—(N-ethyl-N-methylsulfamoyl)-6-((2S)-4-fluoro-2-(5-fluoro-2-((tetrahydro-2H-pyran-4-yl)oxy)phenyl)pyrrolidin-1-yl)imidazo[1,2-a]pyridine-3-carboxamide;
N—(N-ethyl-N-methylsulfamoyl)-6-(4-fluoro-2-(7-fluoro-2,3-dihydrobenzo[b][1,4]dioxin-5-yl)pyrrolidin-1-yl)imidazo[1,2-a]pyridine-3-carboxamide;
6-(2-(2,5-difluorophenyl)piperidin-1-yl)-N-((1-methylcyclopropyl)sulfonyl)imidazo[1,2-a]pyridine-3-carboxamide;
6-(2-(2,5-difluorophenyl)piperidin-1-yl)-N—(N-ethyl-N-methylsulfamoyl)imidazo[1,2-a]pyridine-3-carboxamide;
6-(2-(7-fluoro-2,3-dihydrobenzo[b][1,4]dioxin-5-yl)pyrrolidin-1-yl)-N—(N-(2-fluoroethyl)-N-methylsulfamoyl)imidazo[1,2-a]pyridine-3-carboxamide;
N—(N-ethyl-N-methylsulfamoyl)-6-(2-(7-fluoro-2,3-dihydrobenzo[b][1,4]dioxin-5-yl)pyrrolidin-1-yl)imidazo[1,2-a]pyridine-3-carboxamide;
6-(2-(5-fluoro-2-(((R)-tetrahydrofuran-3-yl)oxy)phenyl)pyrrolidin-1-yl)-N-((1-methylcyclopropyl)sulfonyl)imidazo[1,2-a]pyridine-3-carboxamide;
6-(2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;
6-(2-(5-fluoro-2-((tetrahydrofuran-3-yl)oxy)phenyl)pyrrolidin-1-yl)-N—(N-methyl-N-propylsulfamoyl)imidazo[1,2-a]pyridine-3-carboxamide;
6-(2-(5-fluoro-2-((tetrahydrofuran-3-yl)oxy)phenyl)pyrrolidin-1-yl)-N—(N-(2-fluoro-2-methylpropyl)-N-methylsulfamoyl)imidazo[1,2-a]pyridine-3-carboxamide;
N—(N-ethyl-N-methylsulfamoyl)-6-(2-(5-fluoro-2-(2-fluoroethoxy)phenyl)pyrrolidin-1-yl)imidazo[1,2-a]pyridine-3-carboxamide;
6-(2-(5-fluoro-2-(2-fluoroethoxy)phenyl)pyrrolidin-1-yl)-N—(N-(2-fluoroethyl)-N-methylsulfamoyl)imidazo[1,2-a]pyridine-3-carboxamide;
6-(2-(5-fluoro-2-(2-fluoroethoxy)phenyl)pyrrolidin-1-yl)-N—(N-methyl-N-propylsulfamoyl)imidazo[1,2-a]pyridine-3-carboxamide;
6-(2-(5-fluoro-2-(2-fluoroethoxy)phenyl)pyrrolidin-1-yl)-N—(N-(2-fluoro-2-methylpropyl)-N-methylsulfamoyl)imidazo[1,2-a]pyridine-3-carboxamide;
N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-(2-fluoroethyl)-N-methylsulfamoyl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide;
6-(2-(5-fluoro-2-((tetrahydro-2H-pyran-4-yl)oxy)phenyl)pyrrolidin-1-yl)-N-(2-fluoro-2-methylpropyl)-N-methylsulfamoyl)imidazo[1,2-a]pyridine-3-carboxamide;
1-(6-(4-fluoro-2-(5-fluoro-2-((tetrahydro-2H-pyran-4-yl)oxy)phenyl)pyrrolidin-1-yl)imidazo[1,2-a]pyridin-3-yl)-N-(2-fluoroethyl)-N-methyl-1-oxomethanesulfonamide;
(tert-butylsulfonyl)(6-(4-fluoro-2-(5-fluoro-2-((tetrahydro-2H-pyran-4-yl)oxy)phenyl)pyrrolidin-1-yl)imidazo[1,2-a]pyridin-3-yl)methanone;
6-(2-(2,5-difluorophenyl)pyrrolidin-1-yl)-N—(N-methyl-N-(pyrazin-2-yl)sulfamoyl)imidazo[1,2-a]pyridine-3-carboxamide;
N-((6-(1H-imidazol-1-yl)pyridin-3-yl)sulfonyl)-6-(2-(2,5-difluorophenyl)pyrrolidin-1-yl)imidazo[1,2-a]pyridine-3-carboxamide;
N—(N,N-diethylsulfamoyl)-6-(4-fluoro-2-(5-fluoro-2-((tetrahydrofuran-3-yl)oxy)phenyl)pyrrolidin-1-yl)imidazo[1,2-a]pyridine-3-carboxamide;
N—(N-ethyl-N-(2-fluoroethyl)sulfamoyl)-6-(4-fluoro-2-(5-fluoro-2-(((R)-tetrahydrofuran-3-yl)oxy)phenyl)pyrrolidin-1-yl)imidazo[1,2-a]pyridine-3-carboxamide;
6-(4-fluoro-2-(5-fluoro-2-((tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide;
6-(4-fluoro-2-(5-fluoro-2-((tetrahydrofuran-3-yl)oxy)phenyl)pyrrolidin-1-yl)-N—(N-methyl-N-(thiazol-2-yl)sulfamoyl)imidazo[1,2-a]pyridine-3-carboxamide;
6-(4-fluoro-2-(5-fluoro-2-((tetrahydrofuran-3-yl)oxy)phenyl)pyrrolidin-1-yl)-N—(N-methyl-N-(6-methylpyridazin-3-yl)sulfamoyl)imidazo[1,2-a]pyridine-3-carboxamide N-(tert-butylsulfonyl)-6-(2-(5-fluoro-2-((tetrahydro-2H-pyran-4-yl)oxy)phenyl)pyrrolidin-1-yl)imidazo[1,2-a]pyridine-3-carboxamide;
N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide;
N—(N-(2-ethoxyethyl)-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-methyl-N-(6-methylpyridazin-3-yl)sulfamoyl)imidazo[1,2-a]pyridine-3-carboxamide;

6-(4-fluoro-2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide;
6-(4-fluoro-2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide;
6-(2-(2,5-difluorophenyl)pyrrolidin-1-yl)-N—(N-methyl-N-(1-methyl-1H-pyrazol-3-yl)sulfamoyl)imidazo[1,2-a]pyridine-3-carboxamide;
6-(2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;
6-(4-fluoro-2-(5-fluoro-2-((tetrahydrofuran-3-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;
6-(4-fluoro-2-(5-fluoro-2-((tetrahydrofuran-3-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;
N-(tert-butylsulfonyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;
N—(N,N-diethylsulfamoyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;
6-(4-fluoro-2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;
6-(4-fluoro-2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide;
6-(4-fluoro-2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;
6-(4-fluoro-2-(5-fluoro-2-((tetrahydro-2H-pyran-4-yl)oxy)phenyl)pyrrolidin-1-yl)-N—(N-(2-fluoroethyl)-N-methylsulfamoyl)imidazo[1,2-a]pyridine-3-carboxamide;
6-(4-fluoro-2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide;
6-(4-fluoro-2-(5-fluoro-2-((tetrahydrofuran-3-yl)oxy)phenyl)pyrrolidin-1-yl)-N—(N-methyl-N-propylsulfamoyl)imidazo[1,2-a]pyridine-3-carboxamide;
N—(N-ethyl-N-(2-fluoroethyl)sulfamoyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;
6-((2R,4S)-4-fluoro-2-(5-fluoro-2-((tetrahydrofuran-3-yl)oxy)phenyl)pyrrolidin-1-yl)-N—(N-methyl-N-(pyridin-2-yl)sulfamoyl)imidazo[1,2-a]pyridine-3-carboxamide;
6-(4-fluoro-2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide;
6-(2-(5-fluoro-2-((tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide;
N—(N,N-dimethylsulfamoyl)-6-(2-(5-fluoro-2-((tetrahydrofuran-3-yl)oxy)phenyl)pyrrolidin-1-yl)imidazo[1,2-a]pyridine-3-carboxamide;
6-(2-(5-fluoro-2-((tetrahydrofuran-3-yl)oxy)phenyl)pyrrolidin-1-yl)-N—(N-methyl-N-propylsulfamoyl)imidazo[1,2-a]pyridine-3-carboxamide;
N—(N-cyclopropyl-N-methylsulfamoyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;
N—(N-(2,2-difluoroethyl)-N-methylsulfamoyl)-6-(4-fluoro-2-(5-fluoro-2-((tetrahydro-2H-pyran-4-yl)oxy)phenyl)pyrrolidin-1-yl)imidazo[1,2-a]pyridine-3-carboxamide;
6-(4-fluoro-2-(5-fluoro-2-((tetrahydro-2H-pyran-4-yl)oxy)phenyl)pyrrolidin-1-yl)-N—(N-(2-fluoro-2-methylpropyl)-N-methylsulfamoyl)imidazo[1,2-a]pyridine-3-carboxamide;
6-(2-(5-fluoro-2-((tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide; and
N—(N,N-diethylsulfamoyl)-6-(2-(5-fluoro-2-((tetrahydrofuran-3-yl)oxy)phenyl)pyrrolidin-1-yl)imidazo[1,2-a]pyridine-3-carboxamide;

or a pharmaceutically acceptable salt thereof, or a pharmaceutically acceptable solvate thereof or a stereoisomer thereof.

14. The compound according to claim 1, selected from
(R)-6-(2-(2,5-difluorophenyl)pyrrolidin-1-yl)-N-(2-hydroxyethyl)imidazo[1,2-a]pyridine-3-carboxamide;
(S)-6-(2-(2,5-difluorophenyl)pyrrolidin-1-yl)-N-(2-hydroxyethyl)imidazo[1,2-a]pyridine-3-carboxamide;
(3S)—N-(6-(2-(2,5-difluorophenyl)pyrrolidin-1-yl)imidazo[1,2-a]pyridin-3-yl)-3-hydroxypyrrolidine-1-carboxamide;
(6-(2-(2,5-difluorophenyl)pyrrolidin-1-yl)imidazo[1,2-a]pyridin-3-yl)((S)-3-hydroxypyrrolidin-1-yl)methanone;
(6-((S)-2-(2,5-difluorophenyl)pyrrolidin-1-yl)imidazo[1,2-a]pyridin-3-yl)((S)-3-hydroxypyrrolidin-1-yl)methanone;
(6-((R)-2-(2,5-difluorophenyl)pyrrolidin-1-yl)imidazo[1,2-a]pyridin-3-yl)((S)-3-hydroxypyrrolidin-1-yl)methanone;
(Z/E)(6-(2-(2,5-difluorophenyl)pyrrolidin-1-yl)imidazo[1,2-a]pyridin-3-yl)(4-fluorophenyl)methanone oxime;
(E/Z)-(6-(2-(2,5-difluorophenyl)pyrrolidin-1-yl)imidazo[1,2-a]pyridin-3-yl)(4-fluorophenyl)methanone oxime;
(R)-6-(2-(2,5-difluorophenyl)pyrrolidin-1-yl)-N-(4-fluorophenyl)-N-methylimidazo[1,2-a]pyridine-3-carboxamide;
(S)-6-(2-(2,5-difluorophenyl)pyrrolidin-1-yl)-N-(4-fluorophenyl)-N-methylimidazo[1,2-a]pyridine-3-carboxamide;
6-((S)-2-(2,5-difluorophenyl)pyrrolidin-1-yl)-N-((1r,4S)-4-hydroxycyclohexyl)imidazo[1,2-a]pyridine-3-carboxamide;
6-((R)-2-(2,5-difluorophenyl)pyrrolidin-1-yl)-N-((1r,4R)-4-hydroxycyclohexyl)imidazo[1,2-a]pyridine-3-carboxamide;
(S)-(6-(2-(2,5-difluorophenyl)pyrrolidin-1-yl)imidazo[1,2-a]pyridin-3-yl)(4-hydroxypiperidin-1-yl)methanone;
(R)-(6-(2-(2,5-difluorophenyl)pyrrolidin-1-yl)imidazo[1,2-a]pyridin-3-yl)(4-hydroxypiperidin-1-yl)methanone;
(S)-6-(2-(2,5-difluorophenyl)pyrrolidin-1-yl)-N-(3-ethoxy-2-oxopropyl)imidazo[1,2-a]pyridine-3-carboxamide;

Ethyl (S)-2-(6-(2-(2,5-difluorophenyl)pyrrolidin-1-yl)imidazo[1,2-a]pyridine-3-carboxamido)acetate;
(R)-6-(2-(2,5-difluorophenyl)pyrrolidin-1-yl)-N-(3-ethoxy-2-oxopropyl)imidazo[1,2-a]pyridine-3-carboxamide;
Ethyl (R)-2-(6-(2-(2,5-difluorophenyl)pyrrolidin-1-yl)imidazo[1,2-a]pyridine-3-carboxamido)acetate;
(S)-(6-(2-(2,5-difluorophenyl)pyrrolidin-1-yl)imidazo[1,2-a]pyridine-3-carbonyl)glycine;
(S)-2-(6-(2-(2,5-difluorophenyl)pyrrolidin-1-yl)imidazo[1,2-a]pyridine-3-carboxamido)acetic acid;
(R)-(6-(2-(2,5-difluorophenyl)pyrrolidin-1-yl)imidazo[1,2-a]pyridine-3-carbonyl)glycine;
(R)-2-(6-(2-(2,5-difluorophenyl)pyrrolidin-1-yl)imidazo[1,2-a]pyridine-3-carboxamido)acetic acid;
((S)-3-aminopyrrolidin-1-yl)(6-((S)-2-(2,5-difluorophenyl)pyrrolidin-1-yl)imidazo[1,2-a]pyridin-3-yl)methanone;
((S)-3-aminopyrrolidin-1-yl)(6-((R)-2-(2,5-difluorophenyl)pyrrolidin-1-yl)imidazo[1,2-a]pyridin-3-yl)methanone;
(R)-6-(2-(2,5-difluorophenyl)pyrrolidin-1-yl)-N-(2-hydroxyethyl)imidazo[1,2-a]pyridine-3-carboxamide;
(S)-6-(2-(2,5-difluorophenyl)pyrrolidin-1-yl)-N-(2-hydroxyethyl)imidazo[1,2-a]pyridine-3-carboxamide;
(6-((R)-2-(2,5-difluorophenyl)pyrrolidin-1-yl)imidazo[1,2-a]pyridin-3-yl)(4-hydroxyazepan-1-yl)methanone;
6-((R)-2-(2,5-difluorophenyl)pyrrolidin-1-yl)-N-((1r,3S,5R,7S)-3-hydroxyadamantan-1-yl)imidazo[1,2-a]pyridine-3-carboxamide;
(R)-6-(2-(2,5-difluorophenyl)pyrrolidin-1-yl)-N-(1,3-dihydroxy-2-methylpropan-2-yl)imidazo[1,2-a]pyridine-3-carboxamide;
6-((R)-2-(2,5-difluorophenyl)pyrrolidin-1-yl)-N—((S)-2,3-dihydroxypropyl)imidazo[1,2-a]pyridine-3-carboxamide;
(R)-(6-(2-(2,5-difluorophenyl)pyrrolidin-1-yl)imidazo[1,2-a]pyridin-3-yl)(3-hydroxy-3-methylazetidin-1-yl)methanone;
(R)-6-(2-(2,5-difluorophenyl)pyrrolidin-1-yl)-N-(piperidin-1-yl)imidazo[1,2-a]pyridine-3-carboxamide;
6-((R)-2-(2,5-difluorophenyl)pyrrolidin-1-yl)-N—((S)-1-hydroxypropan-2-yl)imidazo[1,2-a]pyridine-3-carboxamide;
(R)-6-(2-(2,5-difluorophenyl)pyrrolidin-1-yl)-N-(1-hydroxy-2-methylpropan-2-yl)imidazo[1,2-a]pyridine-3-carboxamide;
(R)-6-(2-(2,5-difluorophenyl)pyrrolidin-1-yl)-N-(tetrahydro-2H-pyran-4-yl)imidazo[1,2-a]pyridine-3-carboxamide;
(R)—N-(tert-butylsulfonyl)-6-(2-(2,5-difluorophenyl)pyrrolidin-1-yl)imidazo[1,2-a]pyridine-3-carboxamide;
(R)-6-(2-(2,5-difluorophenyl)pyrrolidin-1-yl)-N-((1-methylcyclopropyl)sulfonyl)imidazo[1,2-a]pyridine-3-carboxamide;
6-((R)-2-(2,5-difluorophenyl)pyrrolidin-1-yl)-N-((6-((S)-3-hydroxypyrrolidin-1-yl)pyridin-3-yl)sulfonyl)imidazo[1,2-a]pyridine-3-carboxamide;
(R)-6-(2-(2,5-difluorophenyl)pyrrolidin-1-yl)-N—(N-ethyl-N-methylsulfamoyl)imidazo[1,2-a]pyridine-3-carboxamide;
(R)—N-((4-(1H-1,2,4-triazol-1-yl)phenyl)sulfonyl)-6-(2-(2,5-difluorophenyl)pyrrolidin-1-yl)imidazo[1,2-a]pyridine-3-carboxamide;
6-((R)-2-(2,5-difluorophenyl)pyrrolidin-1-yl)-N-((4-((S)-3-hydroxypyrrolidin-1-yl)phenyl)sulfonyl)imidazo[1,2-a]pyridine-3-carboxamide;
(R)-6-(2-(2,5-difluorophenyl)pyrrolidin-1-yl)-N—(N-methyl-N-propylsulfamoyl)imidazo[1,2-a]pyridine-3-carboxamide;
(R)-6-(2-(2,5-difluorophenyl)pyrrolidin-1-yl)-N—(N-(2-fluoroethyl)-N-methylsulfamoyl)imidazo[1,2-a]pyridine-3-carboxamide;
(R)-6-(2-(2,5-difluorophenyl)pyrrolidin-1-yl)-N—(N-(2-methoxyethyl)-N-methylsulfamoyl)imidazo[1,2-a]pyridine-3-carboxamide;
(R)-6-(2-(2,5-difluorophenyl)pyrrolidin-1-yl)-N—(N-ethyl-N-(2-fluoroethyl)sulfamoyl)imidazo[1,2-a]pyridine-3-carboxamide;
(R)-6-(2-(2,5-difluorophenyl)pyrrolidin-1-yl)-N—(N-methyl-N-(2,2,2-trifluoroethyl)sulfamoyl)imidazo[1,2-a]pyridine-3-carboxamide;
(R)-6-(2-(2,5-difluorophenyl)pyrrolidin-1-yl)-N—(N-(2-fluoro-2-methylpropyl)-N-methylsulfamoyl)imidazo[1,2-a]pyridine-3-carboxamide;
(R)-6-(2-(2,5-difluorophenyl)pyrrolidin-1-yl)-N—(N-methyl-N-(pyridin-3-yl)sulfamoyl)imidazo[1,2-a]pyridine-3-carboxamide;
(R)—N—(N-(cyclopropylmethyl)-N-(pyridin-3-yl)sulfamoyl)-6-(2-(2,5-difluorophenyl)pyrrolidin-1-yl)imidazo[1,2-a]pyridine-3-carboxamide;
(R)-6-(2-(2,5-difluorophenyl)pyrrolidin-1-yl)-N—(N-methyl-N-(pyrazin-2-yl)sulfamoyl)imidazo[1,2-a]pyridine-3-carboxamide;
(R)—N-((6-(1H-imidazol-1-yl)pyridin-3-yl)sulfonyl)-6-(2-(2,5-difluorophenyl)pyrrolidin-1-yl)imidazo[1,2-a]pyridine-3-carboxamide;
(R)-6-(2-(2,5-difluorophenyl)pyrrolidin-1-yl)-N—(N-methyl-N-(pyridin-2-yl)sulfamoyl)imidazo[1,2-a]pyridine-3-carboxamide;
(R)-6-(2-(2,5-difluorophenyl)pyrrolidin-1-yl)-N—(N-methyl-N-(thiazol-2-yl)sulfamoyl)imidazo[1,2-a]pyridine-3-carboxamide;
6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide;
6-(2-(2,5-difluorophenyl)piperidin-1-yl)-N-((4-((S)-3-hydroxypyrrolidin-1-yl)phenyl)sulfonyl)imidazo[1,2-a]pyridine-3-carboxamide;
6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide;
6-(2-(7-fluoro-2,3-dihydrobenzo[b][1,4]dioxin-5-yl)pyrrolidin-1-yl)-N-((1-methylcyclopropyl)sulfonyl)imidazo[1,2-a]pyridine-3-carboxamide;
6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide;
6-(2-(2,5-difluorophenyl)piperidin-1-yl)-N-((6-((S)-3-hydroxypyrrolidin-1-yl)pyridin-3-yl)sulfonyl)imidazo[1,2-a]pyridine-3-carboxamide;
6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide;
6-(2-(7-fluoro-2,3-dihydrobenzo[b][1,4]dioxin-5-yl)piperidin-1-yl)-N-((1-methylcyclopropyl)sulfonyl)imidazo[1,2-a]pyridine-3-carboxamide;
(R)-6-(2-(5-fluoro-2-methoxyphenyl)pyrrolidin-1-yl)-N—(N-methyl-N-propylsulfamoyl)imidazo[1,2-a]pyridine-3-carboxamide;

(R)-6-(2-(5-fluoro-2-methoxyphenyl)pyrrolidin-1-yl)-N—(N-(2-fluoro-2-methylpropyl)-N-methylsulfamoyl)imidazo[1,2-a]pyridine-3-carboxamide;

(R)—N—(N-ethyl-N-methylsulfamoyl)-6-(2-(5-fluoro-2-methoxyphenyl)pyrrolidin-1-yl)imidazo[1,2-a]pyridine-3-carboxamide;

(R)-6-(2-(5-fluoro-2-methoxyphenyl)pyrrolidin-1-yl)-N—(N-(2-fluoroethyl)-N-methylsulfamoyl)imidazo[1,2-a]pyridine-3-carboxamide;

N—(N-ethyl-N-methylsulfamoyl)-6-((2R,4S)-4-fluoro-2-(5-fluoro-2-(2-fluoroethoxy)phenyl)pyrrolidin-1-yl)imidazo[1,2-a]pyridine-3-carboxamide;

N-(tert-butylsulfonyl)-6-((2R,4S)-4-fluoro-2-(5-fluoro-2-(2-fluoroethoxy)phenyl)pyrrolidin-1-yl)imidazo[1,2-a]pyridine-3-carboxamide;

N-(tert-butylsulfonyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-methylsulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N-((1-methylcyclopropyl)sulfonyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

N—(N-ethyl-N-methylsulfamoyl)-6-(2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-methylsulfamoyl)-6-(2-(5-fluoro-2-(((R)-tetrahydrofuran-3-yl)oxy)phenyl)pyrrolidin-1-yl)imidazo[1,2-a]pyridine-3-carboxamide;

N-(tert-butylsulfonyl)-6-(2-(5-fluoro-2-(((R)-tetrahydrofuran-3-yl)oxy)phenyl)pyrrolidin-1-yl)imidazo[1,2-a]pyridine-3-carboxamide;

N-(tert-butylsulfonyl)-6-(2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N-ethyl-N-methylsulfamoyl)-6-((2R,4S)-4-fluoro-2-(7-fluoro-2,3-dihydrobenzo[b][1,4]dioxin-5-yl)pyrrolidin-1-yl)imidazo[1,2-a]pyridine-3-carboxamide;

6-((R)-2-(5-fluoro-2-(((R)-tetrahydrofuran-3-yl)oxy)phenyl)pyrrolidin-1-yl)-N-((1-methylcyclopropyl)sulfonyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-methyl-N-propylsulfamoyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-(2-fluoro-2-methylpropyl)-N-methylsulfamoyl)imidazo[1,2-a]pyridine-3-carboxamide;

(R)—N—(N-ethyl-N-methylsulfamoyl)-6-(2-(5-fluoro-2-(2-fluoroethoxy)phenyl)pyrrolidin-1-yl)imidazo[1,2-a]pyridine-3-carboxamide;

(R)-6-(2-(5-fluoro-2-(2-fluoroethoxy)phenyl)pyrrolidin-1-yl)-N—(N-(2-fluoroethyl)-N-methylsulfamoyl)imidazo[1,2-a]pyridine-3-carboxamide;

(R)-6-(2-(5-fluoro-2-(2-fluoroethoxy)phenyl)pyrrolidin-1-yl)-N—(N-methyl-N-propylsulfamoyl)imidazo[1,2-a]pyridine-3-carboxamide;

(R)-6-(2-(5-fluoro-2-(2-fluoroethoxy)phenyl)pyrrolidin-1-yl)-N—(N-(2-fluoro-2-methylpropyl)-N-methylsulfamoyl)imidazo[1,2-a]pyridine-3-carboxamide;

(R)—N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-(2-fluoroethyl)-N-methylsulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-(2-fluoro-2-methylpropyl)-N-methylsulfamoyl)imidazo[1,2-a]pyridine-3-carboxamide;

1-(6-((2S,4R)-4-fluoro-2-(5-fluoro-2-((tetrahydro-2H-pyran-4-yl)oxy)phenyl)pyrrolidin-1-yl)imidazo[1,2-a]pyridin-3-yl)-N-(2-fluoroethyl)-N-methyl-1-oxomethanesulfonamide;

(tert-butylsulfonyl)(6-((2S,4R)-4-fluoro-2-(5-fluoro-2-((tetrahydro-2H-pyran-4-yl)oxy)phenyl)pyrrolidin-1-yl)imidazo[1,2-a]pyridin-3-yl)methanone;

(S)-(6-(2-(2,5-difluorophenyl)pyrrolidin-1-yl)imidazo[1,2-a]pyridin-3-yl)(3-hydroxyazetidin-1-yl)methanone;

(R)-(6-(2-(2,5-difluorophenyl)pyrrolidin-1-yl)imidazo[1,2-a]pyridin-3-yl)(3-hydroxyazetidin-1-yl)methanone;

(R)-6-(2-(2,5-difluorophenyl)pyrrolidin-1-yl)-N—(N-methyl-N-(pyrazin-2-yl)sulfamoyl)imidazo[1,2-a]pyridine-3-carboxamide;

(R)—N-((6-(1H-imidazol-1-yl)pyridin-3-yl)sulfonyl)-6-(2-(2,5-difluorophenyl)pyrrolidin-1-yl)imidazo[1,2-a]pyridine-3-carboxamide;

N—(N,N-diethylsulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-(2-fluoroethyl)sulfamoyl)-6-((2R,4S)-4-fluoro-2-(5-fluoro-2-(((R)-tetrahydrofuran-3-yl)oxy)phenyl)pyrrolidin-1-yl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(thiazol-2-yl)sulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(6-methylpyridazin-3-yl)sulfamoyl)imidazo[1,2-a]pyridine-3-carboxamide (R)—N-(tert-butylsulfonyl)-6-(2-(5-fluoro-2-((tetrahydro-2H-pyran-4-yl)oxy)phenyl)pyrrolidin-1-yl)imidazo[1,2-a]pyridine-3-carboxamide;

(R)—N—(N-ethyl-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide;

(R)—N—(N-(2-ethoxyethyl)-N-methylsulfamoyl)-6-(2-(5-fluoro-2-((tetrahydro-2H-pyran-4-yl)oxy)phenyl)pyrrolidin-1-yl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(6-methylpyridazin-3-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-propylsulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-(2-methoxyethyl)-N-methylsulfamoyl)imidazo[1,2-a]pyridine-3-carboxamide;

(R)-6-(2-(2,5-difluorophenyl)pyrrolidin-1-yl)-N—(N-methyl-N-(1-methyl-1H-pyrazol-3-yl)sulfamoyl)imidazo[1,2-a]pyridine-3-carboxamide;

(R)-6-(2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;

N-(tert-butylsulfonyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N,N-diethylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(1-methyl-1H-pyrazol-3-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(1,3,4-thiadiazol-2-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(5-methyl-1,3,4-thiadiazol-2-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-(2-fluoroethyl)-N-methylsulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(thiazol-2-yl)sulfamoyl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-propylsulfamoyl)imidazo[1,2-a]pyridine-3-carboxamide;

N—(N-ethyl-N-(2-fluoroethyl)sulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

6-((2R,4S)-4-fluoro-2-(5-fluoro-2-(((R)-tetrahydrofuran-3-yl)oxy)phenyl)pyrrolidin-1-yl)-N—(N-methyl-N-(pyridin-2-yl)sulfamoyl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-methyl-N-(pyridin-2-yl)sulfamoyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-(2-methoxyethyl)-N-methylsulfamoyl)imidazo[1,2-a]pyridine-3-carboxamide;

N—(N,N-dimethylsulfamoyl)-6-((R)-2-(5-fluoro-2-(((R)-tetrahydrofuran-3-yl)oxy)phenyl)pyrrolidin-1-yl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-methyl-N-propylsulfamoyl)imidazo[1,2-a]pyridine-3-carboxamide;

N—(N-cyclopropyl-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

N—(N-(2,2-difluoroethyl)-N-methylsulfamoyl)-6-((2R,4S)-4-fluoro-2-(5-fluoro-2-((tetrahydro-2H-pyran-4-yl)oxy)phenyl)pyrrolidin-1-yl)imidazo[1,2-a]pyridine-3-carboxamide;

6-((2R,4S)-4-fluoro-2-(5-fluoro-2-((tetrahydro-2H-pyran-4-yl)oxy)phenyl)pyrrolidin-1-yl)-N—(N-(2-fluoro-2-methylpropyl)-N-methylsulfamoyl)imidazo[1,2-a]pyridine-3-carboxamide;

6-((R)-2-(5-fluoro-2-(((R)-tetrahydrofuran-3-yl)oxy)phenyl)pyrrolidin-1-yl)-N—(N-(2-fluoroethyl)-N-methylsulfamoyl)imidazo[1,2-a]pyridine-3-carboxamide;

N—(N,N-diethylsulfamoyl)-6-((R)-2-(5-fluoro-2-(((R)-tetrahydrofuran-3-yl)oxy)phenyl)pyrrolidin-1-yl)imidazo[1,2-a]pyridine-3-carboxamide;

N—(N-ethyl-N-methylsulfamoyl)-6-((2S,4R)-4-fluoro-2-(5-fluoro-2-(((R)-tetrahydrofuran-3-yl)oxy)phenyl)pyrrolidin-1-yl)imidazo[1,2-a]pyridine-3-carboxamide;

6-((2S,4R)-4-fluoro-2-(5-fluoro-2-(((R)-tetrahydrofuran-3-yl)oxy)phenyl)pyrrolidin-1-yl)-N-((1-methylcyclopropyl)sulfonyl)imidazo[1,2-a]pyridine-3-carboxamide;

N—(N-ethyl-N-methylsulfamoyl)-6-((2S,4R)-4-fluoro-2-(5-fluoro-2-((tetrahydro-2H-pyran-4-yl)oxy)phenyl)pyrrolidin-1-yl)imidazo[1,2-a]pyridine-3-carboxamide; and (R)-6-(2-(2,5-difluorophenyl)pyrrolidin-1-yl)-N—(N-methyl-N-propylsulfamoyl)imidazo[1,2-a]pyridine-3-carboxamide;

or a pharmaceutically acceptable salt thereof, or a pharmaceutically acceptable solvate thereof or a stereoisomer thereof.

15. A pharmaceutical composition comprising at least one compound as claimed in the claim 1 and at least one pharmaceutically acceptable excipient.

16. A method of treating conditions, diseases and/or disorders treatable by inhibition of Trk kinase activity selected from pain, psoriasis, psoriatic arthritis, rheumatoid arthritis, atopic dermatitis or any combination thereof comprising administering a therapeutically effective amount of a compound as claimed in claim 1.

17. The method as claimed in claim 16, wherein pain includes chronic and acute pain.

18. The method as claimed in claim 16, wherein the pain is related to cancer, surgery, bone fracture, skeletal pain caused by tumor metastasis, osteoarthritis, psoriatic arthritis, rheumatoid arthritis, interstitial cystitits, chronic pancreatitis, visceral pain, inflammatory pain, migraine, chronic lower back pain, bladder pain syndrome or neuropathic pain.

19. The compound of claim 1 having TrkA inhibitory activity using TR-FRET assay of less than about 1 μM.

\* \* \* \* \*